(12) United States Patent
Chua et al.

(10) Patent No.: US 7,956,064 B2
(45) Date of Patent: Jun. 7, 2011

(54) FUSED TRICYCLIC COMPOUNDS AS SERINE-THREONINE PROTEIN KINASE AND PARP MODULATORS

(75) Inventors: Peter C. Chua, San Diego, CA (US); Jeffrey P. Whitten, Santee, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 766 days.

(21) Appl. No.: 11/849,230

(22) Filed: Aug. 31, 2007

(65) Prior Publication Data

US 2009/0105233 A1 Apr. 23, 2009
US 2009/0264423 A2 Oct. 22, 2009

Related U.S. Application Data

(60) Provisional application No. 60/842,061, filed on Sep. 1, 2006, provisional application No. 60/844,542, filed on Sep. 13, 2006, provisional application No. 60/846,683, filed on Sep. 22, 2006, provisional application No. 60/873,936, filed on Dec. 7, 2006, provisional application No. 60/895,716, filed on Mar. 19, 2007.

(51) Int. Cl.
*A61K 31/44* (2006.01)
*C07D 471/12* (2006.01)

(52) U.S. Cl. .......................................... 514/292; 546/81
(58) Field of Classification Search ........................ None
See application file for complete search history.

(56) References Cited

U.S. PATENT DOCUMENTS

| 5,624,677 | A | 4/1997 | El-Rashidy et al. |
| 2006/0029950 | A1 | 2/2006 | Whitten et al. |
| 2006/0074089 | A1 | 4/2006 | Whitten et al. |
| 2006/0264634 | A1 | 11/2006 | Whitten et al. |
| 2009/0239859 | A1* | 9/2009 | Chua et al. ................. 514/232.8 |

FOREIGN PATENT DOCUMENTS

| EP | 0 552 745 A2 | 7/1993 |
| JP | 5-197241 A | 8/1993 |
| JP | 10-282804 A | 10/1998 |
| JP | 2002-14550 A | 1/2002 |
| JP | 2002-132065 A | 5/2002 |
| JP | 2002-156808 A | 5/2002 |
| WO | WO 2008/016707 | * 2/2008 |

OTHER PUBLICATIONS

Hansen et al. Tetrahedron, 2005, 61, 9955-60.*
Wermuth. The Practice of Medicinal Chemistry, 1996, pp. 203-237.*
Calabrese et al., Clin. Cancer Res. (2003) 9:2711-2718.
Calabrese et al., J. Nat'l Cancer Inst. (2004) 96(1):56-67.
Curtin, Expert Reviews in Molecular Medicine (2005) 7(4).
Jagtap, Nature Rev.: Drug Discovery (2005) 4:421-440.
Li et al., Pain (2005) 115(1-2)182-190.
Paola et al., Eur. J. Pharmacology (2005) 527(1-3):163-171.
Parhar et al., Int. J. Colorectal Dis. (2006) 22(6):601-609.
Ruzzene et al., Biochem J. (2002) 364(Pt. 1):41-47.
U.S. Appl. No. 60/803,864, filed Jun. 3, 2006 (Lim et al.).
U.S. Appl. No. 60/811,990, filed Jun. 8, 2006 (Pierre et al.).
U.S. Appl. No. 60/811,992, filed Jun. 8, 2006 (Nagasawa et al.).
U.S. Appl. No. 60/904,694, filed Mar. 1, 2007 (Nagasawa et al.).
Veuger et al., Cancer Res. (2003) 63:6008-6015.
Ashford et al., Arzneimittel-Forschung (1971) 21(7):937-939.
International Search Report and Written Opinion for PCT/US07/77464, mailed Aug. 5, 2008, 10 pages.

* cited by examiner

*Primary Examiner* — Noble Jarrell
(74) *Attorney, Agent, or Firm* — Cooley LLP

(57) ABSTRACT

The invention relates in part to fused tricyclic compounds having certain biological activities that include, but are not limited to, inhibiting cell proliferation, modulating protein kinase activity and modulating polymerase activity. The fused tricyclic compounds of the invention can modulate casein kinase (CK) activity and/or poly(ADP-ribose)polymerase (PARP) activity. The invention also relates in part to methods for using such fused tricyclic compounds.

14 Claims, 9 Drawing Sheets

SEQUENCE LISTING

<160> NUMBER OF SEQ ID NOS: 4

<210> SEQ ID NO 1
<211> LENGTH: 391
<212> TYPE: PRT
<213> ORGANISM: Homo sapiens
<220> FEATURE:
<221> NAME/KEY: DOMAIN
<222> LOCATION: (1)...(391)
<223> OTHER INFORMATION: casein kinase II alpha 1 subunit isoform a

<400> SEQUENCE: 1

```
Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270
```

```
Leu Gly Arg His Ser Arg Lys Arg Trp Glu Arg Phe Val His Ser Glu
            275                 280                 285

Asn Gln His Leu Val Ser Pro Glu Ala Leu Asp Phe Leu Asp Lys Leu
        290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Ser Thr Pro Val Ser Ser Ala Asn Met Met
            340                 345                 350

Ser Gly Ile Ser Ser Val Pro Thr Pro Ser Pro Leu Gly Pro Leu Ala
            355                 360                 365

Gly Ser Pro Val Ile Ala Ala Asn Pro Leu Gly Met Pro Val Pro
        370                 375                 380

Ala Ala Ala Gly Ala Gln Gln
385                 390
```

<210> SEQ ID NO 2
<211> LENGTH: 391
<212> TYPE: PRT
<213> ORGANISM: Homo sapiens
<220> FEATURE:
<221> NAME/KEY: DOMAIN
<222> LOCATION: (1)...(391)
<223> OTHER INFORMATION: casein kinase II alpha 1 subunit isoform a

<400> SEQUENCE: 2

```
Met Ser Gly Pro Val Pro Ser Arg Ala Arg Val Tyr Thr Asp Val Asn
 1               5                  10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
```

```
              225                 230                 235                 240
Gln Leu Val Arg Ile Ala Lys Val Leu Gly Thr Glu Asp Leu Tyr Asp
                    245                 250                 255

Tyr Ile Asp Lys Tyr Asn Ile Glu Leu Asp Pro Arg Phe Asn Asp Ile
                260                 265                 270

Leu Gly Arg His Ser Arg Lys Arg Trp Glu Arg Phe Val His Ser Glu
            275                 280                 285

Asn Gln His Leu Val Ser Pro Glu Ala Leu Asp Phe Leu Asp Lys Leu
        290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
                340                 345                 350

Ser Gly Ile Ser Ser Val Pro Thr Pro Ser Pro Leu Gly Pro Leu Ala
            355                 360                 365

Gly Ser Pro Val Ile Ala Ala Ala Asn Pro Leu Gly Met Pro Val Pro
        370                 375                 380

Ala Ala Ala Gly Ala Gln Gln
385                 390

<210> SEQ ID NO 3
<211> LENGTH: 255
<212> TYPE: PRT
<213> ORGANISM: Homo sapiens
<220> FEATURE:
<221> NAME/KEY: DOMAIN
<222> LOCATION: (1)...(255)
<223> OTHER INFORMATION: casein kinase Ii alpha 1 subunit isoform b

<400> SEQUENCE: 3

Met Tyr Glu Ile Leu Lys Ala Leu Asp Tyr Cys His Ser Met Gly Ile
1               5                   10                  15

Met His Arg Asp Val Lys Pro His Asn Val Met Ile Asp His Glu His
            20                  25                  30

Arg Lys Leu Arg Leu Ile Asp Trp Gly Leu Ala Glu Phe Tyr His Pro
        35                  40                  45

Gly Gln Glu Tyr Asn Val Arg Val Ala Ser Arg Tyr Phe Lys Gly Pro
    50                  55                  60

Glu Leu Leu Val Asp Tyr Gln Met Tyr Asp Tyr Ser Leu Asp Met Trp
65                  70                  75                  80

Ser Leu Gly Cys Met Leu Ala Ser Met Ile Phe Arg Lys Glu Pro Phe
                85                  90                  95

Phe His Gly His Asp Asn Tyr Asp Gln Leu Val Arg Ile Ala Lys Val
            100                 105                 110

Leu Gly Thr Glu Asp Leu Tyr Asp Tyr Ile Asp Lys Tyr Asn Ile Glu
        115                 120                 125

Leu Asp Pro Arg Phe Asn Asp Ile Leu Gly Arg His Ser Arg Lys Arg
    130                 135                 140

Trp Glu Arg Phe Val His Ser Glu Asn Gln His Leu Val Ser Pro Glu
145                 150                 155                 160

Ala Leu Asp Phe Leu Asp Lys Leu Leu Arg Tyr Asp His Gln Ser Arg
                165                 170                 175

Leu Thr Ala Arg Glu Ala Met Glu His Pro Tyr Phe Tyr Thr Val Val
            180                 185                 190
```

-continued

```
Lys Asp Gln Ala Arg Met Gly Ser Ser Met Pro Gly Gly Ser Thr
            195                 200                 205

Pro Val Ser Ser Ala Asn Met Met Ser Gly Ile Ser Ser Val Pro Thr
        210                 215                 220

Pro Ser Pro Leu Gly Pro Leu Ala Gly Ser Pro Val Ile Ala Ala Ala
225                 230                 235                 240

Asn Pro Leu Gly Met Pro Val Pro Ala Ala Ala Gly Ala Gln Gln
                245                 250                 255

<210> SEQ ID NO 4
<211> LENGTH: 1014
<212> TYPE: PRT
<213> ORGANISM: Homo sapiens
<220> FEATURE:
<221> NAME/KEY: DOMAIN
<222> LOCATION: (1)...(1014)
<223> OTHER INFORMATION: poly (ADP-ribose) polymerase family, member 1

<400> SEQUENCE: 4

Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300
```

-continued

```
Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
            325                 330                 335

Lys Glu Phe Arg Glu Ile Ser Tyr Leu Lys Lys Leu Lys Val Lys Lys
        340                 345                 350

Gln Asp Arg Ile Phe Pro Pro Glu Thr Ser Ala Ser Val Ala Ala Thr
    355                 360                 365

Pro Pro Pro Ser Thr Ala Ser Ala Pro Ala Ala Val Asn Ser Ser Ala
370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
        435                 440                 445

Ala Asn Ile Arg Val Val Ser Glu Asp Phe Leu Gln Asp Val Ser Ala
    450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
        515                 520                 525

Gly Gly Ala Ala Val Asp Pro Asp Ser Gly Leu Glu His Ser Ala His
    530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu Gln Phe Met Lys Leu Tyr Glu Glu Lys Thr Gly Asn
    610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
    690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
```

```
            725                 730                 735
Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
            755                 760                 765

Leu Asp Ile Glu Val Ala Tyr Ser Leu Leu Arg Gly Gly Ser Asp Asp
            770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
            805                 810                 815

Tyr Val Lys Asn Thr His Ala Thr Thr His Ser Ala Tyr Asp Leu Glu
            820                 825                 830

Val Ile Asp Ile Phe Lys Ile Glu Arg Glu Gly Glu Cys Gln Arg Tyr
            835                 840                 845

Lys Pro Phe Lys Gln Leu His Asn Arg Arg Leu Leu Trp His Gly Ser
            850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
            885                 890                 895

Phe Ala Asp Met Val Ser Lys Ser Ala Asn Tyr Tyr His Thr Ser Gln
            900                 905                 910

Gly Asp Pro Ile Gly Leu Ile Leu Leu Gly Glu Val Ala Leu Gly Asn
            915                 920                 925

Met Tyr Glu Leu Lys His Ala Ser His Ile Ser Arg Leu Pro Lys Gly
            930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
            965                 970                 975

Ser Gly Val Ile Asp Thr Ser Leu Leu Tyr Asn Glu Tyr Ile Val Tyr
            980                 985                 990

Asp Ile Ala Gln Val Asn Leu Lys Tyr Leu Leu Lys Leu Lys Phe Asn
            995                 1000                1005

Phe Lys Thr Ser Leu Trp
            1010
```

FUSED TRICYCLIC COMPOUNDS AS SERINE-THREONINE PROTEIN KINASE AND PARP MODULATORS

CROSS-REFERENCE TO RELATED APPLICATIONS

This application claims priority under 35 U.S.C. §119(e) to U.S. Provisional Application Ser. No. 60/842,061 filed Sep. 1, 2006; U.S. Provisional Application Ser. No. 60/844,542 filed Sep. 13, 2006; U.S. Provisional Application Ser. No. 60/846,683 filed Sep. 22, 2006; U.S. Provisional Application Ser. No. 60/873,936 filed Dec. 7, 2006; and U.S. Provisional Application Ser. No. 60/859,716 filed Mar. 19, 2007. The contents of these documents are incorporated herein by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

File Name 532232003200Seqlist.txt

Date of Creation Aug. 28, 2008

Size(bytes) 18011 bytes

FIELD OF THE INVENTION

The invention relates in part to molecules having certain biological activities that include, but are not limited to, inhibiting cell proliferation, modulating serine-threonine protein kinase activity and modulating polymerase activity. Molecules of the invention can modulate casein kinase (CK) activity (e.g., CK2 activity) and/or poly(ADP-ribose)polymerase (PARP) activity. The invention also relates in part to methods for using such molecules.

DISCLOSURE OF THE INVENTION

The present invention in part provides chemical compounds having certain biological activities that include, but are not limited to, inhibiting cell proliferation, inhibiting angiogenesis, modulating protein kinase activity and modulating polymerase activity. Certain molecules can modulate casein kinase 2 (CK2) activity and/or a poly(ADP-ribose) polymerase (PARP) activity and can affect biological functions that include but are not limited to, inhibiting gamma phosphate transfer from ATP to a protein or peptide substrate, inhibiting angiogenesis, inhibiting cell proliferation and inducing cell apoptosis, for example. The present invention also in part provides methods for preparing novel chemical compounds, and analogs thereof, and methods of using the foregoing. Also provided are compositions comprising the above-described molecules in combination with other agents, and methods for using such molecules in combination with other agents.

The compounds of the invention have the general formula (A):

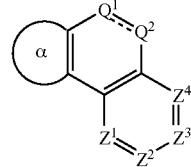

(A)

wherein the group labeled α represents a 5-6 membered aromatic or heteroaromatic ring fused onto the ring containing $Q^1$, wherein α is a 6-membered aryl ring optionally containing one or more nitrogen atoms as ring members, or a five membered aryl ring selected from thiophene and thiazole;

$Q^1$ is C=X, $Q^2$ is $NR^5$, and the bond between $Q^1$ and $Q^2$ is a single bond; or $Q^1$ is C—X—$R^5$, $Q^2$ is N, and the bond between $Q^1$ and $Q^2$ is a double bond; and wherein X represents O, S or $NR^4$, and $Z^1$-$Z^8$ and $R^4$ and $R^5$ are as defined below;

provided that when $Q^1$ in Formula (A) is C—NHΦ, where Φ is optionally substituted phenyl:

if the ring labeled α is a six-membered ring containing at least one N as a ring member, at least one $R^3$ present must be a polar substituent, or if each $R^3$ is H, then Φ must be substituted; and if the ring labeled α is phenyl, and three of $Z^1$-$Z^4$ represent CH, then $Z^2$ cannot be C—OR", and $Z^3$ cannot be $NH_2$, $NO_2$, NHC(=O)R" or NHC(=O)—OR", where R" is C1-C4 alkyl.

The invention also includes the pharmaceutically acceptable salts of compounds of formula (A). Thus in each compound of the invention, Formula (A) represents a fused tricyclic ring system which is linked through either $Q^1$ or $Q^2$ to a group $R^5$, which is further described below.

Thus, provided herein are compounds of Formulae I, II, III and IV:

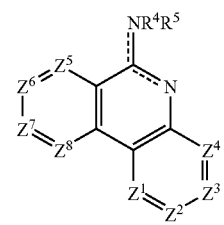

Formula I

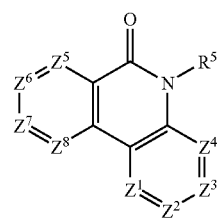

Formula II

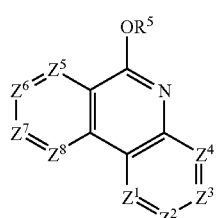

Formula III

-continued

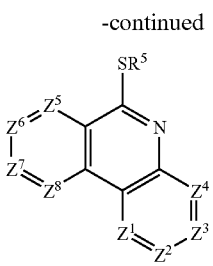

Formula IV and pharmaceutically acceptable salts, esters, prodrugs and tautomers thereof; wherein:
each $Z^1$, $Z^2$, $Z^3$, and $Z^4$ is N or $CR^3$;
each of $Z^5$, $Z^6$, $Z^7$ and $Z^8$ is $CR^6$ or N;
each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group,
or each $R^3$ and each $R^6$ can be halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$,
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or more N, O or S;
and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR''SO_2R'$, $NR''CONR'_2$, NR'COOR', NR'COR', CN, COOR', $CONR'_2$, OOCR', COR', and $NO_2$,
wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;
and wherein two R' can be linked to form a 3-7 membered ring optionally containing up to three heteroatoms selected from N, O and S,
$R^4$ is H or optionally substituted member selected from the group consisting of C1-C6 alkyl, C2-C6 heteroalkyl, and C1-C6 acyl;
each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and
in each —$NR^4R^5$, $R^4$ and $R^5$ together with N may form an optionally substituted 3-8 membered ring, which may optionally contain an additional heteroatom selected from N, O and S as a ring member;
provided that when —$NR^4R^5$ in Formula (I) is —NHΦ, where Φ is optionally substituted phenyl:
if at least one of $Z^5$-$Z^8$ is N, at least one $R^3$ present must be a polar substituent, or if each $R^3$ is H, then Φ must be substituted; and
if each of $Z^5$-$Z^8$ is $CR^6$, and three of $Z^1$-$Z^4$ represent CH, then $Z^2$ cannot be C—OR", and $Z^3$ cannot be $NH_2$, $NO_2$, NHC(=O)R" or NHC(=O)—OR", where R" is C1-C4 alkyl.

In certain embodiments, provided are compounds having the structure of Formulae I, II, III, and IV, and pharmaceutically acceptable salts, esters and tautomers thereof; wherein:
each $Z^1$, $Z^2$, $Z^3$, and $Z^4$ is N or $CR^3$;
each of $Z^5$, $Z^6$, $Z^7$ and $Z^8$ is N or $CR^6$;
none, one or two of $Z^1$-$Z^4$ are N and none, one or two of $Z^5$-$Z^8$ are N;
each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group,
or each $R^3$ and each $R^6$ is independently halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, polar substituent, carboxy bioisostere, COOH or $NO_2$,
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or more N, O or S;
and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$,
wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;
and wherein two R' can be linked to form a 3-7 membered ring optionally containing up to three heteroatoms selected from N, O and S;
$R^4$ is H or an optionally substituted member selected from the group consisting of C1-C6 alkyl, C2-C6 heteroalkyl, and C1-C6 acyl;
each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —NR⁴R⁵, R⁴ and R⁵ together with N may form an optionally substituted 3-8 membered ring, which may optionally contain an additional heteroatom selected from N, O and S as a ring member;

provided that when —NR⁴R⁵ in Formula (I) is —NHΦ, where Φ is optionally substituted phenyl:
  if all of $Z^5$-$Z^8$ are CH or one of $Z^5$-$Z^8$ is N, at least one of $Z^1$-$Z^4$ is CR³ and at least one R³ must be a non-hydrogen substituent; or
  if each R³ is H, then Φ must be substituted; or
if all of $Z^5$-$Z^8$ are CH or one of $Z^5$-$Z^8$ is N, then $Z^2$ is not C—OR", and $Z^3$ is not NH₂, NO₂, NHC(=O)R" or NHC(=O)—OR", where R" is C1-C4 alkyl.

In certain embodiments, one, two, three or four of $Z^5$, $Z^6$, $Z^7$ and $Z^8$ are N. For embodiments in which two of $Z^5$, $Z^6$, $Z^7$ and $Z^8$ are N, the ring nitrogen atoms may be adjacent (e.g., nitrogen atoms at $Z^5$ and $Z^6$, $Z^6$ and $Z^7$, or $Z^7$ and $Z^8$) or may be separated by one or two ring positions (e.g., nitrogen atoms at $Z^5$ and $Z^7$, $Z^6$ and $Z^8$ or $Z^5$ and $Z^8$). In certain embodiments, at least one R³ substituent is a polar substituent, such as a carboxylic acid or a salt, an ester or a bioisostere thereof. In some embodiments, at least one R³ is a carboxylic acid-containing substituent or a carboxylate bioisostere, or a salt or ester thereof, for example. In some embodiments, at least one R³ is a carboxylic acid-containing substituent or a salt thereof.

The term "polar substituent" as used herein refers to any substituent having an electric dipole, and optionally a dipole moment (e.g., an asymmetrical polar substituent has a dipole moment and a symmetrical polar substituent does not have a dipole moment). Polar substituents include substituents that accept or donate a hydrogen bond, and groups that would carry at least a partial positive or negative charge in aqueous solution at physiological pH levels. In certain embodiments, a polar substituent is one that can accept or donate electrons in a non-covalent hydrogen bond with another chemical moiety. In certain embodiments, a polar substituent is selected from a carboxy, a carboxy bioisostere or other acid-derived moiety that exists predominately as an anion at a pH of about 7 to 8. Other polar substituents include, but are not limited to, groups containing an OH or NH, an ether oxygen, an amine nitrogen, an oxidized sulfur or nitrogen, a carbonyl, a nitrile, and a nitrogen-containing or oxygen-containing heterocyclic ring whether aromatic or non-aromatic. In some embodiments, the polar substituent represented by R³ is a carboxylate or a carboxylate bioisostere.

"Carboxylate bioisostere" or "carboxy bioisostere" as used herein refers to a moiety that is expected to be negatively charged to a substantial degree at physiological pH. In certain embodiments, the carboxylate bioisostere is a moiety selected from the group consisting of:

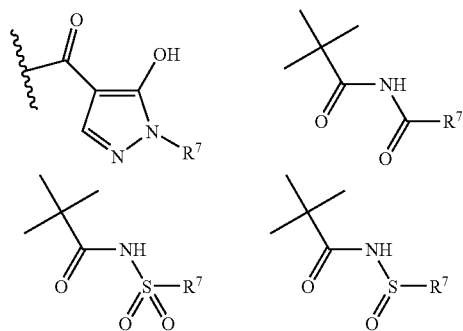

-continued

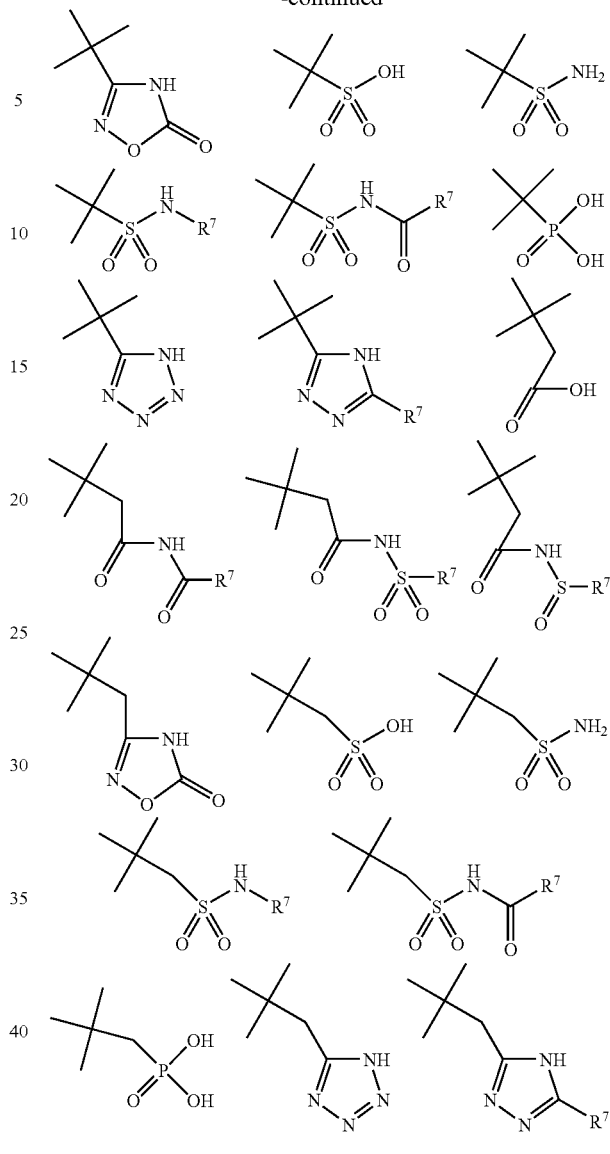

and salts and prodrugs of the foregoing, wherein each R⁷ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring; or R⁷ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring. In certain embodiments, the polar substituent is selected from the group consisting of carboxylic acid, carboxylic ester, carboxamide, tetrazole, triazole, carboxymethanesulfonamide, oxadiazole, oxothiadiazole, thiazole, aminothiazole and hydroxythiazole. In some embodiments, at least one R³ present is a carboxylic acid or a salt, or ester or a bioisostere thereof. In certain embodiments, at least one R³ present is a carboxylic acid-containing substituent or a salt, ester or bioisostere thereof. In the latter embodiments, the R³ substituent may be a C1-C10 alkyl or C1-C10 alkenyl linked to a carboxylic acid (or salt, ester or bioisostere thereof), for example, and in some embodiments, the R³ substituent is not —NHCOOCH₂CH₃.

In certain embodiments, at least one of $Z^1$-$Z^4$ and $Z^5$-$Z^8$ is a nitrogen atom, and one or more ring nitrogen atoms can be positioned in the ring containing $Z^1$-$Z^4$ or in the ring containing $Z^5$-$Z^8$ such that each ring is independently an optionally substituted pyridine, pyrimidine or pyridazine ring. For example, one or more ring nitrogen atoms within the ring containing $Z^5$-$Z^8$ may be arranged as follows:

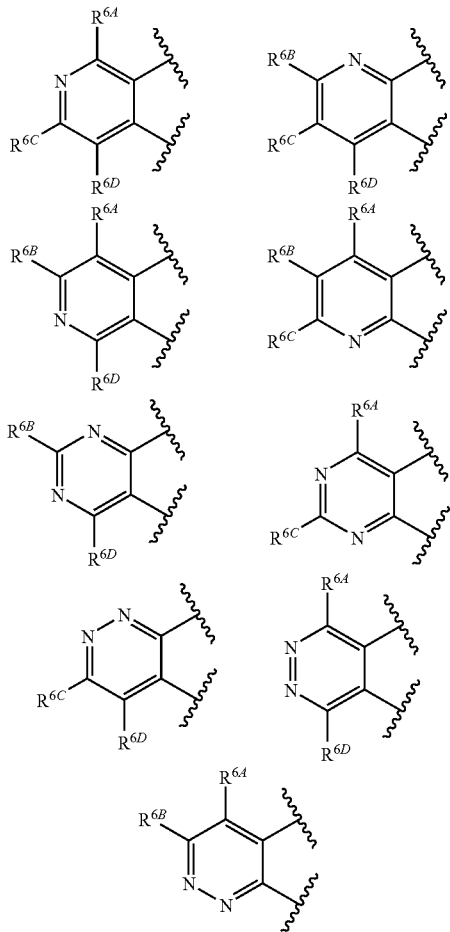

where each $R^{6A}$, $R^{6B}$, $R^{6C}$ and $R^{6D}$ independently is selected from $R^6$ substituents defined above with respect to compounds of Formula I, II, III or IV. In certain embodiments, no two adjacent $Z^1$-$Z^4$ or $Z^5$-$Z^8$ both are N.

A polar substituent may be at any position on the ring containing $Z^1$-$Z^4$ in Formula I, II, III or IV, and the ring may include one, two, three or four polar substituents. In certain embodiments, each of $Z^1$-$Z^4$ may be $CR^3$ and one of the $R^3$ substituents may be a polar substituent (e.g., a carboxylate or carboxylic acid ester, or a tetrazole) arranged at any one of the positions in the ring containing $Z^1$-$Z^4$:

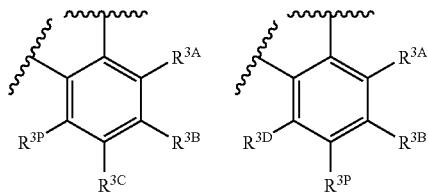

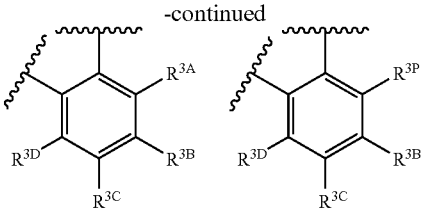

where $R^{3P}$ is a polar substituent and each $R^{3A}$, $R^{3B}$, $R^{3C}$ and $R^{3D}$ independently is selected from $R^3$ substituents, as defined above with respect to compounds of Formula I, II, III or IV.

In certain embodiments of the compounds in the foregoing Formulae, $R^4$ is H. In some embodiments, $R^4$ is H or $CH_3$ and $R^5$ is an optionally substituted 3-8 membered ring, which can be aromatic, nonaromatic, and carbocyclic or heterocyclic, or $R^5$ is a $C_{1-10}$ alkyl group substituted with such an optionally substituted 3-8 membered ring. In specific embodiments, $R^5$ is an optionally substituted five-, six-, or seven-membered carbocyclic or heterocyclic ring, and sometimes is an optionally substituted phenyl ring.

In some embodiments pertaining to compounds of Formula I, $R^4$ is H or $CH_3$ and $R^5$ is a phenyl substituted with one or more halogen (e.g., F, Cl) or acetylene substituents, which substituents sometimes are on the phenyl ring at the 3-position, 4-position or 5-position, or combinations thereof (e.g., the 3- and 5-positions).

$R^5$ in certain embodiments is a $C_{1-2}$ alkyl substituted with an optionally substituted phenyl, pyridyl or morpholino ring substituent, or substituted with —$NR^4R^4$ where $R^4$ is as defined above (e.g., $R^5$ may be —$N(CH_3)_2$). The polar group represented by $R^3$ in some embodiments is a carboxy, carboxyalkyl (e.g., carboxymethyl), tetrazole or amide (e.g., —$CONH_2$) substituent. In other embodiments, $R^3$ represents a carboxylate bioisostere.

An $R^6$ substituent in certain embodiments, such as $R^{6B}$, sometimes is a —$NR^4R^5$ substituent, such as a —NH—(C1-C6 alkyl) moiety (e.g., —NH—$CH_3$), for example. In some embodiments, the compound has the structure of Formula I; $R^4$ is H or $CH_3$; $R^5$ is an optionally substituted five-, six-, or seven-membered carbocyclic or heterocyclic ring, and sometimes is an optionally substituted phenyl ring; and one $R^3$ is a carboxylic acid or a salt, an ester or a carboxylate bioisostere. In some embodiments, the compound has the structure of Formula I; $R^4$ is H or $CH_3$; $R^5$ is an optionally substituted five-, six-, or seven-membered carbocyclic or heterocyclic ring, and sometimes is an optionally substituted phenyl ring; and one or two of $Z^5$, $Z^6$, $Z^7$ and $Z^8$ are N.

In some embodiments of compounds of Formulae I, II, III or IV, each of $Z^1$, $Z^2$, $Z^3$, and $Z^4$ is $CR^3$, and at least one $R^3$ is H, or at least two $R^3$ are H. Often, at least one $R^6$ is H, or at least two $R^6$ are H. In some embodiments, (i) each $Z^1$, $Z^2$, $Z^3$, $Z^4$, $Z^5$, $Z^6$ and $Z^8$ is $CR^3$ and $Z^7$ is nitrogen; or (ii) each $Z^1$, $Z^2$, $Z^3$, $Z^1$, $Z^1$, $Z^7$ and $Z^8$ is $CR^3$ and $Z^5$ is nitrogen; or (iii) each $Z^1$, $Z^2$, $Z^3$, $Z^4$, $Z^6$, and $Z^8$ is $CR^3$ and each of $Z^5$ and $Z^7$ is nitrogen. Each $R^3$ and/or each $R^6$ present in certain embodiments is hydrogen, except that at least one $R^3$ present is a polar substituent. In some embodiments, each $R^{3A}$, $R^{3C}$, $R^{3D}$, $R^{6A}$, $R^{6B}$, $R^{6C}$ and $R^{6D}$ is H and $R^{3B}$ is a polar substituent (e.g., carboxylate, carboxylic acid, tetrazole).

Also provided herein are compounds of Formula (A) represented by one of Formulae V, VI, VII or VIII:

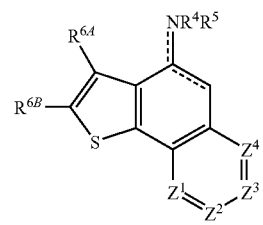

Formula V

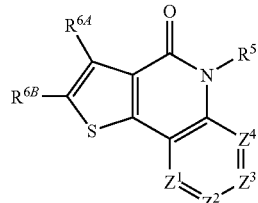

Formula VI

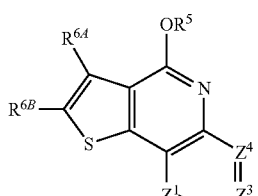

Formula VII

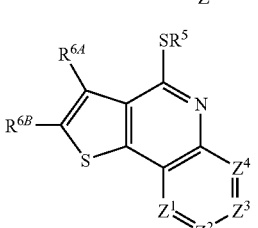

Formula VIII and pharmaceutically acceptable salts, esters, prodrugs and tautomers thereof; where $Z^1, Z^2, Z^3, Z^4, R^4$ and $R^5$ are defined above with respect to compounds of Formulae I, II, III and IV, and each $R^{6A}$ and $R^{6B}$ is independently selected from an $R^6$ substituent defined above with respect to compounds of Formulae I, II, III and IV. As with compounds of Formulae I, II, III and IV, at least one $R^3$ present is a polar substituent, such as a polar substituent described above. Embodiments described with respect to compounds of Formulae I, II, III and IV also may be applied to compounds of Formulae V, VI, VII and VIII.

In certain embodiments, provided are compounds having a structure of Formulae V, VI, VII and VIII, and pharmaceutically acceptable salts, esters and tautomers thereof; wherein:

each $Z^1$, $Z^2$, $Z^3$, and $Z^4$ independently is N or $CR^3$ and none, one or two of $Z^1$, $Z^2$, $Z^3$, and $Z^4$ is N;

each $R^3$, $R^{6A}$ and $R^{6B}$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$, $R^{6A}$ and $R^{6B}$ independently is halo, OR, NR$_2$, NROR, NRNR$_2$, SR, SOR, SO$_2$R, SO$_2$NR$_2$, NRSO$_2$R, NRCONR$_2$, NRCOOR, NRCOR, CN, COOR, polar substituent, carboxy bioisostere, CONR$_2$, OOCR, COR, or NO$_2$, wherein each R is independently H or C1-C8 alkyl, C2-C8 heteroalkyl, C2-C8 alkenyl, C2-C8 heteroalk-enyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, $R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —NR$^4$R$^5$, $R^4$ and $R^5$ together with N may form an optionally substituted 3-8 membered ring, which may optionally contain an additional heteroatom selected from N, O and S as a ring member;

provided that if $R^5$ in Formula IV is phenyl, substituted phenyl, —CH(CH$_3$)—(CH$_2$)$_3$—NEt$_2$, —(CH$_2$)$_3$-piperazine-(CH$_2$)$_3$—NH$_2$, cyclohexane or butyl, then one or more of $R^3$ present is a non-hydrogen moiety.

In some embodiments pertaining to compounds of Formulae V, VI, VII and VIII, each of $Z^1$, $Z^2$, $Z^3$, and $Z^4$ is $CR^3$, and at least one $R^3$ is H, or at least two $R^3$ are H. Often, at least one of $R^{6A}$ and $R^{6B}$ is H, and sometimes each of $R^{6A}$ and $R^{6B}$ is H. In certain embodiments, each $R^3$ and/or each of $R^{6A}$ and $R^{6B}$ present is H, except that at least one $R^3$ present is a polar substituent. In some embodiments, each $R^{3A}$, $R^{3C}$, $R^{3D}$, $R^{6A}$ and $R^{6B}$ is H and $R^{3B}$ is a polar substituent (e.g., carboxylate bioisostere, carboxylic acid, tetrazole).

In certain embodiments pertaining to compounds of Formula V, $R^4$ is H or CH$_3$ and $R^5$ is an optionally substituted five-, six- or seven-membered carbocyclic or heterocyclic ring (e.g., optionally substituted phenyl ring). In some embodiments pertaining to compounds of Formula V, $R^4$ is H or CH$_3$ and $R^5$ is a phenyl ring substituted with one or more halogen (e.g., F, Cl) or acetylene substituents, which substituents sometimes are at the 3-position, 4-position or 5-position, or a combination thereof (e.g., the 3- and 5-positions). $R^5$ in certain embodiments is a $C_{1-3}$ alkyl substituted with an optionally substituted phenyl, pyridyl, morpholino or pyrrolyl substituent, or a $C_{1-3}$ alkyl substituted with a hydroxyl substituent or substituted with a substituent —NR$^4$R$^4$, where $R^4$ is as defined above (e.g., $R^5$ can be —N(CH$_3$)$_2$). An $R^6$ substituent in certain embodiments, such as $R^{6A}$ or $R^{6B}$, sometimes is a —$NR^4R^5$ substituent, such as a —NH—(C1-C6 alkyl) moiety (e.g., —NH—CH$_3$), for example.

Provided also are compounds of Formulae IX, X, XI and XII:

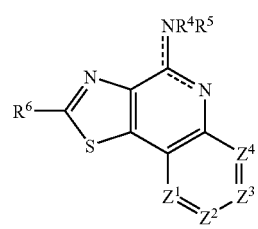

Formula IX

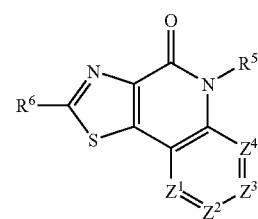

Formula X

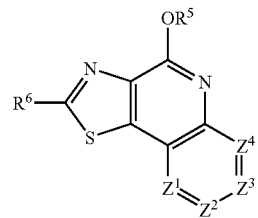

Formula XI

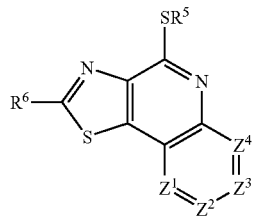

Formula XII and pharmaceutically acceptable salts, esters, prodrugs and tautomers thereof; where $Z^1$, $Z^2$, $Z^3$, $Z^4$, $R^4$, $R^5$ and $R^6$ are defined above with respect to compounds of Formulae I, II, III and IV. As with compounds of Formulae I, II, III and IV, at least one $R^3$ present is a polar substituent, such as a polar substituent described above (e.g., carboxylic acid, carboxylate, tetrazole). For compounds of Formula IX, $R^4$ and $R^5$ are not both hydrogen, and independently are H, —$Y^0$ or -$LY^1$, where $Y^0$ is an optionally substituted 5-membered ring or optionally substituted 6-membered ring (e.g., heterocyclic ring or carbocyclic ring each being aryl or non-aryl), $Y^1$ is an optionally substituted 5-membered aryl ring or optionally substituted 6-membered aryl ring, and L is a C1-C20 alkyl linker or C1-C20 alkylene linker. In some embodiments, provided are compounds having a structure of Formulae IX, X, XI and XII, and pharmaceutically acceptable salts, esters and tautomers thereof; wherein:

each $Z^1$, $Z^2$, $Z^3$, and $Z^4$ is N or $CR^3$ and none, one or two of $Z^1$, $Z^2$, $Z^3$, and $Z^4$ is N;

each $R^3$ and $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ and $R^6$ can be halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, polar substituent, carboxy bioisostere, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member.

Embodiments described with respect to compounds of Formulae I, II, III, IV, V, VI, VII and VIII also may be applied to compounds of Formulae IX, X, XI and XII. In some embodiments pertaining to compounds of Formulae IX, X, XI and XII, each of $Z^1$, $Z^2$, $Z^3$, and $Z^4$ is $CR^3$, and at least one $R^3$ is H, or at least two $R^3$ are H. $R^6$ often is H, and in certain embodiments, each $R^6$ and $R^3$ present is H, except that at least one $R^3$ present is a polar substituent. In some embodiments, each $R^{3A}$, $R^{3C}$, $R^{3D}$ and $R^6$ is H and $R^{3B}$ is a polar substituent (e.g., carboxylate, carboxylic acid, tetrazole).

In certain embodiments pertaining to compounds of Formula IX, $R^4$ is H or $CH_3$ and $R^5$ is an optionally substituted five-, six- or seven-membered carbocyclic or heterocyclic ring (e.g., optionally substituted phenyl ring). In some embodiments pertaining to compounds of Formula IX, $R^4$ is H or $CH_3$ and $R^5$ is a phenyl ring substituted with one or more halogen (e.g., F, Cl) or acetylene substituents, which substituents sometimes are at the 3-position, 4-position or 5-position, or a combination thereof (e.g., the 3- and 5-positions). $R^5$ in certain embodiments is a $C_{1-3}$ alkyl substituted with an optionally substituted phenyl, pyridyl, morpholino or pyrrolyl substituent, or a $C_{1-3}$ alkyl substituted with a hydroxyl substituent or substituted with a —$NR^4R^4$ (e.g., —$N(CH_3)_2$) substituent. $R^6$ in certain embodiments sometimes is a —$NR^4R^5$ substituent, such as a —NH—(C1-C6 alkyl) moiety (e.g., —NH—$CH_3$), for example.

Also provided herein are compounds of Formulae XIII, XIV, XV and XVI:

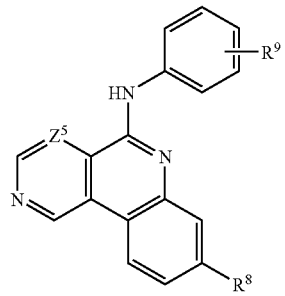

Formula XIII

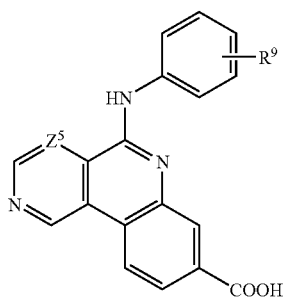

Formula XIV

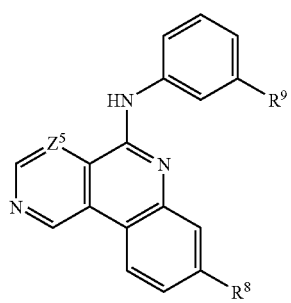

Formula XV

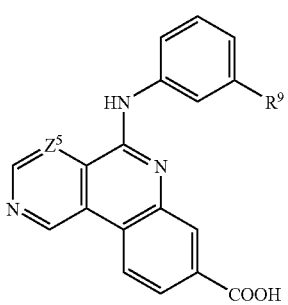

Formula XVI and pharmaceutically acceptable salts, esters, prodrugs and tautomers thereof; wherein:
and pharmaceutically acceptable salts, esters, prodrugs and tautomers thereof; wherein:

$Z^5$ is N or $CR^{6A}$;
each $R^{6A}$, $R^{6B}$, $R^{6C}$ and $R^8$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^{6A}$, $R^{6B}$, $R^{6C}$ and $R^8$ independently is halo, $CF_3$, CFN, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, carboxy bioisostere, $CONR_2$, OOCR, COR, or $NO_2$, $R^9$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-$C_{12}$ heteroaryl, C7-C12 arylalkyl, or C6-C12 heteroarylalkyl group, or $R^9$ is independently halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

n is 0 to 4; and
p is 0 to 4.

In certain embodiments for compounds of Formulae XIII, XIV, XV and XVI, $Z^5$ is N. In some embodiments, $R^8$ is a caboxy moiety, such as a carboxylate or carboxylic acid. In certain embodiments, $R^9$ is selected from —C≡CR, —C≡CH, —$CH_3$, —$CH_2CH_3$, —$CF_3$, —CFN, —C≡N, —OR or halogen. In some embodiments $R^9$ is selected from halogen, —C≡CR or —C≡CH. In certain embodiments $R^9$ is selected from halogen or —C≡CH, and in some embodiments $R^9$ is halogen, is chloro, is bromo or is —C≡CH.

Also provided herein is a pharmaceutical composition comprising a compound described herein and a pharmaceutically acceptable carrier. Pharmaceutical compositions can be utilized in treatments described herein.

Provided also are methods for identifying a candidate molecule that interacts with a CK2 or PARP protein, which comprise: contacting a composition containing a CK2 or PARP protein and a compound described herein with a candidate molecule under conditions in which the compound and the protein interact, and determining whether the amount of the compound that interacts with the protein is modulated relative to a control interaction between the compound and the protein without the candidate molecule, whereby a candidate molecule that modulates the amount of the compound interacting with the protein relative to the control interaction is identified as a candidate molecule that interacts with the protein. In certain embodiments, the protein is a CK2 protein, such as a CK2 protein comprising the amino acid sequence of SEQ ID NO: 1, 2 or 3 or a substantially identical variant thereof, for example.

SEQ ID NO: 1 (NP 001886; casein kinase II alpha 1 subunit
isoform a [Homo sapiens])

```
  1 msgpvpsrar vytdvnthrp reywdyeshv vewgnqddyq lvrklgrgky sevfeainit 61 nnekvvvkil kpvkkkkikr eikilenlrg gpniitladi vkdpvsrtpa lvfehvnntd 121 fkqlyqtltd ydirfymyei lkaldychsm gimhrdvkph nvmidhehrk lrlidwglae 181 fyhpgqeynv rvasryfkgp ellvdyqmyd ysldmwslgc mlasmifrke pffhghdnyd 241 qlvriakvlg tedlydyidk ynieldprfn dilgrhsrkr werfvhsenq hlvspealdf 301 ldkllrydhq srltareame hpyfytvvkd qarmgsssmp ggstpvssan mmsgissvpt 361 psplgplags pviaaanplg mpvpaaagaq q
```

SEQ ID NO: 2 (NP 808227; casein kinase II alpha 1 subunit
isoform a [Homo sapiens])

```
  1 msgpvpsrar vytdvnthrp reywdyeshv vewgnqddyq lvrklgrgky sevfeainit 61 nnekvvvkil kpvkkkkikr eikilenlrg gpniitladi vkdpvsrtpa lvfehvnntd 121 fkqlyqtltd ydirfymyei lkaldychsm gimhrdvkph nvmidhehrk lrlidwglae 181 fyhpgqeynv rvasryfkgp ellvdyqmyd ysldmwslgc mlasmifrke pffhghdnyd 241 qlvriakvlg tedlydyidk ynieldprfn dilgrhsrkr werfvhsenq hlvspealdf 301 ldkllrydhq srltareame hpyfytvvkd qarmgsssmp ggstpvssan mmsgissvpt 361 psplgplags pviaaanplg mpvpaaagaq q
```

SEQ ID NO: 3 (NP 808228; casein kinase II alpha 1 subunit
isoform b [Homo sapiens])

```
  1 myeilkaldy chsmgimhrd vkphnvmidh ehrklrlidw glaefyhpgq eynvrvasry 61 fkgpellvdy qmydysldmw slgcmlasmi frkepffhgh dnydqlvria kvlgtedlyd 121 yidkynield prfndilgrh srkrwerfvh senqhlvspe aldfldkllr ydhqsrltar 181 eamehpyfyt vvkdqarmgs ssmpggstpv ssanmmsgis svptpsplgp lagspviaaa 241 nplgmpvpaa agaqq
```

In some embodiments, the protein is a PARP protein, such as a PARP protein comprising the amino acid sequence of SEQ ID NO: 4 or a substantially identical variant thereof, for example.

SEQ ID NO: 4 (NP 001609; poly (ADP-ribose) polymerase family,
member 1 [Homo sapiens])

```
  1 maessdklyr veyaksgras ckkcsesipk dslrmaimvq spmfdgkvph wyhfscfwkv 61 ghsirhpdve vdgfselrwd dqqkvkktae aggvtgkgqd gigskaektl gdfaaeyaks 121 nrstckgcme kiekgqvrls kkmvdpekpq lgmidrwyhp gcfvknreel gfrpeysasq 181 lkgfsllate dkealkkqlp gvksegkrkg devdgvdeva kkkskkekdk dsklekalka 241 qndliwnikd elkkvcstnd lkellifnkq qvpsgesail drvadgmvfg allpceecsg 301 qlvfksdayy ctgdvtawtk cmvktqtpnr kewvtpkefr eisylkklkv kkqdrifppe 361 tsasvaatpp pstasapaav nssasadkpl snmkiltlgk lsrnkdevka mieklggklt 421 gtankaslci stkkevekmn kkmeevkean irvvsedflq dvsastkslq elflahilsp 481 wgaevkaepv evvaprgksg aalskkskgq vkeeginkse krmkltlkgg aavdpdsgle 541 hsahvlekgg kvfsatlglv divkgtnsyy klqlleddke nrywifrswg rvgtvigsnk 601 leqmpskeda ieqfmklyee ktgnawhskn ftkypkkfyp leidygqdee avkkltvnpg 661 tksklpkpvq dlikmifdve smkkamveye idlqkmplgk lskrqiqaay silsevqqav 721 sqgssdsqil dlsnrfytli phdfgmkkpp llnnadsvqa kvemldnlld ievaysllrg 781 gsddsskdpi dvnyeklktd ikvvdrdsee aeiirkyvkn thatthsayd levidifkie
```

```
841 regecqrykp fkqlhnrrll whgsrttnfa gilsqglria ppeapvtgym fgkgiyfadm 901 vsksanyyht sqgdpiglil lgevalgnmy elkhashisr lpkgkhsvkg lgkttpdpsa 961 nisldgvdvp lgtgissgvi dtsllyneyi vydiaqvnlk yllklkfnfk tslw
```

In certain embodiments the protein is in a cell or in a cell-free system. The protein, the compound or the molecule in some embodiments is in association with a solid phase. In certain embodiments, the interaction between the compound and the protein is detected via a detectable label, where in some embodiments the protein comprises a detectable label and in certain embodiments the compound comprises a detectable label. The interaction between the compound and the protein sometimes is detected without a detectable label.

Also provided are methods for modulating the activity of a CK2 protein or PARP protein, which comprise contacting a system comprising the protein with a compound described herein in an amount effective for modulating the activity of the protein. In certain embodiments the activity of the protein is inhibited, and sometimes the protein is a CK2 protein, such as a CK2 protein comprising the amino acid sequence of SEQ ID NO: 1, 2 or 3 or a substantially identical variant thereof, for example. In some embodiments the protein is a PARP protein, such as a PARP protein comprising the amino acid sequence of SEQ ID NO: 4 or a substantially identical variant thereof, for example. In certain embodiments, the system is a cell, and in other embodiments the system is a cell-free system. The protein or the compound may be in association with a solid phase in certain embodiments.

Provided also are methods for inhibiting cell proliferation, which comprise contacting cells with a compound described herein in an amount effective to inhibit proliferation of the cells. The cells sometimes are in a cell line, such as a cancer cell line (e.g., breast cancer, prostate cancer, pancreatic cancer, lung cancer, hemopoietic cancer, colorectal cancer, skin cancer, ovary cancer cell line), for example. In some embodiments, the cancer cell line is a breast cancer, prostate cancer or pancreatic cancer cell line. The cells sometimes are in a tissue, can be in a subject, at times are in a tumor, and sometimes are in a tumor in a subject. In certain embodiments, the method further comprises inducing cell apoptosis. Cells sometimes are from a subject having macular degeneration.

Also provided are methods for treating a condition related to aberrant cell proliferation, which comprise administering a compound described herein to a subject in need thereof in an amount effective to treat the cell proliferative condition. In certain embodiments the cell proliferative condition is a tumor-associated cancer. The cancer sometimes is of the breast, prostate, pancreas, lung, colorectum, skin, or ovary. In some embodiments, the cell proliferative condition is a non-tumor cancer, such as a hematopoietic cancer, for example. The cell proliferative condition is macular degeneration in some embodiments.

Provided also are methods for treating cancer or an inflammatory disorder in a subject in need of such treatment, comprising: administering to the subject a therapeutically effective amount of a therapeutic agent as described herein; and administering to the subject a molecule that inhibits PARP or CK2 in an amount that is effective to enhance a desired effect of the therapeutic agent. The therapeutic agent sometimes is a compound of formula TA1-1, TA2, TA3-1, TA4-1, TA5-1 or TA6-1 as described herein, or a pharmaceutically acceptable salt of one of these compounds. In certain embodiments, the molecule that inhibits PARP or CK2 is a compound of Formula I, II, III, IV, V, VI, VII, VIII, IX, X, XI or XII as described herein, or a pharmaceutically acceptable salt thereof. In some embodiments, the molecule that inhibits PARP or CK2 is a known compound shown above, or a compound in one of the Tables provided herein, or a pharmaceutically acceptable salt of one of these compounds. In some embodiments, the desired effect of the therapeutic agent that is enhanced by the molecule that inhibits PARP or CK2 is a reduction in cell proliferation. In certain embodiments, the desired effect of the therapeutic agent that is enhanced by the molecule that inhibits PARP or CK2 is an increase in apoptosis in at least one type of cell. The therapeutic agent in certain embodiments is:

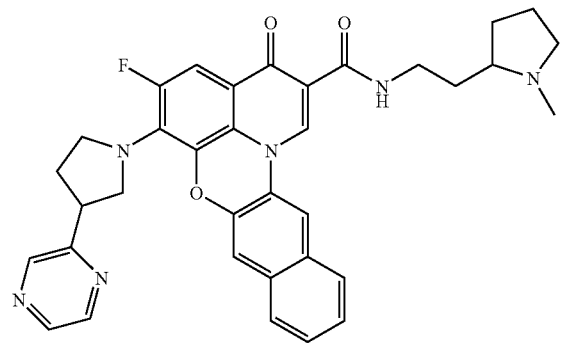

or a pharmaceutically acceptable salt thereof, or a specific isomer or mixture of isomers thereof. In some embodiments, the therapeutic agent and the molecule that inhibits PARP or CK2 are administered at substantially the same time. The therapeutic agent and molecule that inhibits PARP or CK2 sometimes are used concurrently by the subject. The therapeutic agent and the molecule that inhibits PARP or CK2 are combined into one pharmaceutical composition in certain embodiments. Some embodiments are directed to a pharmaceutical composition comprising a therapeutic agent of any of formulas TA1-1, TA2, TA3-1, TA4-1, TA5-1 or TA6 admixed with a molecule that inhibits PARP or CK2, or a pharmaceutically acceptable salt thereof. In some pharmaceutical compositions, the molecule that inhibits PARP or CK2 is a PARP inhibitor and is a known compound shown above, or is GPI 15427, GPI 16539. In some embodiments, the molecule that inhibits PARP or CK2 is a compound of Formula I, II, III, IV, V, VI, VII, VIII, IX, X, XI or XII as described herein, or a pharmaceutically acceptable salt thereof. In some embodiments the therapeutic agent is a compound of formula TA2 or a pharmaceutically acceptable salt thereof. A therapeutic composition in certain embodiments comprises a therapeutically effective amount of a therapeutic agent of the formula TA2:

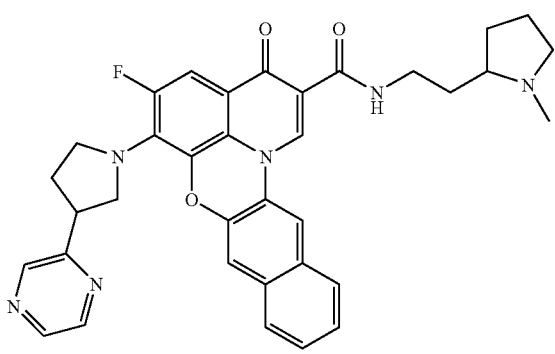

or a pharmaceutically acceptable salt thereof, or a specific isomer or mixture of isomers thereof, admixed with an amount of a PARP inhibitor or a pharmaceutically acceptable salt of a PARP inhibitor, wherein the PARP inhibitor is selected from the group consisting of GPI 15427, GPI 16539, and the known compounds shown above; and where the amount of the PARP inhibitor or the pharmaceutically acceptable salt of a PARP inhibitor is an amount that is effective to enhance a desired effect of the therapeutic agent.

Also provided are compositions comprising a compound described herein and an isolated protein. The protein sometimes is a CK2 protein, such as a CK2 protein comprising the amino acid sequence of SEQ ID NO: 1, 2 or 3 or a substantially identical variant thereof, for example. In some embodiments, the protein is a PARP protein, such as a PARP protein comprising the amino acid sequence of SEQ ID NO: 4 or a substantially identical variant thereof, for example. Certain compositions comprise a compound described herein in combination with a cell. The cell may be from a cell line, such as a cancer cell line. In the latter embodiments, the cancer cell line is sometimes a breast cancer, prostate cancer, pancreatic cancer, lung cancer, hemopoietic cancer, colorectal cancer, skin cancer, ovary cancer cell line.

These and other embodiments of the invention are described in the description that follows.

MODES OF CARRYING OUT THE INVENTION

Figure 1:
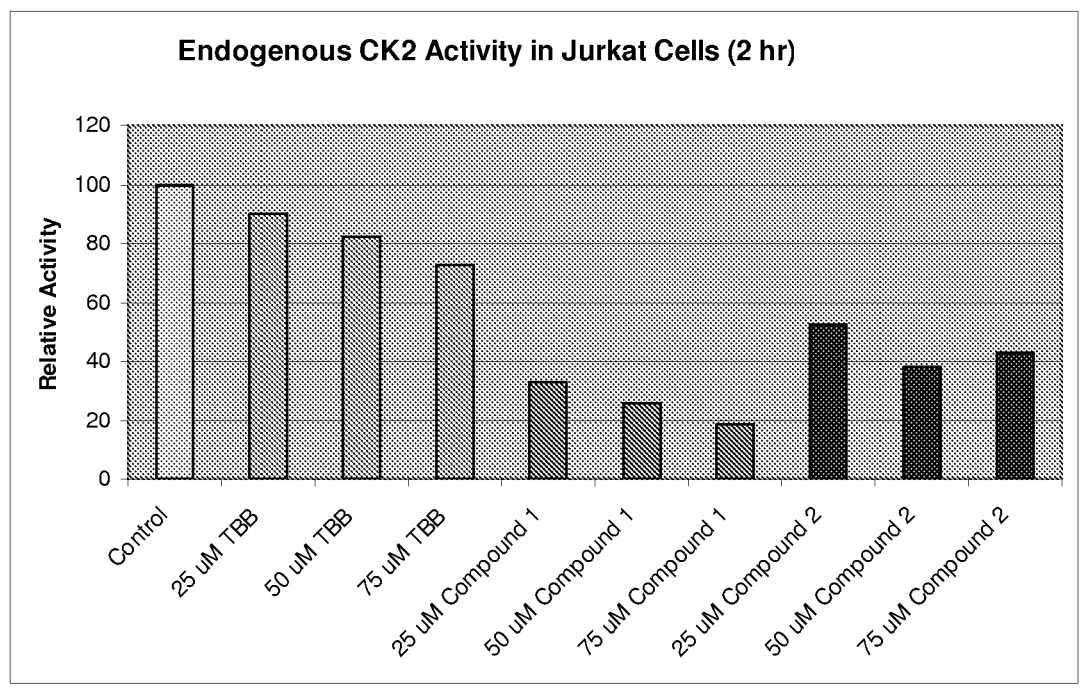
FIG. 1 depicts assay data showing inhibition of CK2 activity.

Compounds of Formulae I, II, III, IV, V, VI, VII, VIII, IX, X, XI, XII, XIII, XIV, XV and XVI can exert biological activities that include, but are not limited to, inhibiting cell proliferation, modulating protein kinase activity and modulating polymerase activity. Compounds of such Formulae can modulate CK2 activity and/or PARP activity, for example. Such compounds therefore can be utilized in multiple applications by a person of ordinary skill in the art. For example, compounds described herein may find uses that include, but are not limited to, (i) modulation of protein kinase activity (e.g., CK2 activity), (ii) modulation of polymerase activity (e.g., PARP activity), (iii) modulation of cell proliferation, (iv) modulation of apoptosis, and (v) treatments of cell proliferation related disorders (e.g., administration alone or co-administration with another molecule).

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed. The compounds of the invention may also exist in more than one tautomeric form; the depiction herein of one tautomer is for convenience only, and is also understood to encompass other tautomers of the form shown.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or $C_{1-10}$. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described.

Typically, the alkyl, alkenyl and alkynyl substituents of the invention contain 1-10C (alkyl) or 2-10C (alkenyl or alkynyl).

Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often optionally substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, C≡CR', COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" substituents are 2-10C alkynyl groups that are optionally substituted, and are of the formula —C≡C—$R^a$, wherein $R^a$ is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each $R^a$ group is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and wherein two R' can be linked to form a 3-7 membered ring optionally containing up to three heteroatoms selected from N, O and S. In some embodiments, $R^a$ of —C≡C—$R^a$ is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)$NR_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", as used herein includes fluoro, chloro, bromo and iodo. Fluoro and chloro are often preferred.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems.

As used herein, the term "heteroatom" refers to any atom that is not carbon or hydrogen, such as nitrogen, oxygen or sulfur.

Illustrative examples of heterocycles include but are not limited to tetrahydrofuran, 1,3 dioxolane, 2,3 dihydrofuran, pyran, tetrahydropyran, benzofuran, isobenzofuran, 1,3 dihydro isobenzofuran, isoxazole, 4,5 dihydroisoxazole, piperidine, pyrrolidine, pyrrolidin 2 one, pyrrole, pyridine, pyrimidine, octahydro pyrrolo[3,4 b]pyridine, piperazine, pyrazine, morpholine, thiomorpholine, imidazole, imidazolidine 2,4 dione, 1,3 dihydrobenzimidazol 2 one, indole, thiazole, benzothiazole, thiadiazole, thiophene, tetrahydro thiophene 1,1 dioxide, diazepine, triazole, guanidine, diazabicyclo[2.2.1] heptane, 2,5 diazabicyclo[2.2.1]heptane, 2,3,4,4a,9,9a hexahydro 1H β carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

As used herein, the term "inorganic substituent" refers to substituents that do not contain carbon or contain carbon bound to elements other than hydrogen (e.g., elemental carbon, carbon monoxide, carbon dioxide, and carbonate). Examples of inorganic substituents include but are not limited to nitro, halogen, azido, cyano, sulfonyls, sulfinyls, sulfonates, phosphates, etc.

The terms "treat" and "treating" as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

The invention in part provides pharmaceutical compositions comprising at least one compound within the scope of the invention as described herein, and methods of using compounds described herein. For example, the invention in part provides methods for identifying a candidate molecule that interacts with a CK2 or PARP protein, which comprises contacting a composition containing a CK2 or PARP protein and a molecule described herein with a candidate molecule and determining whether the amount of the molecule described herein that interacts with the protein is modulated, whereby a candidate molecule that modulates the amount of the molecule described herein that interacts with the protein is identified as a candidate molecule that interacts with the protein.

Also provided are methods for modulating the activity of a CK2 protein or PARP protein, which comprises contacting a system comprising the protein with a compound described herein in an amount effective for modulating (e.g., inhibiting) the activity of the protein. The system in such embodiments can be a cell-free system or a system comprising cells. Also provided are methods for reducing cell proliferation, and optionally inducing apoptosis, which comprises contacting cells with a compound described herein in an amount effective to reduce proliferation of the cells. The cells in such embodiments can be in a cell line, in a tissue or in a subject (e.g., a research animal or human). In related embodiments, provided are compositions comprising a compound described herein in combination with a protein or cell, such as an isolated protein (e.g., isolated CK2 or other serine-threonine protein kinase protein or PARP protein) or a cell in a cell line (e.g., HCT-116 cell line).

Provided also are methods for modulating a serine-threonine protein kinase activity. Serine-threonine protein kinases catalyze the transfer of a gamma phosphate from adenosine triphosphate to a serine or threonine amino acid in a peptide or protein substrate. Thus, included herein are methods which comprise contacting a system comprising a serine-threonine protein kinase protein with a compound described herein in an amount effective for modulating (e.g., inhibiting) the activity of the protein. In some embodiments, the activity of the serine-threonine protein kinase is the catalytic activity of the protein (e.g., catalyzing the transfer of a gamma phosphate from adenosine triphosphate to a peptide or protein substrate). In certain embodiments, provided are methods for identifying a candidate molecule that interacts with a serine-threonine protein kinase, which comprise: contacting a composition containing a serine-threonine protein kinase and a compound described herein with a candidate molecule under conditions in which the compound and the protein interact, and determining whether the amount of the compound that interacts with the protein is modulated relative to a control interaction between the compound and the protein without the candidate molecule, whereby a candidate molecule that modulates the amount of the compound interacting with the protein relative to the control interaction is identified as a candidate molecule that interacts with the protein. Systems in such embodiments can be a cell-free system or a system comprising cells (e.g., in vitro). The protein, the compound or the molecule in some embodiments is in association with a solid phase. In certain embodiments, the interaction between the compound and the protein is detected via a detectable label, where in some embodiments the protein comprises a detectable label and in certain embodiments the compound comprises a detectable label. The interaction between the compound and the protein sometimes is detected without a detectable label.

The serine-threonine protein kinase can be from any source, such as a mammal, ape or human, for example. Examples of serine-threonine protein kinases that can be inhibited by compounds disclosed herein include without limitation human versions of CK2, CK2α2, Pim-1, CDK1/cyclinB, c-RAF, Mer, MELK, DYRK2, Flt3, Flt3 (D835Y), Flt4, HIPK3, HIPK2, ZIPK and ZIPK. A serine-threonine protein kinase sometimes is a member of a sub-family containing one or more of the following amino acids at positions corresponding to those listed in human CK2: leucine at position 45, methionine at position 163 and isoleucine at position 174. Examples of such protein kinases include without limitation human versions of CK2, STK10, HIPK2, HIPK3, DAPK3, DYK2 and PIM-1. Nucleotide and amino acid sequences for serine-threonine protein kinases and reagents are publicly available (e.g., World Wide Web URLs ncbi.nlm.nih.gov/sites/entrez/ and Invitrogen.com).

The invention also in part provides methods for treating a condition related to aberrant cell proliferation. For example, provided are methods of treating a cell proliferative condition in a subject, which comprises administering a compound described herein to a subject in need thereof in an amount effective to treat the cell proliferative condition. The subject may be a research animal (e.g., rodent, dog, cat, monkey), optionally containing a tumor such as a xenograft tumor (e.g., human tumor), for example, or may be a human. A cell proliferative condition sometimes is a tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma).

Also provided are methods for treating a condition related to inflammation or pain. For example, provided are methods of treating pain in a subject, which comprise administering a compound described herein to a subject in need thereof in an amount effective to treat the pain. Provided also are methods of treating inflammation in a subject, which comprises administering a compound described herein to a subject in need thereof in an amount effective to treat the inflammation. The subject may be a research animal (e.g., rodent, dog, cat, monkey), for example, or may be a human. Conditions associated with inflammation and pain include without limitation acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, osteoporosis, Parkinson's disease, periodontal disease, polyarteritis, polychondritis, psoriasis, scleroderma, sinusitis, Sjögren's syndrome, spastic colon, systemic candidiasis, tendonitis, urinary track infections, vaginitis, inflammatory cancer (e.g., inflammatory breast cancer) and the like. Methods for determining effects of compounds herein on pain or inflammation are known. For example, formalin-stimulated pain behaviors in research animals can be monitored after administration of a compound described herein to assess treatment of pain (e.g., Li et al., *Pain* 115(1-2): 182-90 (2005)). Also, modulation of pro-inflammatory molecules (e.g., IL-8, GRO-alpha, MCP-1, TNFalpha and iNOS) can be monitored after administration of a compound described herein to assess treatment of inflammation (e.g., Parhar et al., *Int J Colorectal Dis.* 22(6): 601-9 (2006)), for example. Thus, also provided are methods for determining whether a compound herein reduces inflammation or pain, which comprise contacting a system with a compound described herein in an amount effective for modulating (e.g., inhibiting) the activity of a pain signal or inflammation signal. Provided also are methods for identifying a compound that reduces inflammation or pain, which comprise: contacting a system with a compound of Formula I, II, III, IV, V, VI, VII, VIII, IX, X, XI, XII, XIII, XIV, XV or XVI; and detecting a pain signal or inflammation signal, whereby a compound that modulates the pain signal relative to a control molecule is identified as a compound that reduces inflammation of pain. Non-limiting examples of pain signals are formalin-stimulated pain behaviors and examples of inflammation signals include without limitation a level of a pro-inflammatory molecule.

The invention also in part pertains to methods for modulating angiogenesis in a subject, and methods for treating a condition associated with aberrant angiogenesis in a subject. Thus, provided are methods for determining whether a compound herein modulates angiogenesis, which comprise contacting a system with a compound described herein in an amount effective for modulating (e.g., inhibiting) angiogenesis or a signal associated with angiogenesis. Signals associated with angiogenesis are levels of a pro-angiogenesis growth factor such as VEGF. Methods for assessing modulation of angiogenesis also are known, such as analyzing human endothelial tube formation (BD BioCoat™ Angiogenesis System from BD Biosciences). Provided also are methods for identifying a compound that modulates angiogenesis, which comprise contacting a system with a compound of Formula I, II, III, IV, V, VI, VII, VIII, IX, X, XI, XII, XIII, XIV, XV or XVI; and detecting angiogenesis in the system or an angiogenesis signal, whereby a compound that modulates the angiogenesis or angiogenesis signal relative to a control molecule is identified as a compound that modulates angiogenesis. Also provided are methods for treating an angiogenesis condition, which comprise administering a compound described herein to a subject in need thereof in an amount effective to treat the angiogenesis condition. Angiogenesis conditions include without limitation solid tumor cancers, varicose disease and the like.

Any suitable formulation of a compound described above can be prepared for administration. Any suitable route of administration may be used, including, but not limited to, oral, parenteral, intravenous, intramuscular, transdermal, topical and subcutaneous routes. Depending on the subject to be treated, the mode of administration, and the type of treatment desired—e.g., prevention, prophylaxis, therapy; the compounds are formulated in ways consonant with these parameters. Preparation of suitable formulations for each route of administration are known in the art. A summary of such formulation methods and techniques is found in *Remington's Pharmaceutical Sciences*, latest edition, Mack Publishing Co., Easton, Pa., which is incorporated herein by reference. The formulation of each substance or of the combination of two substances will generally include a diluent as well as, in some cases, adjuvants, buffers, preservatives and the like. The substances to be administered can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised, and can be applied to compounds of the invention. See, for example, U.S. Pat. No. 5,624,677, the methods of which are incorporated herein by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the appropriate dosage of the a compound described above often is 0.01-15 mg/kg, and sometimes 0.1-10 mg/kg. Dosage levels are dependent on the nature of the condition, drug efficacy, the condition of the patient, the judgment of the practitioner, and the frequency and mode of administration; however, optimization of such parameters is within the ordinary level of skill in the art.

Therapeutic Combinations

The invention provides methods to treat conditions such as cancer and inflammation by administering to a subject in need of such treatment a therapeutically effective amount of a therapeutic agent that binds to certain DNA segments and administering to the same subject a PARP or CK2 modulator in an amount that is effective to enhance the activity of the therapeutic agent. A PARP or CK2 modulator is an agent that inhibits or enhances a biological activity of a PARP protein or a CK2 protein, and is generically referred to hereafter as a "modulator." The therapeutic agent and the modulator may be administered together, either as separate pharmaceutical compositions or admixed in a single pharmaceutical composition. The therapeutic agent and the modulator may also be administered separately, including at different times and with different frequencies, as long as the modulator is administered at a time that increases the potency of the therapeutic agent. The modulator may be administered by any known route, such as orally, intravenously, intramuscularly, nasally, and the like; and the therapeutic agent may also be administered by any conventional route. In many embodiments, at least one and optionally both of the modulator and the therapeutic agent may be administered orally.

In some embodiments, the modulator and the therapeutic agent are administered at the same time, whether in separate dosages or admixed in a single dosage. Where the frequency of administration of the two materials can be adjusted to match, the modulator and therapeutic agent are preferably combined into a single pharmaceutical composition, so the treated patient may receive a single oral dosage or a single injection, for example.

The amount of each of these materials to be administered will vary with the route of administration, the condition of the subject, other treatments being administered to the subject, and other parameters. The therapeutic agents of the invention may, of course, cause multiple desired effects; and the amount of modulator to be used in combination with the therapeutic agent should be an amount that increases one or more of these desired effects. The modulator is to be administered in an amount that is effective to enhance a desired effect of the therapeutic agent. An amount is "effective to enhance a desired effect of the therapeutic agent", as used herein, if it increases by at least about 25% at least one of the desired effects of the therapeutic agent alone. Preferably, it is an amount that increases a desired effect of the therapeutic agent by at least 50% or by at least 100% (i.e., it doubles the effective activity of the therapeutic agent.) In some embodiments, it is an amount that increases a desired effect of the therapeutic agent by at least 200%.

The amount of a modulator that increases a desired effect of a therapeutic agent may be determined using in vitro methods, such as cell proliferation assays. The therapeutic agents of the invention are useful to counter hyperproliferative disorders such as cancer, thus they reduce cell proliferation. Thus, for example, a suitable amount of a modulator could be the amount needed to enhance an antiproliferative effect of a therapeutic agent by at least 25% as determined in a cell proliferation assay.

The modulator used in the present invention enhances at least one desired effect produced by the therapeutic agent it is used with, thus the combinations of the invention provide a synergistic effect, not merely an additive effect. The modulators themselves are at times useful for treating the same types of conditions, and thus may also have some direct effect in such assays. In that event, the "amount effective to increase a desired effect" must be a synergistic enhancement of the activity of the therapeutic agent that is attributable to enhancement by the modulator of an effect of the therapeutic agent, rather than a simple additive effect that would be expected with separate administration of the two materials. In many cases, the modulator can be used in an amount (concentration) that would not be expected to have any apparent effect on the treated subject or the in vitro assay, so the increased effect achieved with the combination is directly attributable to a synergistic effect.

The present invention includes methods and compositions for treating a patient having a cell proliferation disorder or an inflammatory disorder with a therapeutic agent as described herein, and a "modulator" described above, where the timing of administration of the modulator permits it to enhance a desired effect of the therapeutic agent.

Modulators of PARP and CK2 are known. Inhibitors of PARP are well known in the art, and some have been shown to potentiate the activity of other drugs for certain uses. For example, it has been reported that treating a carcinoma cell colony with a PARP inhibitor at a concentration that had no substantial growth inhibition or cellular toxicity alone increased the activity of cytotoxic agents temozolomide and topotecan substantially. C. R. Calabrese, et al., *Clin. Cancer Res.*, vol. 9, 2711-18 (July 2003). This effect is believed to be related to the role PARP plays in DNA repair: because PARP promotes repair of damaged DNA, it is thought to increase the effects of compounds that act by damaging DNA. These include compounds that alkylate DNA, which may include temozolomide, and topoisomerase inhibitors such as topotecan. Id.

The present invention relates to the use of a "modulator" as described above in combination with a therapeutic agent that can act by binding to regions of DNA that can form certain quadruplex structures; the therapeutic agents have anticancer activity on their own, but their activity is enhanced when they are used in combination with a modulator. This synergistic effect allows the therapeutic agent to be administered in a lower dosage while achieving equivalent or higher levels of at least one desired effect.

The therapeutic agents of the invention are compounds that bind to certain motifs in nucleic acids. The therapeutic agent to be used can be selected from several different classes of compounds, such as those that bind to quadruplex-forming regions of DNA. The therapeutic agents are useful for the treatment of cancer and other indications such as inflammatory disorders, and methods for making and using them are known in the art. Several preferred classes of these therapeutic agents are described below. Each class of therapeutic agents can be used in combination with any active PARP inhibitor, including but not limited to those disclosed herein.

In one aspect, the therapeutic agent can be a compound of formula (TA1-1):

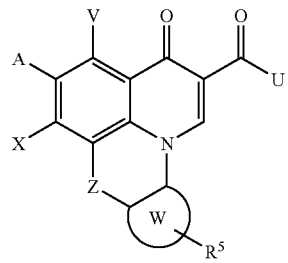
(TA1-1)

and pharmaceutically acceptable salts, esters and prodrugs thereof;

wherein V is H, halo, or $NR_1R_2$;
A is H, fluoro, or $NR^1_2$;
Z is O, S, $NR_1$ or $CH_2$;
U is $OR^2$ or $NR^1R^2$;
X is $OR^2$, $NR^1R^2$, halo, azido, or $SR^2$;
n is 1-3;
wherein in $NR^1R^2$, $R^1$ and $R^2$ may form a double bond or a ring, each of which is optionally substituted;
$R^1$ is H or a $C_{1-6}$ alkyl;
$R^2$ is H or a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted heterocyclic ring, aryl or heteroaryl;
$R^5$ is a substituent at any position on W; and is H, $OR^2$, $C_{1-6}$ alkyl, $C_{2-6}$ alkenyl, each optionally substituted by halo, =O or one or more heteroatoms; or $R^5$ is an inorganic substituent; and
W is an optionally substituted aryl or heteroaryl, which may be monocyclic or fused with a single or multiple ring and optionally containing a heteroatom;
or a compound having formula (TA1-2):

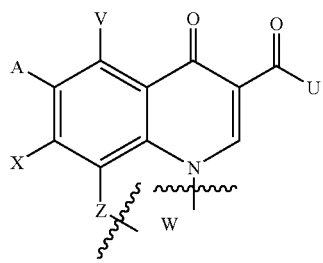
(TA1-2)

wherein V, A, X, Z and U are as defined in formula TA1-1, and W is selected from the group consisting of

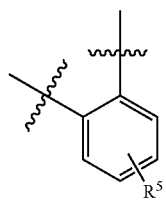 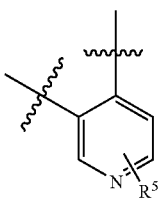 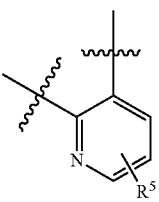

-continued

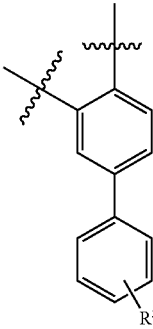 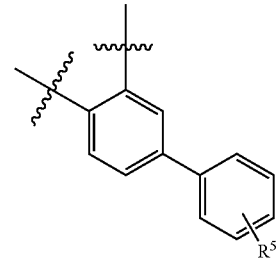

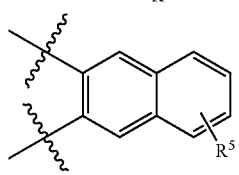 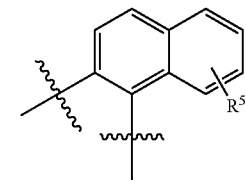

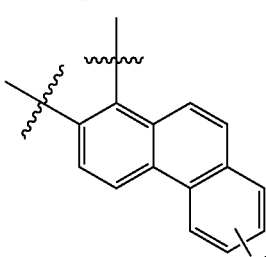 

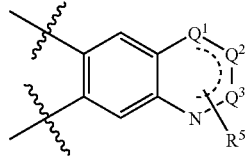 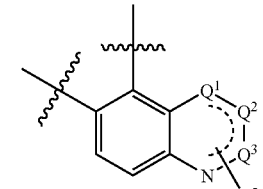

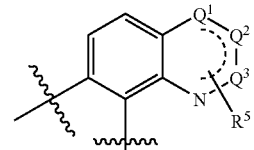 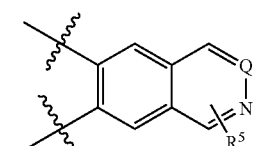

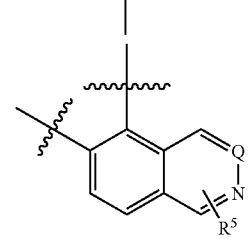 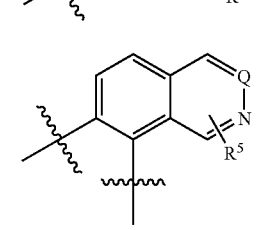

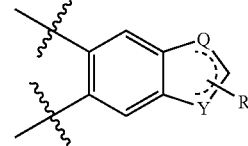 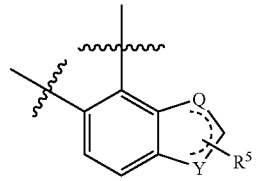

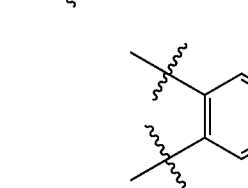

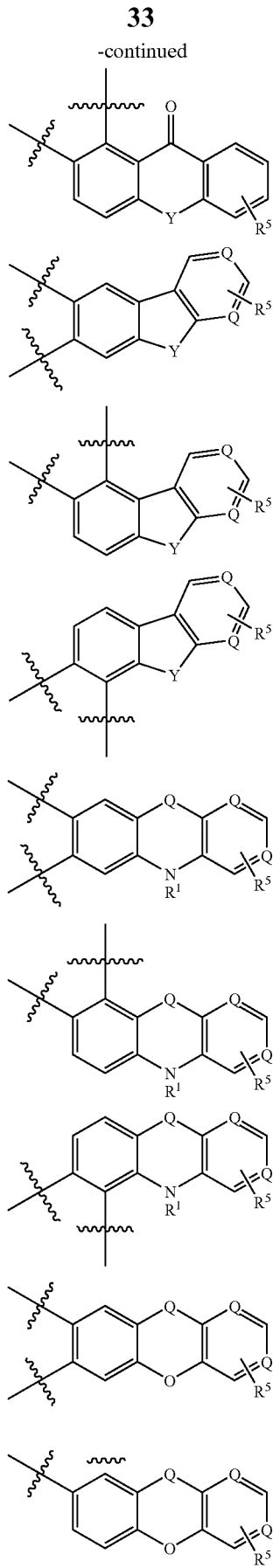

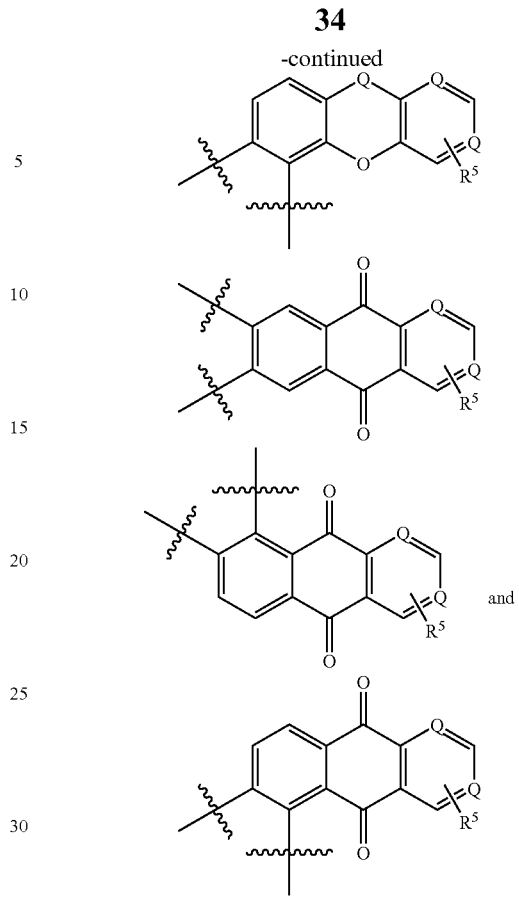

wherein Q, $Q^1$, $Q^2$, and $Q^3$ are independently CH or N;
Y is independently O, CH, =O or $NR^1$; and
$R^5$ is as defined in formula 1.

Compounds of this structure, and methods for making and using them, are described in U.S. patent application Ser. No. 11/106,909, to Whitten, et al., which is entitled SUBSTITUTED QUINOBENZOXAZINE ANALOGS AND METHODS OF USING THEREOF, and was filed on Apr. 15, 2005.

In a specific embodiment of the therapeutic agents of formula (TA1-1), the therapeutic agent is a compound having formula (TA1-1A):

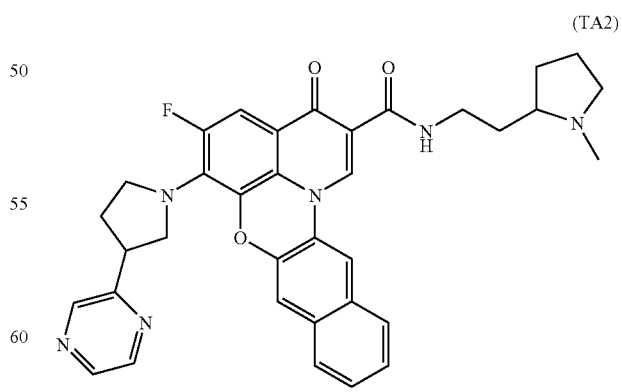

(TA2)

or a pharmaceutically acceptable salt, esters or prodrug thereof, or a specific isomer or mixture of isomers thereof.

In another aspect, the therapeutic agent of the combinations of the invention is a compound of this formula:

(TA3-1)

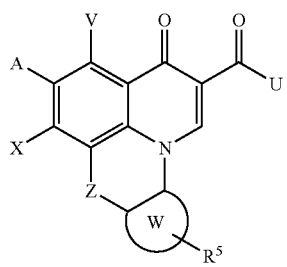

and pharmaceutically acceptable salts, esters and prodrugs thereof;

wherein V is H, halo, or $NR_1R_2$;

A is H, fluoro, or $NR^1_2$;

Z is O, S, $NR_1$ or $CH_2$;

U is $OR^2$ or $NR^1R^2$;

X is $OR^2$, $NR^1R^2$, halo, azido, or $SR^2$;

n is 1-3;

wherein in $NR^1R^2$, $R^1$ and $R^2$ may form a double bond or a ring, each of which is optionally substituted;

$R^1$ is H or a $C_{1-6}$ alkyl;

$R^2$ is H or a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted heterocyclic ring, aryl or heteroaryl;

$R^5$ is a substituent at any position on W; and is H, $OR^2$, $C_{1-6}$ alkyl, $C_{2-6}$ alkenyl, each optionally substituted by halo, =O or one or more heteroatoms; or $R^5$ is an inorganic substituent; and W is an optionally substituted aryl or heteroaryl, which may be monocyclic or fused with a single or multiple ring and optionally containing a heteroatom;

or a compound having formula (TA3-2)

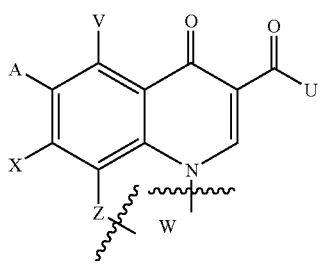

wherein V, A, X, Z and U are as defined in formula I, and W is selected from the group consisting of

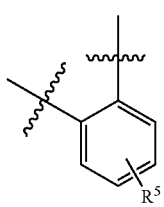 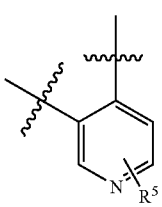 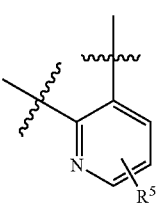

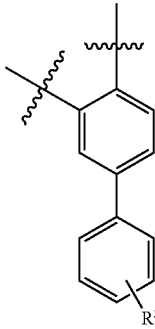 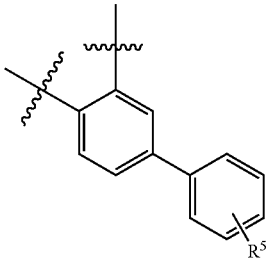

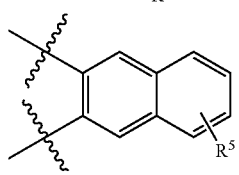 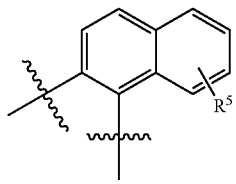

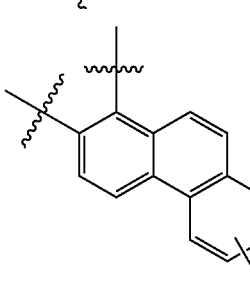

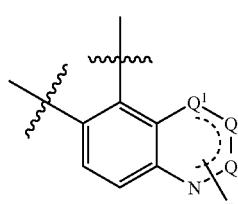

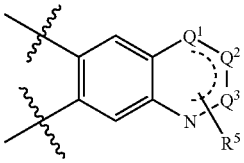

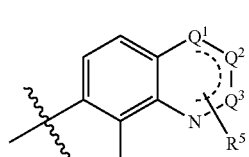

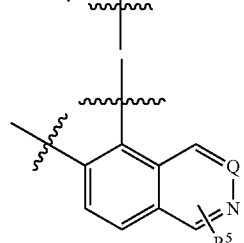

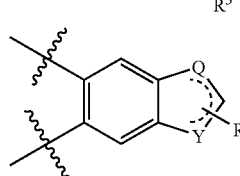

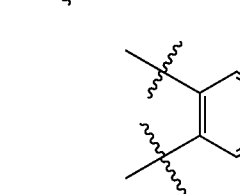

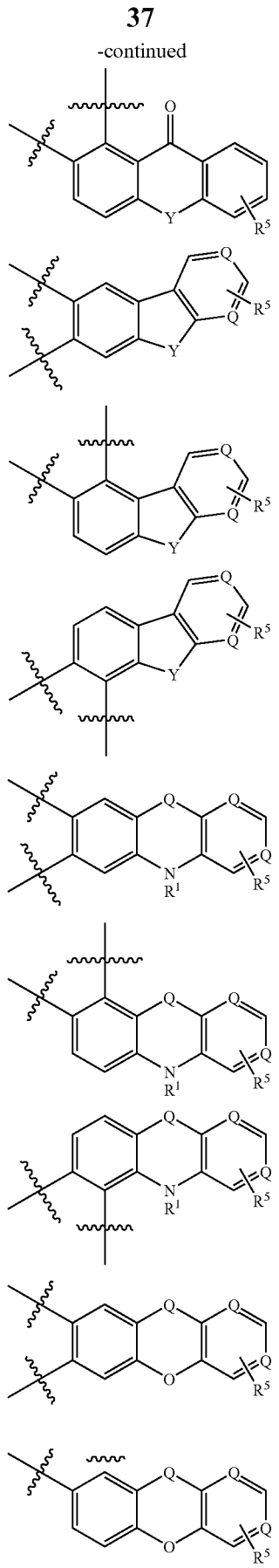

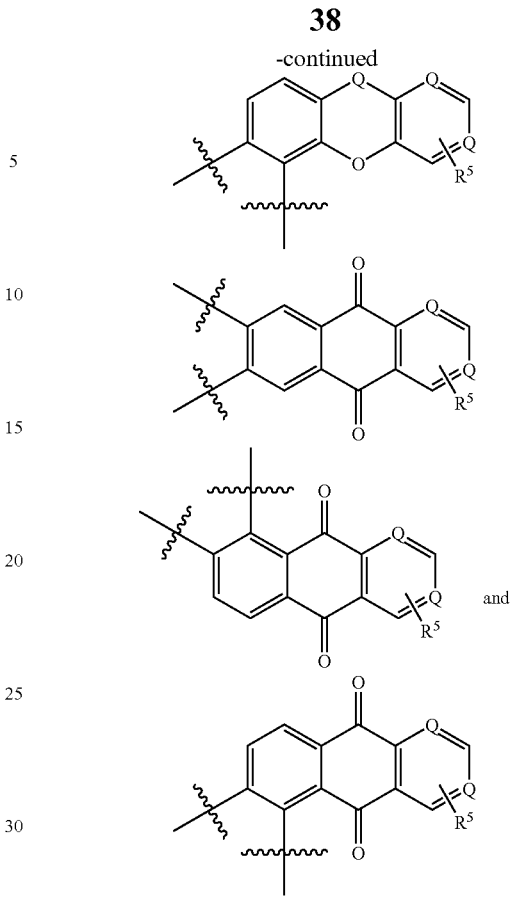

wherein Q, Q¹, Q², and Q³ are independently CH or N;
Y is independently O, CH, =O or NR¹; and
R⁵ is as defined in formula 1.

The preparation and activity of these compounds of formula (TA3-1) are described in U.S. Patent Application Ser. No. 60/811,992, filed Jun. 8, 2006, to Nagasawa, et al., entitled QUINOLONE ANALOGS DERIVATIZED WITH SULFONIC ACID, SULFONATE OR SULFONAMIDE.

In another aspect, the therapeutic agent of the combinations of the invention is a compound of this formula:

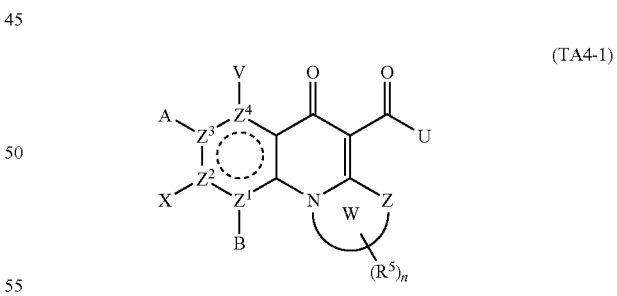

(TA4-1)

and pharmaceutically acceptable salts, esters and prodrugs thereof;

wherein B, X, A, or V is absent if $Z^2$, $Z^3$, or $Z^4$, respectively, is N, and independently H, halo, azido, $R^2$, $CH_2R^2$, $SR^2$, $OR^2$ or $NR^1R^2$ if $Z^2$, $Z^3$, or $Z^4$, respectively, is C; or A and V, A and X, or X and B may form a carbocyclic ring, heterocyclic ring, aryl or heteroaryl, each of which may be optionally substituted and/or fused with a cyclic ring;

Z is O, S, $NR_1$, $CH_2$, or C=O;

$Z^1$, $Z^2$, $Z^3$ and $Z^4$ are C or N, provided any two N are non-adjacent;

W together with N and Z forms an optionally substituted 5- or 6-membered ring that is fused to an optionally substituted saturated or unsaturated ring; said saturated or unsaturated ring may contain a heteroatom and is monocyclic or fused with a single or multiple carbocyclic or heterocyclic rings;

U is $R^2$, $OR^2$, $NR^1R^2$, $NR^1$—$(CR^1{}_2)_n$—$NR^3R^4$, or $N=CR^1R^2$, wherein in $N=CR^1R^2R^1$ and $R^2$ together with C may form a ring, provided U is not H, and when U is OH, $OR^2$ or $NH_2$, then at least one of $Z^1$-$Z^4$ is N;

in each $NR^1R^2$, $R^1$ and $R^2$ together with N may form an optionally substituted ring;

in $NR^3R^4$, $R^3$ and $R^4$ together with N may form an optionally substituted ring;

$R^1$ and $R^3$ are independently H or $C_{1-6}$ alkyl;

each $R^2$ is H, or a $C_{1-10}$ alkyl or $C_{2-10}$ alkenyl each optionally substituted with a halogen, one or more non-adjacent heteroatoms, a carbocyclic ring, a heterocyclic ring, an aryl or heteroaryl, wherein each ring is optionally substituted; or $R^2$ is an optionally substituted carbocyclic ring, heterocyclic ring, aryl or heteroaryl;

$R^4$ is H, a $C_{1-10}$ alkyl or $C_{2-10}$ alkenyl optionally containing one or more non-adjacent heteroatoms selected from N, O and S, and optionally substituted with a carbocyclic or heterocyclic ring; or $R^3$ and $R^4$ together with N may form an optionally substituted ring;

each $R^5$ is a substituent at any position on ring W; and is H, $OR^2$, amino, alkoxy, amido, halogen, cyano or an inorganic substituent; or $R^5$ is $C_{1-6}$ alkyl, $C_{2-6}$ alkenyl, $C_{2-6}$ alkynyl, —$CONHR^1$, each optionally substituted by halo, carbonyl or one or more non-adjacent heteroatoms; or two adjacent $R^5$ are linked to obtain a 5-6 membered optionally substituted carbocyclic or heterocyclic ring that may be fused to an additional optionally substituted carbocyclic or heterocyclic ring; and n is 1-6.

In the above formula (TA4-1), B may be absent when $Z^1$ is N, or is H or a halogen when $Z^1$ is C.

In the above formula (TA4-1), W together with N and Z forms an optionally substituted 5- or 6-membered ring that is fused to an optionally substituted aryl or heteroaryl selected from the group consisting of:

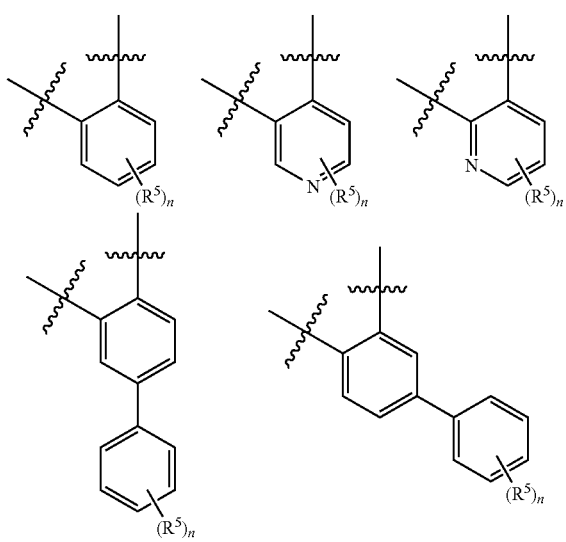

-continued

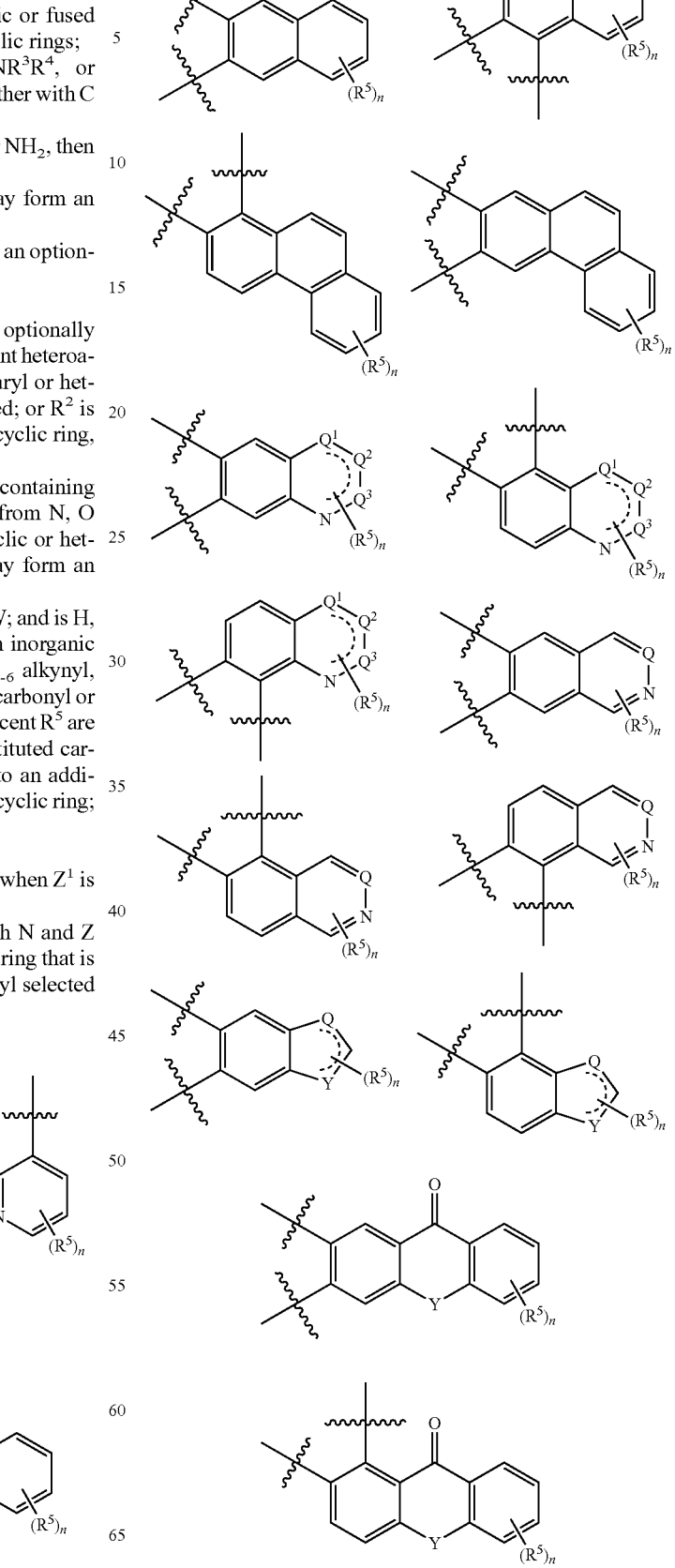

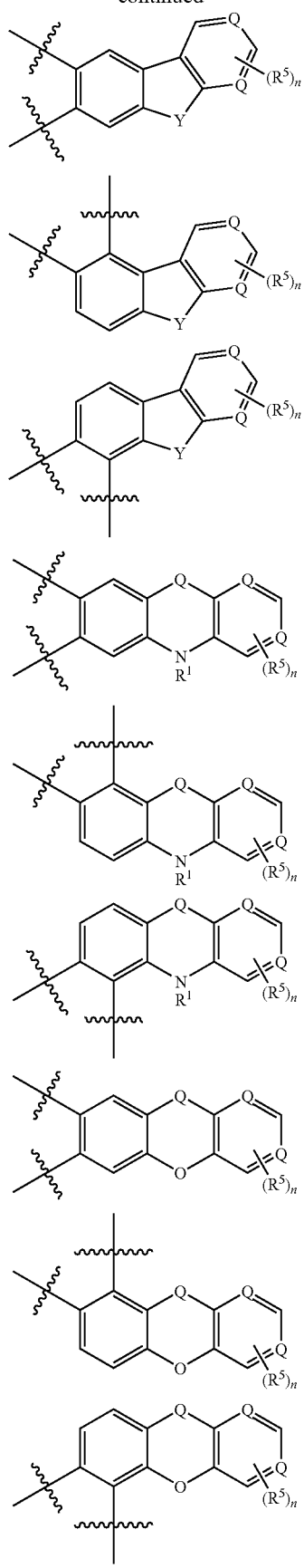

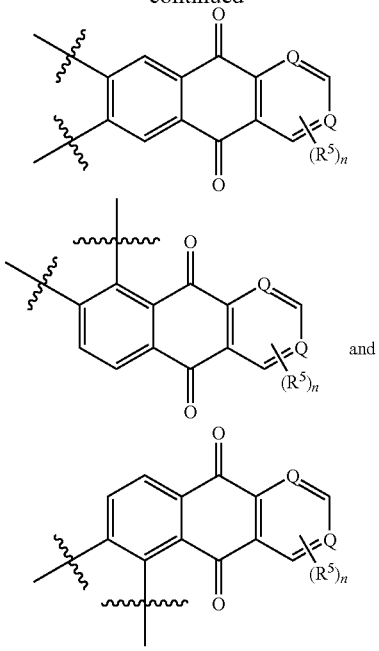

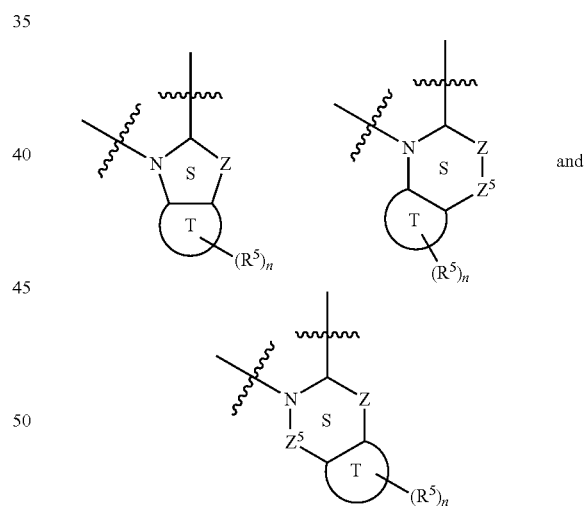

wherein each Q, $Q^1$, $Q^2$, and $Q^3$ is independently CH or N; Y is independently O, CH, C=O or $NR^1$; n and $R^5$ is as defined above.

In other embodiments, W together with N and Z form a group having the formula selected from the group consisting of wherein Z is O, S, $CR^1$, $NR^1$, or C=O;
each $Z^5$ is $CR^6$, $NR^1$, or C=O, provided Z and $Z^5$ if adjacent are not both $NR^1$;
each $R^1$ is H, $C_{1-6}$ alkyl, $COR^2$ or $S(O)_p R^2$ wherein p is 1-2;
$R^6$ is H, or a substituent known in the art, including but not limited to hydroxyl, alkyl, alkoxy, halo, amino, or amido; and ring S and ring T may be saturated or unsaturated.

In some embodiments, W together with N and Z forms a 5- or 6-membered ring that is fused to a phenyl. In other embodiments, W together with N and Z forms a 5- or 6-membered ring that is optionally fused to another ring, when U is $NR^1R^2$, provided U is not $NH_2$. In certain embodiments, W together with N and Z forms a 5- or 6-membered ring that is not fused to another ring, when U is $NR^1R^2$ (e.g., $NH_2$).

In yet another embodiment, the compounds of the present invention have the general formula (TA4-2A) or (TA4-2B):

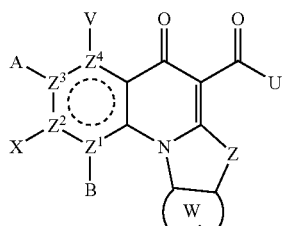
(TA4-2A)

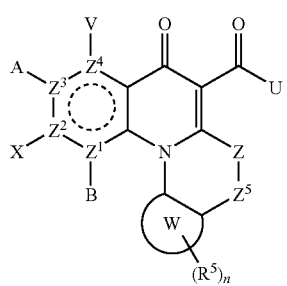
(TA4-2B)

wherein A, B, V, X, U, Z, $Z^1$, $Z^2$, $Z^3$, $Z^4$ and n are as described for TA4-1;

$Z^5$ is O, $NR^1$, $CR^6$, or C=O;

$R^6$ is H, $C_{1-6}$ alkyl, hydroxyl, alkoxy, halo, amino or amido; and

Z and $Z^5$ may optionally form a double bond.

In the above formula (TA4-1), (TA4-2A) and (TA4-2B), U may be $NR^1R^2$, wherein $R^1$ is H, and $R^2$ is a $C_{1-10}$ alkyl optionally substituted with a heteroatom, a $C_{3-6}$ cycloalkyl, aryl or a 5-14 membered heterocyclic ring containing one or more N, O or S. For example, $R^2$ may be a $C_{1-10}$ alkyl substituted with an optionally substituted morpholine, thiomorpholine, imidazole, aminodithiadazole, pyrrolidine, piperazine, pyridine or piperidine. In other examples, $R^1$ and $R^2$ together with N form an optionally substituted piperidine, pyrrolidine, piperazine, morpholine, thiomorpholine, imidazole, or aminodithiazole.

The compounds of formula (TA4-1), and methods of making and using them, are described in U.S. patent application Ser. No. 11/228,636, to Whitten, et al., entitled QUINOLONE ANALOGS, and filed on Sep. 16, 2005.

In yet another aspect, the therapeutic agent to be combined with a PARP inhibitor can be selected from compounds having this formula:

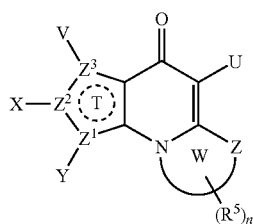
(TA5-1)

and pharmaceutically acceptable salts, esters and prodrugs thereof;

wherein V, X, and Y are absent if attached to a heteroatom other than Nitrogen, and independently H, halo, azido, $R^2$, $CH_2R^2$, $SR^2$, $OR^2$ or $NR^1R^2$ when attached to C or N; or wherein V and X, or X and Y may form a carbocyclic ring, heterocyclic ring, aryl or heteroaryl, each of which may be optionally substituted and/or fused with a cyclic ring;

$Z^1$, $Z^2$ and $Z^3$ are C, N, O or S;

Z is O, S, $NR^2$, $CH_2$ or C=O;

W together with N and Z forms an optionally substituted 5- or 6-membered ring that is fused to an optionally substituted aryl or heteroaryl, wherein said aryl or heteroaryl may be monocyclic or fused with a single or multiple ring, and wherein said ring optionally contains a heteroatom;

U is —C(=O)$R^2$, —COO$R^2$, —CONR$^1$R$^2$, —CONR$^1$—(CR$^1_2$)$_n$—NR$^3$R$^4$, SO$_3$R$^2$, SO$_2$NR$^1$R$^2$, SO$_2$NR$^1$NR$^1$R$^2$, SO$_2$NR$^1$OR$^2$, SO$_2$NR$^1$—(CR$^1_2$)$_n$—NR$^3$R$^4$ or SO$_2$NR$^1$NR$^1$—(CR$^1_2$)$_n$—NR$^3$R$^4$ or SO$_2$NR$^1$—O—(CR$^1_2$)$_n$—NR$^3$R;

wherein in each $NR^1R^2$, $R^1$ and $R^2$ together with N may form an optionally substituted ring;

in $NR^3R^4$, $R^3$ and $R^4$ together with N may form an optionally substituted ring;

$R^1$ and $R^3$ are independently H or $C_{1-6}$ alkyl;

each $R^2$ is H, or a $C_{1-10}$ alkyl or $C_{2-10}$ alkenyl each optionally substituted with a halogen, one or more non-adjacent heteroatoms selected from N, O and S, a carbocyclic ring, a heterocyclic ring, an aryl or heteroaryl, wherein each ring is optionally substituted; or $R^2$ is an optionally substituted carbocyclic ring, heterocyclic ring, aryl or heteroaryl; or $R^2$ is $COR^1$ or $S(O)_xR^1$ wherein x is 1-2;

$R^4$ is H, a $C_{1-10}$ alkyl or $C_{2-10}$ alkenyl optionally containing one or more non-adjacent heteroatoms selected from N, O and S, and optionally substituted with a carbocyclic or heterocyclic ring; or $R^3$ and $R^4$ together with N may form an optionally substituted ring;

each $R^5$ is a substituent at any position on W; and is H, $OR^2$, amino, alkoxy, amido, halogen, cyano or an inorganic substituent; or $R^5$ is $C_{1-6}$ alkyl, $C_{2-6}$ alkenyl, —CONHR$^1$, each optionally substituted by halo, carbonyl or one or more non-adjacent heteroatoms; or two adjacent $R^5$ are linked to obtain a 5-6 membered optionally substituted carbocyclic or heterocyclic ring, optionally fused to an additional optionally substituted carbocyclic or heterocyclic ring; and n is 1-6.

In the above formula (TA5-1), ring T may form an optionally substituted 5-membered ring selected from the group consisting of:

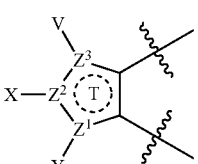 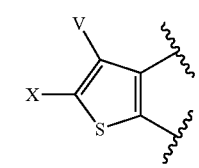

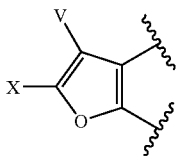 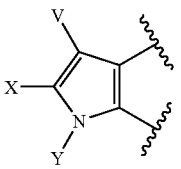

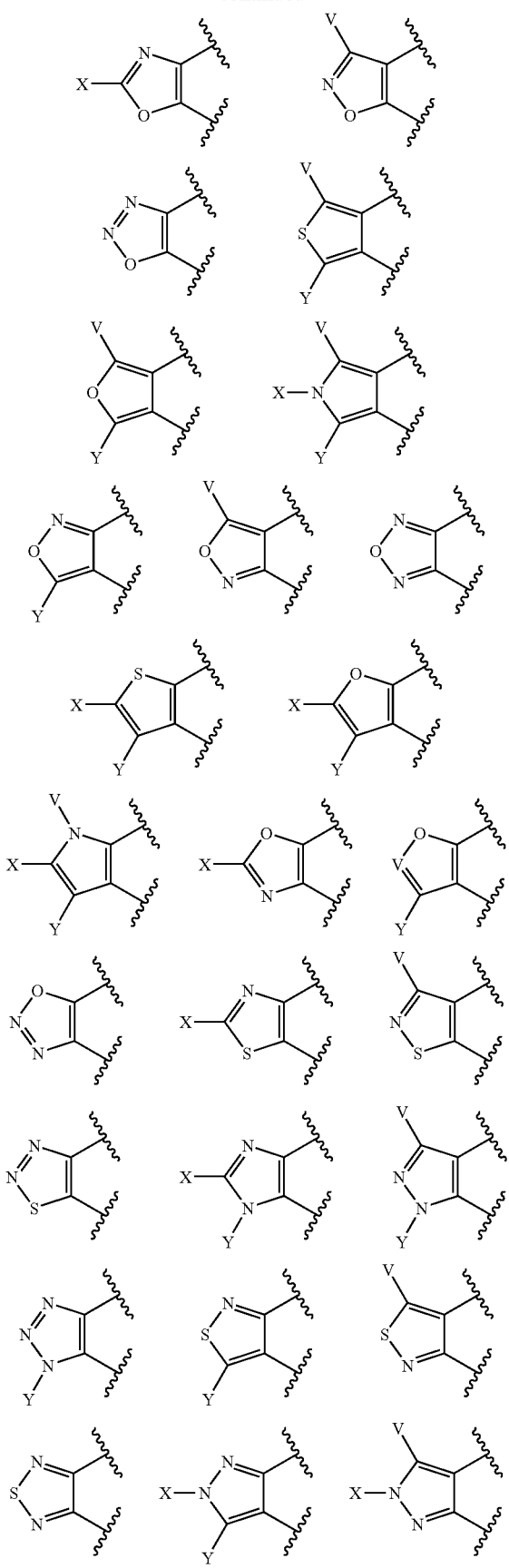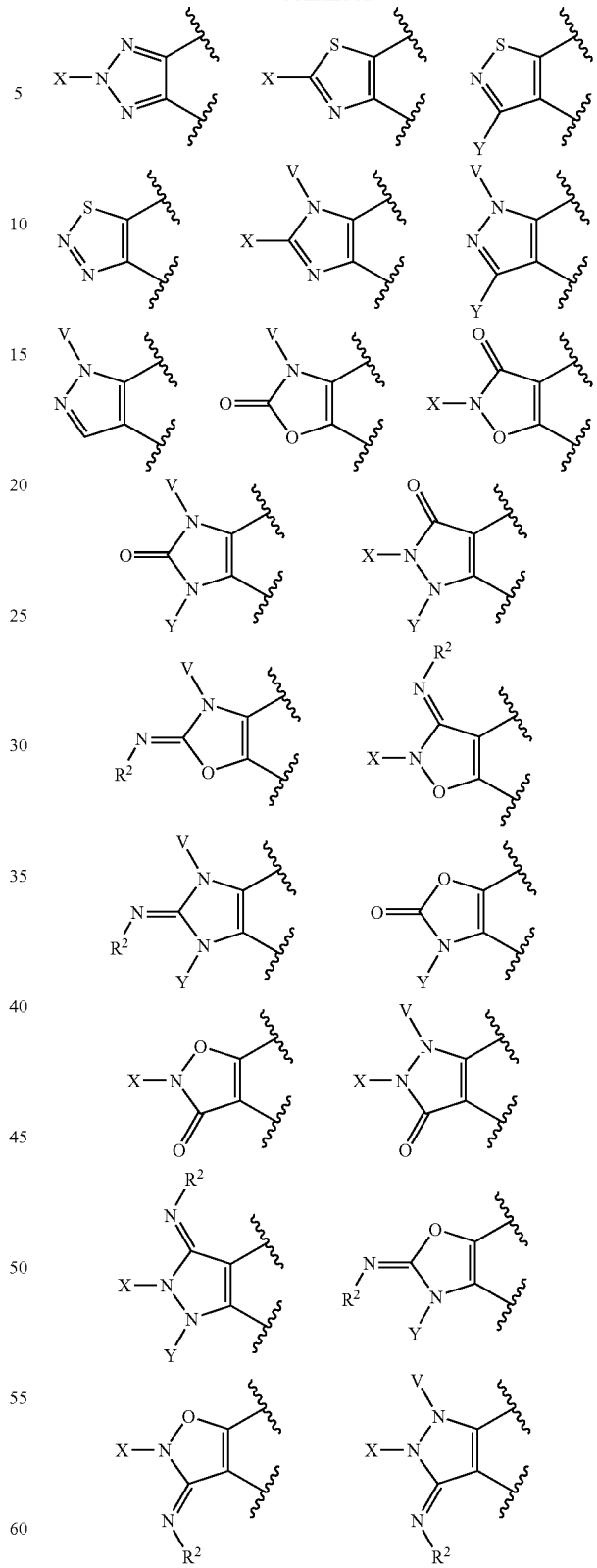
In the above formula (TA5-1), W together with N and Z may form an optionally substituted 5- or 6-membered aryl or heteroaryl ring that is fused to an optionally substituted aryl or heteroaryl selected from the group consisting of:

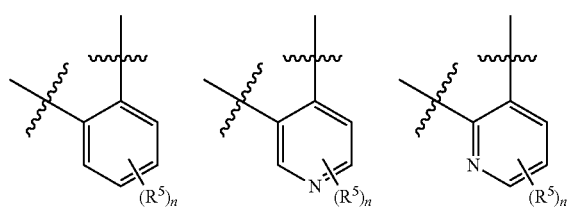
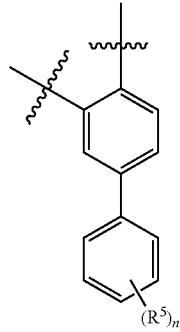
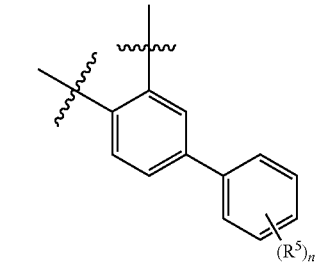
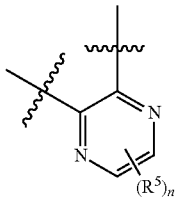
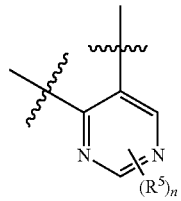
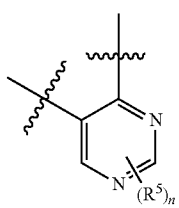
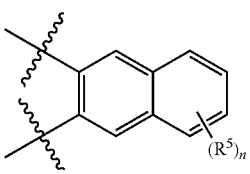
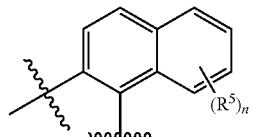
-continued
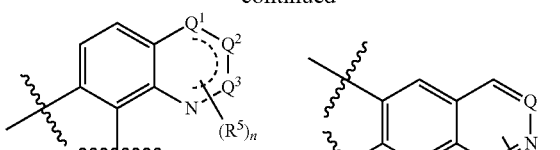
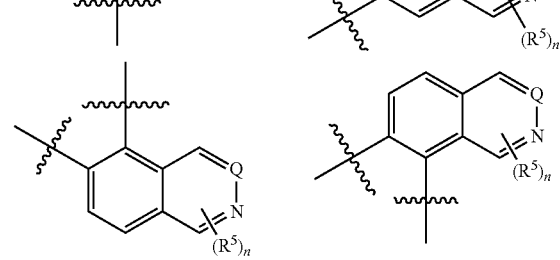
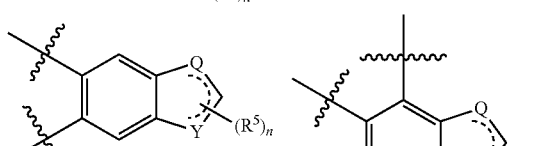
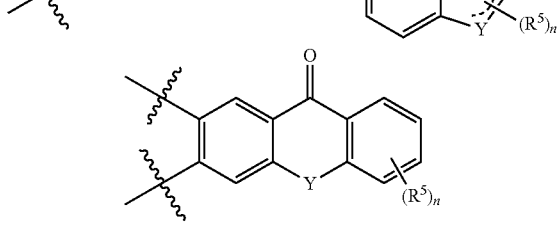
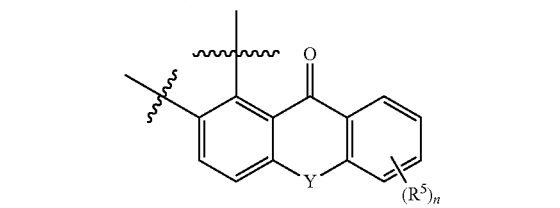
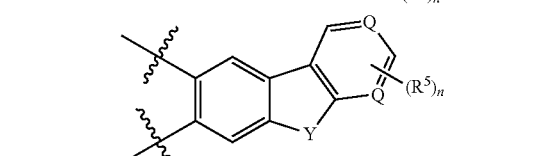
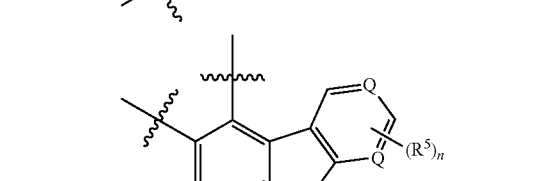
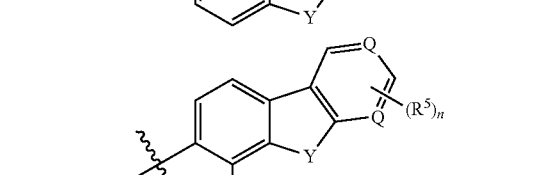
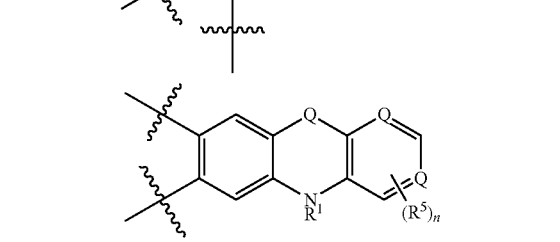

-continued

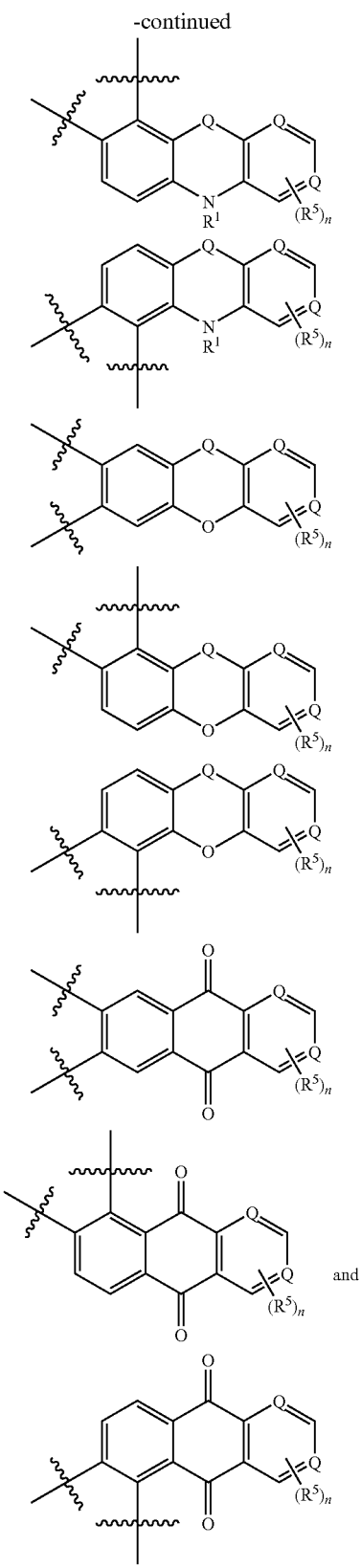

wherein each Q, Q¹, Q², and Q³ is independently CH or N;
P is independently O, CH, C=O or NR¹;
n and R⁵ is as defined above.

In other embodiments of these compounds, W together with N and Z may form a group having the formula selected from the group consisting of

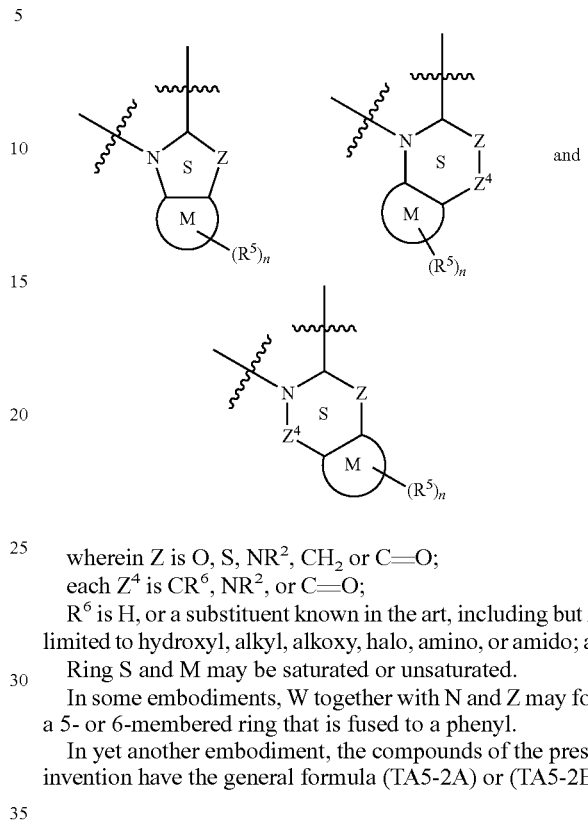

wherein Z is O, S, NR², CH₂ or C=O;
each Z⁴ is CR⁶, NR², or C=O;
R⁶ is H, or a substituent known in the art, including but not limited to hydroxyl, alkyl, alkoxy, halo, amino, or amido; and
Ring S and M may be saturated or unsaturated.

In some embodiments, W together with N and Z may form a 5- or 6-membered ring that is fused to a phenyl.

In yet another embodiment, the compounds of the present invention have the general formula (TA5-2A) or (TA5-2B):

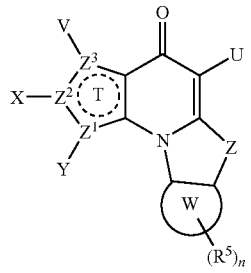
(TA5-2A)

(TA5-2B)

wherein U, V, W, X, Y, Z, Z¹, Z², Z³, R⁵ and n are as described above for TA5-1;
Z⁴ is CR⁶, NR², or C=O; and
Z and Z⁴ may optionally form a double bond.

In the above formula (TA5-1), (TA5-2A) and (TA5-2B), U may be SO₂NR¹R², wherein R¹ is H, and R² is a C$_{1-10}$ alkyl optionally substituted with a heteroatom, a C$_{3-6}$ cycloalkyl, aryl or a 5-14 membered heterocyclic ring containing one or more N, O or S. For example, $R^2$ may be a $C_{1-10}$ alkyl substituted with an optionally substituted morpholine, thiomorpholine, imidazole, aminodithiadazole, pyrrolidine, piperazine, pyridine or piperidine. In other examples, $R^1$ and $R^2$ together with N form an optionally substituted piperidine, pyrrolidine, piperazine, morpholine, thiomorpholine, imidazole, or aminodithiazole.

In other embodiments of these compounds, U is $SO_2NR^1$—$(CR^1_2)_n$—$NR^3R^4$; n is 1-4; each $R^1$ is H or alkyl; and $R^3$ and $R^4$ in $NR^3R^4$ together form an optionally substituted piperidine, pyrrolidine, piperazine, morpholine, thiomorpholine, imidazole, or aminodithiazole. In some examples, U is $SO_2NH$—$(CH_2)_n$—$NR^3R^4$ wherein $R^3$ and $R^4$ together with N form an optionally substituted pyrrolidine, which may be linked to $(CH_2)_n$ at any position in the pyrrolidine ring. In one embodiment, $R^3$ and $R^4$ together with N form an N-methyl substituted pyrrolidine.

In one embodiment, the present invention provides compounds having formula (TA5-1), (TA5-2A) or (TA5-2B), wherein:

each of V and Y if present is independently H or halogen (e.g., chloro or fluoro);

X is —$(R^5)R^1R^2$, wherein $R^5$ is C or N and wherein in each —$(R^5)R^1R^2$, $R^1$ and $R^2$ together may form an optionally substituted aryl or heteroaryl ring;

Z is NH or N-alkyl (e.g., N—$CH_3$);

W together with N and Z forms an optionally substituted 5- or 6-membered ring that is fused with an optionally substituted aryl or heteroaryl ring; and U is —$SO_2R^5R^6$—$(CH_2)_n$—$CHR^2$—$NR^3R^4$, wherein $R^5$ is $CR^1$ or N; $R^1$ is H or alkyl; $R^6$ is H or $C_{1-10}$ alkyl and wherein in the —$CHR^2$—$NR^3R^4$ moiety each $R^3$ or $R^4$ together with the C may form an optionally substituted heterocyclic or heteroaryl ring, or wherein in the —$CHR^2$—$NR^3R^4$ moiety each $R^3$ or $R^4$ together with the N may form an optionally substituted carbocyclic, heterocyclic, aryl or heteroaryl ring.

In another embodiment, the present invention provides compounds having formula (TA5-1), (TA5-2A) or (TA5-2B), wherein:

V and Y if present is H or halogen (e.g., chloro or fluoro);

X if present is —$(R^5)R^1R^2$, wherein $R^5$ is C or N and wherein in each —$(R^5)R^1R^2$, $R^1$ and $R^2$ together may form an optionally substituted aryl or heteroaryl ring;

Z is NH or N-alkyl (e.g., N—$CH_3$);

W together with N and Z forms an optionally substituted 5- or 6-membered ring that is fused with an optionally substituted aryl or heteroaryl ring; and U is —$SO_2R^5R^6$—$(CH_2)_n$—$CHR^2$—$NR^3R^4$, $R^5$ is $CR^1$ or N;

$R^6$ is H or alkyl and wherein in the —$CHR^2$—$NR^3R^4$ moiety each $R^3$ or $R^4$ together with the C may form an optionally substituted heterocyclic or heteroaryl ring, or wherein in the —$CHR^2$—$NR^3R^4$ moiety each $R^3$ or $R^4$ together with the N may form an optionally substituted carbocyclic, heterocyclic, aryl or heteroaryl ring.

In yet another embodiment, the compounds of the present invention have the general formula (TA5-3):

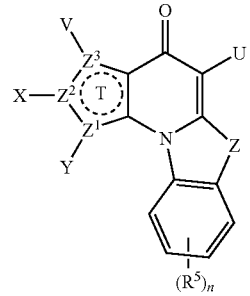

(TA5-3)

wherein U, V, X, Y, Z, $Z^1$, $Z^2$, $Z^3$, $R^5$ and n are as described above.

In yet another embodiment, the compounds of the present invention have the general formula (TA5-4A) or (TA5-4B):

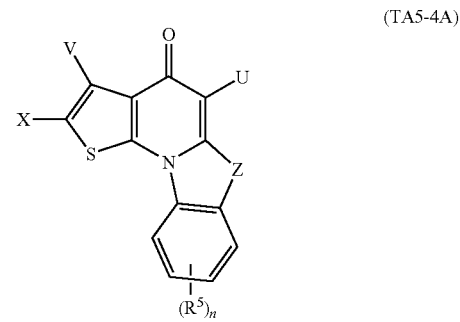

(TA5-4A)

(TA5-4B)

wherein U, V, X, Z, $R^5$ and n are as described above for TA5-1.

Compounds of Formula (TA5-1), and methods for making and using them, are described in U.S. Patent Application Ser. No. 60/811,990, to Pierre, et al., entitled PYRIDINONE ANALOGS, which was filed Jun. 8, 2006, and in U.S. Provisional Patent Application 60/904,694 to Nagasawa, et al., filed on Mar. 1, 2007.

In still another aspect, the therapeutic agent for the combinations of the invention can be a compound of the formula:

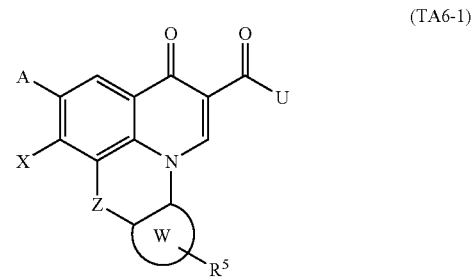

(TA6-1)

and pharmaceutically acceptable salts, esters and prodrugs thereof, wherein X is H, $OR^2$, $NR^1R^2$, halogen, azido, $SR^2$ or $CH_2R$;

A is H, halogen, $NR^1R^2$, $SR^2$, $OR^2$, $CH_2R^2$, azido or $NR^1$—$(CR^1{}_2)_n$—$NR^3R^4$;

Z is O, S, $NR_1$ or $CH_2$;

U is $R^2$, $OR^2$, $NR^1R^2$ or $NR^1$—$(CR^1{}_2)_n$—$NR^3R^4$ provided U is not H;

W is an optionally substituted aryl or heteroaryl, which may be monocyclic or fused with a single or multiple ring optionally containing a heteroatom;

wherein $R^1$ and $R^2$ together with N in $NR^1R^2$, and $R^3$ and $R^4$ together with N in $NR^3R^4$ may independently form an optionally substituted 5-6 membered ring containing N, and optionally O or S;

$R^1$ and $R^3$ are independently H or a $C_{1-6}$ alkyl; and $R^2$ and $R^4$ are independently H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally cycloalkyl, substituted heterocyclic ring, aryl or heteroaryl;

$R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

provided X and A both are not H, and further provided that $R^5$ is cyano or —$CONHR^1$ when A is H, halogen or $NR^1R^2$;

or a compound having formula (TA6-1A)

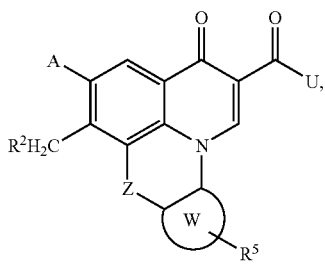

(TA6-1A)

and pharmaceutically acceptable salts, esters and prodrugs thereof;

A is H, halogen, azido, $SR^2$, $OR^2$, $CH_2R^2$, $NR^1R^2$, or $NR^1$—$(CR^1{}_2)_n$—$NR^3R^4$;

Z, U, W, $R^1$, $R^2$, $R^3$ and $R^4$ are as defined in formula TA6-1; and $R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

wherein each optionally substituted moiety in formula TA6-1 and -1A is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, =O, aryl or one or more heteroatoms selected from N, O and S; or is substituted with an aryl, a carbocyclic or a heterocyclic ring.

In the above formula TA6-1 or TA6-1A, W may be selected from the group consisting of

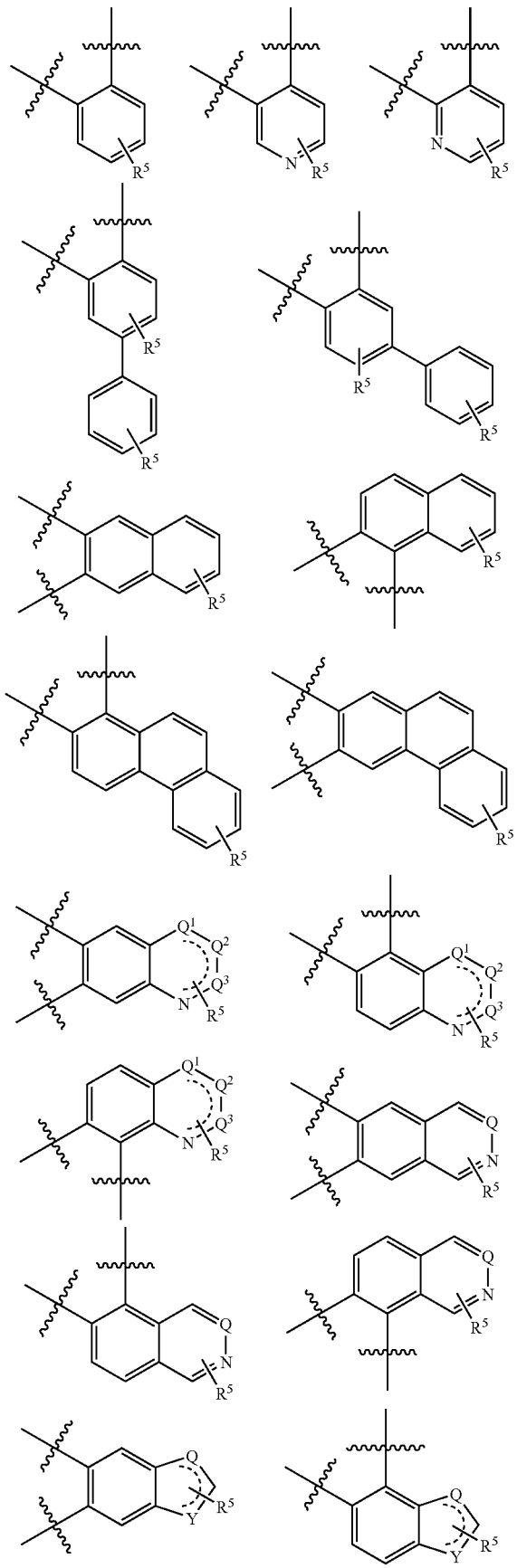

-continued

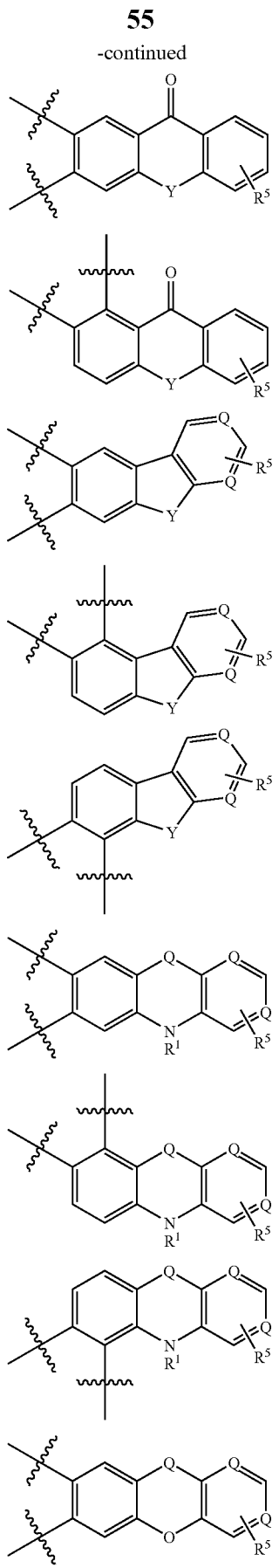

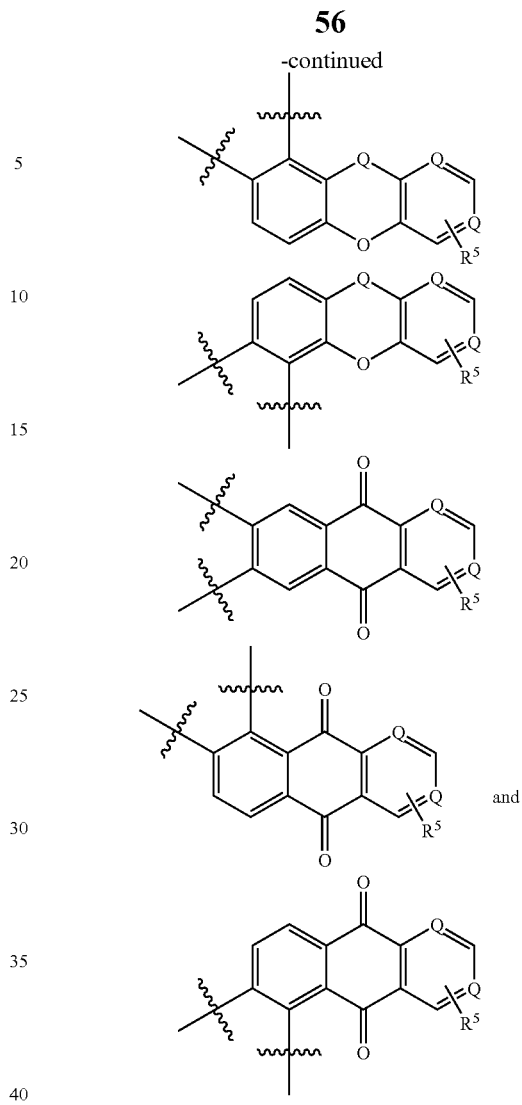

wherein Q, $Q^1$, $Q^2$, and $Q^3$ are independently CH or N;
Y is independently O, CH, =O or $NR^1$; and
$R^5$ is as defined in formula 1.

In some embodiments of these compounds, each W in the above formula TA6-1 or TA6-1A may be an optionally substituted phenyl, pyridine, biphenyl, naphthalene, phenanthrene, quinoline, isoquinoline, quinazoline, cinnoline, phthalazine, quinoxaline, indole, benzimidazole, benzoxazole, benzthiazole, benzofuran, anthrone, xanthone, acridone, fluorenone, carbazolyl, pyrimido[4,3-b]furan, pyrido[4,3-b]indole, pyrido[2,3-b]indole, dibenzofuran, acridine or acridizine. In one embodiment, W is an optionally substituted phenyl.

The compounds of formula (TA6-1), and methods for making and using them, are described in U.S. patent application Ser. No. 11/404,947, to Whitten, et al., which was filed on Apr. 14, 2006, and is entitled QUINOBENZOXAZINE ANALOGS AND METHODS OF USING THEREOF.

The present invention utilizes the above therapeutic agents in combination with at least one modulator. Examples of PARP inhibitors are known in the art, and are disclosed, for example, in C. R. Calebrese, et al., *Clin. Cancer Res*. vol. 9, 2711-18 (2003); S. J. Veuger, et al., *Cancer Res*. vol. 63, 6008-15 (2003); C. R. Calabrese et al., *J. Nat'l. Cancer Inst*. 96(1), 56-67 (2004); "Potent Novel PARP Inhibitors," *Expert*

Reviews in Molecular Medicine, vol. 7(4) (March 2005); and P. Jagtap, *Nature Rev.: Drug Discovery*, vol. 4, 421-40 (20045). The PARP inhibitors disclosed in these documents are suitable for use in the methods and compositions of the present invention. Additional PARP inhibitors that can be used include, for example, 10-(4-methyl-piperazin-1-ylmethyl)-2H-7-oxa-1,2-diaza-benzo[de]anthracen-3-one (GPI 15427) and 2-(4-methyl-piperazin-1-yl)-5H-benzo[c][1,5]naphthyridin-6-one (GPI 16539). See Di Paola, et al., *Eur. J. Pharmacology*, 527(1-3), 163-71 (2005). Representative, but non-limiting, examples of PARP inhibitors that are suitable for use in the invention include the known compounds shown hereafter, including the pharmaceutically acceptable salts thereof, and individual isomers or mixtures of isomers thereof.

-continued

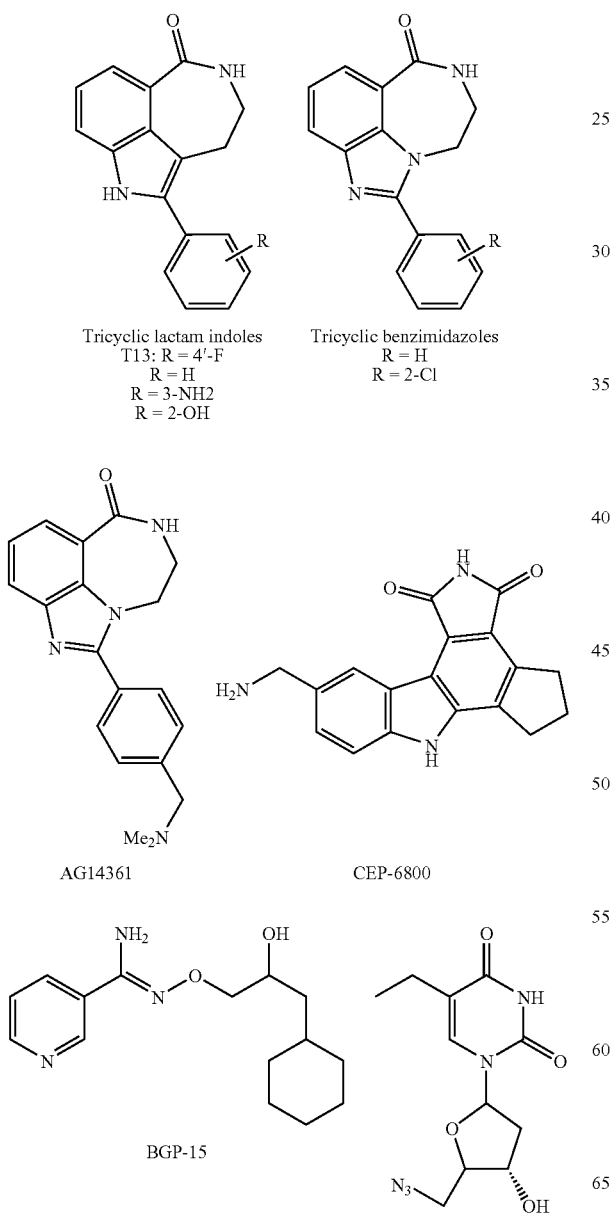

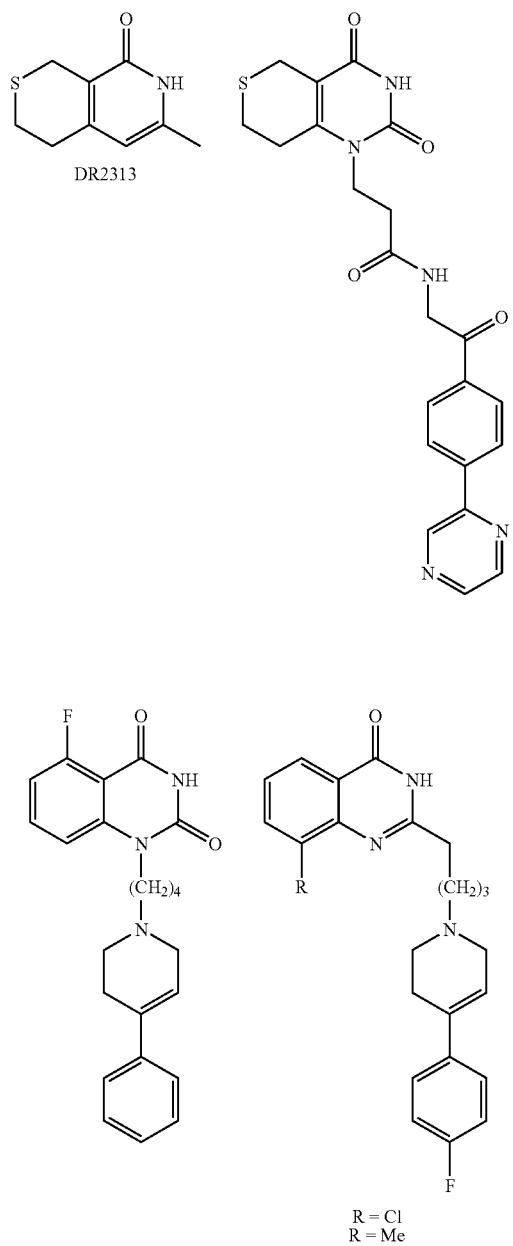

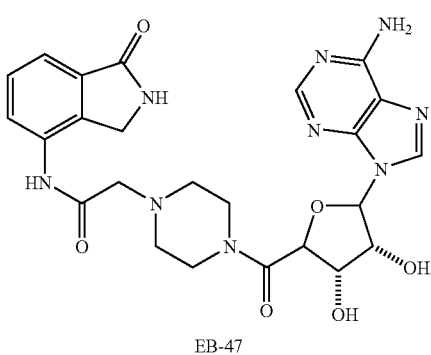

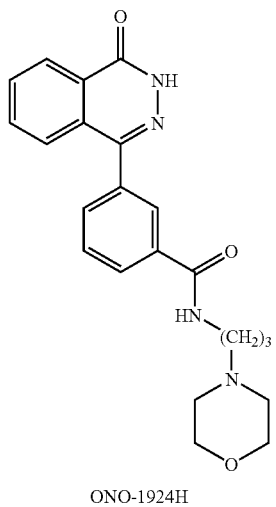

ONO-1924H

PJ-34

NU-1025

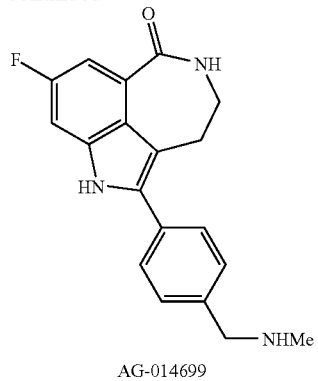

NU-1085

AG-014699

Modulators that can be utilized in combination with a therapeutic agent described above also include compounds having structures of Formula I, II, III, IV, V, VI, VII, VIII, IX, X, XI or XII described herein.

The compound TA1-1A is a preferred therapeutic agent for use in the methods and compositions of the invention. More detail on suitable methods for its formulation and administration are provided in U.S. Provisional Application Ser. No. 60/803,864 to Lim, et al., which was filed on Jun. 3, 2006.

The invention also in part provides pharmaceutical compositions comprising at least one therapeutic agent within the scope of the invention as described herein in combination with at least one modulator. Optionally, the composition may comprise a diluent or other pharmaceutically acceptable excipients.

For administration to animal or human subjects, the appropriate dosage of the therapeutic agent is typically 0.01-15 mg/kg, preferably 0.1-10 mg/kg. Dosage levels are dependent on the nature of the condition, drug efficacy, the condition of the patient, the judgment of the practitioner, and the frequency and mode of administration; however, optimization of such parameters is within the ordinary level of skill in the art.

Similarly, the dosage of a modulator, such as a compound of Formula I, II, III, IV, V, VI, VII, VIII, IX, X, XI or XII described herein, is typically between about 0.01-15 mg/kg, and about 0.1-10 mg/kg. A modulator may be separately active for treating a cancer. For combination therapies described above, when used in combination with a therapeutic agent, the dosage of a modulator will frequently be two-fold to ten-fold lower than the dosage required when the modulator is used alone to treat the same condition or subject. Determination of a suitable amount of the modulator for use in combination with a therapeutic agent is readily determined by methods known in the art.

Also provided are methods for modulating the activity of a PARP protein, which comprises contacting a system comprising the PARP protein with a composition described herein in an amount effective for modulating (e.g., inhibiting) the activity of the protein. The system in such embodiments can be a cell-free system or a system comprising cells. Also provided are methods for reducing cell proliferation, and optionally inducing apoptosis, which comprises contacting cells with a composition or a combination therapy as described herein, wherein a therapeutic agent is administered in an amount effective to reduce proliferation of the cells, and a PARP inhibitor is administered in an amount sufficient to enhance the efficacy of the therapeutic agent. The cells in such embodiments can be in a cell line, in a tissue or in a subject (e.g., a research animal or human).

The invention also in part provides methods for treating a condition related to aberrant cell proliferation. For example, provided are methods of treating a cell proliferative condition in a subject, which comprises administering a therapeutic agent described herein and a PARP inhibitor described herein to a subject in need of treatment for a cell proliferative disorder; the therapeutic agent and the PARP inhibitor are administered in amounts effective to treat the cell proliferative condition. The subject may be a research animal (e.g., rodent, dog, cat, monkey), optionally containing a tumor such as a xenograft tumor (e.g., human tumor), for example, or may be a human.

A cell proliferative condition sometimes is a tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma).

Any suitable formulation of the therapeutic agent and the PARP inhibitor can be prepared for administration, either together or separately. Any suitable route of administration may be used for each component, including but not limited to oral, parenteral, intravenous, intramuscular, transdermal, topical and subcutaneous routes. The two substances used together (PARP inhibitor and therapeutic agent) may be administered separately or together. When administered together, they may be in separate dosage forms, or they may be combined into a single combination drug. Thus, provided herein are pharmaceutical compositions comprising a therapeutic agent as described herein and at least one PARP inhibitor, and a pharmaceutically acceptable excipient.

The following examples illustrate and do not limit the invention.

Example 1

Processes for Synthesizing Compounds of Formulae I, II, III and IV

Process 1

3-bromo-4-pyridine carboxylic acid (3.0 g, 14.9 mmol) in ethanol (100 mL) was treated with concentrated sulfuric acid (5 mL).

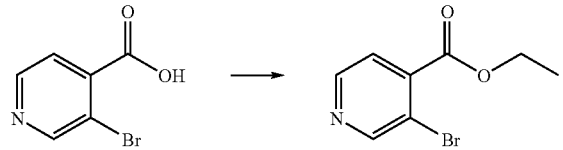

The mixture was brought to reflux at which time everything went into solution. After 12 hours at reflux, LCMS indicated that the reaction was complete. The reaction mixture was cooled to room temperature and concentrated on a rotary evaporator to a third of its original volume. The mixture was then diluted with 250 mL of ethyl acetate and washed twice with saturated aqueous sodium bicarbonate. Concentration on a rotary evaporator yielded 3.25 g of the ethyl ester as a yellowish oil which was sufficiently pure enough for subsequent chemical transformations. LCMS (ESI) 216.2 (M+1)$^+$.

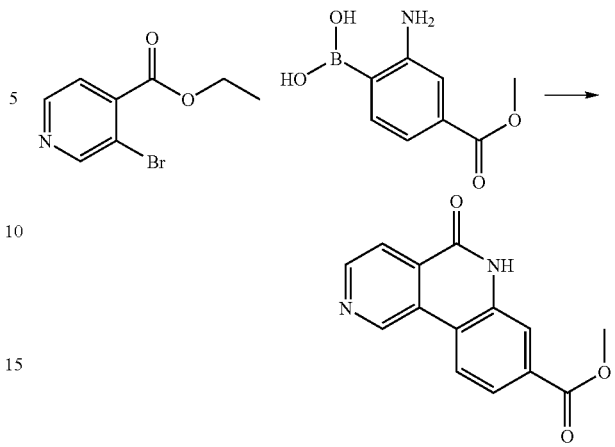

Ethyl 3-bromo-4-pyridine carboxylate 1.15 g, 5.0 mmol), 2-amino-4-methoxycarbonyl-phenylboronic acid (1.04 g, 4.5 mmol), sodium acetate (1.64 g, 20 mmol), 1,1'-bis(diphenylphosphino)ferrocene palladium (II) chloride (complexed with dichloromethane) (182 mg, 0.25 mmol) and dimethylformamide (7.5 mL) were combined in a flask. The flask was evacuated and filled with nitrogen twice and heated to 125° C. with stirring for 12 hours or until LCMS indicated the absence of any starting material. The mixture was cooled to room temperature and water (100 mL) was added to form a brown precipitate. The precipitate was filtered to yield 637 mg of methyl 5-oxo-5,6-dihydrobenzo[c][2,6]naphthyridine-8-carboxylate. LCMS (ESI) 255.4 (M+1)$^+$.

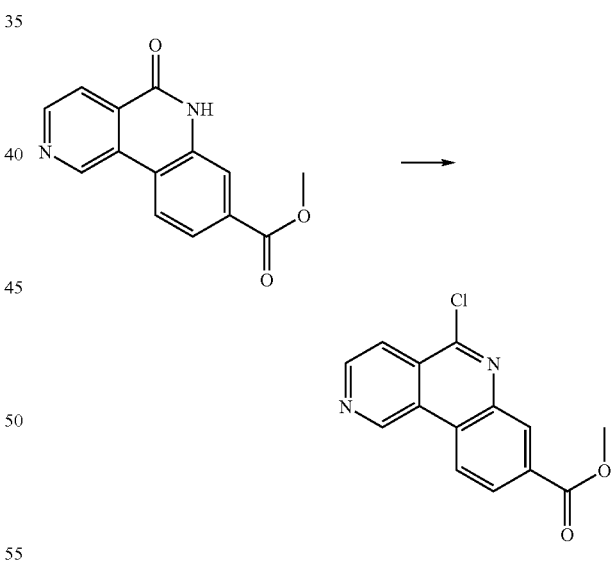

Methyl 5-oxo-5,6-dihydrobenzo[c][2,6]naphthyridine-8-carboxylate (200 mg, 0.787 mmol) was combined with phosphorus oxychloride (1 mL) and heated to reflux. After 2 hours, LCMS indicated the absence of any starting material. The volatiles were removed under reduced pressure. The residue was taken up in dichloromethane (50 mL) and washed twice with saturated aqueous sodium bicarbonate. The organic phase was dried over sodium sulfate and concentrated on a rotary evaporator to give methyl 5-chlorobenzo[c][2,6]naphthyridine-8-carboxylate (140 mg) as a grayish solid. LCMS (ESI) 273.3 (M+1)$^+$.

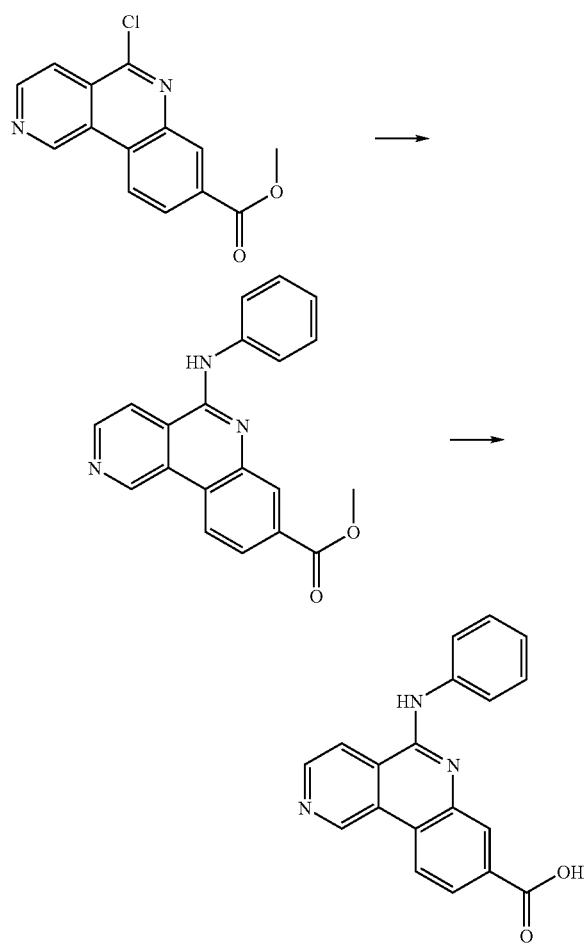

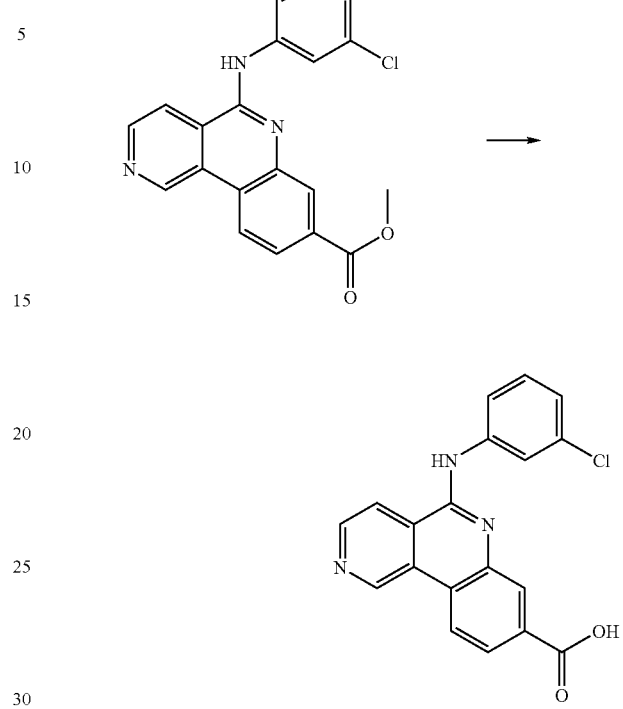

Methyl 5-chlorobenzo[c][2,6]naphthyridine-8-carboxylate (20 mg, 0.074 mmol) was combined with aniline (60 mg, 0.65 mmol) and N-methylpyrrolidinone (0.2 mL) in a microwave tube and the mixture was heated to 120° C. for 10 minutes at which time LCMS indicated that the reaction was complete as indicated by the absence of any starting material. The mixture was then purified by HPLC to yield the ester (22 mg) or it could be treated with 6N sodium hydroxide to yield the acid (19 mg). LCMS (ESI) 316.3 (M+1)⁺. ¹HNMR (400 MHz, CD₃OD) 10.17 (1H, s), 9.67 (1H, br), 8.99 (1H, d, 5.9 Hz), 8.83 (1H, d, 8.6 Hz), 8.62 (1H, d, 5.9 Hz), 8.24 (1H, d, 1.6 Hz), 8.04 (1H, s), 8.02 (1H, s), 7.93 (1H, dd, 8.2, 1.6 Hz), 7.43 (1H, d, 7.4 Hz), 7.41 (1H, d, 7.4 Hz), 7.10 (1H, m).

Methyl 5-chlorobenzo[c][2,6]naphthyridine-8-carboxylate (232 mg, 0.853 mmol) was combined with meta-chloroaniline (217 mg, 1.71 mmol) and N-methyl pyrrolidinone (1 mL) in a flask and the mixture was heated to 80° C. for 2 hours at which time LCMS indicated that the reaction was complete as indicated by the absence of any starting material. The mixture was dissolved in CH₂Cl₂, washed with saturated aqueous sodium bicarbonate and dried over Na₂SO₄. The material was purified by flash chromatography (SiO₂, 1:1 to 9:1 gradient of EtOAc/Hexanes) to obtain the ester. The material was dissolved in methanol and 6N aqueous NaOH and the mixture stirred at 50° C. for 30 minutes. The volatiles were removed in vacuo. The residue was triturated from acetic acid/THF/methanol using a mixture of hexanes and ethylacetate. Filtration and drying provided 147 mg of 5-(3-chlorophenylamino)benzo[c][2,6]naphthyridine-8-carboxylic acid. LCMS (ESI) 350 (M+1)⁺. ¹HNMR (400 MHz, DMSO-d₆) δ 10.21 (s, 1H), 9.72 (br s, 1H), 9.02 (d, J=5.6, 1H), 8.89 (d, J=8.8, 1H), 8.62 (d, J=5.6, 1H), 8.31 (br s, 1H), 8.28 (d, J=1.6, 1H), 8.10 (br d, J=8, 1H), 7.99 (dd, J=2, J=8.4, 1H), 7.46 (t, J=8.0, 1H), 7.16 (br d, J=7.2, 1H) ppm.

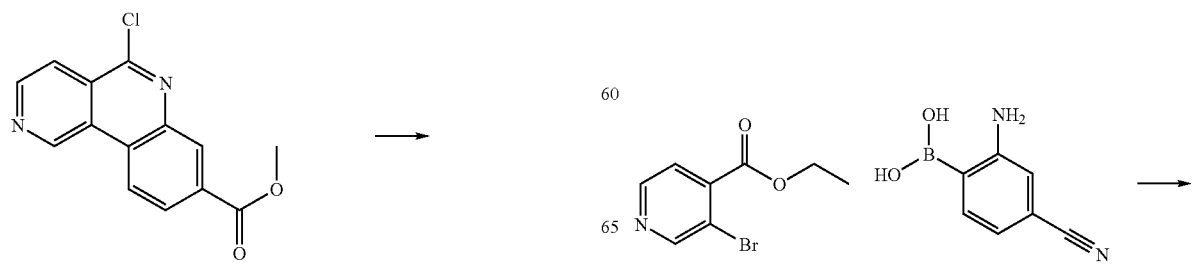

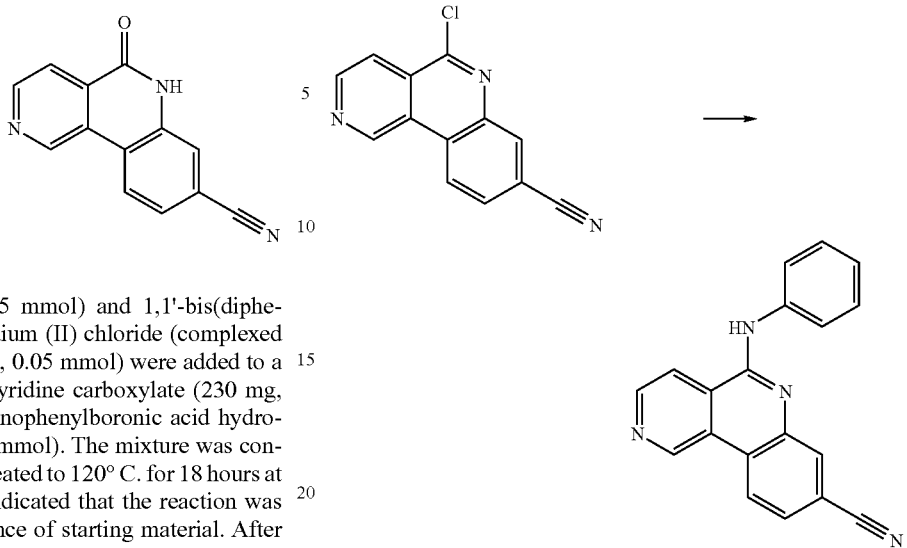

Sodium acetate (410 mg, 5 mmol) and 1,1'-bis(diphenylphosphino)ferrocene palladium (II) chloride (complexed with dichloromethane) (36 mg, 0.05 mmol) were added to a mixture of ethyl 3-bromo-4-pyridine carboxylate (230 mg, 1.0 mmol) and 2-amino-4-cyanophenylboronic acid hydrochloric acid salt (179 mg, 0.9 mmol). The mixture was connected to an exit bubbler and heated to 120° C. for 18 hours at which time LCMS analysis indicated that the reaction was done based on the disappearance of starting material. After cooling to room temperature, water was added and the dark solids were filtered and washed with dichloromethane to give 5-oxo-5,6-dihydrobenzo[c][2,6]naphthyridine-8-carbonitrile (156 mg) as a gray solid which was sufficiently pure enough for subsequent chemical transformations. LCMS (ESI) 222.4 (M+1)$^+$. $^1$HNMR (400 MHz, DMSO-d$_6$) 12.2 (1H, s), 9.96 (1H, s), 8.90 (1H, d, 5.1 Hz), 8.77 (1H, d, 8.2 Hz), 8.13 (1H, d, 5.1 Hz), 7.73 (1H, dd 8.2, 1.6 Hz), 7.70 (1H, d, 1.6 Hz).

A mixture of the 5-chlorobenzo[c][2,6]naphthyridine-8-carbonitrile (30 mg, 0.13 mmol), aniline (60 mg, 0.65 mmol) and dimethylformamide (0.2 mL) was heated to 120° C. in a microwave reactor for 10 minutes. LCMS indicated that absence of starting material. The mixture was diluted with water and left to stand for a few minutes as 5-(phenylamino)benzo[c][2,6]naphthyridine-8-carbonitrile (25 mg) precipitated as an off-white solid. LCMS (ESI) 297.3 (M+1)$^+$.

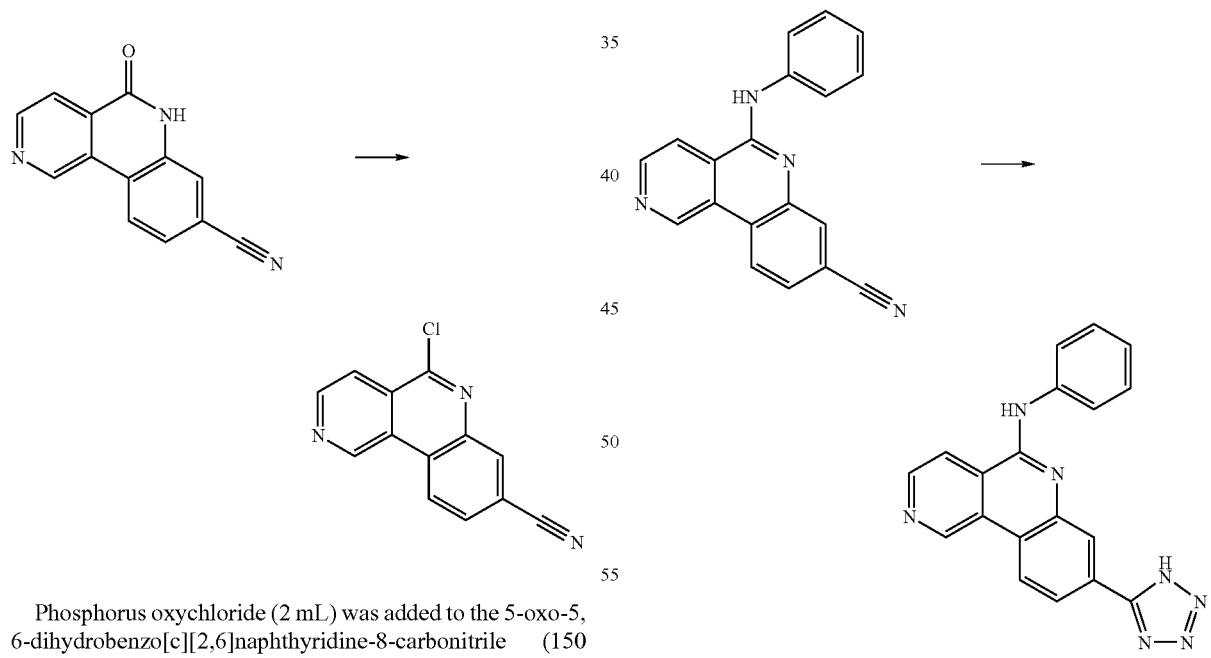

Phosphorus oxychloride (2 mL) was added to the 5-oxo-5,6-dihydrobenzo[c][2,6]naphthyridine-8-carbonitrile (150 mg, 0.66 mmol). The mixture was heated reflux for 3 hours at which time LCMS analysis indicated the absence of any starting material. Volatiles were removed under vacuum and the crude product was dissolved in dichloromethane, washed with brine and saturated aqueous sodium bicarbonate and dried over sodium sulfate. After concentrating under vacuum, the crude product was triturated with ethyl acetate and hexanes to give 5-chlorobenzo[c][2,6]naphthyridine-8-carbonitrile (125 mg). LCMS (ESI) 240.3 (M+1)$^+$.

Sodium azide (65 mg, 1 mmol) and ammonium chloride (53 mg, 1 mmol) were added to a crude mixture of the 5-(phenylamino)benzo[c][2,6]naphthyridine-8-carbonitrile (25 mg, 0.084 mmol) in dimethylformamide (0.2 mL). The mixture was heated for 18 h at 120° C. at which time LCMS analysis indicated the absence of any starting material. The mixture was diluted with water and purified by preparative HPLC to give N-phenyl-8-(1H-tetrazol-5-yl)benzo[c][2,6]naphthyridin-5-amine (14 mg). LCMS (ESI) 340.3 (M+1)+. 1HNMR (400 MHz, CD3OD) 10.11 (1H, s), 8.96 (1H, d, 5.9 Hz), 8.85 (1H, d, 8.2 Hz), 8.53 (1H, d, 5.5 Hz), 8.47 (1H, s), 8.16 (1H, d, 8.6 Hz), 7.88 (1H, s), 7.86 (1H, d, 0.8 Hz), 7.57-7.51 (3H, m), 7.36-7.31 (2H, m).
Representative compounds are set forth hereafter in Table 1A.
TABLE 1A
| Compound | Molecular Weight | LCMS (ES) m/z |
|---|---|---|
| 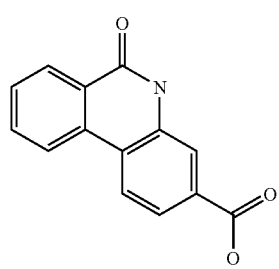 | 239.2 | 240 [M + 1]+ |
| 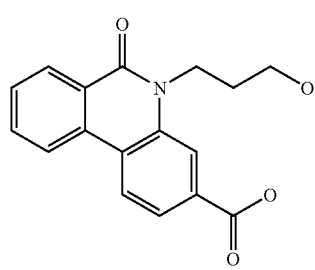 | 297.3 | 298 [M + 1]+ |
| 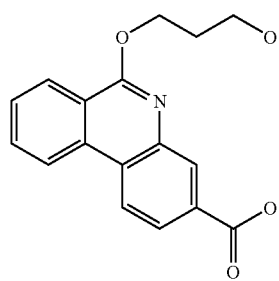 | 297.3 | 298 [M + 1]+ |
| 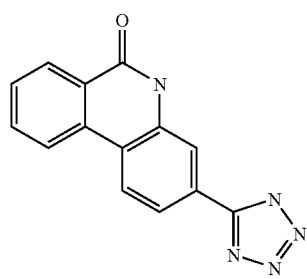 | 263.3 | 264 [M + 1]+ |
TABLE 1A-continued
| | Molecular Weight | LCMS (ES) m/z |
|---|---|---|
| | 240.2 | 241 [M + 1]+ |
| | 254.2 | 255 [M + 1]+ |
| | 309.4 | 310 [M + 1]+ |
| | 314.3 | 315 [M + 1]+ |
| | 321.3 | 322 [M + 1]+ |

TABLE 1A-continued

| Molecular Weight | LCMS (ES) m/z |
|---|---|
| 315.3 | 316 [M + 1]+ |
| 310.4 | 311 [M + 1]+ |
| 264.3 | 265 [M + 1]+ |
| 339.4 | 340 [M + 1]+ |

TABLE 1A-continued

| Molecular Weight | LCMS (ES) m/z |
|---|---|
| 334.4 | 335 [M + 1]+ |
| 329.4 | 330 [M + 1]+ |
| 345.4 | 346 [M + 1]+ |
| 367.8 | 368 [M + 1]+ |

TABLE 1A-continued

| Structure | Molecular Weight | LCMS (ES) m/z |
|---|---|---|
| (4-fluoro-3-chlorophenylamino benzonaphthyridine carboxylic acid) | 367.76 | 368 [M + 1]+ |
| (phenylamino benzonaphthyridine carbonitrile) | 296.33 | 297 [M + 1]+ |
| (dimethylaminoethylamino benzonaphthyridine carbonitrile) | 291.35 | 292 [M + 1]+ |
| (4-fluoro-3-chlorophenylamino benzonaphthyridine methyl ester) | 381.79 | 382 [M + 1]+ |

TABLE 1A-continued

| Structure | Molecular Weight | LCMS (ES) m/z |
|---|---|---|
| (3-methoxyphenylamino benzonaphthyridine methyl ester) | 359.38 | 360 [M + 1]+ |
| (3-fluorophenylamino benzonaphthyridine carboxylic acid) | 333.32 | 334 [M + 1]+ |
| (phenethylamino benzonaphthyridine carboxylic acid) | 343.38 | 345 [M + 1]+ |
| (3-chlorophenylamino benzonaphthyridine carboxylic acid) | 349.77 | 350 [M + 1]+ |

TABLE 1A-continued

| Molecular Weight | LCMS (ES) m/z | Structure |
|---|---|---|
| 357.34 | 358 [M + 1]+ | 3-fluorophenylamino-benzo[c][2,7]naphthyridine with tetrazole |
| 391.79 | 392 [M + 1]+ | 4-chloro-3-fluorophenylamino-benzo[c][2,7]naphthyridine with tetrazole |
| 349.77 | 350 [M + 1]+ | 4-chlorophenylamino-benzo[c][2,7]naphthyridine-carboxylic acid |
| 339.35 | 340 [M + 1]+ | 3-ethynylphenylamino-benzo[c][2,7]naphthyridine-carboxylic acid |
| 373.80 | 374 [M + 1]+ | 3-chlorophenylamino-benzo[c][2,7]naphthyridine with tetrazole |
| 329.35 | 330 [M + 1]+ | benzylamino-benzo[c][2,7]naphthyridine-carboxylic acid |
| 353.38 | 354 [M + 1]+ | N-phenyl-benzo[c][2,7]naphthyridine with 3-methyl-1,2,4-oxadiazole |
| 377.82 | 378 [M + 1]+ | 2-(3-chlorophenyl)ethylamino-benzo[c][2,7]naphthyridine-carboxylic acid |

TABLE 1A-continued
| | Molecular Weight | LCMS (ES) m/z |
|---|---|---|
| 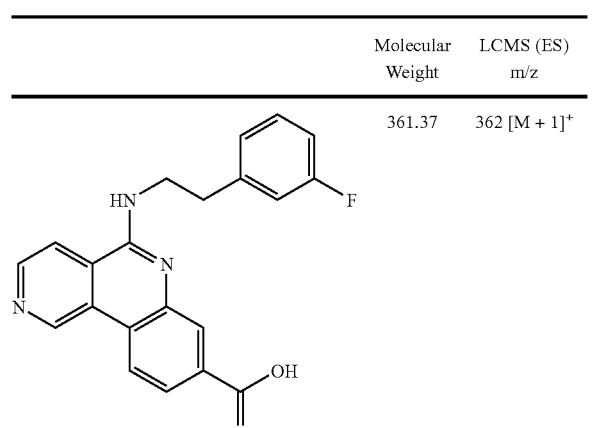 | 361.37 | 362 [M + 1]+ |
| 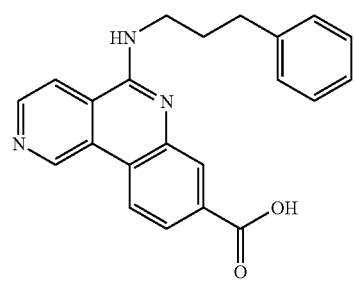 | 357.41 | 358 [M + 1]+ |
| 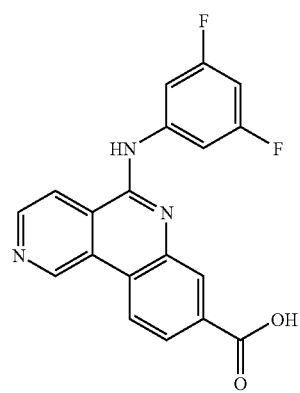 | 351.31 | 352 [M + 1]+ |
| 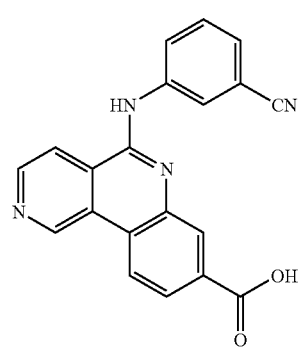 | 340.33 | 341 [M + 1]+ |
TABLE 1A-continued
| | Molecular Weight | LCMS (ES) m/z |
|---|---|---|
| 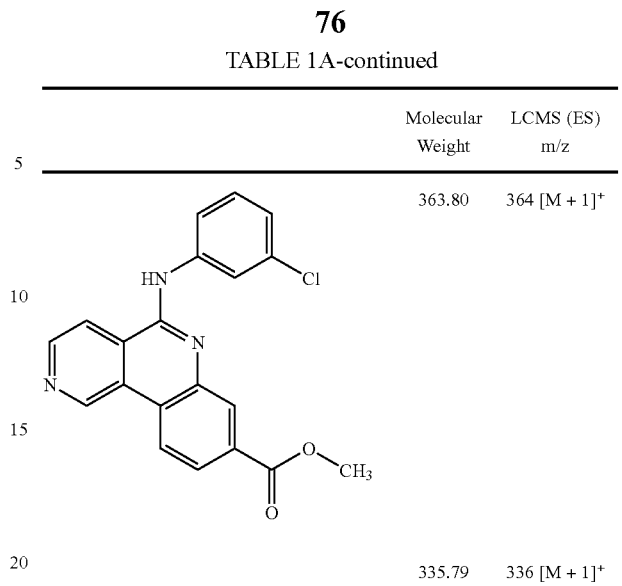 | 363.80 | 364 [M + 1]+ |
| 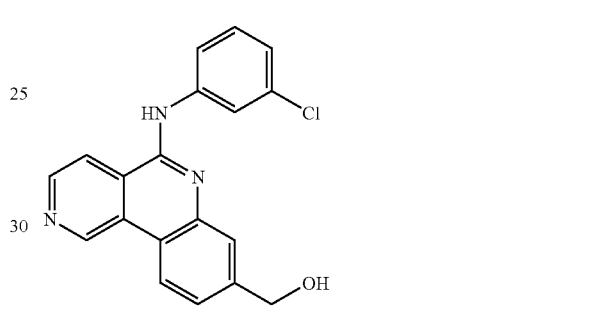 | 335.79 | 336 [M + 1]+ |
| 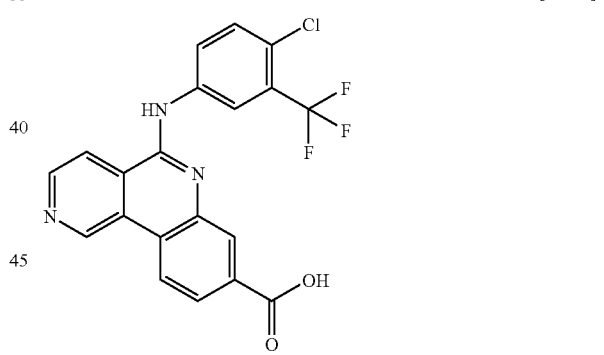 | 417.77 | 418 [M + 1]+ |
| 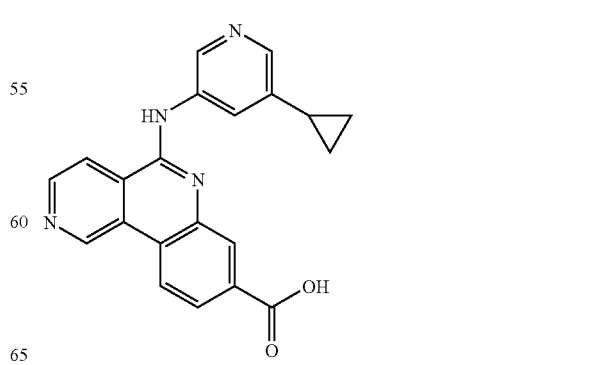 | 356.38 | 357 [M + 1]+ |

TABLE 1A-continued

| | Molecular Weight | LCMS (ES) m/z |
|---|---|---|
| (structure) | 329.35 | 330 [M + 1]+ |
| (structure) | 383.32 | 384 [M + 1]+ |
| (structure) | 279.29 | 280 [M + 1]+ |

Process 2

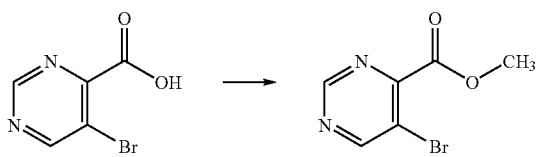

5-bromopyrimidine-4-carboxylic acid (prepared according to the procedure described in U.S. Pat. No. 4,110,450) (1.0 eq, 6.14 g, 30.2 mmol) was suspended in $CH_2Cl_2$ (100 ml). Oxalylchloride (1.1 eq, 2.9 ml, 33.0 mmol) was added followed by 2 drops of DMF. The mixture was stirred at room temperature overnight and the volatiles were removed in vacuo. The residue was taken in MeOH (50 ml) and heated. After evaporation of MeOH in vacuo the compound was dissolved in $CH_2Cl_2$ and poured on a prepacked silica gel column. The material was eluted using 20% Ethyl acetate in hexanes. Evaporation of the solvent provided methyl-5-bromopyrimidine-4-carboxylate as a light orange crystalline solid (2.54 g, 39% yield). LCMS (ES): 95% pure, m/z 217 [M]+; 219 [M+2]+; $^1$H NMR ($CDCl_3$, 400 MHz) δ 4.04 (s, 3H), 9.02 (s, 1H), 9.21 (s, 1H) ppm.

Process 3

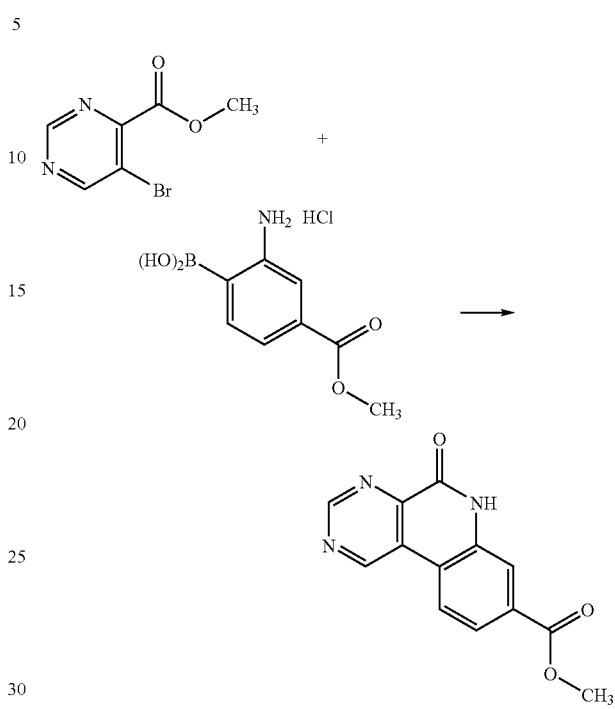

Sodium acetate (4.0 eq, 1.92 g, 23.41 mmol) and 1,1'-bis(diphenylphosphino)ferrocene palladium (II) chloride (complexed with dichloromethane) (0.05 eq, 214 mg, 0.29 mmol) were added to a mixture of methyl-5-bromopyrimidine-4-carboxylate (1.0 eq, 1.27 g, 5.85 mmol), and 2-amino-4-(methoxycarbonyl)phenylboronic acid hydrochloride (1.0 eq, 1.35 g, 5.85 mmol) in anhydrous DMF (10 ml). The Mixture was stirred under nitrogen atmosphere at 120° C. for 18 hours. Water and brine were added and the resulting solid impurities filtered off. The material was extracted with $CH_2Cl_2$ (4×) and the combined extracts dried over $Na_2SO_4$. After evaporation of $CH_2Cl_2$, the remaining DMF was evaporated by heating the residue in vacuo. The resulting solid was triturated in $CH_2Cl_2$, filtered and dried to provide methyl 5-oxo-5,6-dihydropyrimido[4,5-c]quinoline-8-carboxylate as a beige solid (127 mg, 8.5% yield). LCMS (ES): >80% pure, m/z 256 [M+1]+; $^1$H NMR (DMSO-$d_6$, 400 MHz) δ 3.79 (s, 3H), 7.81 (d, J=8.0, 1H), 8.68 (d, J=8.8, 1H), 9.49 (s, 1H), 10.19 (s, 1H), 12.37 (s, 1H) ppm.

Process 4

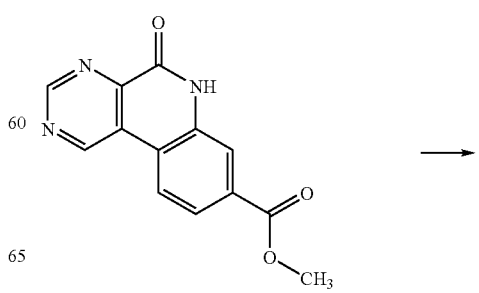

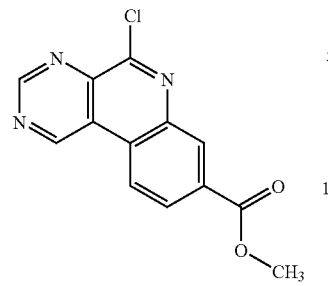

In a vial, methyl 5-oxo-5,6-dihydropyrimido[4,5-c]quinoline-8-carboxylate (1.0 eq, 151 mg, 0.59 mmol) was mixed in toluene (1 ml) with DIEA (1.5 eq, 155 ul, 0.89 mmol) and POCl$_3$ (5 eq, 270 ul, 3.0 mmol). The mixture was stirred at 120° C. for 1 hour and cooled down to room temperature. After adding ice and water the compound was extracted with CH$_2$Cl$_2$ (4×). The solution was filtered over Na$_2$SO$_4$ and filtered through a pad of celite. After evaporation of the volatiles, the material was triturated in a mixture of ethyl acetate and hexanes, filtered and dried to afford methyl 5-chloropyrimido[4,5-c]quinoline-8-carboxylate as a light brown fluffy solid (115 mg, 71% yield). LCMS (ES): 95% pure, m/z 274 [M+1]$^+$. $^1$H NMR (DMSO-d$_6$, 400 MHz) δ 3.96 (s, 3H), 8.37 (dd, J=1.6, J=8.4, 1H), 8.60 (d, J=1.6, 1H), 9.15 (d, J=8.8, 1H), 9.74 (s, 1H), 10.61 (s, 1H) ppm Process 5

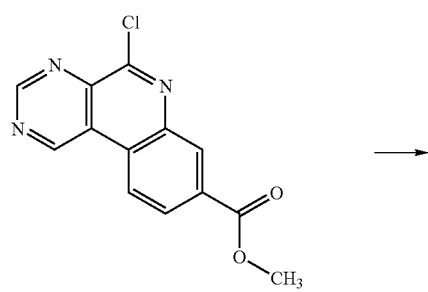

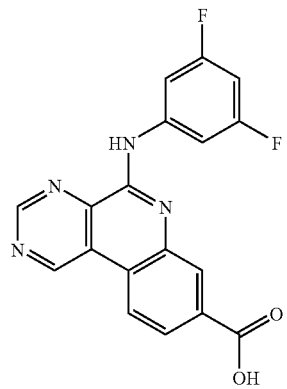

methyl 5-chloropyrimido[4,5-c]quinoline-8-carboxylate (10 mg) was mixed with 3,5-difluoroaniline (100 mg) in NMP (0.1 ml). The mixture was heated under microwaves at 120° C. for 10 minutes. Water was added and the material extracted with CH$_2$Cl$_2$. The solvent was removed. Trituration in a mixture of ethylacetate and hexanes and filtration provided methyl 5-(3,5-difluorophenylamino)pyrimido[4,5-c]quinoline-8-carboxylate. This material was suspended in a 1:1 mixture of THF and MeOH (2 ml) and a 5N aqueous solution of Lithium Hydroxide was added. The mixture was vigorously stirred at room temperature for 5 hours. Water and 6N hydrochloric acid were added to induce precipitation of the expected material. The solid was filtered, washed with water, dried and suspended in MeOH. Filtration and drying gave 5-(3,5-difluorophenylamino)pyrimido[4,5-c]quinoline-8-carboxylic acid as a yellow solid (4 mg, 31% yield). LCMS (ES): 95% pure, m/z 353 [M+1]$^+$. $^1$H NMR (DMSO-d$_6$, 400 MHz) δ 6.90 (br t, J=9.6, 1H), 8.02 (dd, J=1.6, J=8.0, 1H), 8.18 (br d, J=10.8, 2H), 8.34 (d, J=1.6, 1H), 8.86 (d, J=8.4, 1H), 9.65 (s, 1H), 10.40 (s, 1H), 10.44 (s, 1H) ppm.

Process 6

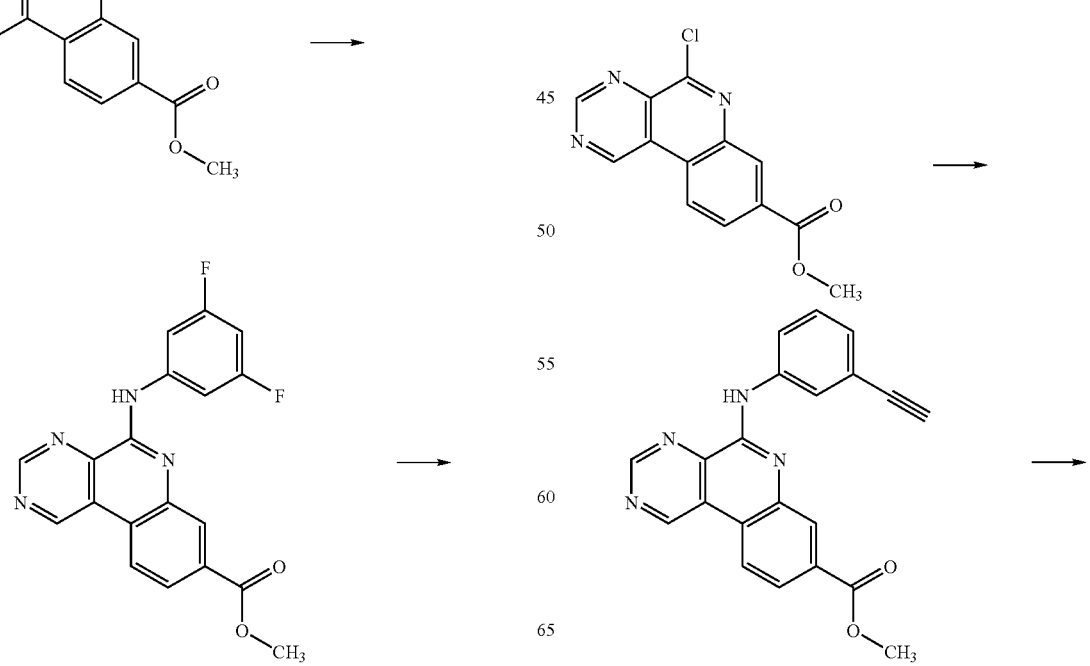

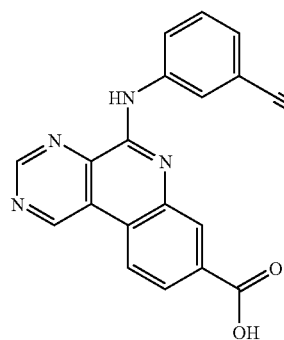

5-(3-ethynylphenylamino)pyrimido[4,5-c]quinoline-8-carboxylic acid was prepared using the same method, starting from methyl 5-chloropyrimido[4,5-c]quinoline-8-carboxylate and 3-ethynylaniline. LCMS (ES): 95% pure, m/z 341 [M+1]$^+$. $^1$H NMR (DMSO-d$_6$, 400 MHz) δ 4.20 (s, 1H), 7.19 (d, J=7.6, 1H), 7.42 (t, J=8.0, 1H), 7.99 (dd, J=1.6, J=8.4, 1H), 8.30 (d, J=1.6, 1H), 8.34 (dd, J=1.6, J=8.0, 1H), 8.49 (br s, 1H), 8.85 (d, J=8.8, 1H), 9.65 (s, 1H), 10.11 (s, 1H), 10.43 (s, 1H) ppm.

Representative analogs (Table 1B) were prepared by the same method using methyl 5-chloropyrimido[4,5-c]quinoline-8-carboxylate and appropriate amines.

TABLE 1B

| Structure | MW | LCMS (ES) m/z |
|---|---|---|
|  | 382.78 | 383 [M + 1]$^+$ |
|  | 368.75 | 369 [M + 1]$^+$ |
| 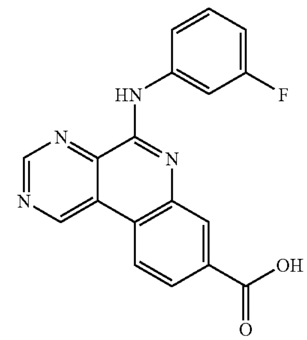 | 334.30 | 335 [M + 1]$^+$ |
| 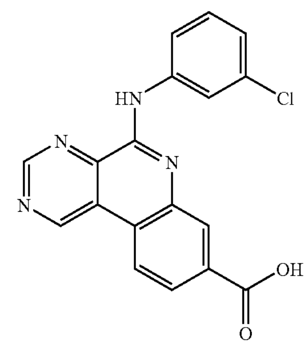 | 350.76 | 351 [M + 1]$^+$ |
| 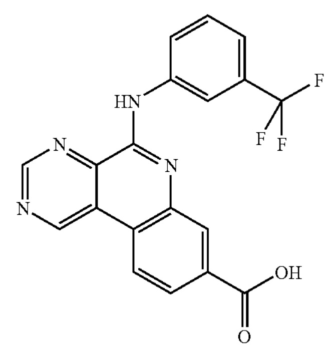 | 384.3114 | 385 [M + 1]$^+$ |
| 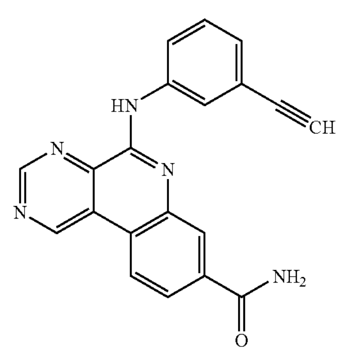 | 339.3501 | 340 [M + 1]+ |

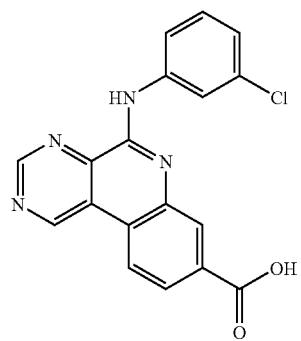
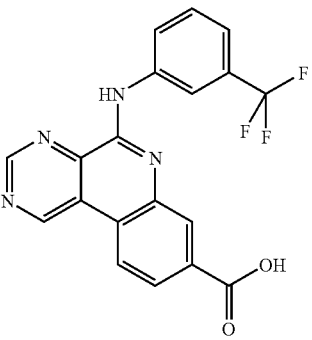
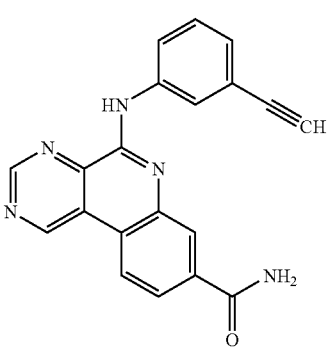

Process 7

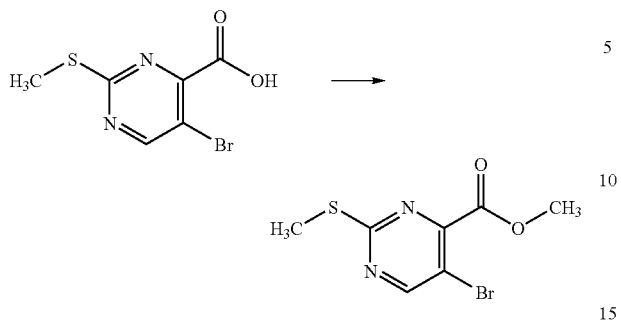

methyl-5-bromo-2-(methylthio)pyrimidine-4-carboxylate was prepared according to the procedure used in process 2 for the preparation of methyl-5-bromopyrimidine-4-carboxylate. LCMS (ES): >90% pure, m/z 263 [M]$^+$, 265 [M+2]$^+$; $^1$H NMR (CDCl$_3$, 400 MHz) δ 2.59 (s, 3H), 4.00 (s, 3H), 8.71 (s, 1H) ppm.

Process 8

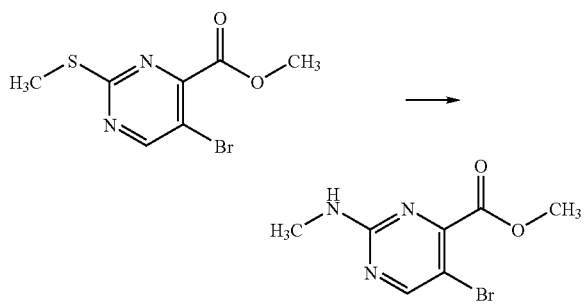

Methyl-5-bromo-2-(methylthio)pyrimidine-4-carboxylate (1.0 eq, 661 mg, 2.52 mmol) was dissolved in CH$_2$Cl$_2$ (10 ml). meta-chloro perbenzoic acid (m-cpba, 77% pure grade, 2.5 eq, 1.42 g, 6.34 mmol) was added and the mixture was stirred at room temperature for 1 hour. To the resulting suspension was added anhydrous THF (10 ml), methylamine hydrochloride (10 eq, 1.7 g, 25.18 mmol) and DIEA (10 eq, 4.3 ml, 24.69 mmol) and the mixture stirred at room temperature overnight. The solvents were removed in vacuo prior to adding CH$_2$Cl$_2$ and a saturated aqueous sodium bicarbonate solution. The two phases were decanted and two further CH$_2$Cl$_2$ extractions were carried out. The combined extracts were dried over Na$_2$SO$_4$ and the solvents evaporated. Purification by flash chromatography on silica gel (20-30% ethylacetate in hexanes) provided methyl 5-bromo-2-(methylamino)pyrimidine-4-carboxylate as an off-white solid (461 mg, 75% yield). LCMS (ES): >95% pure, m/z 246 [M]$^+$, 248 [M+2]$^+$.

Process 9

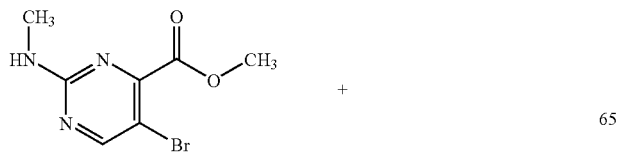

+

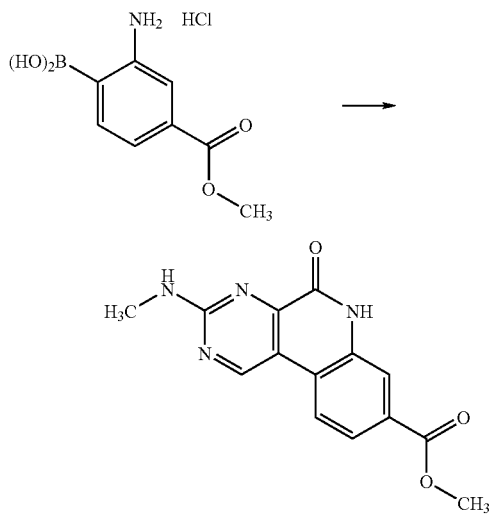

Sodium acetate (3.0 eq, 240 mg, 2.93 mmol) and 1,1'-bis (diphenylphosphino)ferrocene palladium (II) chloride (complexed with dichloromethane) (0.05 eq, 36 mg, 0.049 mmol) were added to a mixture of methyl 5-bromo-2-(methylamino)pyrimidine-4-carboxylate (1.0 eq, 240 mg, 0.975 mmol), and 2-amino-4-(methoxycarbonyl)phenylboronic acid hydrochloride (1.0 eq, 226 mg, 0.98 mmol) in anhydrous DMF (2 ml). The mixture was stirred under microwave heating at 120° C. for 10 min. Addition of water induced precipitation of the expected compound that was filtered and dried. methyl 3-(methylamino)-5-oxo-5,6-dihydropyrimido[4,5-c]quinoline-8-carboxylate (57 mg, 21% yield). LCMS (ES): >80% pure, m/z 285 [M+1]$^+$.

Process 10

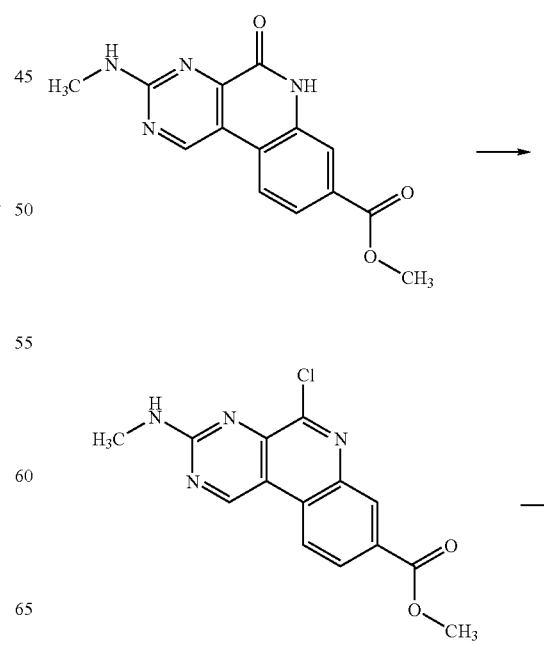

-continued

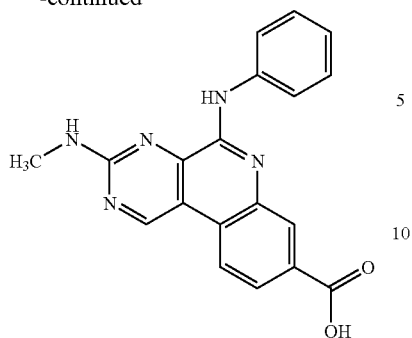

3-(methylamino)-5-(phenylamino)pyrimido[4,5-c]quinoline-8-carboxylic acid was prepared using methods described in process 3 and 4 starting from methyl 3-(methylamino)-5-oxo-5,6-dihydropyrimido[4,5-c]quinoline-8-carboxylate. The final product was purified by flash chromatography and isolated as a yellow solid (0.35 mg). LCMS (ES): >95% pure, m/z 346 [M+1]$^+$.

Process 11

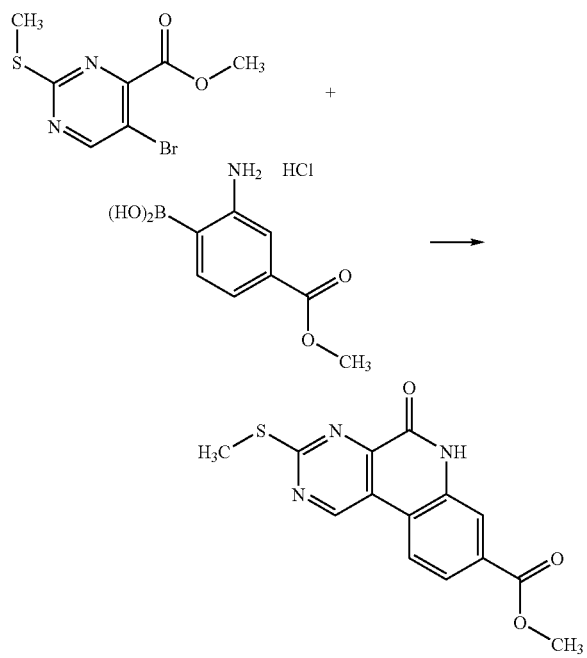

In a microwave vessel, methyl 5-bromo-2-(methylthio)pyrimidine-4-carboxylate (1.0 eq, 274 mg, 1.18 mmol), 2-amino-4-(methoxycarbonyl)phenylboronic acid hydrochloride (1.2 eq, 329 mg, 1.42 mmol), and sodium acetate (3.0 eq, 291 mg, 3.55 mmol) were mixed in anhydrous DMF (2 ml). The mixture was degassed by bubbling nitrogen gas in the solution for 10 min and the reaction heated under microwaves at 120° C. for 30 min. After cooling down the expected material crashed out of NMP. The solid was filtered, suspended in water filtered and dried. The material was triturated in AcOEt and filtered give a yellow solid. The same procedure was repeated 9 times using the same amounts of materials to provide methyl 3-(methylthio)-5-oxo-5,6-dihydropyrimido[4,5-c]quinoline-8-carboxylate (283 mg, 10% yield). LCMS (ES): >95% pure, m/z 302 [M+1]$^+$, $^1$H NMR (DMSO-d$_6$, 400 MHz) δ 2.71 (s, 3H), 3.89 (s, 3H), 7.80 (dd, J=1.6, J=8.4, 1H), 7.97 (d, J=1.6, 1H), 8.59 (d, J=8.8, 1H), 9.98 (s, 1H), 12.34 (s, 1H) ppm.

Process 12

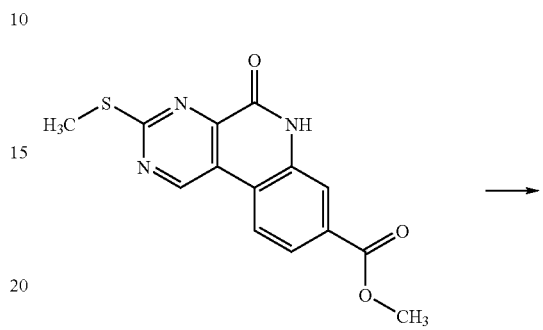

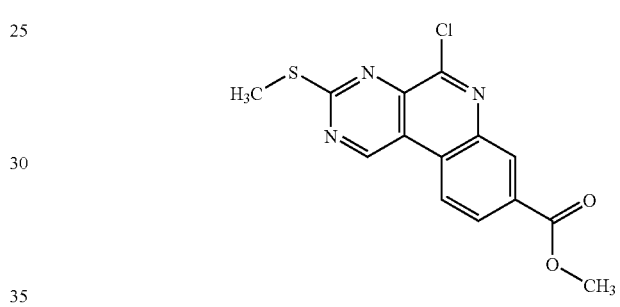

methyl 3-(methylthio)-5-oxo-5,6-dihydropyrimido[4,5-c]quinoline-8-carboxylate (1.0 eq, 279 mg, 0.926 mmol) was suspended in toluene (2 ml). POCl$_3$ (2 ml) and DIEA (0.5 ml) were added and the mixture stirred at 120° C. for 5 hours. The volatiles were removed in vacuo and CH$_2$Cl$_2$ was added. The organic phase was washed with saturated aqueous sodium bicarbonate, washed with water and dried over Na$_2$SO$_4$. The solution was filtered through a pad of celite and the solvents removed in vacuo. The material was triturated in hexanes and AcOEt, filtered and dried to provide methyl 5-chloro-3-(methylthio)pyrimido[4,5-c]quinoline-8-carboxylate as a beige solid (184 mg, 63% yield). LCMS (ES): >95% pure, m/z 320 [M+1]$^+$, 322 [M+3]$^+$.

Process 13

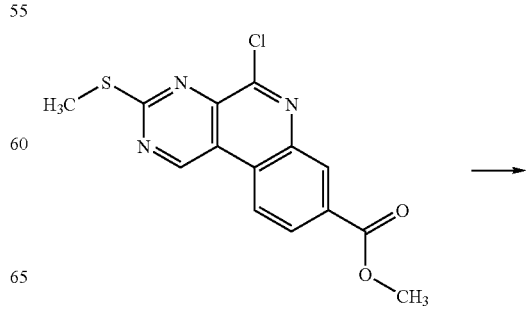

Process 14

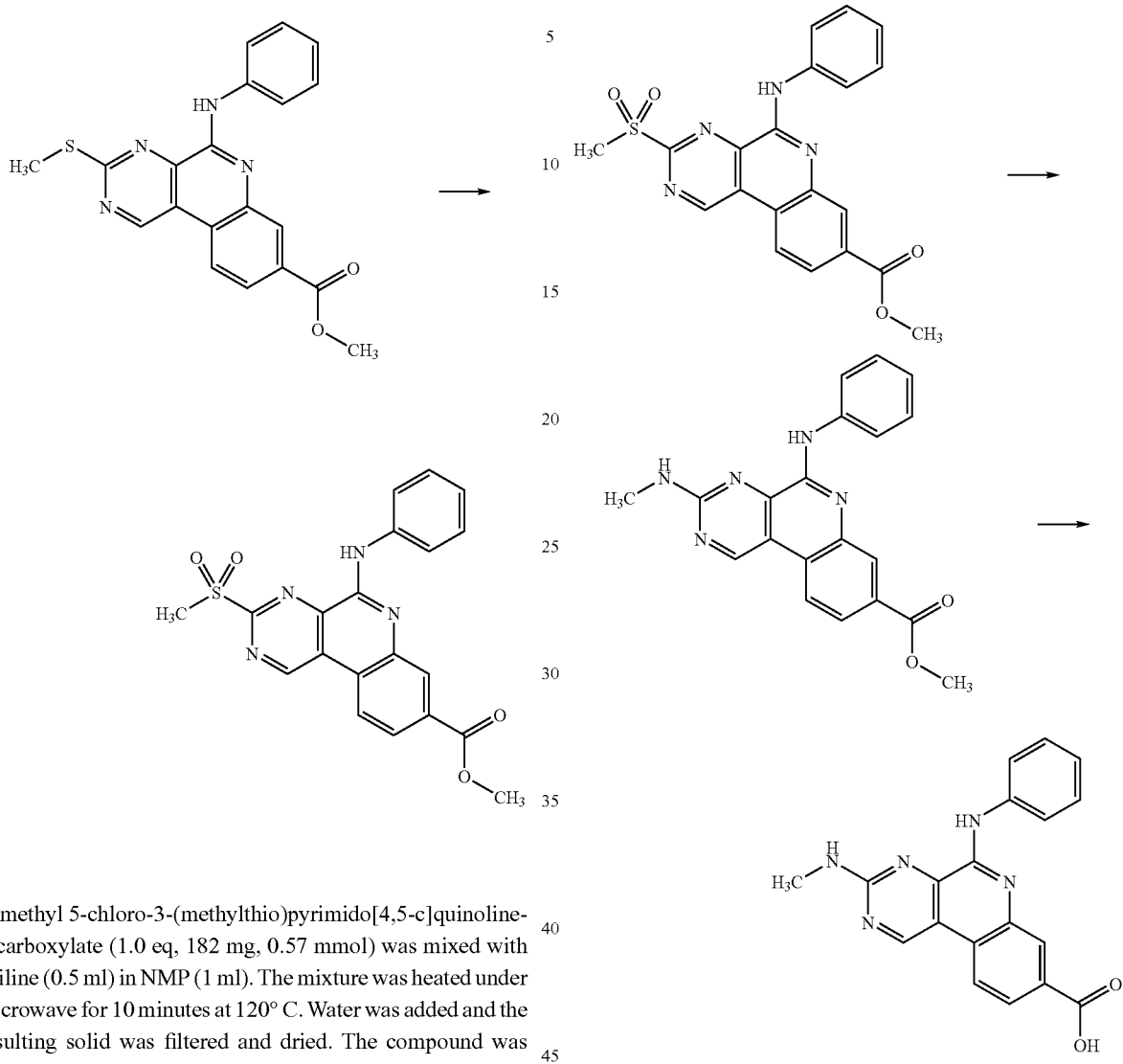

methyl 5-chloro-3-(methylthio)pyrimido[4,5-c]quinoline-8-carboxylate (1.0 eq, 182 mg, 0.57 mmol) was mixed with aniline (0.5 ml) in NMP (1 ml). The mixture was heated under microwave for 10 minutes at 120° C. Water was added and the resulting solid was filtered and dried. The compound was triturated in EtOAc and hexanes and filtered to afford methyl 3-(methylthio)-5-(phenylamino)pyrimido[4,5-c]quinoline-8-carboxylate as a yellow solid. LCMS (ES): >95% pure, m/z 377 [M+1]$^+$. This material was suspended in $CH_2Cl_2$ (4 ml) and meta-chloroperbenzoic acid (77% pure, 2.5 eq, 165 mg, 0.737 mmol) was added in small portions. After one hour, an additional amount (100 mg) of mcpba was added and the mixture stirred for 1.5 hours. After addition of more $CH_2Cl_2$, the organic phase was washed with water (4×), dried over $Na_2SO_4$ and the solution was filtered through a pad of silica gel, eluting with a MeOH/$CH_2Cl_2$ mixture. After evaporation of the solvents, methyl 3-(methylsulfonyl)-5-(phenylamino)pyrimido[4,5-c]quinoline-8-carboxylate was isolated as a yellow solid (166 mg, 72% yield). LCMS (ES): >95% pure, m/z 409 [M+1]$^+$, $^1$H NMR (DMSO-$d_6$, 400 MHz) δ 3.77 (s, 3H), 3.93 (s, 3H), 7.15 (t, J=7.2, 1H), 7.45 (t, J=7.6, 2H), 7.99 (dd, J=2.0, J=8.4, 1H), 8.16 (d, J=7.6, 2H), 8.28 (d, J=2.0, 1H), 8.89 (d, J=8.8, 1H), 9.76 (s, 1H), 10.61 (s, 1H) ppm.

In a closed vial, methyl 3-(methylsulfonyl)-5-(phenylamino)pyrimido[4,5-c]quinoline-8-carboxylate (1.0 eq, 62 mg, 0.152 mmol) was mixed with Methylamine hydrochloride (100 mg), DIEA (260 ul) in DMF (1 ml). The mixture was stirred at 60° C. for 40 min. Addition of water induced precipitation of methyl 3-(methylamino)-5-(phenylamino)pyrimido[4,5-c]quinoline-8-carboxylate which was isolated by filtration. This material was suspended in a 1:1:1 mixture of THF, MeOH and water (4 ml), and vigorously stirred at 60° C. in the presence of LiOH (200 mg) for 1.5 hours. Water aqueous HCl were added and to reach pH=1. The solid was filtered, dried and triturated in AcOEt/hexanes to provide 3-(methylamino)-5-(phenylamino)pyrimido[4,5-c]quinoline-8-carboxylic acid as a yellow solid (40 mg, 74% yield). LCMS (ES): >95% pure, m/z 346 [M+1]$^+$.

The following analogs (table 1C) were prepared using the same method. After purification by preparative HPLC and genevac evaporation the material were isolated as solids.

TABLE 1C
| Structure | Molecular Weight | LCMS (ES) m/z |
|---|---|---|
| 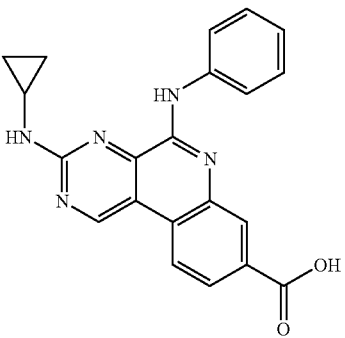 | 371.39 | 372 [M + 1]+ |
| 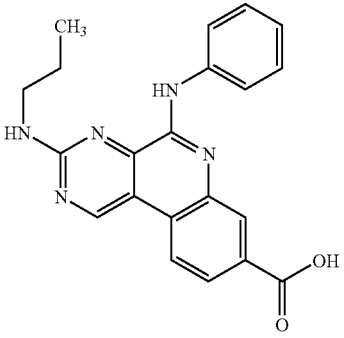 | 373.41 | 374 [M + 1]+ |
| 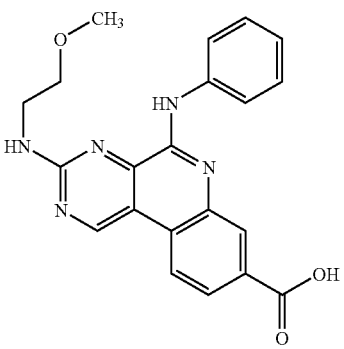 | 389.41 | 390 [M + 1]+ |
| 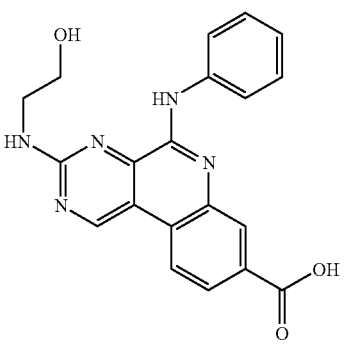 | 375.38 | 376 [M + 1]+ |

TABLE 1C-continued

| Structure | Molecular Weight | LCMS (ES) m/z |
|---|---|---|
| 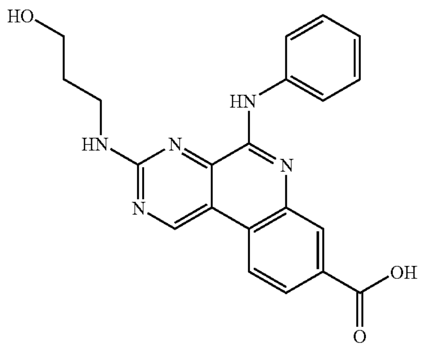 | 389.41 | 390 [M + 1]+ |
| 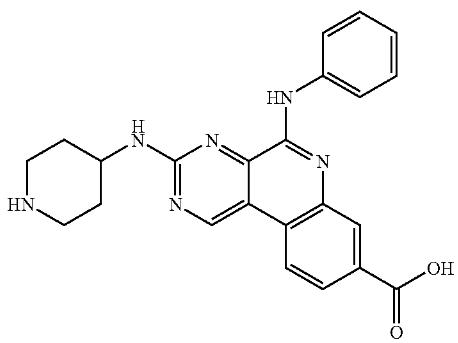 | 414.46 | 415 [M + 1]+ |
| 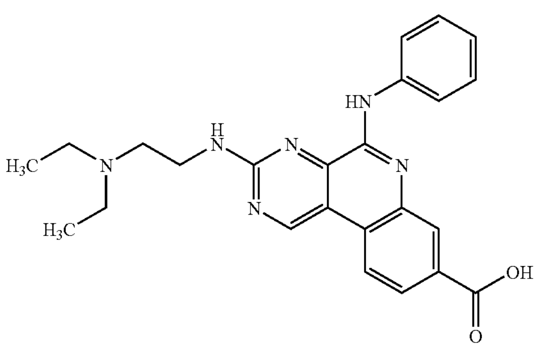 | 430.50 | 431 [M + 1]+ |
| 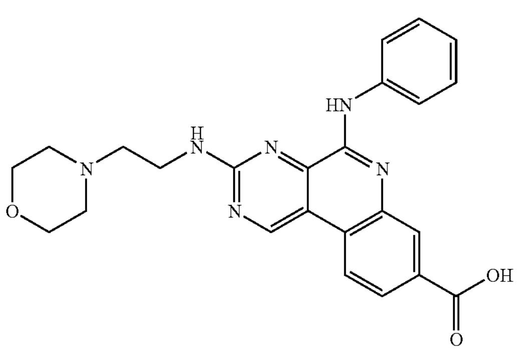 | 444.49 | 445 [M + 1]+ |

TABLE 1C-continued

| Structure | Molecular Weight | LCMS (ES) m/z |
|---|---|---|
| 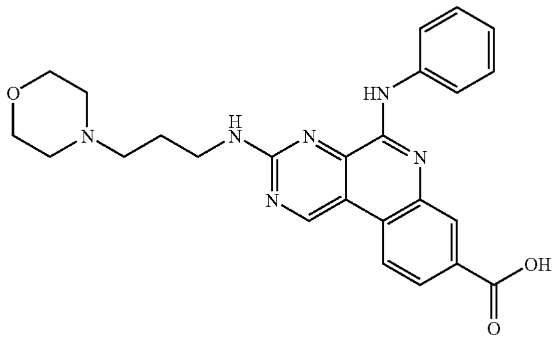 | 458.51 | 459 [M + 1]+ |
| 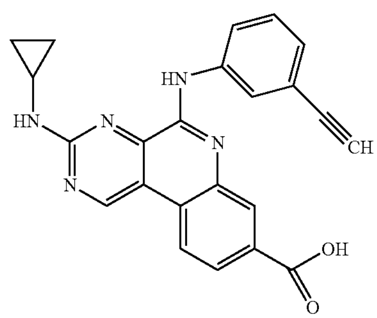 | 395.41 | 396 [M + 1]+ |
| 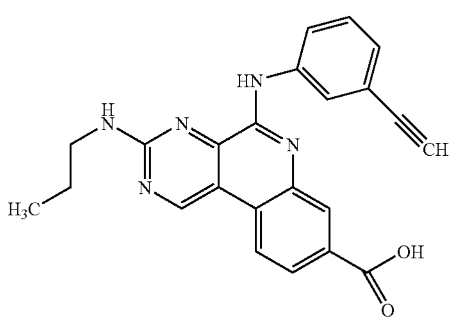 | 397.43 | 398 [M + 1]+ |
| 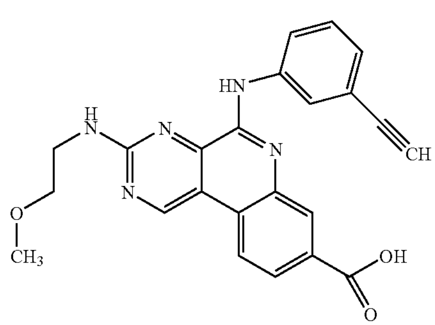 | 413.43 | 414 [M + 1]+ |

TABLE 1C-continued
| Structure | Molecular Weight | LCMS (ES) m/z |
|---|---|---|
| 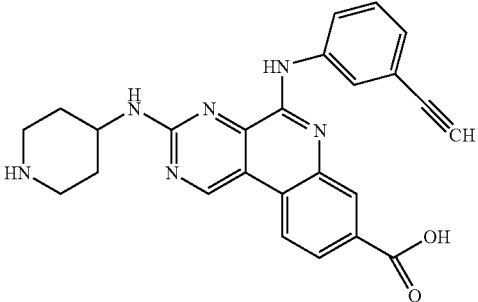 | 438.48 | 439 [M + 1]+ |
| 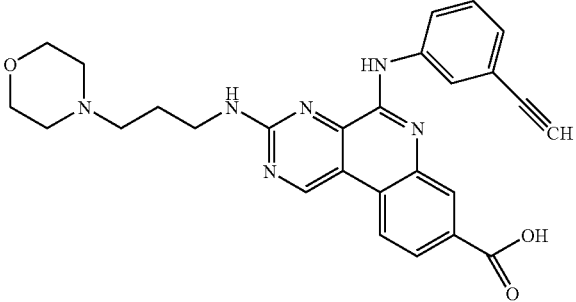 | 482.53 | 483 [M + 1]+ |
| 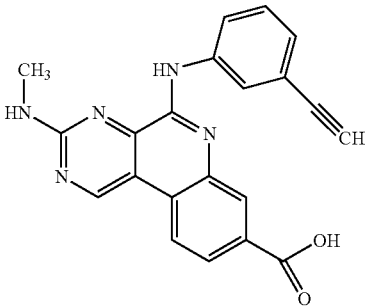 | 369.38 | 370 [M + 1]+ |
| 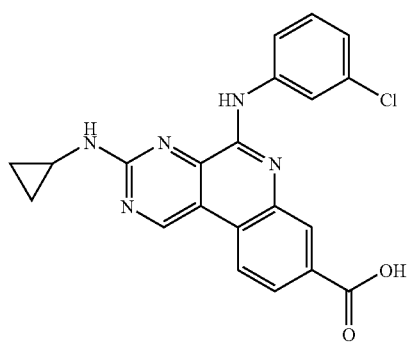 | 405.84 | 406 [M + 1]+ |

TABLE 1C-continued

| Structure | Molecular Weight | LCMS (ES) m/z |
|---|---|---|
| 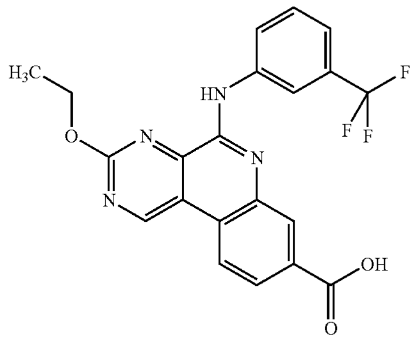 | 428.36 | 429 [M + 1]⁺ |
| 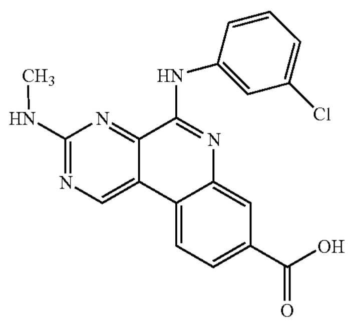 | 379.80 | 380 [M + 1]⁺ |
| 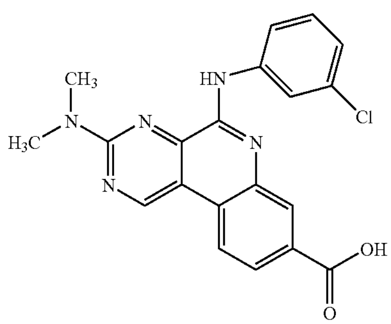 | 393.83 | 394 [M + 1]⁺ |
| 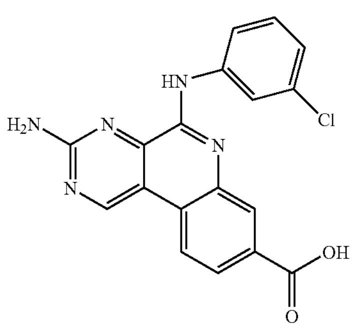 | 365.77 | 366 [M + 1]⁺ |

TABLE 1C-continued

| Structure | Molecular Weight | LCMS (ES) m/z |
|---|---|---|
| 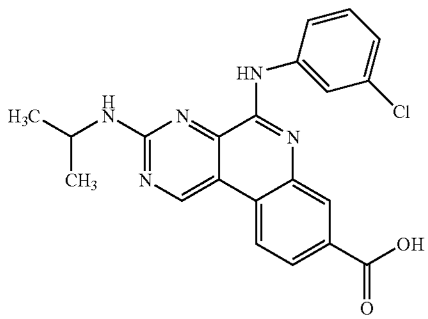 | 407.85 | 408 [M + 1]⁺ |
| 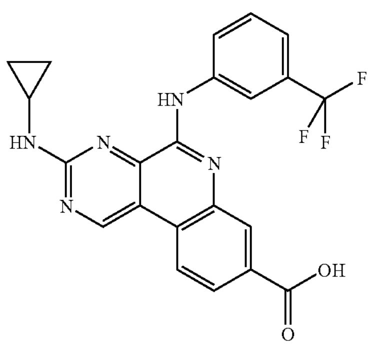 | 439.39 | 440 [M + 1]⁺ |
| 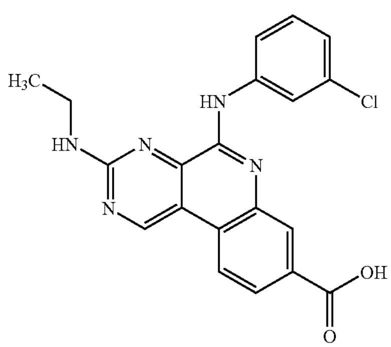 | 393.83 | 397 [M + 1]⁺ |
| 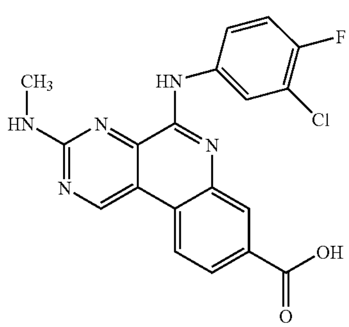 | 397.79 | 398 [M + 1]⁺ |

TABLE 1C-continued
| Structure | Molecular Weight | LCMS (ES) m/z |
|---|---|---|
| 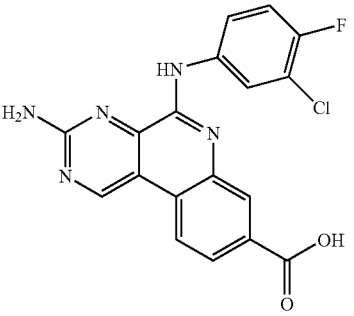 | 383.76 | 384 [M + 1]⁺ |
| 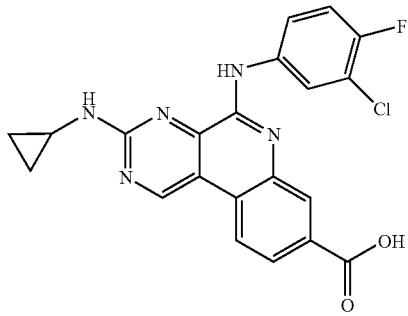 | 423.83 | 424 [M + 1]⁺ |
| 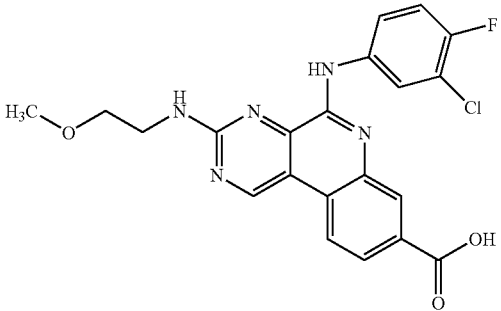 | 441.8 | 442 [M + 1]⁺ |
| 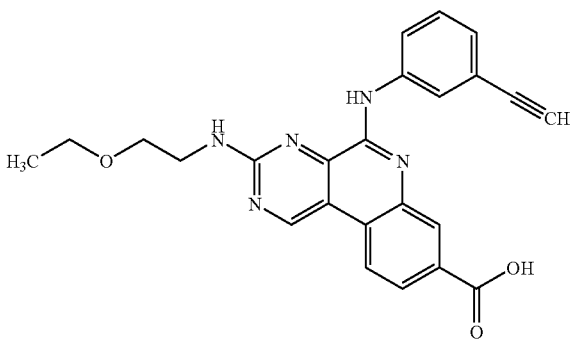 | 427.46 | 428 [M + 1]⁺ |

TABLE 1C-continued

| Structure | Molecular Weight | LCMS (ES) m/z |
|---|---|---|
| 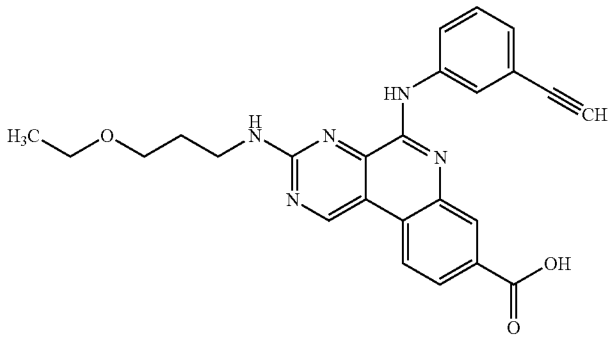 | 441.48 | 442 [M + 1]+ |
| 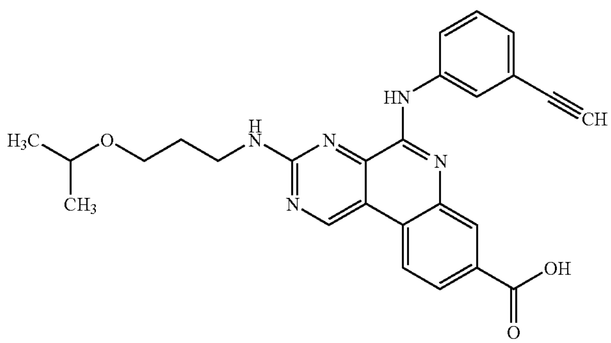 | 455.51 | 456 [M + 1]+ |
| 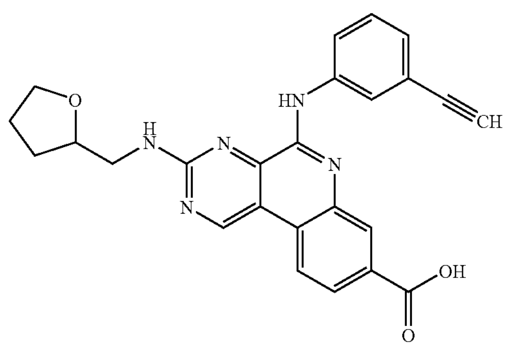 | 439.47 | 440 [M + 1]+ |
| 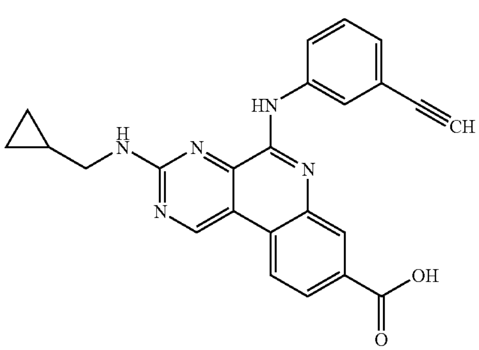 | 409.44 | 410 [M + 1]+ |

TABLE 1C-continued

| Structure | Molecular Weight | LCMS (ES) m/z |
|---|---|---|
| 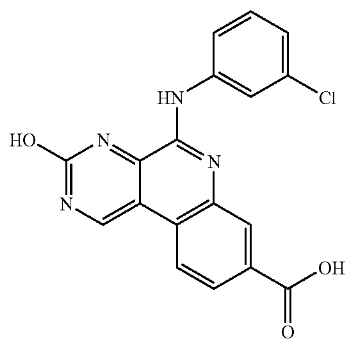 | 366.76 | 367 [M + 1]+ |
| 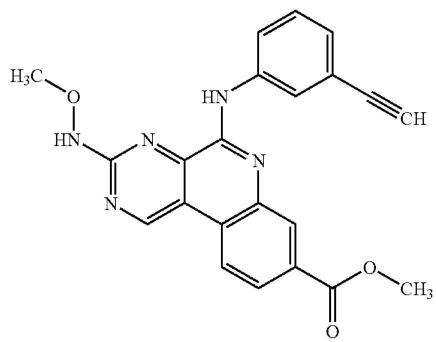 | 399.40 | 400 [M + 1]+ |
| 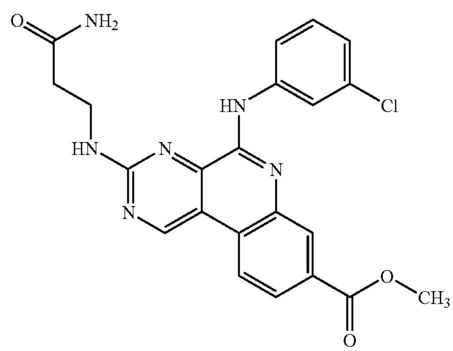 | 450.88 | 451 [M + 1]+ |
| 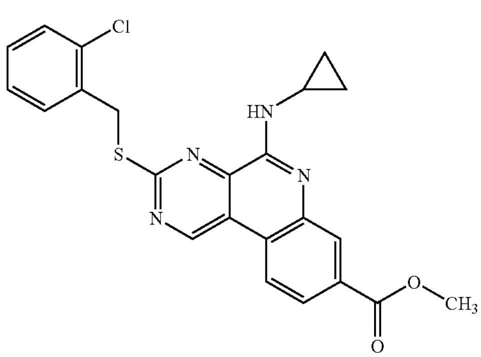 | 450.94 | 451 [M + 1]+ |

TABLE 1C-continued

| Structure | Molecular Weight | LCMS (ES) m/z |
|---|---|---|
| 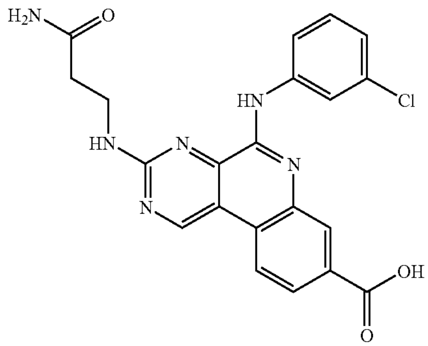 | 436.85 | 437 [M + 1]⁺ |
| 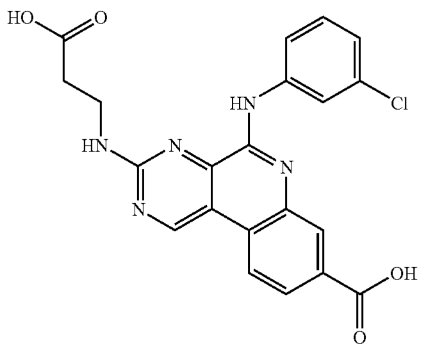 | 437.8 | 438 [M + 1]⁺ |
| 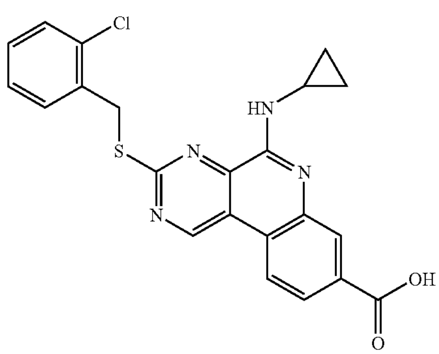 | 436.91 | 437 [M + 1]⁺ |
| 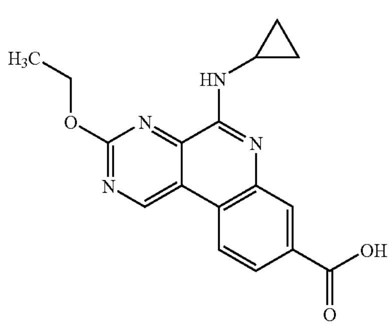 | 324.33 | 325 [M + 1]⁺ |

TABLE 1C-continued

| Structure | Molecular Weight | LCMS (ES) m/z |
|---|---|---|
| 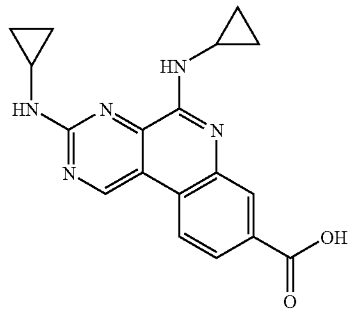 | 335.36 | 336 [M + 1]+ |
| 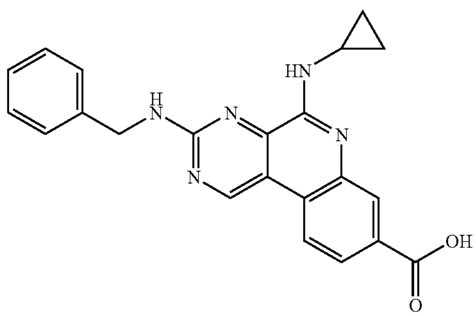 | 385.42 | 386 [M + 1]+ |
| 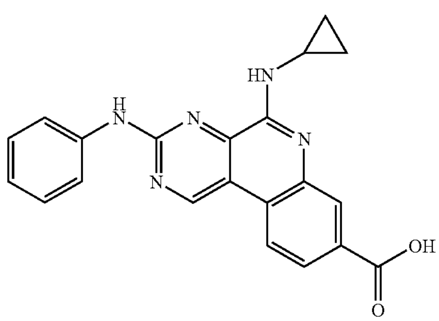 | 371.39 | 372 [M + 1]+ |
| 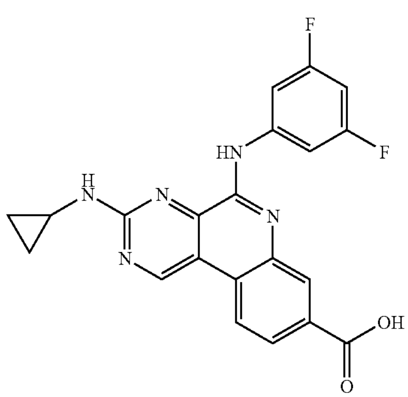 | 407.37 | 408 [M + 1]+ |

TABLE 1C-continued

| Structure | Molecular Weight | LCMS (ES) m/z |
|---|---|---|
| 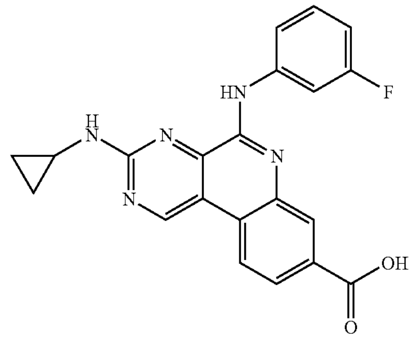 | 389.38 | 390 [M + 1]⁺ |
| 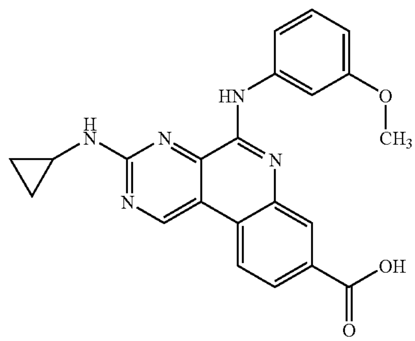 | 401.42 | 402 [M + 1]⁺ |
| 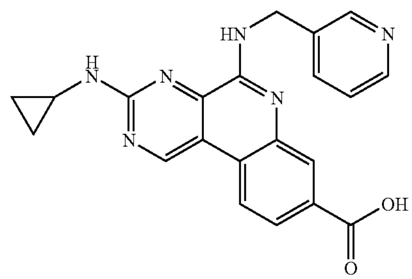 | 386.41 | 387 [M + 1]⁺ |
| 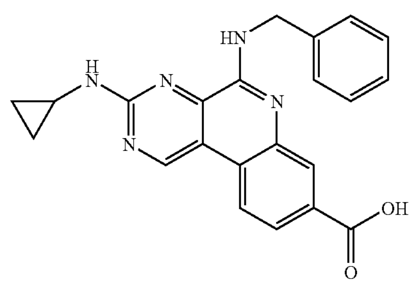 | 385.42 | 386 [M + 1]⁺ |
| 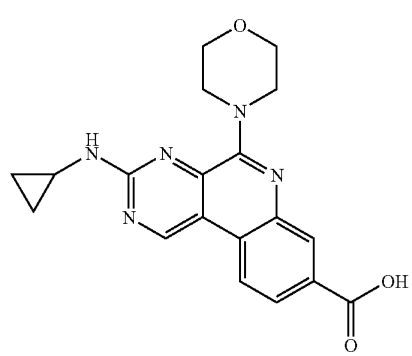 | 365.39 | 366 [M + 1]⁺ |

TABLE 1C-continued

| Structure | Molecular Weight | LCMS (ES) m/z |
|---|---|---|
| 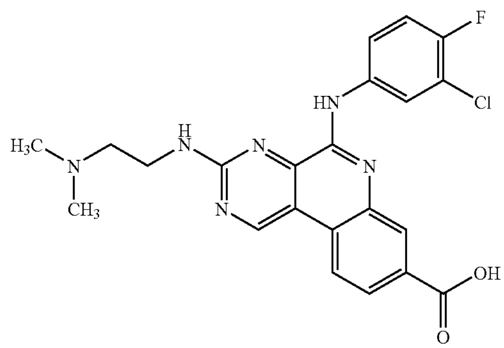 | 454.88 | 455 [M + 1]+ |
| 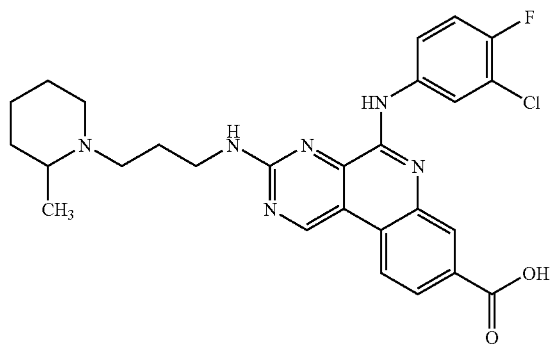 | 523.00 | 524 [M + 1]+ |
| 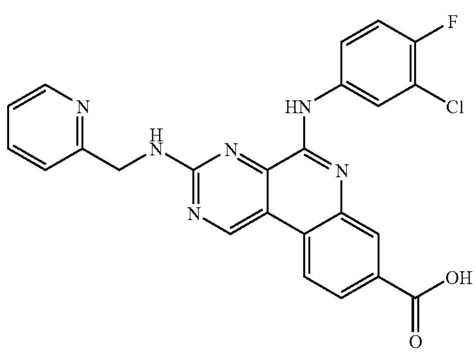 | 474.87 | 475 [M + 1]+ |
| 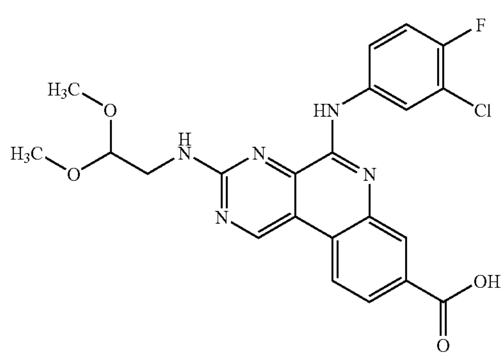 | 471.87 | 472 [M + 1]+ |

TABLE 1C-continued

| Structure | Molecular Weight | LCMS (ES) m/z |
|---|---|---|
| 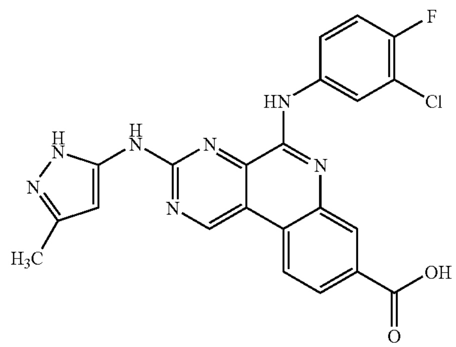 | 463.85 | 464 [M + 1]⁺ |
| | 474.87 | 475 [M + 1]⁺ |
| | 474.87 | 475 [M + 1]⁺ |
| 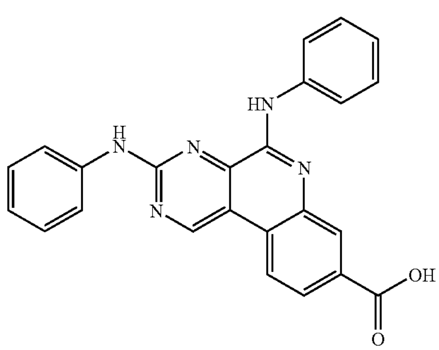 | 407.42 | 408 [M + 1]⁺ |

TABLE 1C-continued

| Structure | Molecular Weight | LCMS (ES) m/z |
|---|---|---|
| 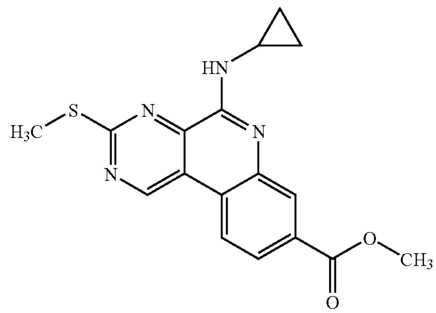 | 340.40 | 341 [M + 1]+ |
| 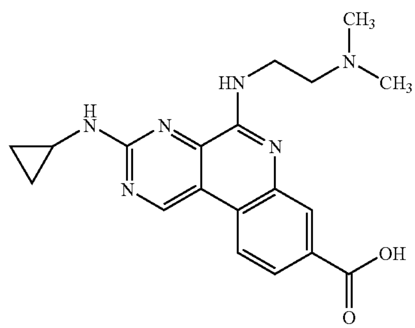 | 366.42 | 367 [M + 1]+ |
| 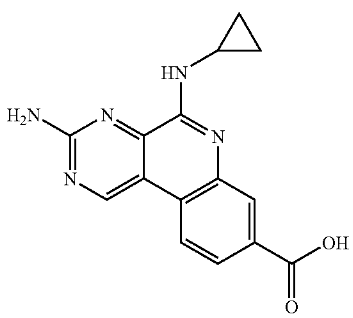 | 295.30 | 296 [M + 1]+ |
| 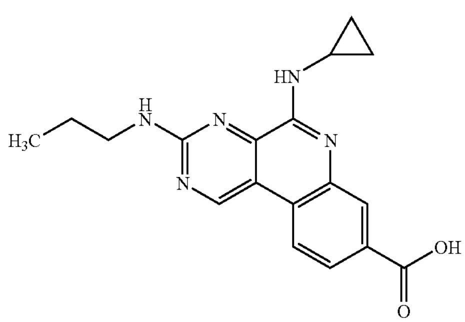 | 337.38 | 338 [M + 1]+ |
| 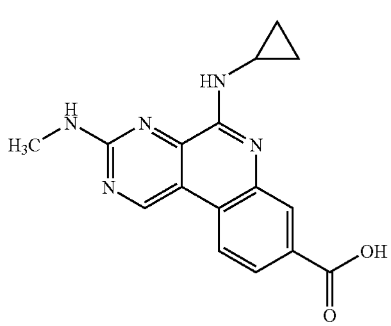 | 309.32 | 310 [M + 1]+ |

TABLE 1C-continued

| Structure | Molecular Weight | LCMS (ES) m/z |
|---|---|---|
| 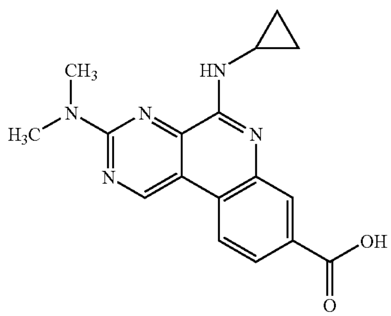 | 323.35 | 324 [M + 1]⁺ |
| 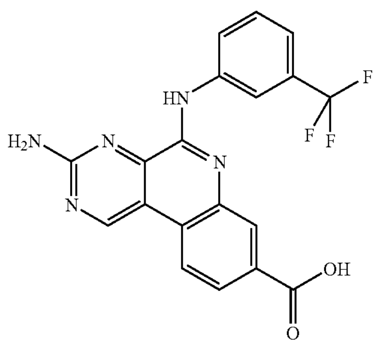 | 399.33 | 400 [M + 1]⁺ |
| 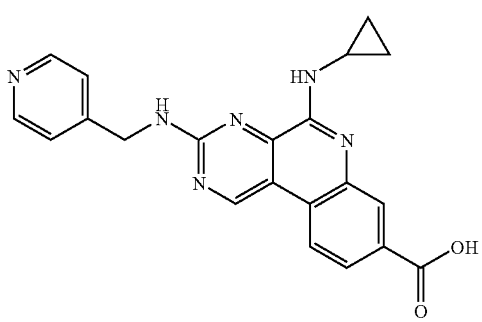 | 386.41 | 387 [M + 1]⁺ |
| 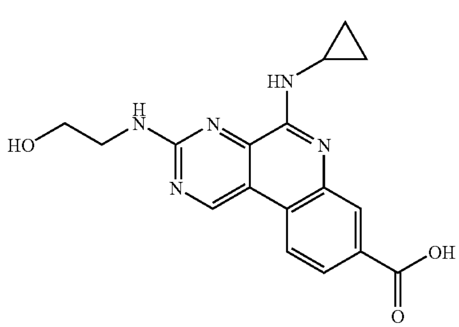 | 339.35 | 340 [M + 1]⁺ |

TABLE 1C-continued

| Structure | Molecular Weight | LCMS (ES) m/z |
|---|---|---|
| | 386.41 | 387 [M + 1]+ |
| 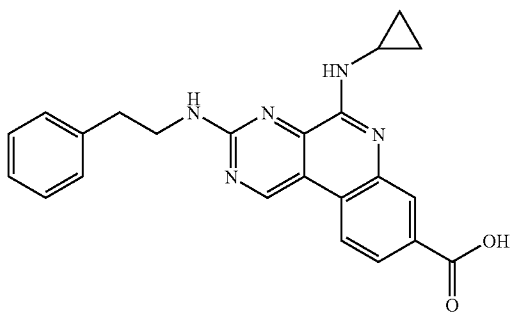 | 399.45 | 400 [M + 1]+ |
| 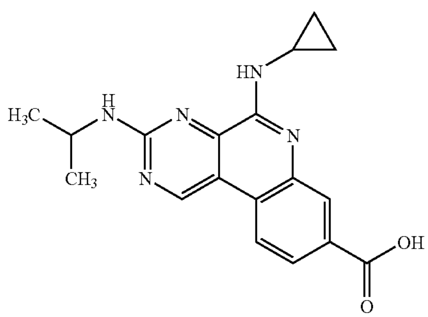 | 337.38 | 338 [M + 1]+ |
| 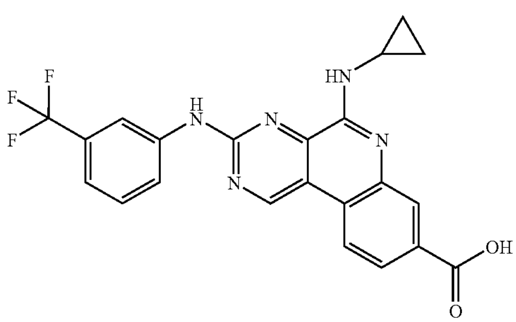 | 439.39 | 440 [M + 1]+ |
| | 386.41 | 387 [M + 1]+ |

TABLE 1C-continued

| Structure | Molecular Weight | LCMS (ES) m/z |
|---|---|---|
| 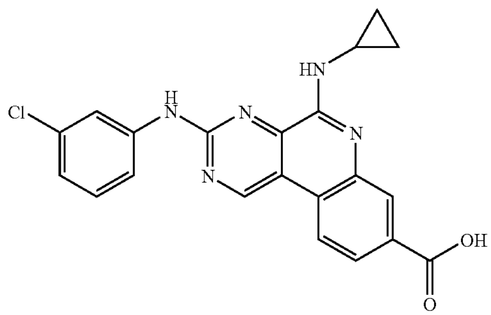 | 405.84 | 406 [M + 1]⁺ |
| 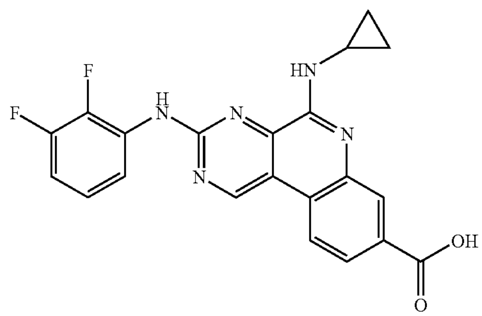 | 407.37 | 408 [M + 1]⁺ |
| 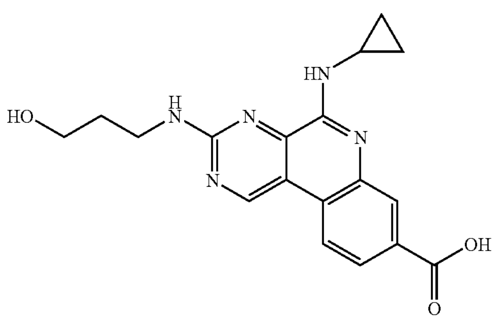 | 353.38 | 354 [M + 1]⁺ |
| 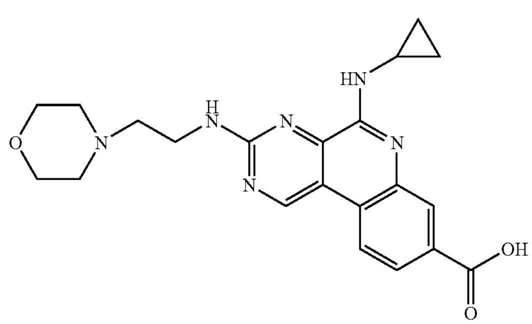 | 408.45 | 409 [M + 1]⁺ |

TABLE 1C-continued

| Structure | Molecular Weight | LCMS (ES) m/z |
|---|---|---|
| 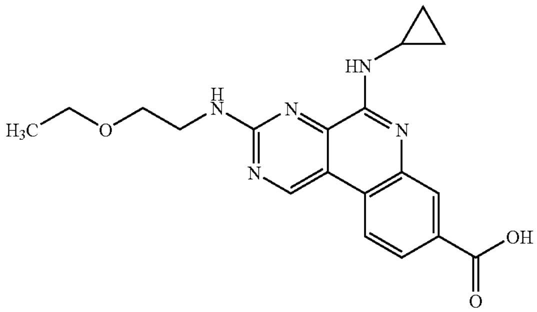 | 367.40 | 368 [M + 1]+ |
| 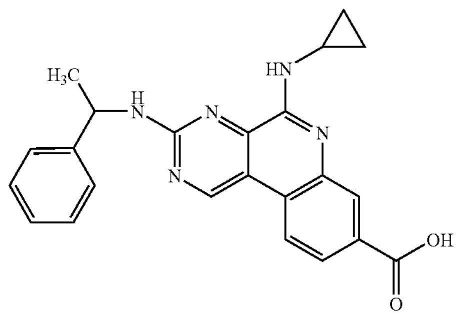 | 399.45 | 400 [M + 1]+ |
| 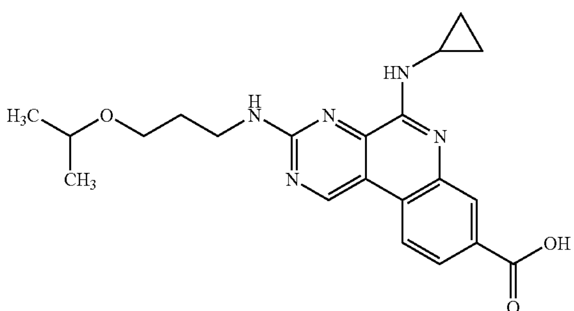 | 395.45 | 396 [M + 1]+ |
| 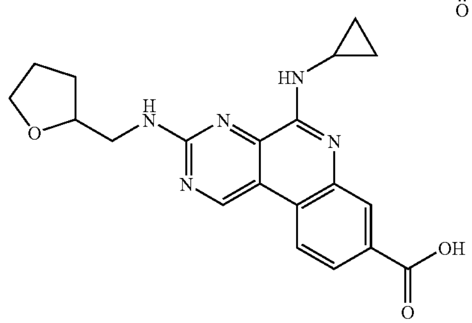 | 379.41 | 380 [M + 1]+ |
| 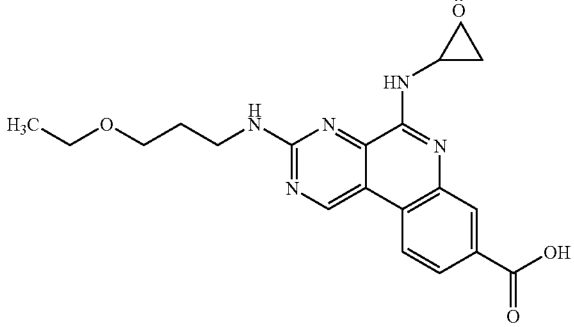 | 381.43 | 382 [M + 1]+ |

Process 15

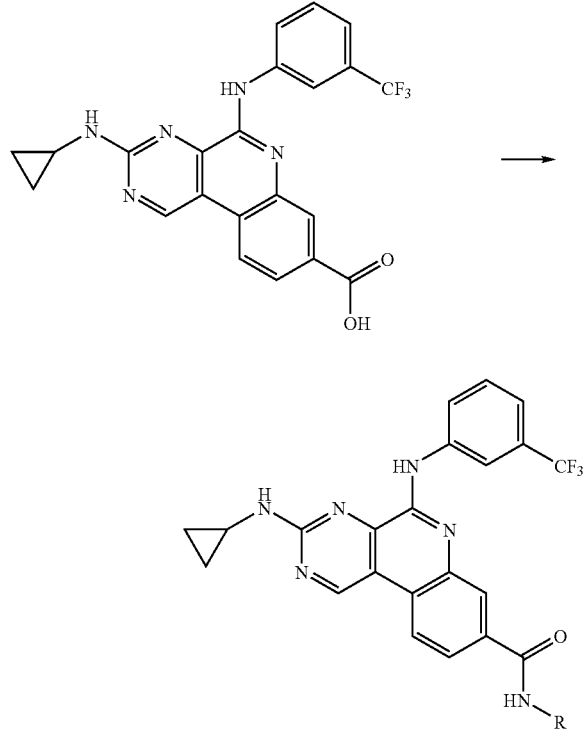

3-(cyclopropylamino)-5-(3-(trifluoromethyl)phenylamino)pyrimido[4,5-c]quinoline-8-carboxylic acid (20 mg) was mixed with 2 equivalent of an appropriate primary amine in NMP (0.5 ml). HOBt (14 mg), triethylamine (13 uL) and EDCI (18 mg) were added and the mixture was stirred at 70° C. for 1 hour. Water and HCl were added and the material was isolated by filtration. This protocol was used to prepare compounds shown in table 1D

TABLE 1D

| Structure | MW | LCMS (ES) m/z |
|---|---|---|
| | 438.41 | 439 [M + 1]+ |
| 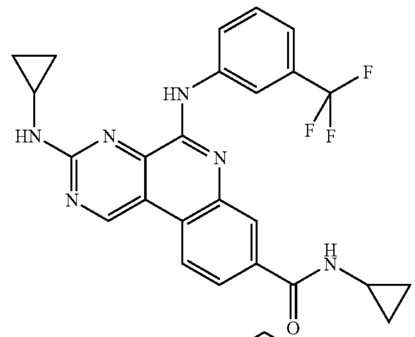 | 478.47 | 479 [M + 1]+ |
| 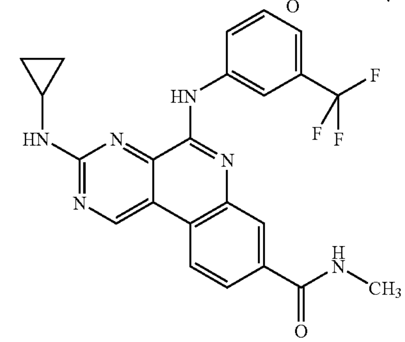 | 452.43 | 453 [M + 1]+ |

Process 16

3-(cyclopropylamino)-5-(3-(trifluoromethyl)phenylamino)pyrimido[4,5-c]quinoline-8-carboxylic acid (100 mg, 0.23 mmol) was reacted with diphenylphosphoryl azide (50 ul, 0.23 mmol) and triethylamine (34 ul, 0.23 mmol) in isopropanol (8 ml). The mixture was stirred at 95° C. for 3 hours. The solvents were removed and the residue partitioned between water and ethylacetate. The organic layer was dried over Na$_2$SO$_4$ and the solvents removed in vacuo. Addition of CH$_2$Cl$_2$ induced formation of a solid that was filtered off and dried to afford isopropyl 3-(cyclopropylamino)-5-(3-(trifluoromethyl)phenylamino)pyrimido[4,5-c]quinolin-8-ylcarbamate. LCMS (ES): 90% pure, m/z 497 [M+1]+.

Example 2

Processes for Synthesizing Compounds of Formulae V, VI, VII and VIII

Process 1

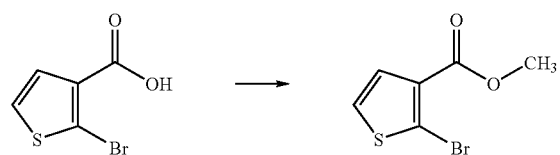

2-bromo-3-thiophene carboxylic acid (1.0 eq, 12.56 g, 60.66 mmol) was suspended in $CH_2Cl_2$ (200 ml). Oxalyl chloride (1.1 eq, 5.9 ml, 67.16 mmol) and 5 drops of DMF were added, inducing formation of gas. The mixture was stirred overnight at room temperature and the volatiles were removed in vacuo. The resulting solid was suspended in dry methanol (150 ml) and the mixture heated to ebullition. Evaporation of the solvents afforded methyl 2-bromo-3-thiophene carboxylate (13.16 g, 98% yield) as a crude brown oil. LCMS (ES): 99% pure, m/z not detected; $^1$H NMR ($CDCl_3$, 400 MHz) δ 3.88 (s, 3H), 7.23 (d, J=5.6, 1H), 7.56 (d, J=5.6, 1H) ppm.

Process 2

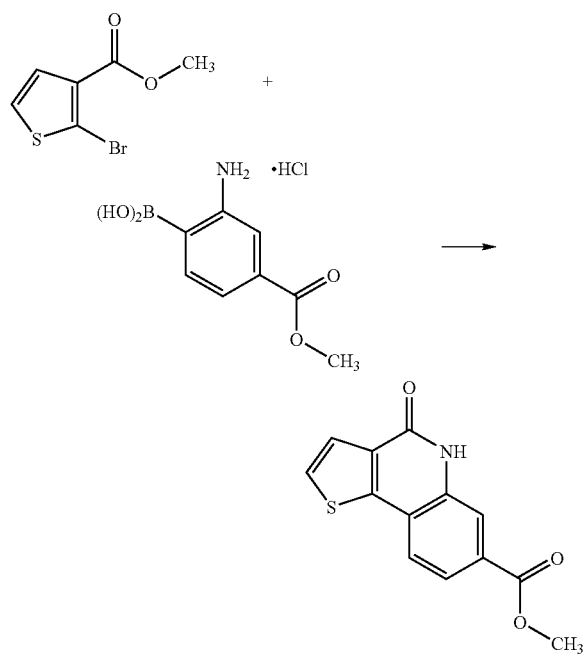

In a microwave vessel, methyl 2-bromo-3-thiophene carboxylate (1.0 eq, 260 mg, 1.18 mmol), 2-amino-4-(methoxycarbonyl)phenylboronic acid hydrochloride (1.1 eq, 300 mg, 1.30 mmol), sodium acetate (3.0 eq, 292 mg, 3.56 mmol) and $PdCl_2(dppf)$ (0.05 eq, 31 mg, 0.059 mmol) were mixed together in anhydrous DMF (2 ml). The mixture was heated in a microwave oven at 120° C. for 10 nm. Water was added and the solid filtered and dried. The material was suspended in $CH_2Cl_2$, filtered and dried to afford methyl 4-oxo-4,5-dihydrothieno[3,2-c]quinoline-7-carboxylate as a yellow solid (152 mg, 50% yield). LCMS (ES): 95% pure, m/z 260 [M+1]+; $^1$H NMR ($CDCl_3$, 400 MHz) δ 3.99 (s, 3H), 7.54 (d, J=5.2, 1H), 7.79 (d, J=4.8, 1H), 7.86 (d, J=8.4, 1H), 7.91 (dd, J=8.4, J=1.6, 1H), 8.03 (d, J=1.2, 1H) ppm.

Process 3

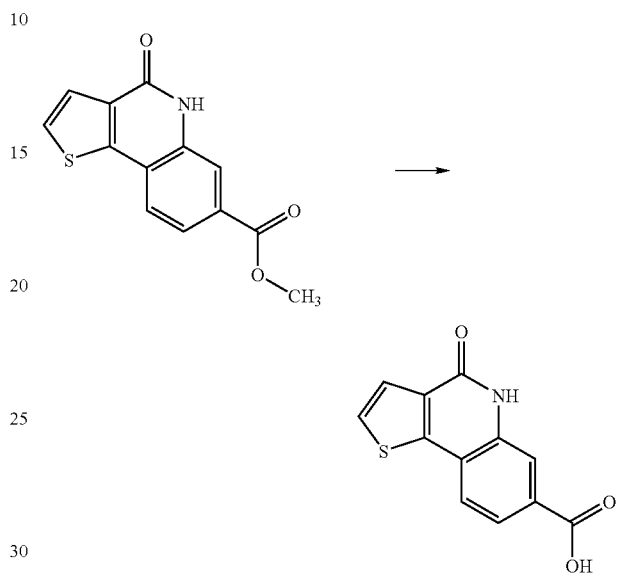

Methyl 4-oxo-4,5-dihydrothieno[3,2-c]quinoline-7-carboxylate (1.0 eq, 618 mg, 2.38 mmol) was suspended in 10 ml of a mixture of MeOH, THF, and water (1:1:1, v:v:v). LiOH (2.0 eq, 114 mg, 4.76 mmol) was added and the mixture was stirred at room temperature for 2 hours. An additional amount of LiOH (114 mg) was added and the mixture was stirred for an hour. LiOH (50 mg) was added and the mixture stirred for an additional 2 hours. Water was added and the solution filtered through a pad of celite. The pad of celite was thoroughly washed with aqueous 1 N NaOH. The solution was acidified with 6 N aqueous HCl to induce precipitation of the expected material. Filtration and drying afforded 4-oxo-4,5-dihydrothieno[3,2-c]quinoline-7-carboxylic acid as a yellow solid (562 mg, 96% yield). LCMS (ES): 95% pure, m/z 246 [M+1]+; $^1$H NMR (DMSO-$d_6$, 400 MHz) δ 7.61 (d, J=5.2, 1H), 7.73 (dd, J=1.6, J=8.0, 1H), 7.88 (d, J=5.6, 1H), 7.92 (d, J=8.4, 1H), 8.02 (d, J=1.6, 1H), 11.92 (s, 1H), 13.21 (br. s, 1H) ppm.

Process 4

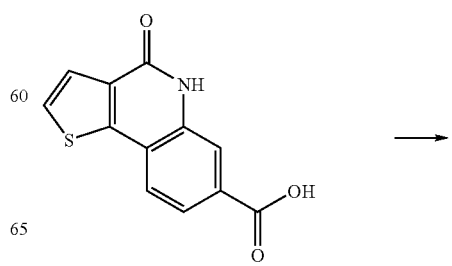

-continued

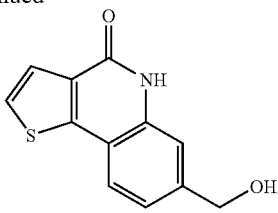

4-oxo-4,5-dihydrothieno[3,2-c]quinoline-7-carboxylic acid (1.0 eq, 38 mg, 0.155 mmol) was suspended in dioxane (1 ml). LiAlH$_4$ (7.0 eq, 40 mg, 1.05 mmol) was added and the mixture stirred at 100° C. for 45 nm. Water was added, then MeOH and CH$_2$Cl$_2$. The solid salts were filtered off and washed with MeOH and CH$_2$Cl$_2$. After evaporation of the volatiles in vacuo, the material was dissolved in a mixture of NMP, MeOH and water and was purified by preparative HPLC. Genevac evaporation afforded 7-(hydroxymethyl)thieno[3,2-c]quinolin-4(5H)-one as an off-white solid (12 mg, 34%). LCMS (ES): 95% pure, m/z 232 [M+1]$^+$; $^1$H NMR (DMSO-d$_6$, 400 MHz) δ 4.56 (s, 2H), 7.15 (d, J=7.6, 1H), 7.39 (br s, 1H), 7.55 (d, J=5.2, 1H), 7.73 (d, J=5.2, 1H), 7.76 (d, J=8.0, 1H), 11.73 (s, 1H) ppm.

Process 5

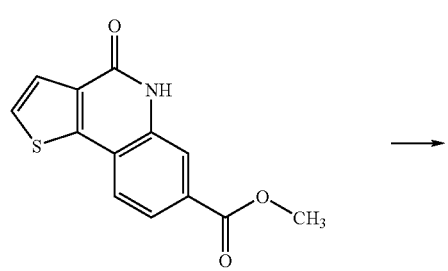

Methyl 4-oxo-4,5-dihydrothieno[3,2-c]quinoline-7-carboxylate (1.0 eq, 17 mg, 0.066 mmol) was suspended in a mixture of chloroform (0.3 ml) and acetic acid (0.1 ml). NBS was added (9.5 eq, 112 mg, 0.63 mmol) and the mixture stirred at 70° C. for 16 hours. Water and aqueous ammonia was added and the material was extracted with CH$_2$Cl$_2$ (2×). The combined extracts were dried over Na$_2$SO$_4$ and the solvent removed in vacuo to provide methyl 2-bromo-4-oxo-4,5-dihydrothieno[3,2-c]quinoline-7-carboxylate (17 mg, 76%). LCMS (ES): >85% pure, m/z 338 [M]$^+$, 340 [M+2]$^+$; $^1$H NMR (CDCl$_3$/CD$_3$OD, 9:1, 400 MHz) δ 3.99 (s, 3H), 7.30 (m, 1H), 7.69 (d, J=8.4, 1H), 7.45 (m, 1H), 7.88 (br d, J=8, 1H), 8.05 (br s, 1H) ppm.

Process 6

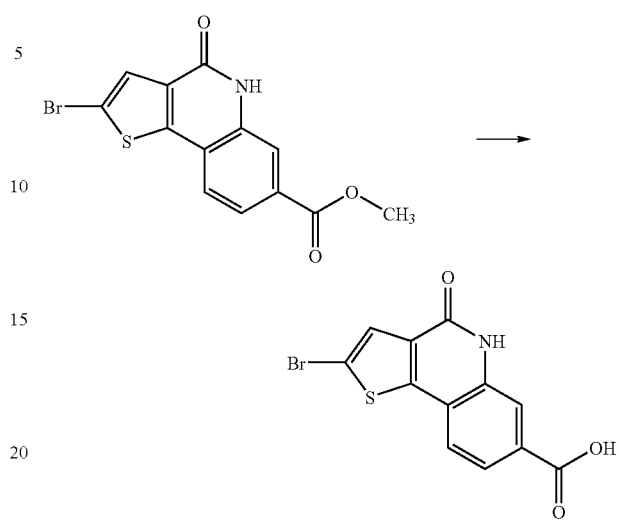

Methyl 2-bromo-4-oxo-4,5-dihydrothieno[3,2-c]quinoline-7-carboxylate (1.0 eq, 17 mg, 0.050 mmol) was suspended in a 1:1:1 mixture of MeOH/THF/water (0.6 ml). LiOH (39 mg) was added and the mixture stirred at room temperature for one hour. Water and 6N HCl was added and the resulting precipitate was filtered. The material was purified by preparative HPLC. Genevac evaporation provided 2-bromo-4-oxo-4,5-dihydrothieno[3,2-c]quinoline-7-carboxylic acid as a solid (2.1 mg, 13% yield). LCMS (ES): >95% pure, m/z 324 [M]$^+$, 326[M+2]$^+$; $^1$H NMR (DMSO-d$_6$, 400 MHz) δ 7.75 (s, 1H), 7.75 (dd, J=1.6, J=8.0, 1H), 7.90 (d, J=8.4, 1H), 8.03 (d, J=1.6, 1H), 12.06 (s, 1H) ppm.

Process 7

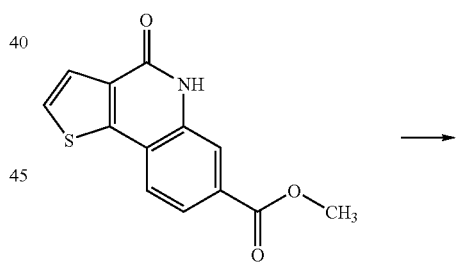

In a closed vessel, Methyl 4-oxo-4,5-dihydrothieno[3,2-c]quinoline-7-carboxylate (44 mg, 0.170 mmol) was suspended in concentrated aqueous ammonia (1 ml). The mixture was stirred at 100° C. overnight. Aqueous 1N NaOH was added and the mixture stirred at room temperature for 2 hours. The solid was filtered and dried to provide 4-oxo-4,5-dihydrothieno[3,2-c]quinoline-7-carboxamide as a brown solid (13 mg, 32% yield). LCMS (ES): 95% pure, m/z 245 [M+1]$^+$.

Process 8

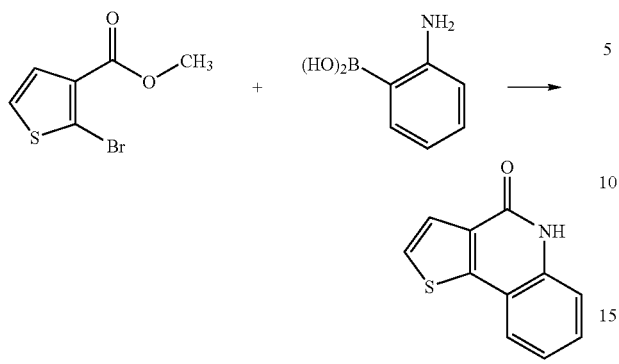

In a microwave vessel, methyl 2-bromo-3-thiophene carboxylate (1.0 eq, 64 mg, 0.29 mmol), 2-amino phenyl boronic acid (1.2 eq, 48 mg, 0.35 mmol), sodium acetate (3.0 eq, 71 mg, 0.86 mmol) and PdCl$_2$(dppf) (0.1 eq, 15 mg, 0.028 mmol) were mixed together in anhydrous DMF (0.2 ml). The mixture was heated in a microwave oven at 120° C. for 5 nm. The material was purified by preparative HPLC. Acetonitrile was evaporated, and the compound was extracted with CH$_2$Cl$_2$ (3×). The combined extracts were washed with water, dried over Na$_2$SO$_4$, and the solvents removed in vacuo. Recrystallization in EtOH provided thieno[3,2-c]quinolin-4(5H)-one as a tan crystalline solid (7 mg, 12% yield). LCMS (ES): 95% pure, m/z 202 [M+1]$^+$; $^1$H NMR (CDCl$_3$/CD$_3$OD, 9:1, 400 MHz) δ 7.28 (m, 1H), 7.33 (m, 1H), 7.43-7.50 (m, 2H), 7.74 (d, J=4.4, 1H), 7.82 (d, J=7.6, 1H) ppm Process 9

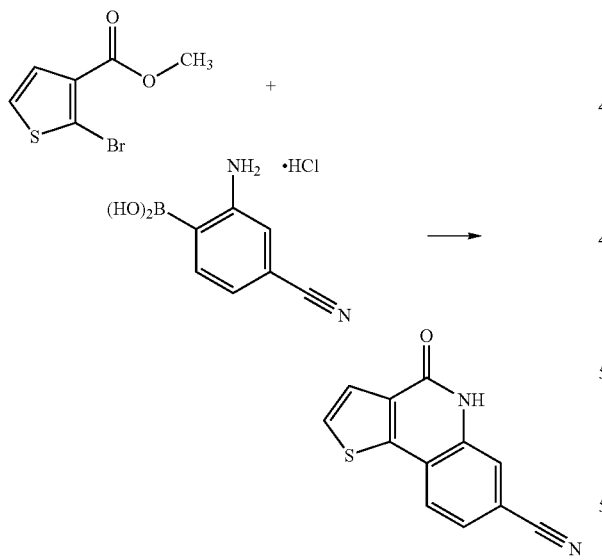

In a microwave vessel, methyl 2-bromo-3-thiophene carboxylate (1.0 eq, 250 mg, 1.13 mmol), 2-amino-3-cyanophenyl boronic acid HCl (1.1 eq, 250 mg, 1.24 mmol), sodium acetate (3.0 eq, 278 mg, 3.39 mmol) and PdCl$_2$(dppf) (0.007 eq, 4.3 mg, 0.0082 mmol) were mixed together in anhydrous DMF (2.5 ml). The mixture was heated in a microwave oven at 120° C. for 10 nm. Water was added and the material extracted with CH$_2$Cl$_2$. The organic extracts were washed with brine, dried over Na$_2$SO$_4$ and the solvents removed in vacuo. The resulting solid was sonicated in AcOEt, filtered and dried to afford 4-oxo-4,5-dihydrothieno[3,2-c]quinoline-7-carbonitrile as a beige solid (121 mg, 48% yield). LCMS (ES): 95% pure, m/z 227 [M+1]$^+$.

Process 10

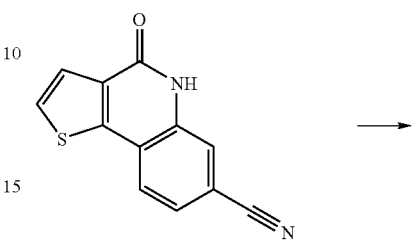

4-oxo-4,5-dihydrothieno[3,2-c]quinoline-7-carbonitrile (1.0 eq, 20 mg, 0.088 mmol) was dissolved in anhydrous DMF (0.15 ml). Sodium azide (4.0 eq, 23 mg, 0.354 mmol) and ammonium chloride (4.0 eq, 19 mg, 0.354 mmol) were added and the mixture stirred at 120° C. overnight. The reaction mixture was cooled down and water was added. Addition of aqueous 6N HCl induced formation of a precipitate. After filtration and drying in vacuo, 7-(1H-tetrazol-5-yl)thieno[3,2-c]quinolin-4(5H)-one was isolated as a greenish solid (18 mg, 76% yield).). LCMS (ES): 95% pure, m/z 270 [M+1]$^+$, 242 [M+1-N$_2$]$^+$; $^1$H NMR (DMSO-d$_6$, 400 MHz) δ 7.64 (d, J=5.2, 1H), 7.86 (dd, J=1.6, J=8.4, 1H), 7.89 (d, J=5.2, 1H), 8.09 (d, J=8.0, 1H), 8.16 (d, J=1.6, 1H), 12.03 (s, 1H) ppm.

Process 11

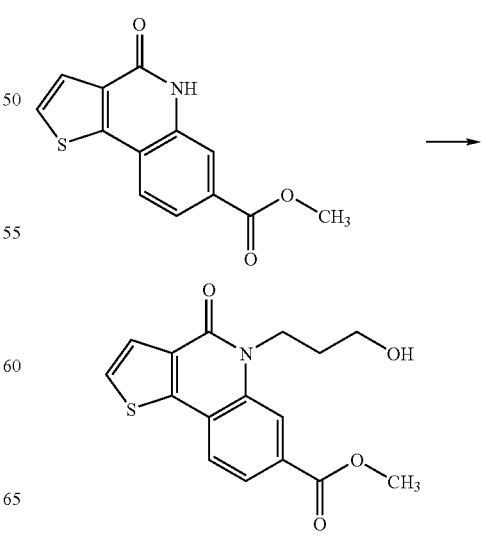

-continued

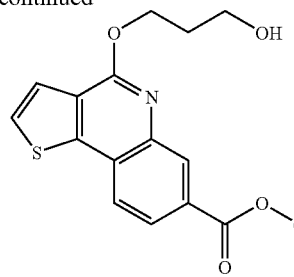

Methyl 4-oxo-4,5-dihydrothieno[3,2-c]quinoline-7-carboxylate (1.0 eq, 18 mg, 0.069 mmol) was dissolved in anhydrous DMF (0.4 ml). K$_2$CO$_3$ (7.0 eq, 70 mg, 0.506 mmol) and 3-bromo-1-propanol (16 eq, 100 ul, 1.144 mmol) were added and the mixture stirred at 100° C. for 1.5 hour. After adding water, the mixture was extracted with CH$_2$Cl$_2$. The combined extracts were dried over Na$_2$SO$_4$ and the solvents removed in vacuo. Compounds 8 and 9 were separated by preparative TLC on silica gel (eluted twice with 30% AcOEt in hexanes, then once with 50% AcOEt in hexanes). The less polar compound is methyl 4-(3-hydroxypropoxy)thieno[3,2-c]quinoline-7-carboxylate (12 mg). LCMS (ES): 80% pure, m/z 318 [M+1]$^+$. The more polar compound is methyl 5-(3-hydroxypropyl)-4-oxo-4,5-dihydrothieno[3,2-c]quinoline-7-carboxylate (19 mg). LCMS (ES): 80% pure, m/z 318 [M+1]$^+$. The two compounds were used for the following step without any further purification.

Process 12

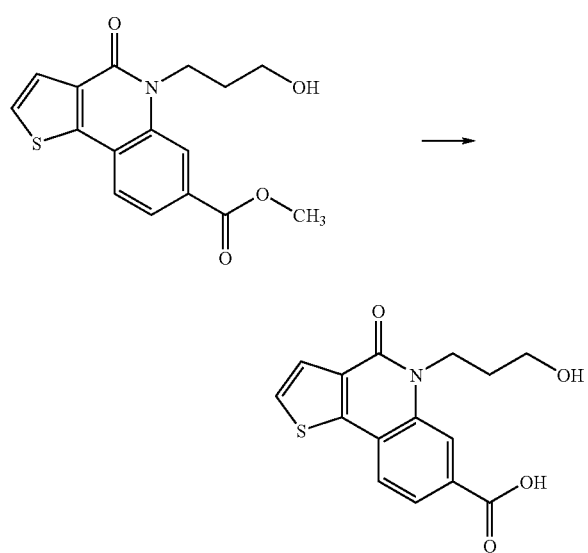

Methyl 5-(3-hydroxypropyl)-4-oxo-4,5-dihydrothieno[3,2-c]quinoline-7-carboxylate (1.0 eq, 19 mg, 0.060 mmol) was dissolved in a 1:1:1 mixture of THF, MeOH and water (0.5 ml). LiOH (40 mg) was added and the resulting mixture stirred at room temperature for 1.5 hours. Water, MeOH and HCl were added and the solution purified by preparative HPLC. Genevac evaporation afforded 5-(3-hydroxypropyl)-4-oxo-4,5-dihydrothieno[3,2-c]quinoline-7-carboxylic acid as a white solid (4 mg, 22% yield). LCMS (ES): 95% pure, m/z 304 [M+1]$^+$. $^1$H NMR (CDCl$_3$/CD$_3$OD, 9:1, 400 MHz) δ 2.08 (qi, J=6.0, 2H), 3.61 (t, J=5.2, 2H), 4.62 (t, J=6.0, 2H), 7.53 (d, J=5.2, 1H), 7.77 (d, J=5.2, 1H), 7.93 (d, J=8.0, 1H), 7.99 (dd, J=1.2, J=8.4, 1H), 8.26 (d, J=0.8, 1H) ppm.

Process 13

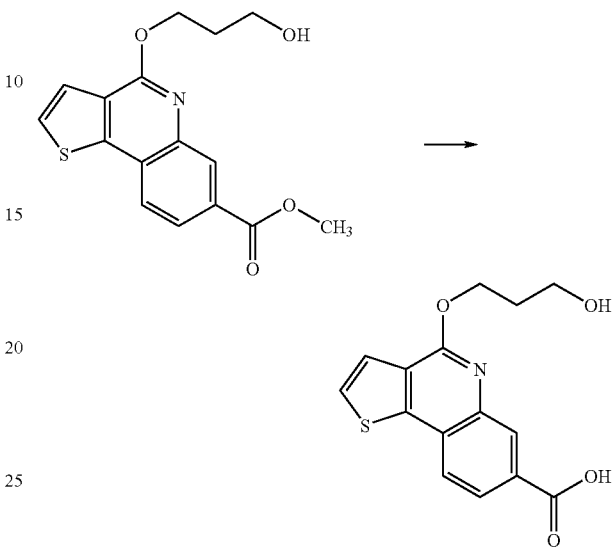

Methyl 4-(3-hydroxypropoxy)thieno[3,2-c]quinoline-7-carboxylate was prepared according to the procedure used in process 12. 4-(3-hydroxypropoxy)thieno[3,2-c]quinoline-7-carboxylic acid was isolated as a solid (3 mg, 26% yield). LCMS (ES): 95% pure, m/z 304 [M+1]$^+$.

Process 14

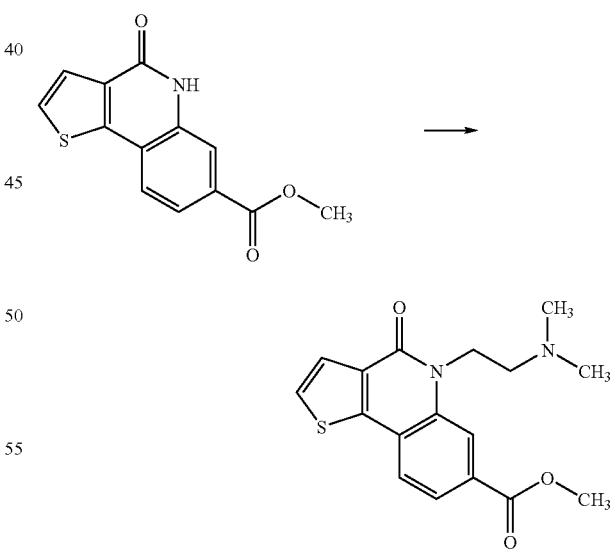

Methyl 5-(2-(dimethylamino)ethyl)-4-oxo-4,5-dihydrothieno[3,2-c]quinoline-7-carboxylate was prepared according to the procedure used in process 11 starting from methyl 4-oxo-4,5-dihydrothieno[3,2-c]quinoline-7-carboxylate and 2-dimethylaminoethyl chloride. LCMS (ES): 95% pure, m/z 331 [M+1]$^+$.

Process 15

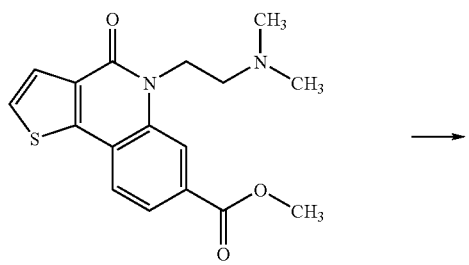

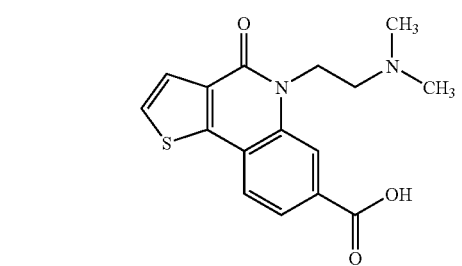

5-(2-(dimethylamino)ethyl)-4-oxo-4,5-dihydrothieno[3,2-c]quinoline-7-carboxylic acid was prepared according to the procedure used in process 12. Preparative HPLC and genevac evaporation provided the material as a TFA salt. LCMS (ES): 95% pure, m/z 317 [M+1]+, 1H NMR (CDCl3/CD3OD, 9:1, 400 MHz) δ 3.06 (s, 6H), 3.50 (t, J=7.6, 2H), 4.88 (t, J=7.6, 2H), 7.53 (d, J=5.2, 1H), 7.73 (d, J=5.6, 1H), 7.89 (d, J=8.4, 1H), 7.95 (br d, J=8.4, 1H), 8.2 (br s, 1H) ppm.

Process 16

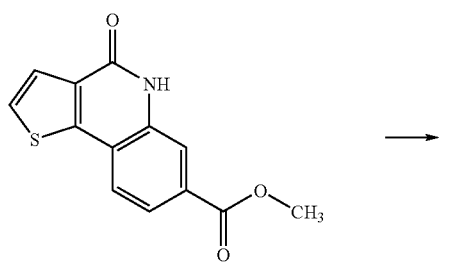

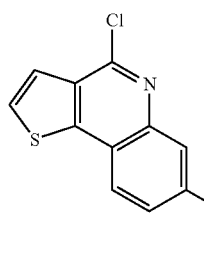

Methyl 4-oxo-4,5-dihydrothieno[3,2-c]quinoline-7-carboxylate (1.0 eq, 1.50 g, 5.79 mmol) was suspended in dry toluene (15 ml). POCl3 (1.2 eq, 0.64 mmol, 6.99 mmol) and DIEA (0.8 eq, 0.81 mmol, 4.65 mmol) were added and the mixture vigorously stirred at 120° C. for 3 hours under nitrogen atmosphere. The mixture was hydrolyzed by addition of ice and water. The compound was extracted with CH2Cl2 (4×). The combined extracts were dried over Na2SO4 and the black solution filtered through a pad of celite. After evaporation of the volatiles in vacuo, the resulting solid was triturated in a mixture of AcOEt and hexanes. Filtration and drying provided methyl 4-chlorothieno[3,2-c]quinoline-7-carboxylate as a yellow fluffy solid (1.14 g, 71% yield). LCMS (ES): 95% pure, m/z 278 [M+1]+, 1H NMR (CDCl3, 400 MHz) δ 4.01 (s, 3H), 7.72 (d, J=4.8, 1H), 7.74 (d, J=5.2, 1H), 8.14 (d, J=8.4, 1H), 8.25 (d, J=8.4, 1H), 8.85 (d, J=1.6, 1H) ppm.

Process 17

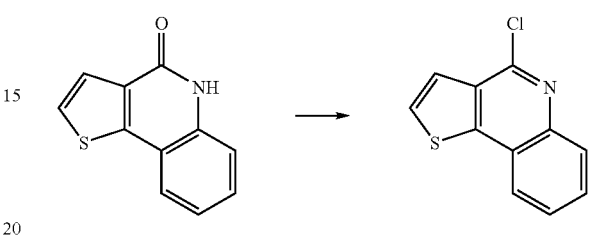

4-chlorothieno[3,2-c]quinoline was prepared according to the procedure used in process 16, starting from thieno[3,2-c]quinolin-4(5H)-one. 4-chlorothieno[3,2-c]quinoline was isolated as a solid (71 mg, 93% yield). LCMS (ES): 95% pure, m/z 220 [M+1]+, 223 [M+3]+.

Process 18

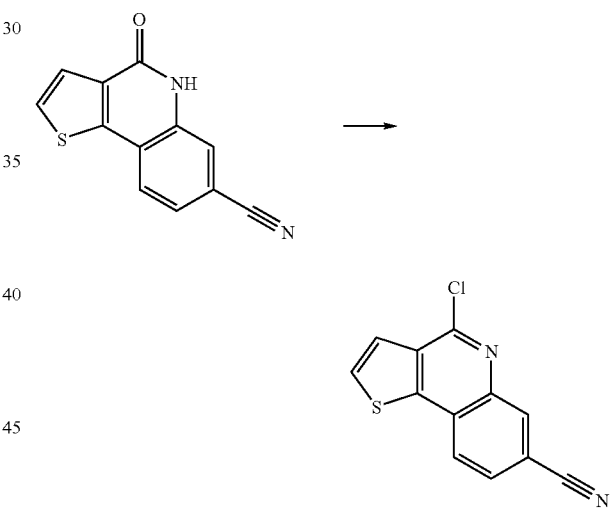

4-chlorothieno[3,2-c]quinoline-7-carbonitrile was prepared according to the procedure used in process 16. 4-chlorothieno[3,2-c]quinoline-7-carbonitrile was isolated as a yellow fluffy solid (833 mg, 77% yield). LCMS (ES): 95% pure, m/z 245 [M+1]+, 247 [M+3]+.

Process 19

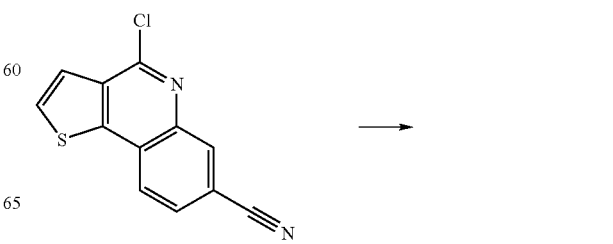

Process 21

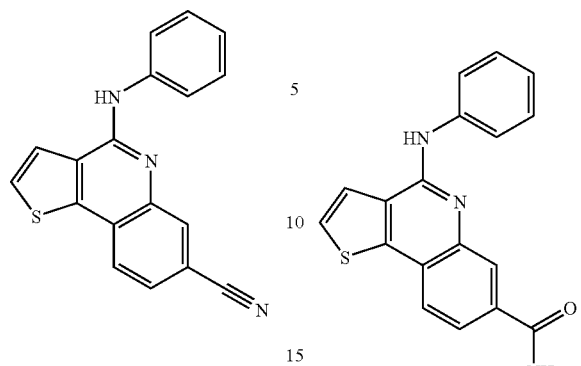

4-chlorothieno[3,2-c]quinoline-7-carbonitrile (1.0 eq, 23 mg, 0.094 mmol), aniline (0.1 ml) and NMP (0.1 ml) were mixed in a vial. The mixture was heated in a microwave oven at 120° C. for 10 nm. Water was added and the resulting solid 4-(phenylamino)thieno[3,2-c]quinoline-7-carbonitrile was filtered and dried. LCMS (ES): 95% pure, m/z 302 [M+1]⁺.

Process 20

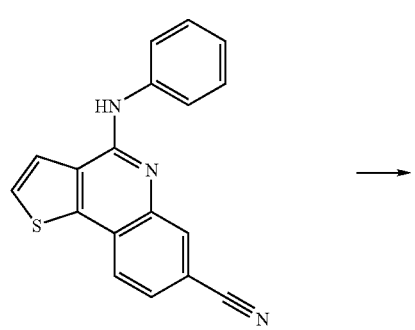

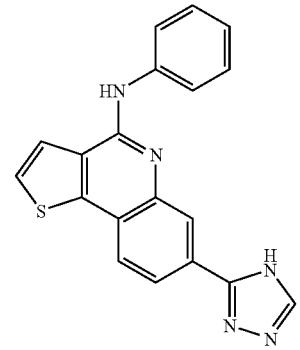

4-(phenylamino)thieno[3,2-c]quinoline-7-carbonitrile (34 mg, 0.113 mmol) was dissolved in NMP (0.3 ml). 30% aqueous $H_2O_2$ (0.2 ml) was added followed by addition of 6N NaOH (50 ul). The mixture was stirred at 50° C. for 2 hours. An extra amount of 30% aqueous $H_2O_2$ (0.3 ml) and 6N NaOH (100 ul) were added and a 70% conversion was achieved after 30 min. Water was added and the solid filtered and dried. The material was further reacted under the same conditions in order to achieve a complete transformation. 4-(phenylamino)thieno[3,2-c]quinoline-7-carboxamide was isolated as solid (30 mg, 83% yield). LCMS (ES): 95% pure, m/z 320 [M+1]⁺.

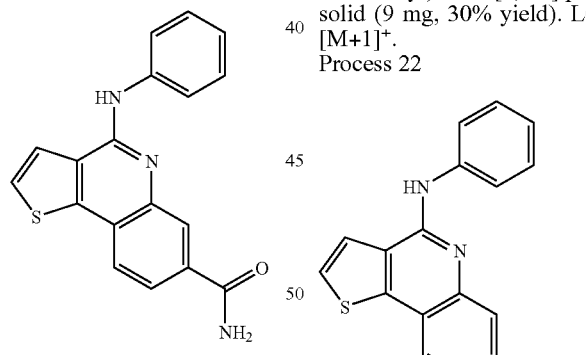

4-(phenylamino)thieno[3,2-c]quinoline-7-carboxamide (28 mg, 0.088 mmol) was suspended in N,N-dimethylformamide dimethylacetal and the mixture stirred at 80° C. under nitrogen atmosphere for 2 hours. The volatiles were removed in vacuo. Acetic acid (0.5 ml) and anhydrous hydrazine (0.1 ml) and the mixture stirred at 115° C. for 1 hour. Water and brine were added and the solid filtered. The material was purified by preparative HPLC. Genevac evaporation and trituration in AcOEt/hexanes afforded N-phenyl-7-(4H-1,2,4-triazol-3-yl)thieno[3,2-c]quinolin-4-amine as an off-white solid (9 mg, 30% yield). LCMS (ES): 94% pure, m/z 344 [M+1]⁺.

Process 22

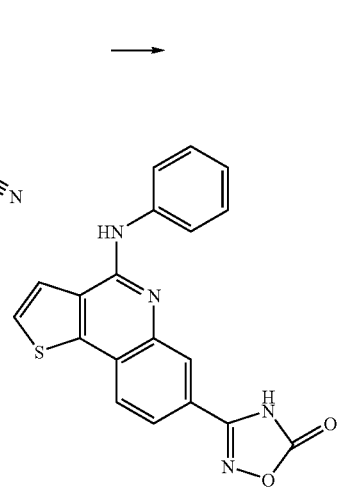

4-(phenylamino)thieno[3,2-c]quinoline-7-carbonitrile (1.0 eq, 27 mg, 0.0897 mmol) and hydroxylamine hydrochloride (10 eq, 62 mg, 0.892 mmol) and $K_2CO_3$ (10 eq, 124 mg, 0.896 mmol) were mixed in EtOH (0.5 ml) and the mixture heated under microwave at 100° C. for 10 min. The solid were removed by filtration and washed with EtOH. The solvents were removed in vacuo. The crude material was suspended in chloroform (0.5 ml). Ethyl chloroformate (20 ul) and triethylamine (20 ul) were added and the mixture stirred at room temperature for 10 min. $CH_2Cl_2$ was added and the organic phase was washed with brine. The organic phase was dried over $Na_2SO_4$ and the solvent removed. The crude material was suspended in NMP (1 ml) and heated under microwave at 160° C. for 10 min. The material was purified by preparative HPLC. Genevac evaporation afforded 3-(4-(phenylamino)thieno[3,2-c]quinolin-7-yl)-1,2,4-oxadiazol-5(4H)-one as an off-white solid (7 mg, 22% yield). LCMS (ES): 95% pure, m/z 361 [M+1]⁺.

Process 23

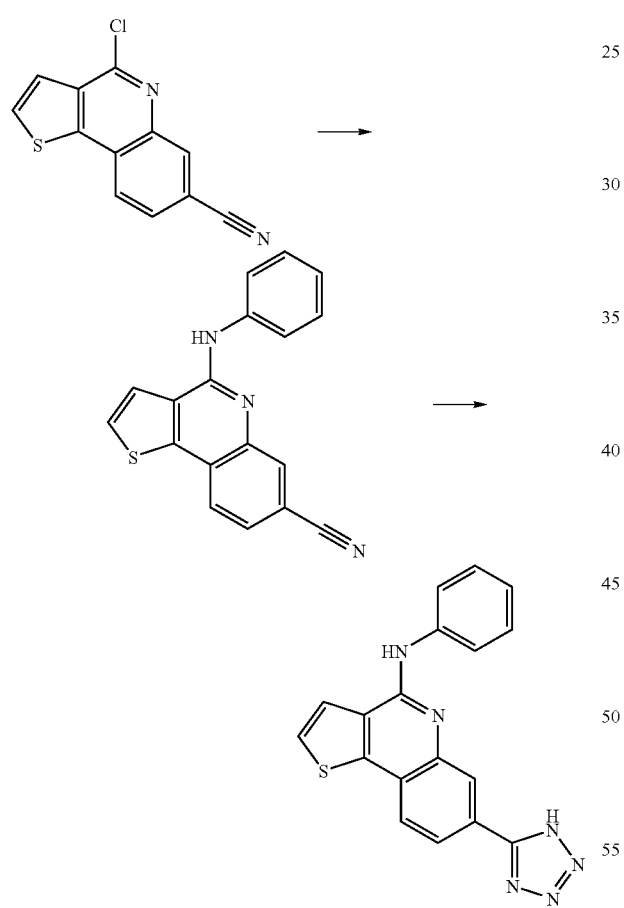

4-chlorothieno[3,2-c]quinoline-7-carbonitrile (1.0 eq, 23 mg, 0.094 mmol), aniline (0.1 ml) and NMP (0.1 ml) were mixed in a vial. The mixture was heated in a microwave oven at 120° C. for 10 nm. Water was added and the resulting solid 4-(phenylamino)thieno[3,2-c]quinoline-7-carbonitrile was filtered and dried. LCMS (ES): 95% pure, m/z 302 [M+1]⁺. This material was mixed in a vial with DMF (0.5 ml), $NH_4Cl$ (50 mg) and $NaN_3$ (50 mg). The mixture was stirred at 120° C.

for 3 hours. After addition of water and filtration, N-phenyl-7-(1H-tetrazol-5-yl)thieno[3,2-c]quinolin-4-amine was isolated as a beige solid (13 mg, 41% yield). LCMS (ES): 95% pure, m/z 345 [M+1]⁺, 317 [M+1-$N_2$]⁺. ¹H NMR (DMSO-$d_6$, 400 MHz) δ 7.07 (t, J=7.2, 1H), 7.40 (t, J=7.6, 2H), 8.00 (dd, J=1.6, J=8.4, 1H), 8.04 (d, J=5.2, 1H), 8.10 (dd, J=1.2, J=8.8, 2H), 8.19 (d, J=8.0, 1H), 8.25 (d, J=5.6, 1H), 8.43 (d, J=1.6, 1H), 9.34 (s, 1H) ppm.

Representative analogs (Table 1C) were prepared by the same method using 4-chlorothieno[3,2-c]quinoline-7-carbonitrile and appropriate amines. The reaction temperatures used for the microwave reactions ranged from 120° C. to 180° C. After synthesis of the tetrazoles, the materials were isolated by preparative HPLC/genevac evaporation. In some instances, the materials precipitated after addition of water to the reaction mixture and were isolated by filtration.

TABLE 1C

| Structure | M.W. | LCMS (ES) m/z |
|---|---|---|
| 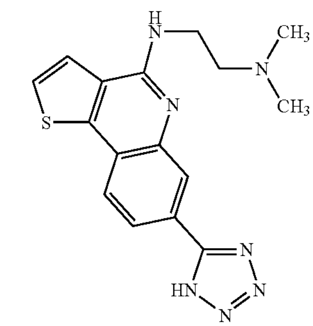 | 339.42 | 340 [M + 1]⁺ |
| 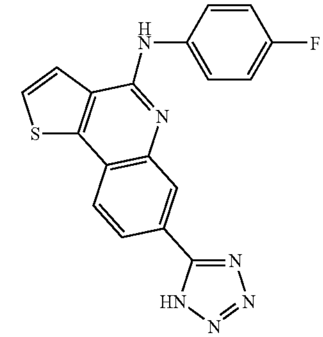 | 362.38 | 363 [M + 1]⁺ |
| 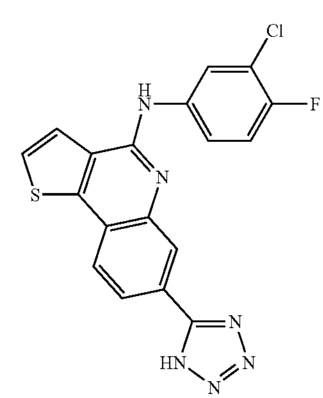 | 396.83 | 397 [M + 1]⁺ |

TABLE 1C-continued

| Structure | M.W. | LCMS (ES) m/z |
|---|---|---|
| (3-methoxyphenyl) | 374.42 | 375 [M + 1]+ |
| (4-chlorophenyl) | 378.84 | 379 [M + 1]+ |
| (3-chloro-4-methoxyphenyl) | 408.86 | 409 [M + 1]+ |
| (2,5-dimethoxyphenyl) | 404.45 | 405 [M + 1]+ |

TABLE 1C-continued

| Structure | M.W. | LCMS (ES) m/z |
|---|---|---|
| (3-trifluoromethoxyphenyl) | 428.39 | 429 [M + 1]+ |
| (3-isopropoxyphenyl) | 402.47 | 403 [M + 1]+ |
| (3,5-dimethoxyphenyl) | 404.45 | 405 [M + 1]+ |
| (4-fluoro-3-methoxyphenyl) | 392.41 | 393 [M + 1]+ |

TABLE 1C-continued

| Structure | M.W. | LCMS (ES) m/z |
|---|---|---|
| | 374.42 | 375 [M + 1]+ |
| 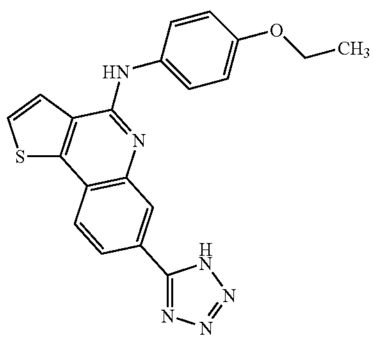 | 388.45 | 389 [M + 1]+ |
| 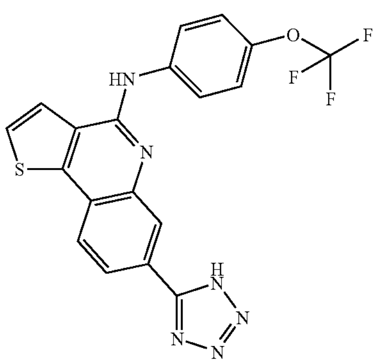 | 428.39 | 429 [M + 1]+ |
| 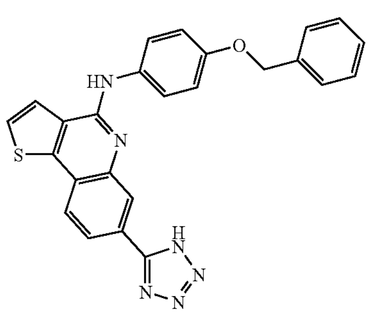 | 450.52 | 451 [M + 1]+ |

TABLE 1C-continued

| Structure | M.W. | LCMS (ES) m/z |
|---|---|---|
| | 404.45 | 405 [M + 1]+ |
| | 416.46 | 417 [M + 1]+ |
| | 412.39 | 413 [M + 1]+ |
| | 374.42 | 375 [M + 1]+ |

TABLE 1C-continued

| Structure | M.W. | LCMS (ES) m/z |
|---|---|---|
| (3-isopropylphenyl-NH, thieno-quinoline, tetrazole) | 386.47 | 387 [M + 1]+ |
| (3-chlorophenyl-NH, thieno-quinoline, tetrazole) | 378.84 | 379 [M + 1]+ |
| (3-(N-methylcarboxamide)phenyl-NH, thieno-quinoline, tetrazole) | 401.44 | 402 [M + 1]+ |
| (3-sulfamoylphenyl-NH, thieno-quinoline, tetrazole) | 423.47 | 424 [M + 1]+ |

TABLE 1C-continued

| Structure | M.W. | LCMS (ES) m/z |
|---|---|---|
| (3-acetamidophenyl-NH, thieno-quinoline, tetrazole) | 401.44 | 402 [M + 1]+ |
| (3-bromophenyl-NH, thieno-quinoline, tetrazole) | 423.29 | 424 [M + 1]+ |
| (3-fluorophenyl-NH, thieno-quinoline, tetrazole) | 362.38 | 363 [M + 1]+ |
| (3-methylphenyl-NH, thieno-quinoline, tetrazole) | 358.42 | 359 [M + 1]+ |

TABLE 1C-continued
| Structure | M.W. | LCMS (ES) m/z |
|---|---|---|
| 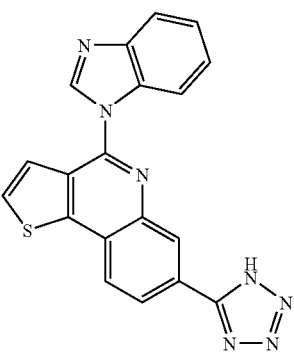 | 369.40 | 370 [M + 1]+ |
| 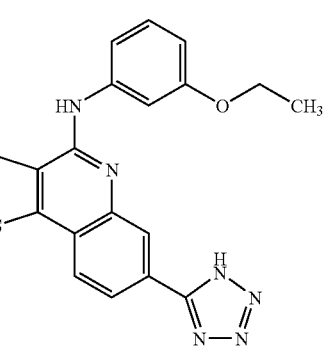 | 388.45 | 389 [M + 1]+ |
| 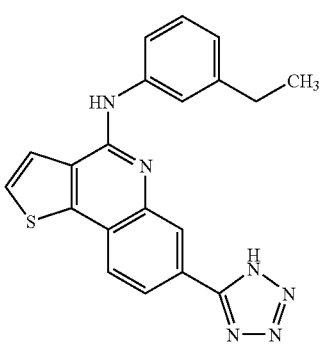 | 372.45 | 373 [M + 1]+ |
| 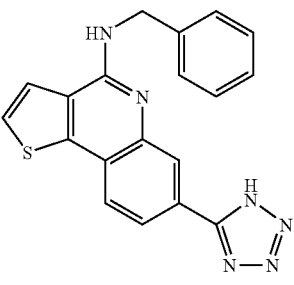 | 358.42 | 359 [M + 1]+ |
| 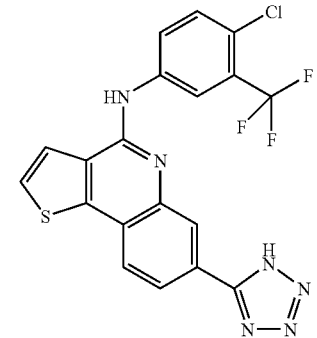 | 446.84 | 447 [M + 1]+ |
| 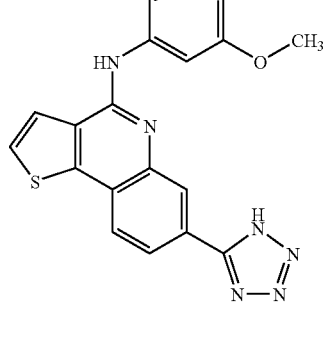 | 388.45 | 389 [M + 1]+ |
| 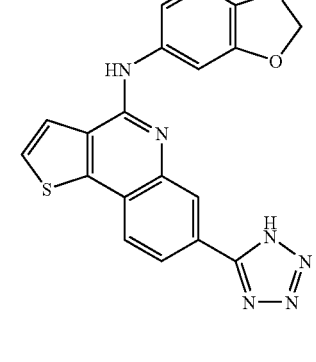 | 388.40 | 389 [M + 1]+ |
| 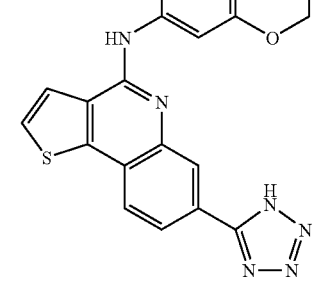 | 402.43 | 403 [M + 1]+ |

TABLE 1C-continued

| Structure | M.W. | LCMS (ES) m/z |
|---|---|---|
| (structure with dimethylaminopropyl amine, thieno[3,2-c]quinoline, tetrazole) | 353.44 | 354 [M + 1]+ |
| (structure with 3-chloro-5-fluorophenyl amine, thieno[3,2-c]quinoline, tetrazole) | 396.83 | 397 [M + 1]+ |
| (structure with 3-ethynylphenyl amine, thieno[3,2-c]quinoline, tetrazole) | 368.41 | 369 [M + 1]+ |
| (structure with 3,5-difluorophenyl amine, thieno[3,2-c]quinoline, tetrazole) | 380.37 | 381 [M + 1]+ |

Process 24

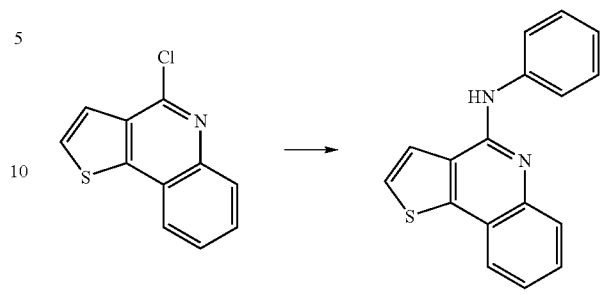

4-chlorothieno[3,2-c]quinoline (23 mg) was mixed with aniline (0.1 ml) and NMP (0.1 ml) and the mixture was heated in a microwave oven at 120° C. for 10 min. NMP (0.8 ml) was added and the compound purified by preparative HPLC. Genevac evaporation afforded N-phenylthieno[3,2-c]quinolin-4-amine as a pinky solid (31 mg, quant.). LCMS (ES): 95% pure, m/z 277 [M+1]+.

Process 25

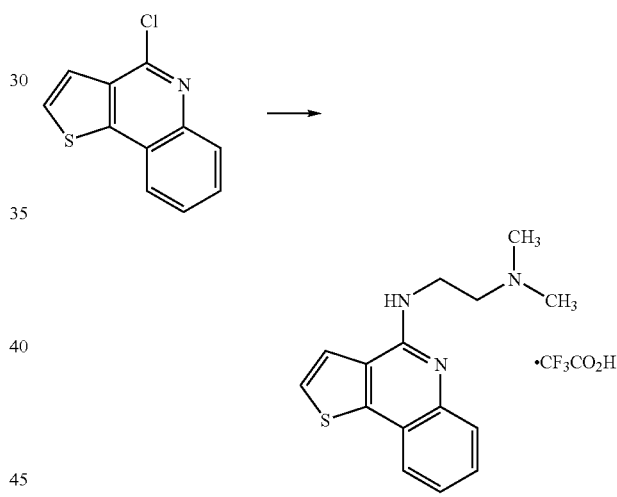

N1,N1-dimethyl-N2-(thieno[3,2-c]quinolin-4-yl)ethane-1,2-diamine was prepared according to the procedure in process 24 using N,N-dimethyl ethylene diamine. Preparative HPLC and genevac evaporation afforded the expected material as a TFA salt. LCMS (ES): 95% pure, m/z 272 [M+1]+.

Process 26

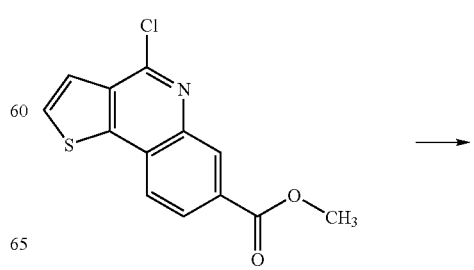

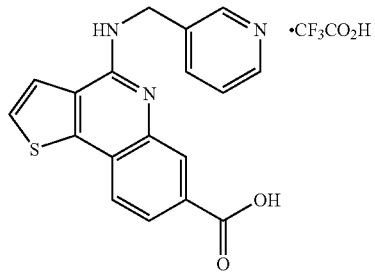

4-chlorothieno[3,2-c]quinoline-7-carboxylate (10 mg, 0.036 mmol) was suspended in NMP (0.1 ml) and 3-aminomethylpyridine (0.1 ml). The mixture was heated in a microwave oven at 120° C. for 10 nm. The reaction mixture was dissolved in a mixture of NMP and MeOH and the ester intermediate purified by preparative HPLC. After genevac evaporation of the solvents, the resulting solid was dissolved in a 1:1 mixture of THF and MeOH (0.6 ml). 5N aqueous LiOH (0.2 ml) was added and the mixture stirred at room temperature for 17 hrs. Water and aqueous HCl were added and the solution of 4-(pyridin-3-ylmethylamino)thieno[3,2-c]quinoline-7-carboxylic acid was purified by preparative HPLC. Removal of the solvents by genevac evaporation provided compound 4-(pyridin-3-ylmethylamino)thieno[3,2-c]quinoline-7-carboxylic acid as a white solid (10 mg, 62% yield). LCMS (ES): 95% pure, m/z 336 [M+1]$^+$. $^1$H NMR (CDCl$_3$, 400 MHz) δ 5.23 (s, 2H), 7.71-7.78 (m, 4H), 8.11 (d, J=5.6, 1H), 8.47 (d, J=8.0, 1H), 8.49 (d, J=0.8, 1H), 8.62 (d, J=5.2, 1H), 8.97 (s, 1H) ppm.

Representative analogs (Table 2) were prepared by the same method, using 4-chlorothieno[3,2-c]quinoline-7-carboxylate and appropriate amines. The reaction temperatures used for the microwave reactions ranged from 120° C. to 180° C. After hydrolysis of the esters, the materials were isolated by preparative HPLC/genevac evaporation. In some instances, the materials precipitated after acidification of the hydrolysis mixture and were isolated by filtration.

TABLE 2

| Structure | M.W. | LCMS (ES) m/z |
|---|---|---|
| 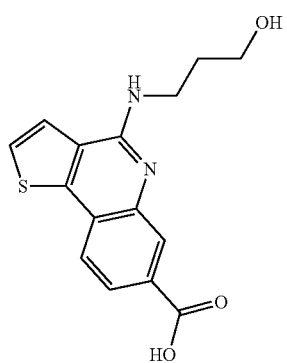 | 302.35 | 303 [M + 1]$^+$ |
| 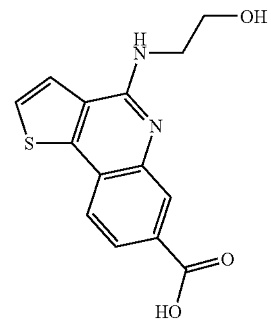 | 288.32 | 289 [M + 1]$^+$ |
| 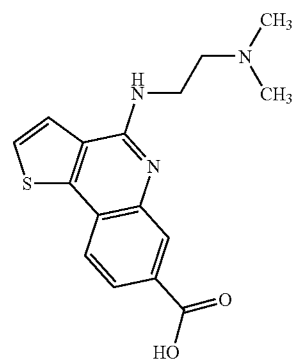 | 315.39 | 316 [M + 1]$^+$ |
| 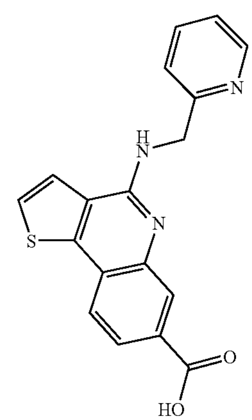 | 335.38 | 336 [M + 1]$^+$ |
| 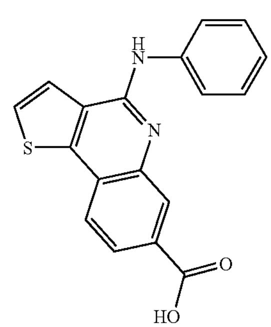 | 320.37 | 321 [M + 1]$^+$ |

TABLE 2-continued

| Structure | M.W. | LCMS (ES) m/z |
|---|---|---|
| (morpholinoethylamino-thienoquinoline carboxylic acid) | 357.43 | 358 [M + 1]+ |
| (pyridin-4-ylmethylamino-thienoquinoline carboxylic acid) | 335.38 | 336 [M + 1]+ |
| (2-methoxyphenylamino-thienoquinoline carboxylic acid) | 350.39 | 351 [M + 1]+ |
| (3-hydroxyphenylamino-thienoquinoline carboxylic acid) | 336.36 | 337 [M + 1]+ |
| (2,4-dimethoxyphenylamino-thienoquinoline carboxylic acid) | 380.42 | 381 [M + 1]+ |
| (pyrrolidin-1-ylethylamino-thienoquinoline carboxylic acid) | 341.43 | 342 [M + 1]+ |
| (morpholino-thienoquinoline carboxylic acid) | 314.36 | 315 [M + 1]+ |
| (phenethylamino-thienoquinoline carboxylic acid) | 348.42 | 349 [M + 1]+ |

TABLE 2-continued
| Structure | M.W. | LCMS (ES) m/z |
|---|---|---|
| 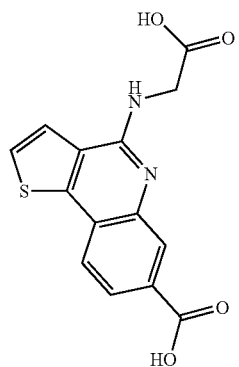 | 302.31 | 303 [M + 1]+ |
| 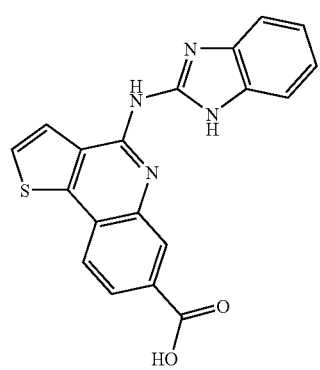 | 360.39 | 361 [M + 1]+ |
| 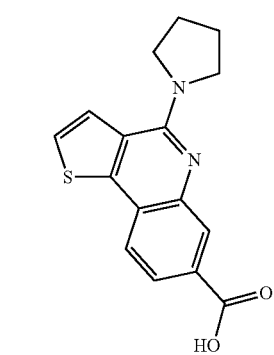 | 298.36 | 299 [M + 1]+ |
| 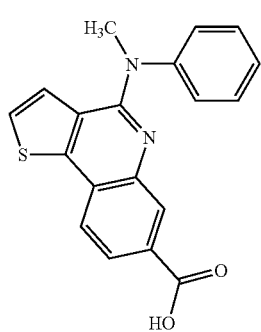 | 334.39 | 335 [M + 1]+ |
TABLE 2-continued
| Structure | M.W. | LCMS (ES) m/z |
|---|---|---|
| 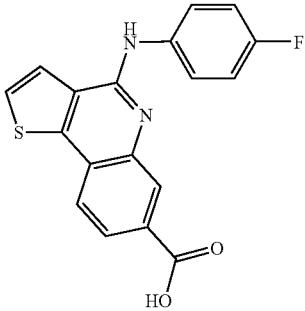 | 338.36 | 339 [M + 1]+ |
| 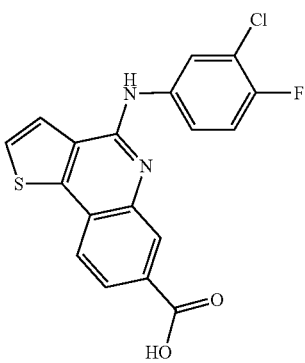 | 372.80 | 373 [M + 1]+ |
| 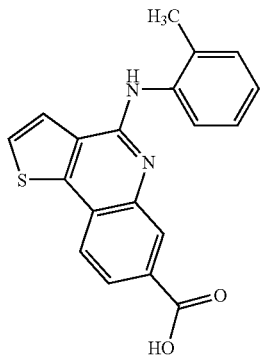 | 334.39 | 335 [M + 1]+ |
| 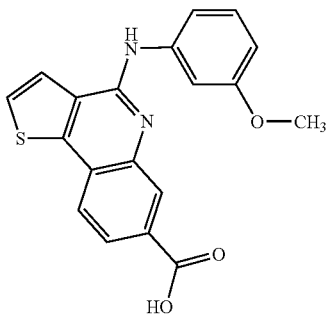 | 350.39 | 351 [M + 1]+ |

TABLE 2-continued
| Structure | M.W. | LCMS (ES) m/z |
|---|---|---|
| 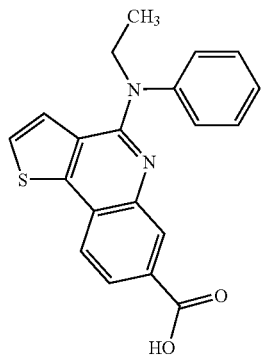 | 348.42 | 349 [M + 1]+ |
| 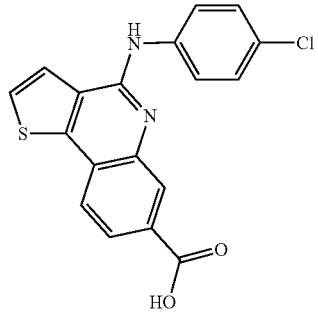 | 354.81 | 355 [M + 1]+ |
| 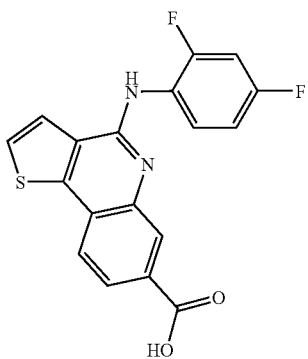 | 356.35 | 357 [M + 1]+ |
| 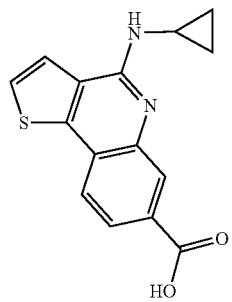 | 284.33 | 285 [M + 1]+ |
TABLE 2-continued
| Structure | M.W. | LCMS (ES) m/z |
|---|---|---|
| 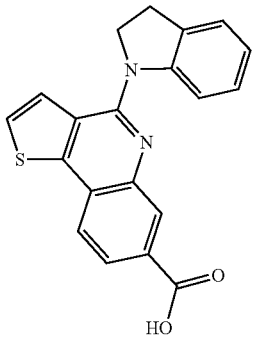 | 346.40 | 347 [M + 1]+ |
| 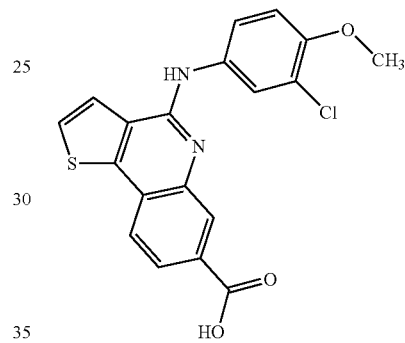 | 384.84 | 385 [M + 1]+ |
| 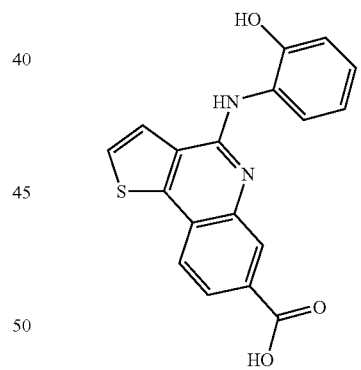 | 336.36 | 337 [M + 1]+ |
| 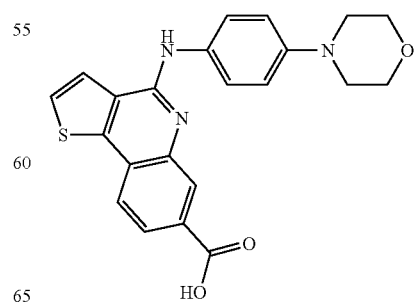 | 405.47 | 406 [M + 1]+ |

TABLE 2-continued

| Structure | M.W. | LCMS (ES) m/z |
|---|---|---|
| (2,5-dimethoxyphenylamino thieno-quinoline carboxylic acid) | 380.42 | 381 [M + 1]+ |
| (phenylamino thieno-quinoline carboxylic acid methyl ester) | 334.39 | 335 [M + 1]+ |
| (3,5-difluorophenylamino thieno-quinoline carboxylic acid) | 356.35 | 357 [M + 1]+ |
| (3-fluorophenylamino thieno-quinoline carboxylic acid) | 338.36 | 339 [M + 1]+ |
| (3-chlorophenylamino thieno-quinoline carboxylic acid) | 354.81 | 355 [M + 1]+ |
| (2-fluoro-5-chlorophenylamino thieno-quinoline carboxylic acid) | 372.80 | 373 [M + 1]+ |
| (3-ethoxyphenylamino thieno-quinoline carboxylic acid) | 364.42 | 365 [M + 1]+ |
| (3-phenoxyphenylamino thieno-quinoline carboxylic acid) | 412.46 | 413 [M + 1]+ |

TABLE 2-continued
| Structure | M.W. | LCMS (ES) m/z |
|---|---|---|
| 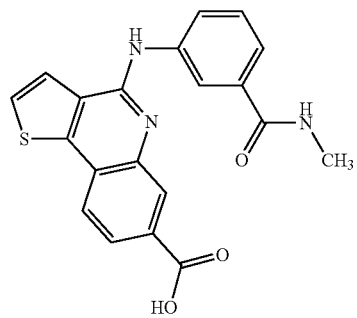 | 377.42 | 378 [M + 1]+ |
| 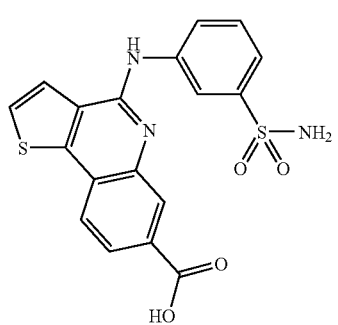 | 399.44 | 400 [M + 1]+ |
| 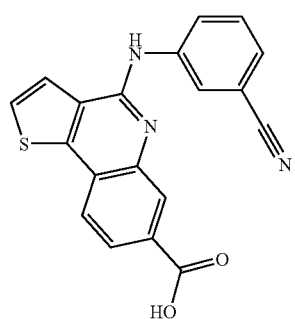 | 345.37 | 346 [M + 1]+ |
| 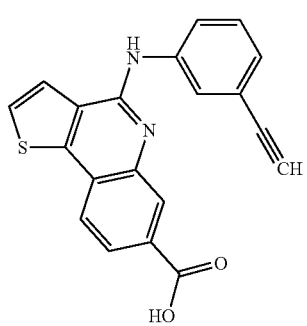 | 344.39 | 345 [M + 1]+ |
| 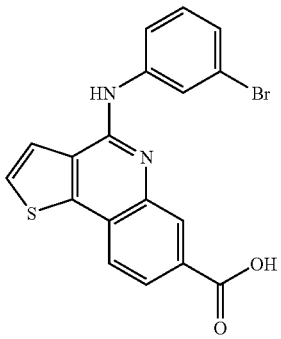 | 399.26 | 400 [M + 1]+ |
| 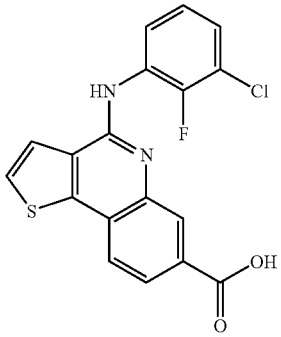 | 372.80 | 373 [M + 1]+ |
| 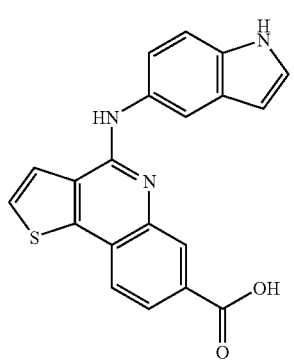 | 359.40 | 360 [M + 1]+ |
| 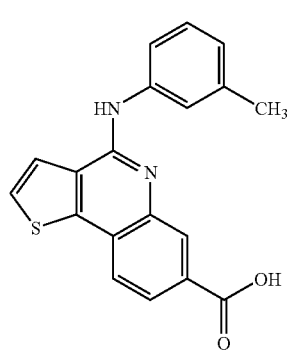 | 334.39 | 335 [M + 1]+ |

TABLE 2-continued
| Structure | M.W. | LCMS (ES) m/z |
|---|---|---|
| 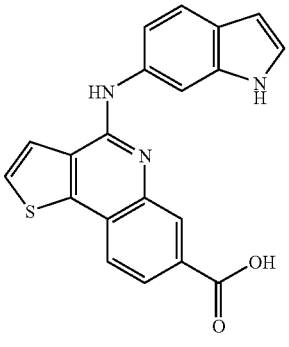 | 359.40 | 360 [M + 1]+ |
| 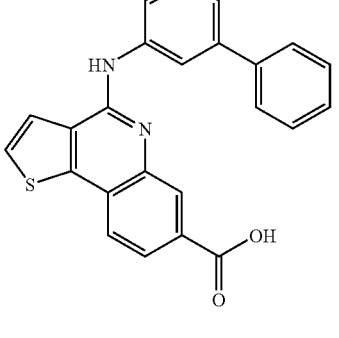 | 396.46 | 397 [M + 1]+ |
| 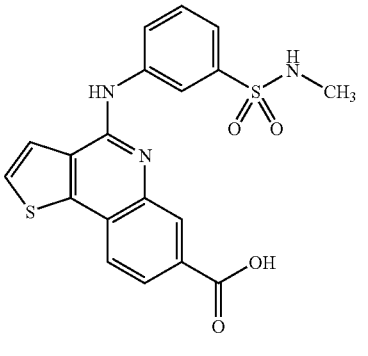 | 413.47 | 414 [M + 1]+ |
| 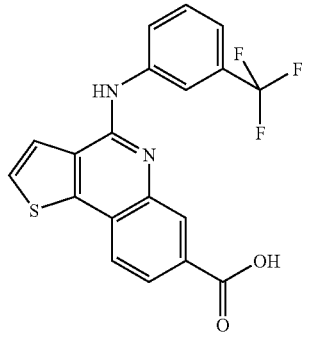 | 388.36 | 389 [M + 1]+ |
TABLE 2-continued
| Structure | M.W. | LCMS (ES) m/z |
|---|---|---|
| 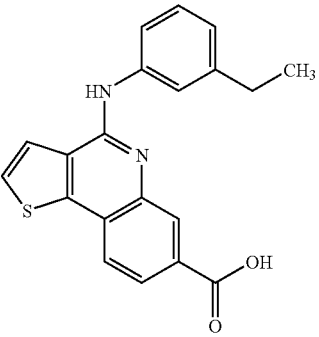 | 348.42 | 349 [M + 1]+ |
| 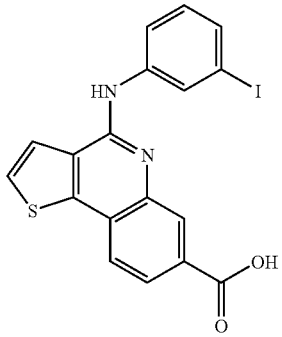 | 446.26 | 447 [M + 1]+ |
| 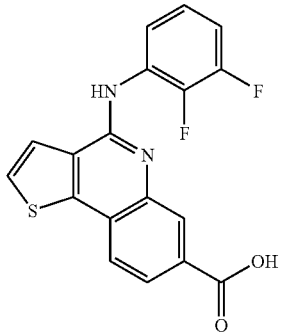 | 356.35 | 357 [M + 1]+ |
| 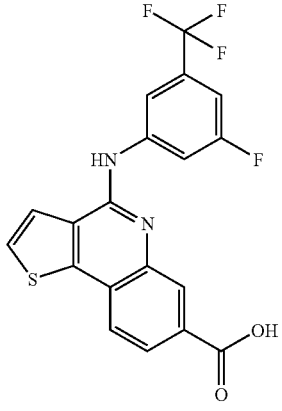 | 406.35 | 407 [M + 1]+ |

TABLE 2-continued

| Structure | M.W. | LCMS (ES) m/z |
|---|---|---|
| (3-carboxy-5-fluoro-phenylamino thieno[3,2-c]quinoline-carboxylic acid) | 382.37 | 383 [M + 1]+ |
| (2,5-difluorophenylamino thieno[3,2-c]quinoline-carboxylic acid) | 356.35 | 357 [M + 1]+ |
| (3-(N-cyclopropylsulfamoyl)phenylamino thieno[3,2-c]quinoline-carboxylic acid) | 439.51 | 440 [M + 1]+ |
| (3,5-dichlorophenylamino thieno[3,2-c]quinoline-carboxylic acid) | 389.26 | 390 [M + 1]+ |

TABLE 2-continued

| Structure | M.W. | LCMS (ES) m/z |
|---|---|---|
| (3,4-difluorophenylamino thieno[3,2-c]quinoline-carboxylic acid) | 356.35 | 357 [M + 1]+ |
| (3-chloro-5-fluoro-phenylamino thieno[3,2-c]quinoline-carboxylic acid) | 372.80 | 373 [M + 1]+ |
| (3-cyano-5-fluoro-phenylamino thieno[3,2-c]quinoline-carboxylic acid) | 363.37 | 364 [M + 1]+ |

Process 27

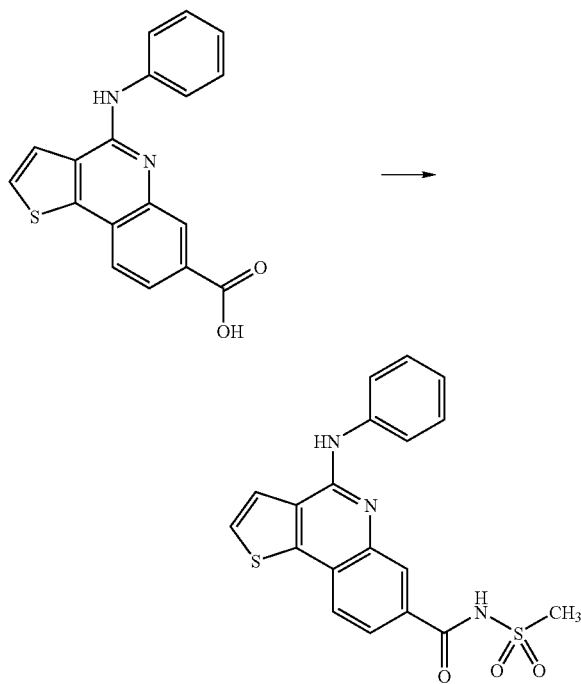

4-(phenylamino)thieno[3,2-c]quinoline-7-carboxylic acid (6 mg) was reacted with methyl sulfonamide (120 mg), EDCI (80 mg) and DMAP (20 mg) in anhydrous DMF (0.5 ml). After 5 hours, water was added and the solution subjected to preparative HPLC. Genevac evaporation provided N-(methylsulfonyl)-4-(phenylamino)thieno[3,2-c]quinoline-7-carboxamide as a solid (6 mg, 81% yield). LCMS (ES): 95% pure, m/z 398 [M+1]$^+$.

Process 28

In a vial, 4-oxo-4,5-dihydrothieno[3,2-c]quinoline-7-carboxylic acid (1.0 eq, 20 mg, 0.081 mmol), N-hydroxybenzotriazole monohydrate (2.0 eq, 22 mg, 0162 mmol), para-methoxybenzylamine (2.0 eq, 21 ul, 0.162 mmol) and triethylamine (2.0 eq, 23 ul, 0.165 mmol) were dissolved in anhydrous DMF (0.5 ml). EDCI (2.0 eq 31 mg, 0.162 mmol) was added and the reaction mixture was stirred at 70° C. overnight. MeOH (0.5 ml) and water (2 ml) were added and the resulting precipitate filtered and dried. The material was triturated in AcOEt, filtered and dried to provide an off-white solid (19 mg, 65% yield). LCMS (ES): 95% pure, m/z 365 [M+1]$^+$, $^1$H NMR (DMSO-d$_6$, 400 MHz) δ 3.71 (s, 3H), 4.40 (d, J=6.0, 2H), 6.88 (d, J=8.8, 2H), 7.24 (d, J=8.8, 2H), 7.60 (d, J=5.6, 1H), 7.69 (dd, J=1.6, J=8.0, 1H), 7.84 (d, J=5.6, 1H), 7.90 (s, 1H), 7.91 (d, J=8.8, 1H), 9.11 (t, J=5.6, 1H) ppm The following representative analogs (Table 3) were prepared by these processes, using 4-oxo-4,5-dihydrothieno[3,2-c]quinoline-7-carboxylic acid and appropriate amines. In some instances, the materials were purified by preparative HPLC and were isolated as dry solids after Genevac evaporation.

TABLE 3

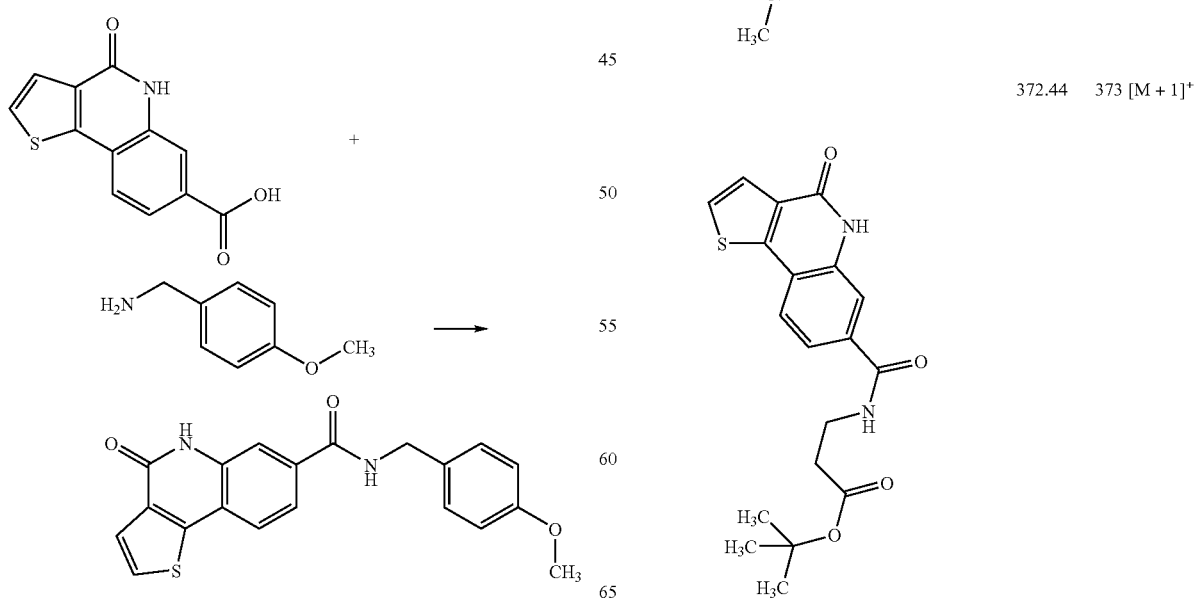

| Structure | M.W. | LCMS (ES) m/z |
|---|---|---|
| 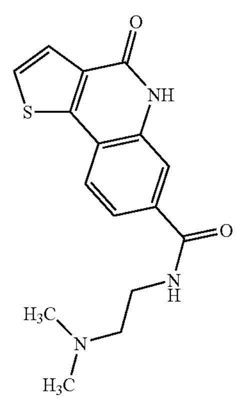 | 315.39 | 316 [M + 1]$^+$ |
| 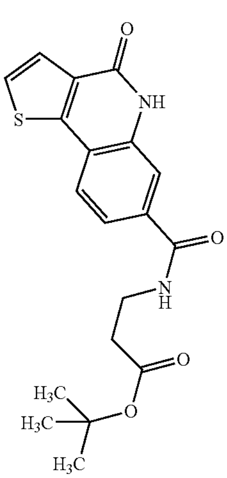 | 372.44 | 373 [M + 1]$^+$ |

TABLE 3-continued

| Structure | M.W. | LCMS (ES) m/z |
|---|---|---|
| (thieno-quinolinone-carboxamide, N-phenyl) | 320.37 | 321 [M + 1]+ |
| (thieno-quinolinone-carboxamide, N-CH2-C(O)-O-CH3) | 316.33 | 316 [M + 1]+ |
| (thieno-quinolinone-carboxamide, N-thiazol-2-yl) | 327.38 | 328 [M + 1]+ |
| (thieno-quinolinone-carboxamide, N-(2,4-dimethoxyphenyl)) | 380.42 | 381 [M + 1]+ |

TABLE 3-continued

| Structure | M.W. | LCMS (ES) m/z |
|---|---|---|
| (thieno-quinolinone-carboxamide, N-(4-morpholinophenyl)) | 405.47 | 406 [M + 1]+ |
| (thieno-quinolinone-carboxamide, N-pyridin-3-yl) | 321.35 | 322 [M + 1]+ |
| (thieno-quinolinone-carboxamide, N-(2-methoxyphenyl)) | 350.39 | 351 [M + 1]+ |
| (thieno-quinolinone-carboxamide, N-(4-chlorophenyl)) | 354.81 | 355 [M + 1]+ |

TABLE 3-continued

| Structure | M.W. | LCMS (ES) m/z |
|---|---|---|
| (thieno-quinolinone carboxamide with histamine/histidine ethyl side chain) | 338.38 | 339 [M + 1]$^+$ |
| (thieno-quinolinone carboxamide with 2-morpholinoethyl side chain) | 357.43 | 358 [M + 1]$^+$ |
| (thieno-quinolinone carboxamide with morpholine amide) | 314.36 | 315 [M + 1]$^+$ |
| (thieno-quinolinone carboxamide with N-propyl amide) | 286.35 | 287 [M + 1]$^+$ |
| (thieno-quinolinone carboxamide with 2-(pyridin-2-yl)ethyl side chain) | 349.41 | 350 [M + 1]$^+$ |
| (thieno-quinolinone carboxamide with 2-methoxyethyl side chain) | 302.35 | 303 [M + 1]$^+$ |
| (thieno-quinolinone carboxamide with 2-(3,4-dimethoxyphenyl)ethyl side chain) | 408.47 | 409 [M + 1]$^+$ |

TABLE 3-continued

| Structure | M.W. | LCMS (ES) m/z |
|---|---|---|
| (thieno-quinolinone with N,N-dimethyl carboxamide) | 272.32 | 273 [M + 1]+ |
| (thieno-quinolinone with 4-acetyl-piperazine carboxamide) | 355.41 | 356 [M + 1]+ |
| (thieno-quinolinone with N-cyclopropyl carboxamide) | 284.33 | 285 [M + 1]+ |
| (thieno-quinolinone with N-benzyl carboxamide) | 334.39 | 335 [M + 1]+ |

TABLE 3-continued

| Structure | M.W. | LCMS (ES) m/z |
|---|---|---|
| (thieno-quinolinone with 2-(methoxycarbonyl)phenyl carboxamide) | 378.40 | 379 [M + 1]+ |
| (thieno-quinolinone with N-Boc-piperazine carboxamide) | 413.49 | 414 [M + 1]+ |
| (thieno-quinolinone with 4-(Boc-amino)piperidine carboxamide) | 427.52 | 428 [M + 1]+ |

TABLE 3-continued
| Structure | M.W. | LCMS (ES) m/z |
|---|---|---|
| 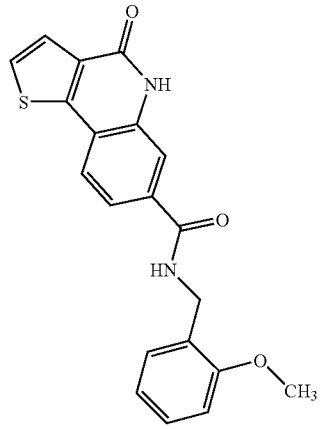 | 364.42 | 365 [M + 1]+ |
| 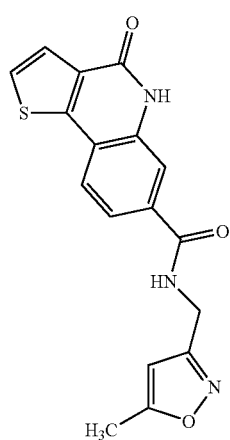 | 339.37 | 340 [M + 1]+ |
| 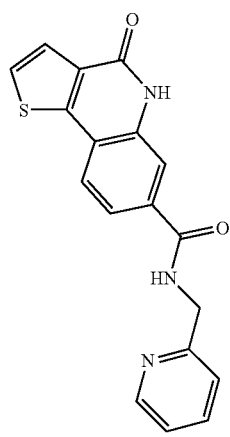 | 335.38 | 336 [M + 1]+ |
TABLE 3-continued
| Structure | M.W. | LCMS (ES) m/z |
|---|---|---|
| 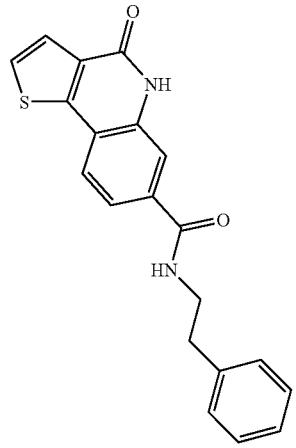 | 348.42 | 349 [M + 1]+ |
| 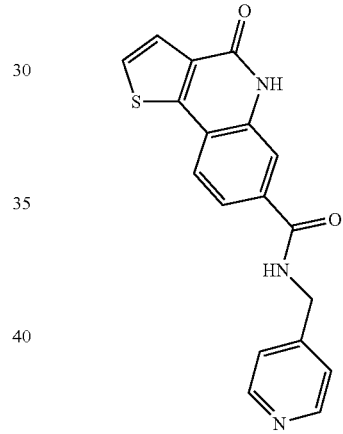 | 335.38 | 336 [M + 1]+ |
| 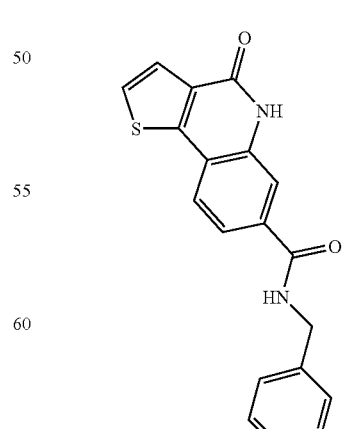 | 335.38 | 336 [M + 1]+ |

TABLE 3-continued

| Structure | M.W. | LCMS (ES) m/z |
|---|---|---|
| 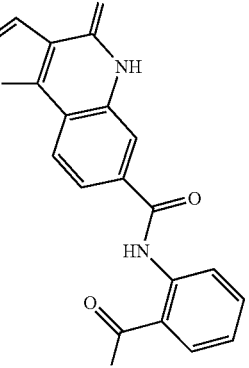 | 467.56 | 468 [M + 1]+ |

The following representative analogs (Table 4) were prepared from their corresponding methyl esters described in Table 3. The compounds were prepared according to the hydrolysis procedure utilized for compound 15.

TABLE 4

| Structure | M.W. | LCMS(ES)m/z |
|---|---|---|
| 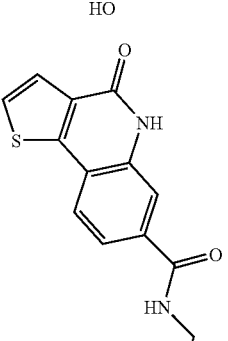 | 364.37 | 365[M + 1]+ |
| 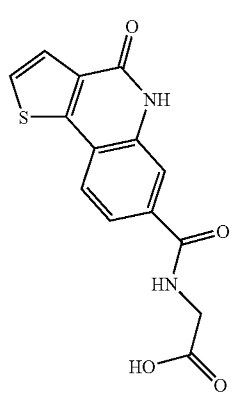 | 302.31 | 303[M + 1]+ |

The following representative analogs (Table 5) were prepared from their corresponding tert-butyl esters or N-Boc protected precursors described in Table 3. The precursors were treated with 30% trifluoroacetic acid in CH$_2$Cl$_2$ for 2 hours. Removal of the volatiles in vacuo afforded the expected materials.

TABLE 5

| Structure | M.W. | LCMS(ES)m/z |
|---|---|---|
| 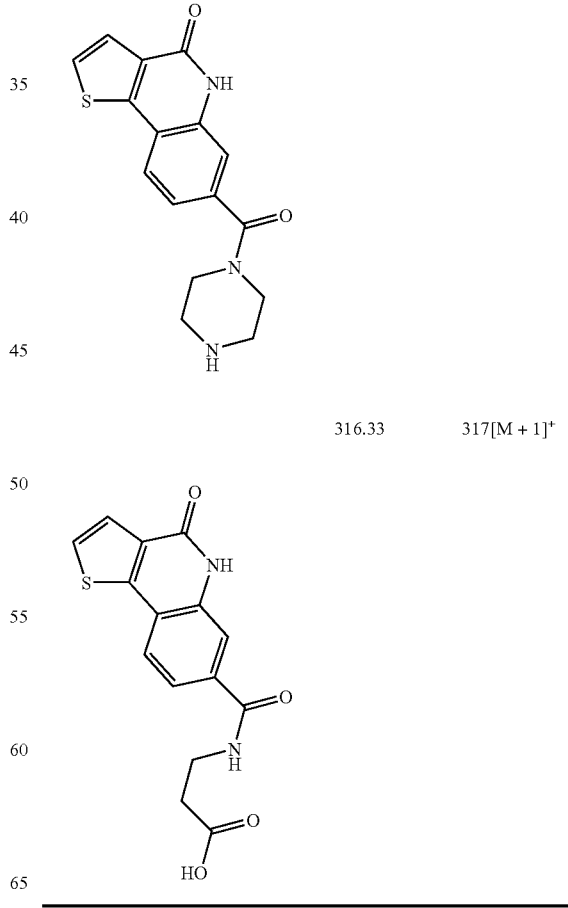 | 327.40 | 328[M + 1]+ |
| 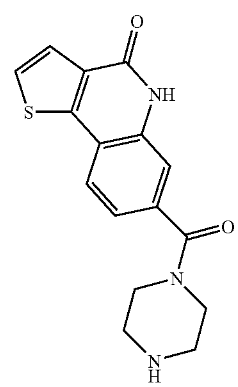 | 313.37 | 314[M + 1]+ |
| 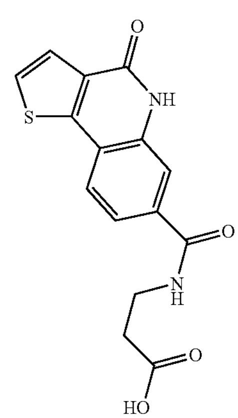 | 316.33 | 317[M + 1]+ |

Process 29

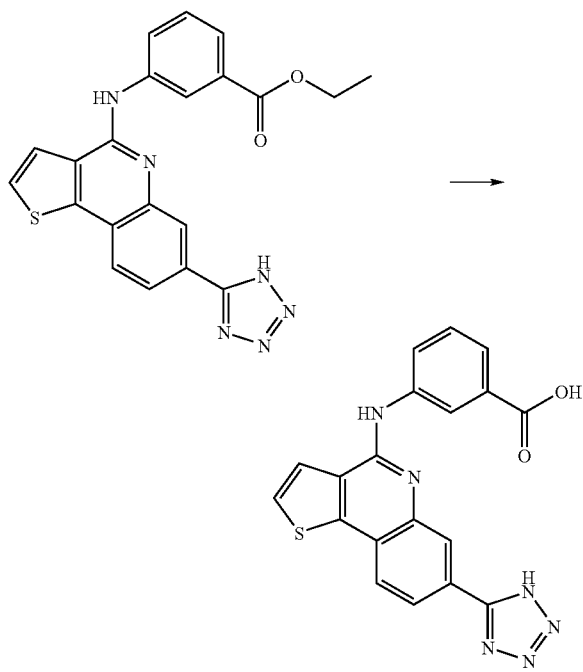

ethyl 3-(7-(1H-tetrazol-5-yl)thieno[3,2-c]quinolin-4-ylamino)benzoate (1.0 eq, 7.6 mg, 0.018 mmol) was suspended in a 1:1:1 mixture of THF, MeOH and water. Lithium Hydroxide was added (40 mg, 1.66 mmol) and the mixture stirred at room temperature for one hour. Water and hydrochloric acid were added and the resulting solid filtered and dried to afford 3-(7-(1H-tetrazol-5-yl)thieno[3,2-c]quinolin-4-ylamino)benzoic acid as a solid. LCMS (ES): 95% pure, m/z 389 [M+1]$^+$.

The following representative analogs (table 6) were prepared by reacting 3-(7-(1H-tetrazol-5-yl)thieno[3,2-c]quinolin-4-ylamino)benzoic acid and appropriate amines using the procedure described in process 28. The materials were purified by preparative HPLC and were isolated as dry solids after Genevac evaporation.

TABLE 6

| Structure | MW | LCMS(ES)m/z |
|---|---|---|
| 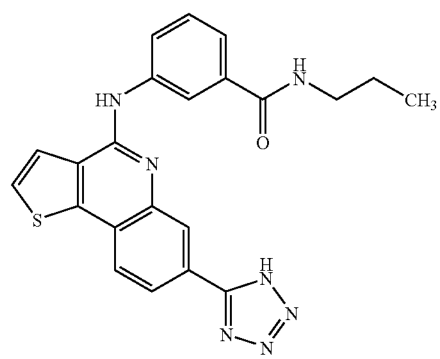 | 429.50 | 430[M + 1]$^+$ |
| 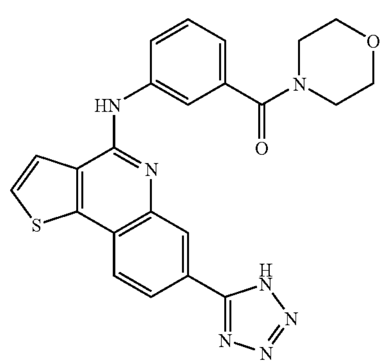 | 457.51 | 458[M + 1]$^+$ |

TABLE 6-continued
| Structure | MW | LCMS(ES)m/z |
|---|---|---|
| 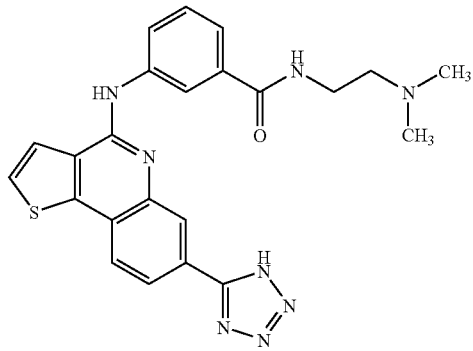 | 458.54 | 459[M + 1]+ |
| 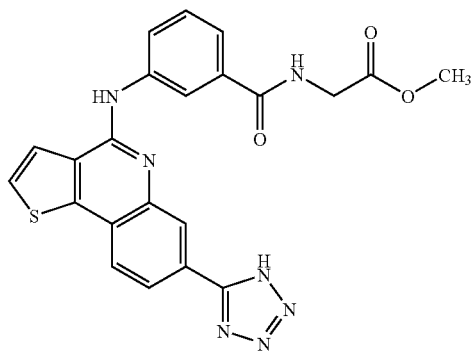 | 459.48 | 460[M + 1]+ |
| 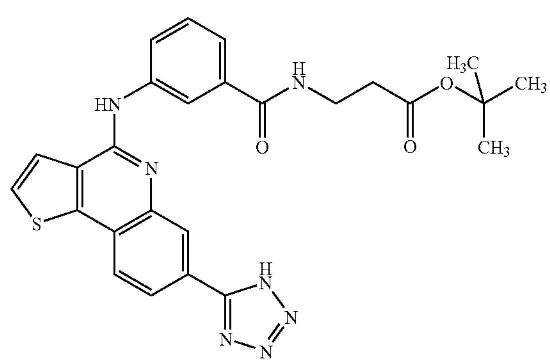 | 515.59 | 516[M + 1]+ |
| 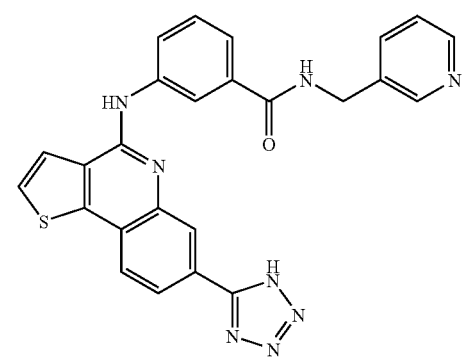 | 478.53 | 479[M + 1]+ |

TABLE 6-continued

| Structure | MW | LCMS(ES)m/z |
|---|---|---|
| 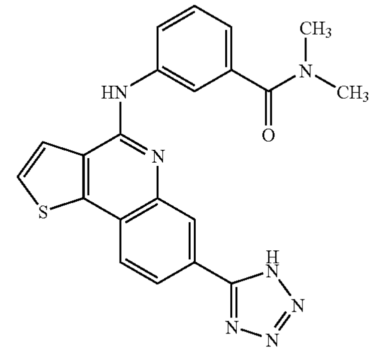 | 415.47 | 416[M + 1]⁺ |
| 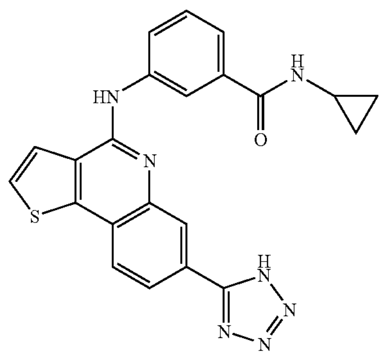 | 427.48 | 428[M + 1]⁺ |
| 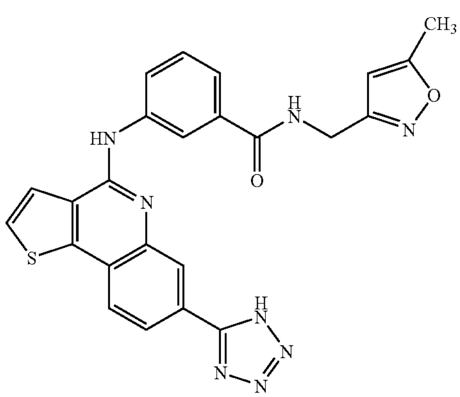 | 482.52 | 483[M + 1]⁺ |
| 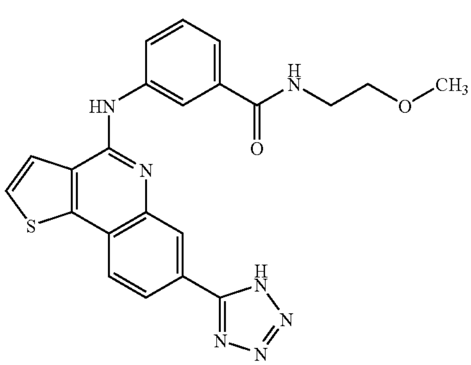 | 445.50 | 446[M + 1]⁺ |

TABLE 6-continued

| Structure | MW | LCMS(ES)m/z |
|---|---|---|
| 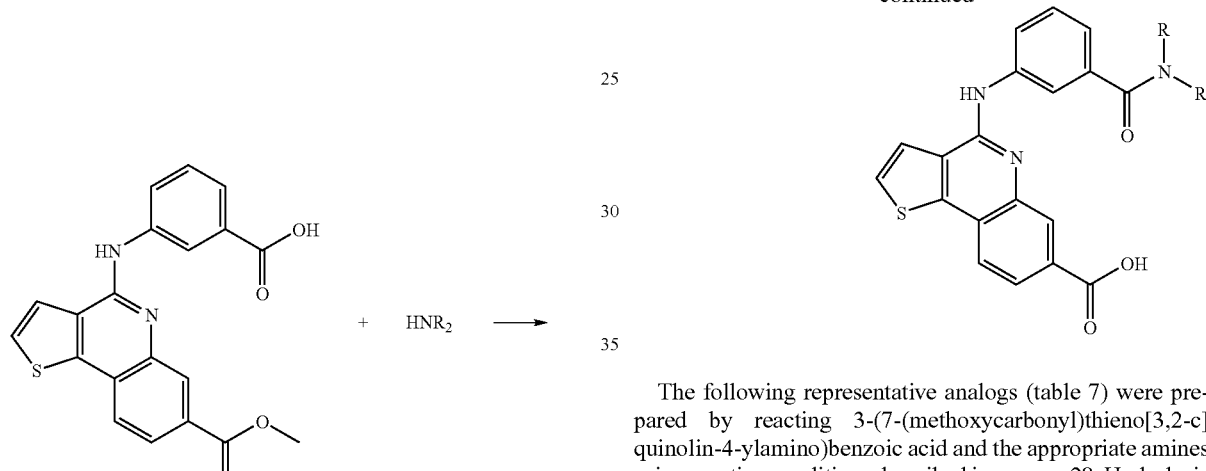 | 498.56 | 499[M + 1]⁺ |

Process 30

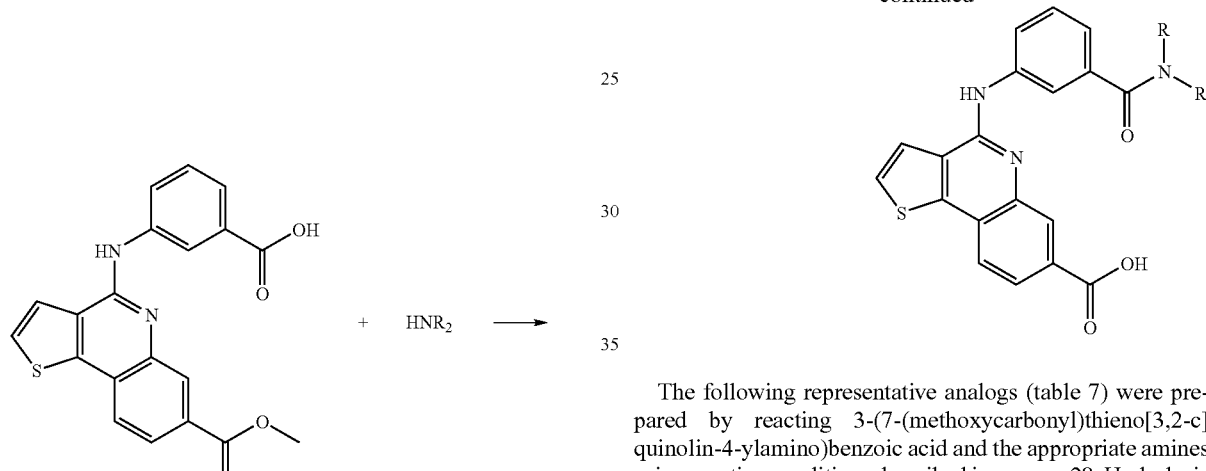

The following representative analogs (table 7) were prepared by reacting 3-(7-(methoxycarbonyl)thieno[3,2-c]quinolin-4-ylamino)benzoic acid and the appropriate amines using reaction conditions described in process 28. Hydrolysis of the ester using conditions described in process 29 afforded the following analogs.

TABLE 7

| Structure | MW | LCMS(ES)m/z |
|---|---|---|
| 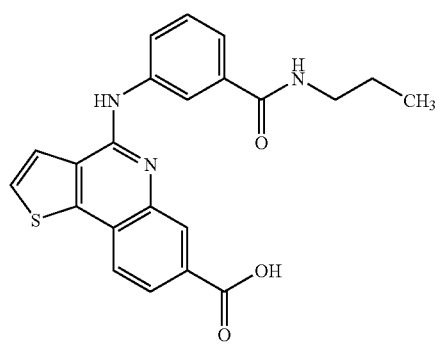 | 405.47 | 406[M + 1]⁺ |

TABLE 7-continued

| Structure | MW | LCMS(ES)m/z |
|---|---|---|
| 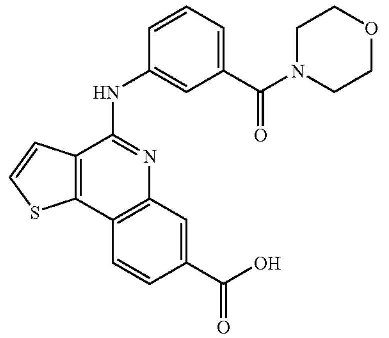 | 433.48 | 434[M + 1]+ |
| 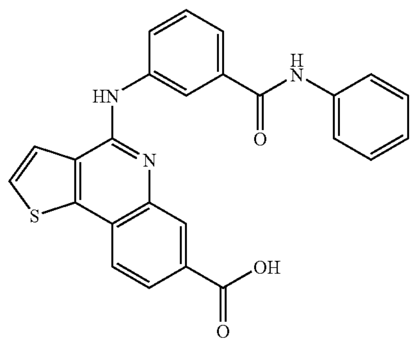 | 439.49 | 440[M + 1]+ |
| 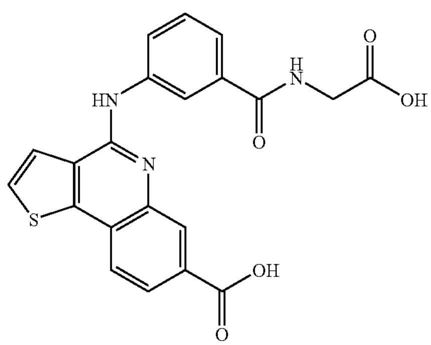 | 421.43 | 422[M + 1]+ |
| 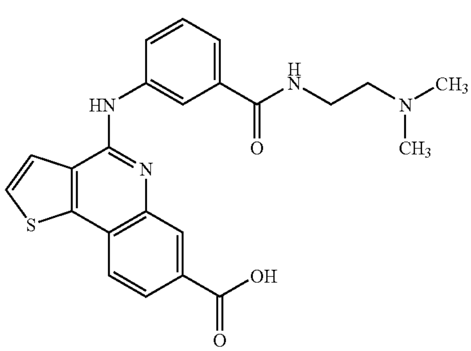 | 434.51 | 435[M + 1]+ |

TABLE 7-continued
| Structure | MW | LCMS(ES)m/z |
|---|---|---|
| 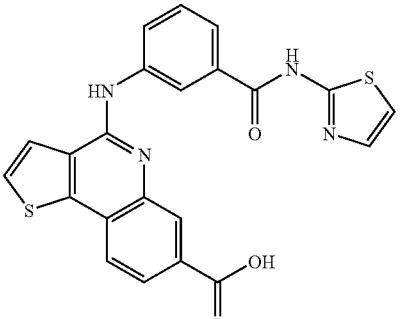 | 446.50 | 447[M + 1]+ |
| 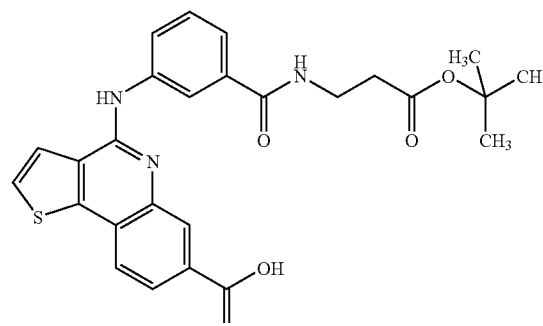 | 491.56 | 492[M + 1]+ |
| 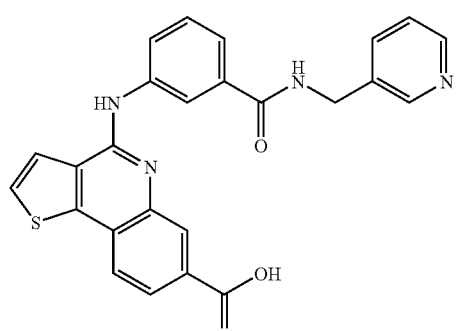 | 454.50 | 455[M + 1]+ |
| 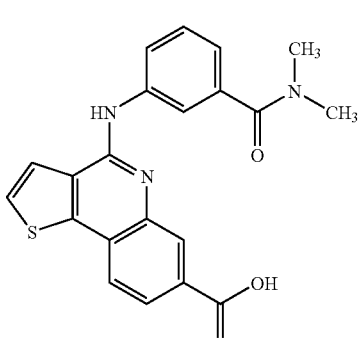 | 391.44 | 392[M + 1]+ |

TABLE 7-continued
| Structure | MW | LCMS(ES)m/z |
|---|---|---|
| 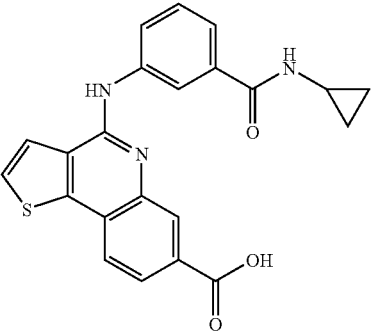 | 403.45 | 404[M + 1]+ |
| 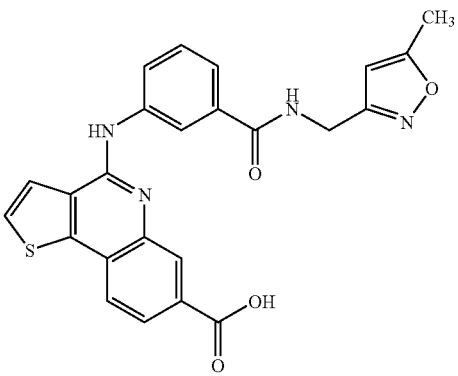 | 458.49 | 459[M + 1]+ |
| 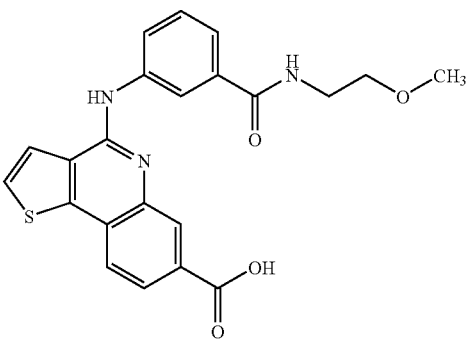 | 421.47 | 422[M + 1]+ |
| 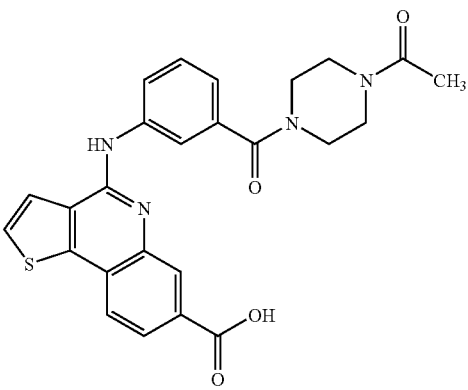 | 474.53 | 475[M + 1]+ |

Process 31
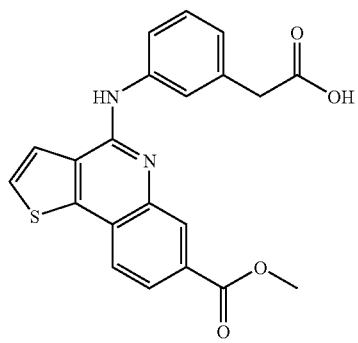
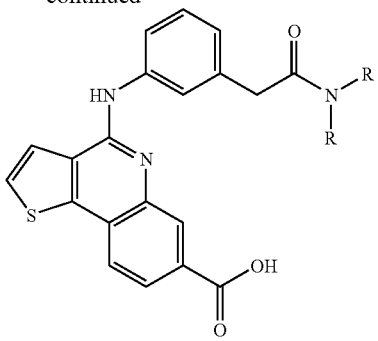
The following representative analogs (table 8) were prepared by reacting 2-(3-(7-(methoxycarbonyl)thieno[3,2-c]quinolin-4-ylamino)phenyl)acetic acid and the appropriate amines using reaction conditions described in process 30.
TABLE 8
| Structure | MW | LCMS(ES)m/z |
|---|---|---|
| 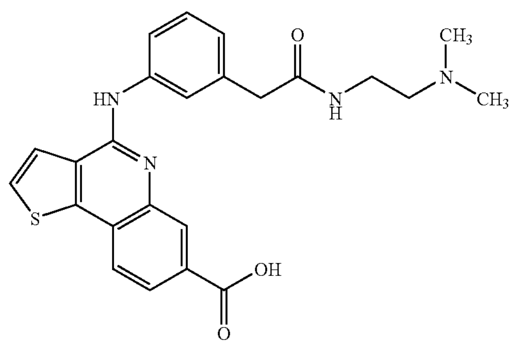 | 448.54 | 449[M + 1]+ |
| 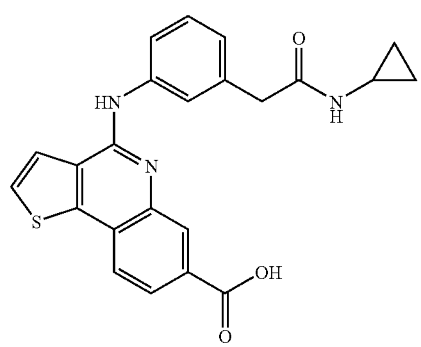 | 417.48 | 418[M + 1]+ |
| 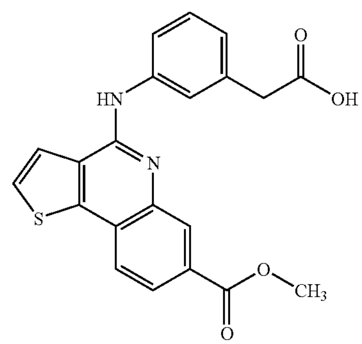 | 392.43 | 393[M + 1]+ |

TABLE 8-continued

| Structure | MW | LCMS(ES)m/z |
|---|---|---|
| 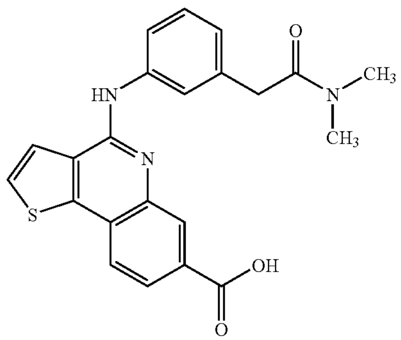 | 405.47 | 406[M + 1]+ |
| 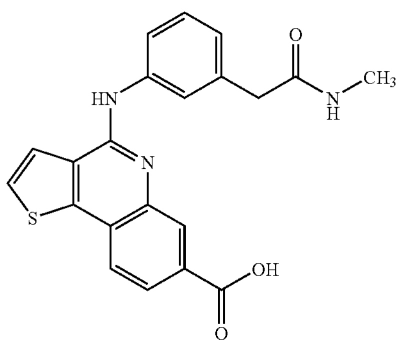 | 391.44 | 392[M + 1]+ |

Example 3

Processes for Synthesizing Compounds of Formulae IX, X, XI and XII

Process 1

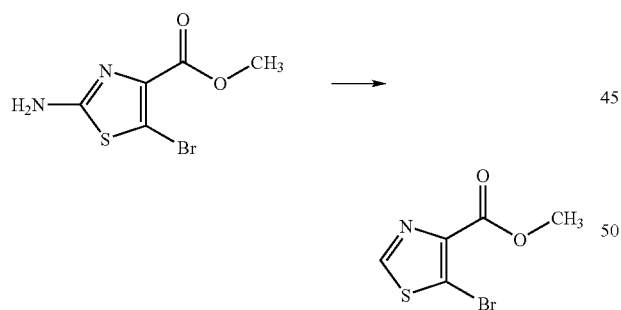

Methyl 2-amino-4-bromothiazole-4-carboxylate (1.0 eq, 100 mg, 0.42 mmol) was dissolved in anhydrous DMF (0.8 ml). The mixture was heated to 80° C. under nitrogen atmosphere. To the hot mixture, a solution of tert-Butyl nitrite (1.2 eq, 60 ul, 0.50 mmol) in DMF (0.8 ml) was added dropwise. After a few minutes, absence of gas evolution indicated completion of the reaction. The mixture was cooled down and poured onto a prepacked silica gel column. Flash chromatography using hexanes, then AcOEt/hexanes (2:8), provided methyl 5-bromothiazole-4-carboxylate as a yellow solid (49 mg, 53% yield). LCMS (ES): 95% pure, m/z 222 [M]+, 224 [M+2]+.

Process 2

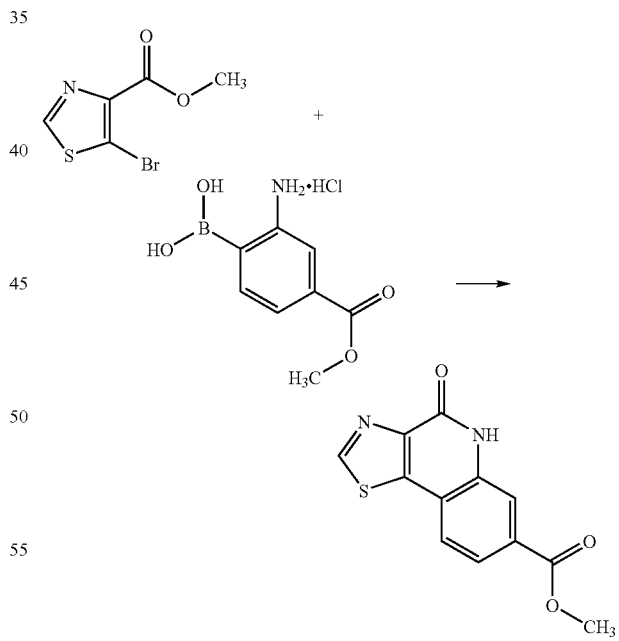

In a microwave vessel, methyl 5-bromothiazole-4-carboxylate (1.0 eq, 97 mg, 0.44 mmol), 2-amino-3-methoxycarbonyl phenyl boronic acid HCl (1.1 eq, 111 mg, 0.48 mmol), sodium acetate (3.0 eq, 107 mg, 1.31 mmol) and PdCl$_2$(dppf) (0.05 eq, 11 mg, 0.022 mmol) were mixed together in anhydrous DMF (1 ml). The mixture was heated in a microwave oven at 120° C. for 10 nm. Water was added and the material extracted with CH$_2$Cl$_2$. The combined extracts were washed with brine, dried over Na$_2$SO$_4$ and the solvents removed by evaporation. The material was dissolved in a mixture of CH$_2$Cl$_2$ and MeOH and the solution filtered through a pad of celite. Evaporation of the volatiles afforded crude methyl 4-oxo-4,5-dihydrothiazolo[4,5-c]quinoline-7-carboxylate as a black solid (44 mg, 39% yield). A small part of the compound was subjected to preparative HPLC for analytical purpose. LCMS (ES): 95% pure, m/z 261 [M+1]$^+$.
Process 3

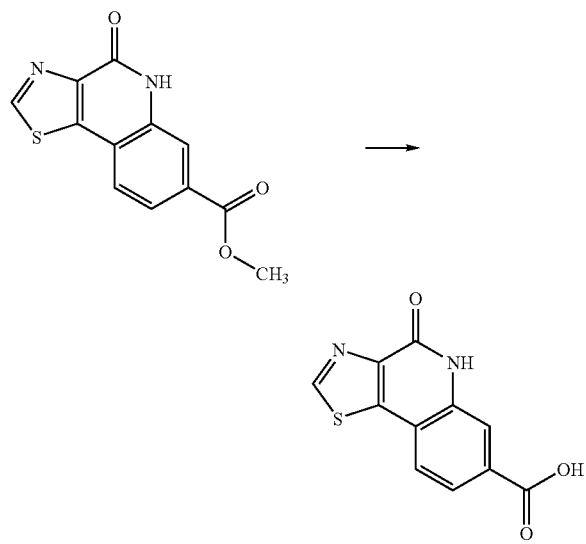

Methyl 4-oxo-4,5-dihydrothiazolo[4,5-c]quinoline-7-carboxylate (35 mg, 0.12 mmol) and LiOH (60 mg, 0.83 mmol) were stirred in a (1:1:1, v:v:v) mixture of THF, MeOH and water (0.6 ml) for 2 hours. 6N aqueous NaOH was added and the solution filtered through celite. The solution was acidified and the resulting solid filtered. Preparative HPLC purification and genevac evaporation provided 4-oxo-4,5-dihydrothiazolo[4,5-c]quinoline-7-carboxylic acid as a white solid (0.8 mg). LCMS (ES): 95% pure, m/z 247 [M+1]$^+$.
Process 4

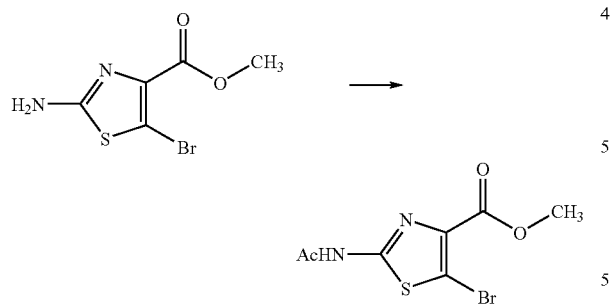

Methyl 2-amino-4-bromothiazole-4-carboxylate (1.0 eq, 2.0 g, 8.44 mmol) was dissolved in CH$_2$Cl$_2$ (4 ml). Acetic anhydride (1.5 eq, 1.2 ml, 12.66 mmol) and triethylamine (1.1 eq, 1.3 ml, 9.28 mmol) were added and the mixture stirred at 100° C. for one hour. The resulting solid was filtered, triturated in AcOEt and then filtered again. After drying, methyl 2-acetamido-5-bromothiazole-4-carboxylate was isolated as a beige solid (1.81 g, 77% yield). LCMS (ES): 95% pure, m/z 280 [M+1]$^+$. $^1$H NMR (CDCl$_3$, 400 MHz) δ 2.25 (s, 3H), 3.95 (s, 3H) ppm.

Process 5

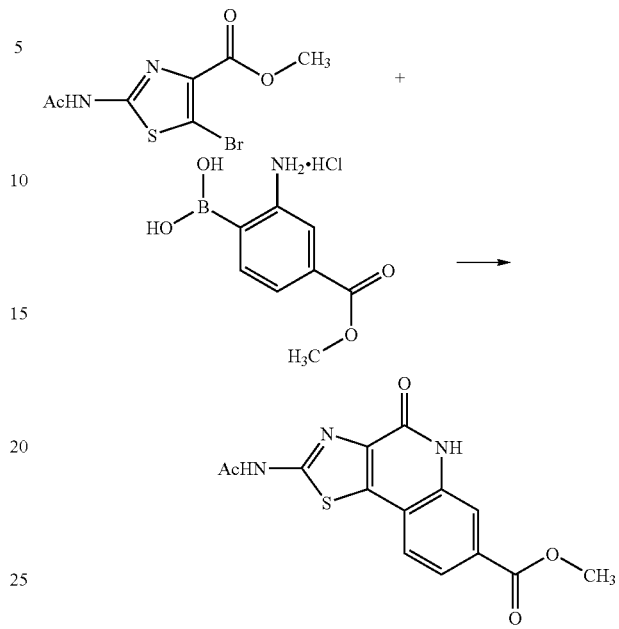

Methyl 2-acetamido-4-oxo-4,5-dihydrothiazolo[4,5-c]quinoline-7-carboxylate was prepared according to the procedure used in process 2, starting from methyl 2-acetamido-5-bromothiazole-4-carboxylate. Methyl 2-acetamido-4-oxo-4,5-dihydrothiazolo[4,5-c]quinoline-7-carboxylate was isolated as a black solid (106 mg, 37% yield). LCMS (ES): 95% pure, m/z 318 [M+1]$^+$.
Process 6

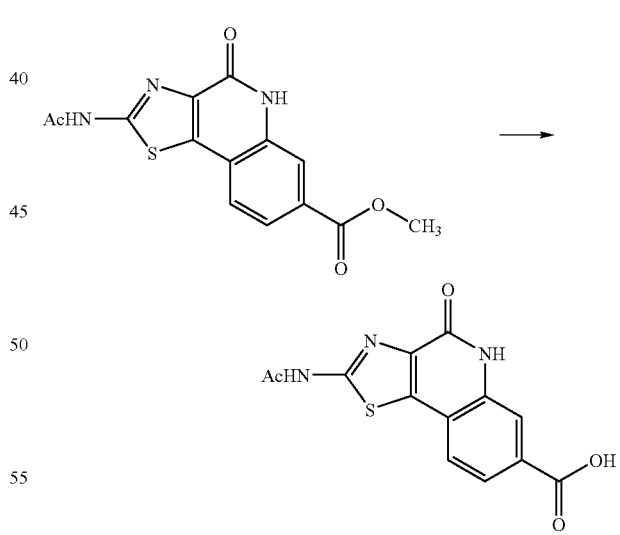

2-acetamido-4-oxo-4,5-dihydrothiazolo[4,5-c]quinoline-7-carboxylic acid was prepared according to the procedure in process 3, starting from. Methyl 2-acetamido-4-oxo-4,5-dihydrothiazolo[4,5-c]quinoline-7-carboxylate.-acetamido-4-oxo-4,5-dihydrothiazolo[4,5-c]quinoline-7-carboxylic acid was isolated as a black solid (14 mg, 44% yield). LCMS (ES): 95% pure, m/z 304 [M+1]$^+$, $^1$H NMR (DMSO-d$_6$, 400 MHz) δ 2.22 (s, 3H), 7.74 (dd, J=1.2, J=8.0, 1H), 7.89 (d, J=8.4, 1H), 8.03 (d, J=1.6, 1H), 12.07 (s, 1H), 12.80 (s, 1H) ppm.

Process 7

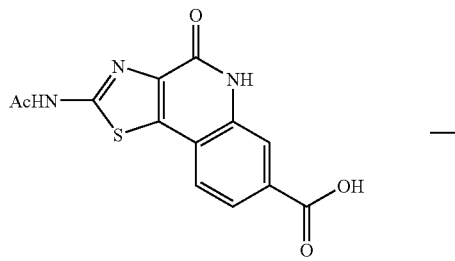

2-acetamido-4-oxo-4,5-dihydrothiazolo[4,5-c]quinoline-7-carboxylic acid (102 mg, 0.34 mmol) was stirred at 120° C. in aqueous 6N HCl overnight. Water was added and the compound was filtered and dried to provide 2-amino-4-oxo-4,5-dihydrothiazolo[4,5-c]quinoline-7-carboxylic acid as a black solid (76 mg, 86% yield). LCMS (ES): 95% pure, m/z 262 [M+1]$^+$, $^1$H NMR (DMSO-d$_6$, 400 MHz) δ 7.60 (d, J=8.4, 1H), 7.70 (dd, J=1.2, J=8.0, 1H), 7.99 (d, J=1.2, 1H), 11.94 (s, 1H) ppm.

Process 8

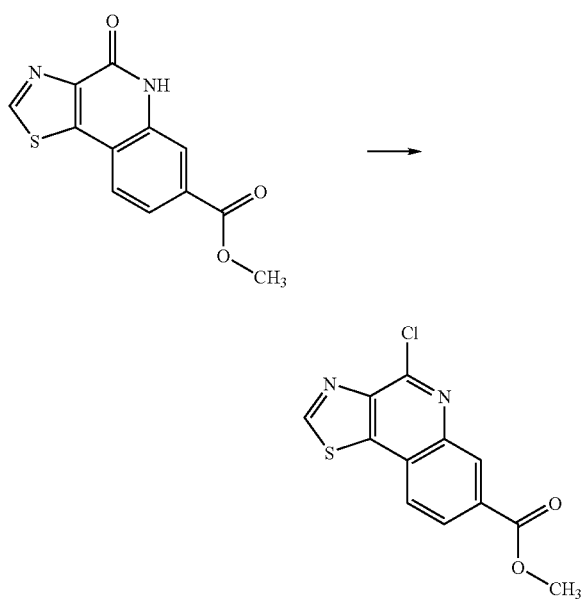

Methyl 4-oxo-4,5-dihydrothiazolo[4,5-c]quinoline-7-carboxylate (1.0 eq, 0.62 g, 2.38 mmol) was suspended in toluene. DIEA (1.5 eq, 122 ul, 3.57 mmol) and POCl$_3$ (2.3 eq, 507 ul, 5.47 mmol) were added and the mixture vigorously stirred at 120° C. for 1 hour. Water, ice and CH$_2$Cl$_2$ were added and the resulting emulsion filtered through celite. The organic phase was decanted and the aqueous phase further extracted with CH$_2$Cl$_2$. The combined organic extracts were dried over Na$_2$SO$_4$ and the solvent removed in vacuo to afford methyl 4-chlorothiazolo[4,5-c]quinoline-7-carboxylate (0.31 g, 47% yield). LCMS (ES): >90% pure, m/z 279[M+1]$^+$.

Process 9

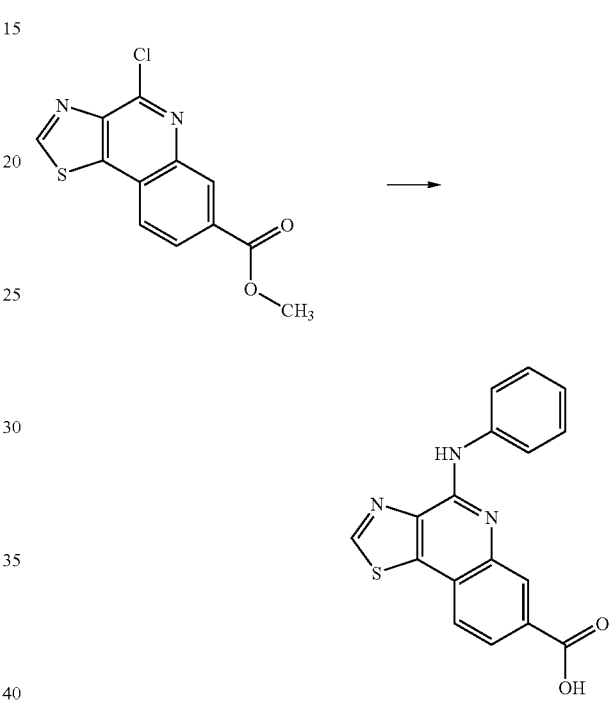

In a microwave vessel, methyl 4-chlorothiazolo[4,5-c]quinoline-7-carboxylate (1.0 eq, 23 mg, 0.084 mmol) and aniline (13 eq, 0.1 ml, 1.1 mmol) were mixed in NMP (0.1 ml). The mixture was heated in a microwave oven at 120° C. for 10 min. The intermediate ester was purified by preparative HPLC and isolated as a solid after genevac evaporation. The solid was stirred in a (1:1:1, v:v:v) mixture of THF, MeOH and water (0.6 ml) with LiOH (41 mg) at room temperature for 2 hours. HCl and water were added, the organic solvents were evaporated and the solution allowed resting for 2 hours. The precipitate that slowly formed was filtered and dried to afford 4-(phenylamino)thiazolo[4,5-c]quinoline-7-carboxylic acid as a solid (8% yield over 2 steps). LCMS (ES): >95% pure, m/z 322 [M+1]$^+$.

Representative analogs (Table 9) were prepared by the same process using methyl 4-chlorothiazolo[4,5-c]quinoline-7-carboxylate and appropriate amines. The reaction temperatures used for the microwave reactions ranged from 120° C. to 180° C. After synthesis of the final compounds, the materials were isolated by preparative HPLC/genevac evaporation. In some instances, the materials precipitated after acidification and were isolated by filtration.

TABLE 9

| Structure | MW | LCMS(ES)m/z |
|---|---|---|
| (3-ethynylphenylamino thiazoloquinoline carboxylic acid) | 345.37 | 346[M + 1]+ |
| (3-fluorophenylamino thiazoloquinoline carboxylic acid) | 339.34 | 340[M + 1]+ |
| (4-fluoro-3-chlorophenylamino thiazoloquinoline carboxylic acid) | 373.79 | 374[M + 1]+ |
| (3-methoxyphenylamino thiazoloquinoline carboxylic acid) | 351.38 | 352[M + 1]+ |

Example 4

Modulation of CK2 and PARP Activity in Cell-Free In Vitro Assays

Modulatory activity of compounds described herein was assessed in vitro in cell-free CK2 assays. Modulatory activity of compounds described herein also are assessed in vitro in cell-free PARP assays. These assays are described hereafter.

CK2 Assay

Test compounds in aqueous solution were added at a volume of 10 microliters, to a reaction mixture comprising 10 microliters Assay Dilution Buffer (ADB; 20 mM MOPS, pH 7.2, 25 mM beta-glycerolphosphate, 5 mM EGTA, 1 mM sodium orthovanadate and 1 mM dithiothreitol), 10 microliters of substrate peptide (RRRDDDSDDD, dissolved in ADB at a concentration of 1 mM), 10 microliters of recombinant human CK2 (25 ng dissolved in ADB; Upstate). Reactions were initiated by the addition of 10 microliters of ATP Solution (90% 75 mM $MgCl_2$, 75 micromolar ATP dissolved in ADB; 10% [$\gamma$-$^{33}$P]ATP (stock 1 mCi/100 μl; 3000 Ci/mmol (Perkin Elmer) and maintained for 10 minutes at 30 degrees C. The reactions were quenched with 100 microliters of 0.75% phosphoric acid, then transferred to and filtered through a phosphocellulose filter plate (Millipore). After washing each well 5 times with 0.75% phosphoric acid, the plate was dried under vacuum for 5 min and, following the addition of 15 ul of scintilation fluid to each well, the residual radioactivity was measured using a Wallac luminescence counter.

PARP Assay

PARP assays are conducted using a chemiluminescent PARP assay kit (Trevigen). Briefly, reactions are performed in Histone-coated strip wells, by adding 10 microliters test compound dissolved in 1×PARP Buffer (prepared by mixing 20×PARP buffer diluted with high-purity water) and 15 microliters diluted PARP-HSA enzyme (diluted in 1×PARP buffer, 0.1 unit per well) to 25 microliters PARP cocktail (prepared from 10×PARP cocktail and 10× activated DNA, both 2.5 microliters per well and 20 microliters per well of 1×PARP buffer). The reactions are incubated at ambient temperature for 60 minutes, then the liquid was removed. After washing the wells four times with PBS (200 ul), 50 microliters of STREP-HRP (Horseradish Peroxidase) solution (diluted 500-fold in 1× Strep-Diluent) was added and the reactions were allowed to incubate for 30 minutes at ambient temperature. The liquid was removed and, after washing the wells four times with PBS (200 ul), 50 microliters each of PeroxyGlo A and B (Chemiluminescent Horseradish Peroxidase substrates) are added and the resulting chemiluminescence quantified on the SpectraMax M5 plate reader.

Tables 10 to 15 show modulatory effects of compounds on CK2 activity.

TABLE 10

| Compound | CK2 Inhibition | PARP Inhibition |
|---|---|---|
| (phenanthridinone carboxylic acid) | 28% (at 5 μM) | $IC_{50}$ = 0.070 μM |

TABLE 10-continued

| Compound | CK2 Inhibition | PARP Inhibition |
|---|---|---|
| (6-oxo-5-(3-hydroxypropyl)-5,6-dihydrophenanthridine-8-carboxylic acid) | 29% (at 5 µM) | $IC_{50} = 0.060$ µM |
| (6-(3-hydroxypropoxy)phenanthridine-8-carboxylic acid) | 38% (at 5 µM) | $IC_{50} = 0.40$ µM |
| (6-oxo-8-(tetrazol-5-yl)-5,6-dihydrophenanthridine) | $IC_{50} = 2$ µM | $IC_{50} = 0.030$ µM |
| (pyrido-fused phenanthridinone carboxylic acid) | $IC_{50} = 0.18$ µM | $IC_{50} = 1.0$ µM |
| (pyrido-fused phenanthridinone methyl ester) | $IC_{50} = 2.5$ µM | $IC_{50} = 0.80$ µM |

TABLE 10-continued

| Compound | CK2 Inhibition | PARP Inhibition |
|---|---|---|
| (6-(2-(dimethylamino)ethylamino)phenanthridine-8-carboxylic acid) | $IC_{50} = 1.0$ µM | 15% (at 1 µM) |
| (6-(phenylamino)phenanthridine-8-carboxylic acid) | $IC_{50} = 1.6$ µM | 9% (at 1 µM) |
| (6-oxo-5-(3-hydroxypropyl)-8-(tetrazol-5-yl)-5,6-dihydrophenanthridine) | 16% (at 2.5 µM) | 33% (at 1 µM) |
| | $IC_{50} = 0.013$ µM | |
| (pyrido-fused 6-(phenylamino)phenanthridine-carboxylic acid) | | |

TABLE 10-continued

| Compound | CK2 Inhibition | PARP Inhibition |
|---|---|---|
| [structure: 6-[(2-dimethylaminoethyl)amino]benzo[c][2,7]naphthyridine-9-carboxylate] | 96% (at 1 µM) | |
| [structure: 9-(tetrazol-5-yl)-6H-benzo[c][2,7]naphthyridin-5-one] | 46% (at 1 µM) | |
| [structure: 6-(phenylamino)-9-(tetrazol-5-yl)-5,6-dihydrobenzo[c][2,7]naphthyridine] | 78% (at 1 µM) | |
| [structure: 6-[(2-dimethylaminoethyl)amino]-9-(tetrazol-5-yl)benzo[c][2,7]naphthyridine] | 62% (at 1 µM) | |

TABLE 11

| Structure | CK2 IC50 (uM) | CK2% inhibition 5 uM | 2.5 uM | 1.0 uM |
|---|---|---|---|---|
| [structure: 4-(3-hydroxypropoxy)thieno[3,2-c]quinoline-8-carboxylic acid] | 1.2 | | | |
| [structure: methyl 4-chlorothieno[3,2-c]quinoline-8-carboxylate] | >10 | | | |

TABLE 11-continued

| Structure | CK2 IC50 (uM) | CK2% inhibition | | |
|---|---|---|---|---|
| | | 5 uM | 2.5 uM | 1.0 uM |
| 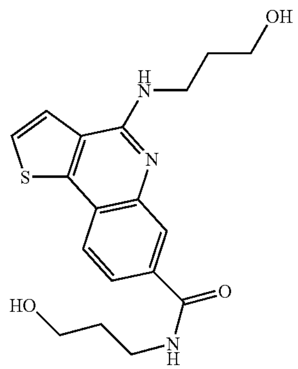 | >10 | | | |
| 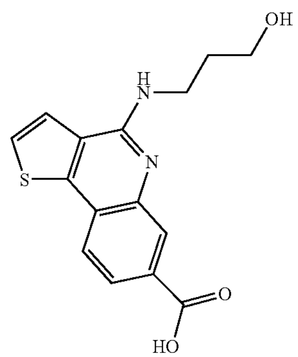 | 0.67 | | | |
| 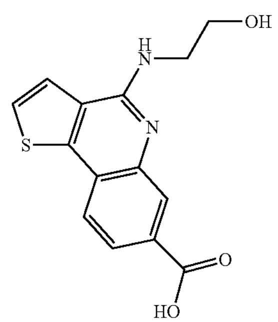 | 1.1 | | | |
| 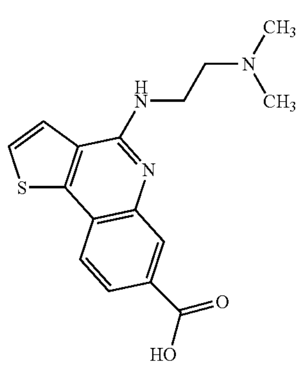 | 0.27 | | | |

TABLE 11-continued

| Structure | CK2 IC50 (uM) | CK2% inhibition | | |
|---|---|---|---|---|
| | | 5 uM | 2.5 uM | 1.0 uM |
| (4-((pyridin-2-ylmethyl)amino)thieno[3,2-c]quinoline-8-carboxylic acid) | 0.95 | | | |
| (4-(phenylamino)thieno[3,2-c]quinoline-8-carboxylic acid) | 0.32 | | | |
| (4-((pyridin-3-ylmethyl)amino)thieno[3,2-c]quinoline-8-carboxylic acid) | 0.9 | | | |
| (4-((2-morpholinoethyl)amino)thieno[3,2-c]quinoline-8-carboxylic acid) | 1.22 | | | |

TABLE 11-continued
| Structure | CK2 IC50 (uM) | CK2% inhibition | | |
|---|---|---|---|---|
| | | 5 uM | 2.5 uM | 1.0 uM |
| 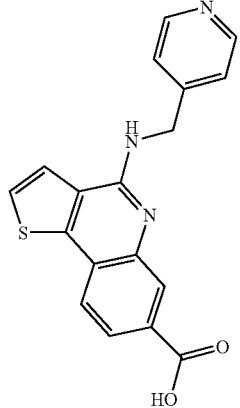 | 0.43 | | | |
| 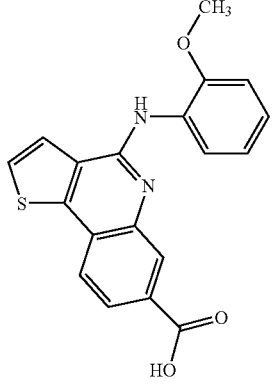 | 0.55 | | | |
| 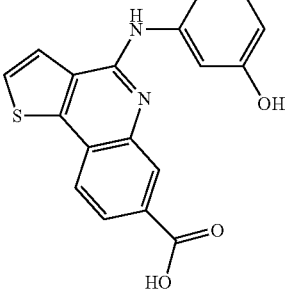 | 0.35 | | | |
| 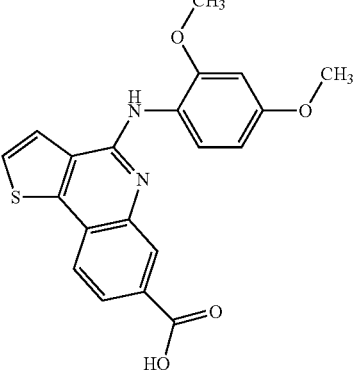 | 2 | | | |

TABLE 11-continued

| Structure | CK2 IC50 (uM) | CK2% inhibition 5 uM | 2.5 uM | 1.0 uM |
|---|---|---|---|---|
| (pyrrolidinyl-ethylamino thieno-quinoline carboxylic acid) | | 84% | | |
| (4-chloro thieno-quinoline) | >5 | | | |
| (4-chloro cyano thieno-quinoline) | | 63% | | |
| (4-phenylamino thieno-quinoline) | | 0% | | |
| (4-(dimethylaminoethylamino) thieno-quinoline) | | 0% | | |

TABLE 11-continued
| Structure | CK2 IC50 (uM) | CK2% inhibition | | |
|---|---|---|---|---|
| | | 5 uM | 2.5 uM | 1.0 uM |
| 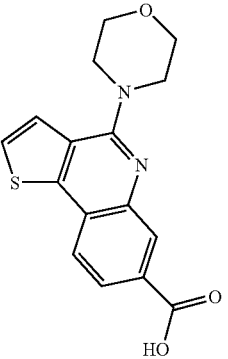 | | 28% | | |
| 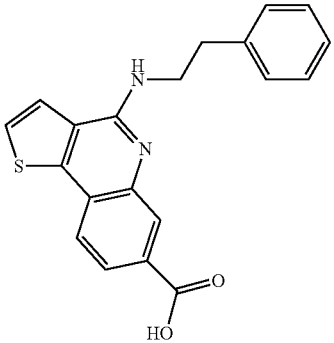 | | 78% | | |
| 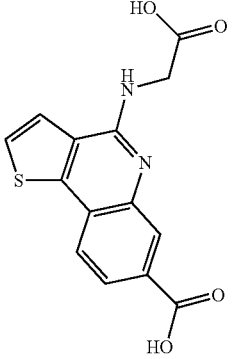 | | 0% | | |
| 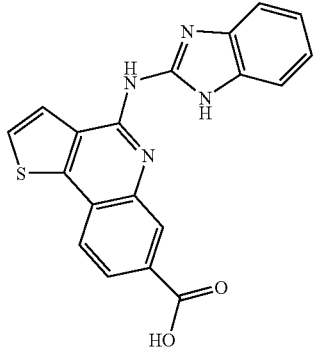 | | 0% | | |

TABLE 11-continued
| Structure | CK2 IC50 (uM) | CK2% inhibition | | |
|---|---|---|---|---|
| | | 5 uM | 2.5 uM | 1.0 uM |
| | | | | 29% |
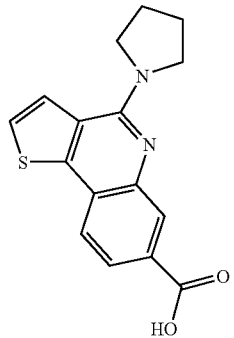
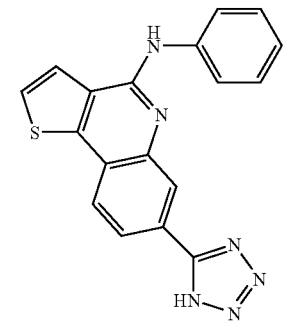
0.19
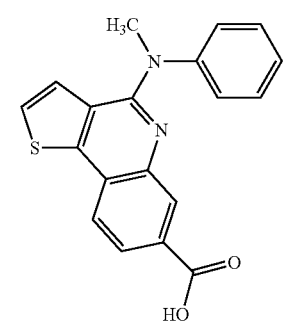
1.5
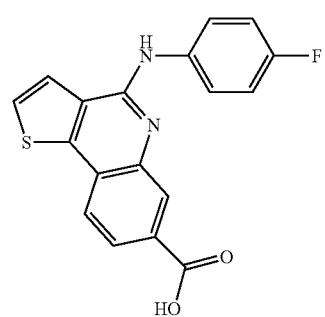
0.31

TABLE 11-continued

| Structure | CK2 IC50 (uM) | CK2% inhibition 5 uM | 2.5 uM | 1.0 uM |
|---|---|---|---|---|
| [4-(3-chloro-4-fluoroanilino)thieno[3,2-c]quinoline-8-carboxylic acid] | 0.15 | | | |
| [4-(2-methylanilino)thieno[3,2-c]quinoline-8-carboxylic acid] | 1.1 | | | |
| [4-(3-methoxyanilino)thieno[3,2-c]quinoline-8-carboxylic acid] | 0.12 | | | |
| [4-(N-ethyl-N-phenylamino)thieno[3,2-c]quinoline-8-carboxylic acid] | | | | 18% |

TABLE 11-continued
| Structure | CK2 IC50 (uM) | CK2% inhibition | | |
|---|---|---|---|---|
| | | 5 uM | 2.5 uM | 1.0 uM |
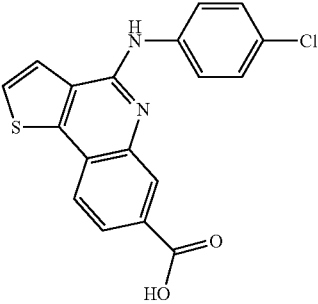
0.21
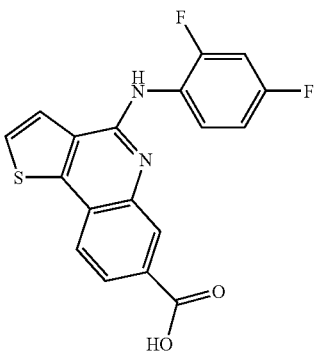
0.67
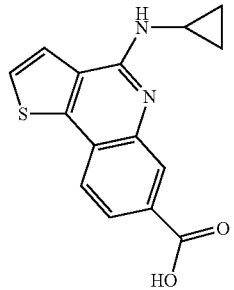
0.97
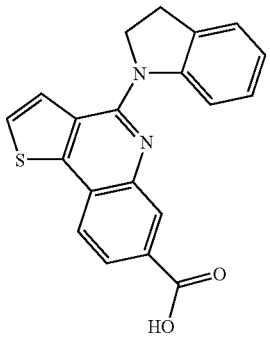
0.58

TABLE 11-continued

| Structure | CK2 IC50 (uM) | CK2% inhibition | | |
|---|---|---|---|---|
| | | 5 uM | 2.5 uM | 1.0 uM |
| | 0.43 | | | |
| 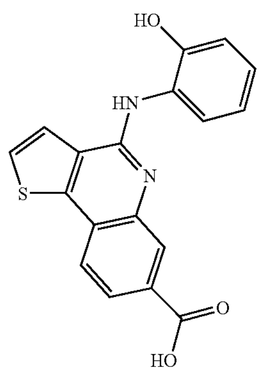 | 0.82 | | | |
| 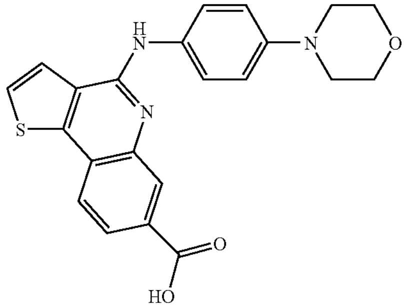 | 1.17 | | | |
| | 0.43 | | | |

TABLE 11-continued
| Structure | CK2 IC50 (uM) | CK2% inhibition | | |
|---|---|---|---|---|
| | | 5 uM | 2.5 uM | 1.0 uM |
| 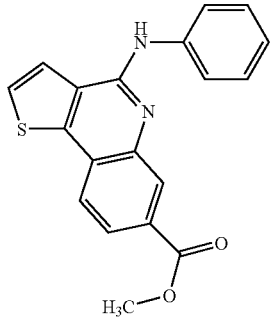 | | 5% | | |
| 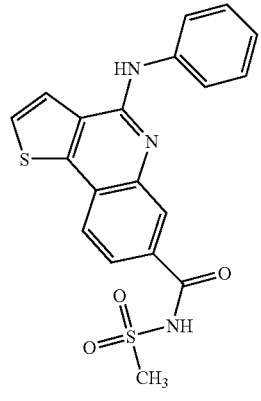 | | 0% | | |
| 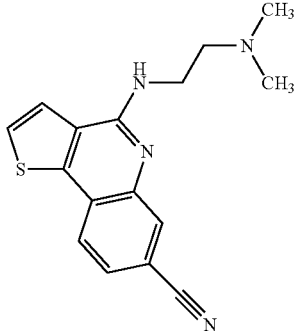 | | 0% | | |
| 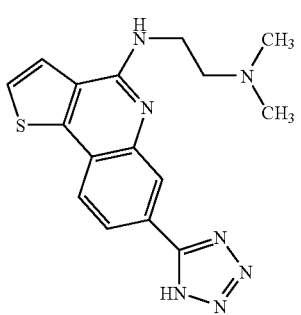 | | 70% | | |

TABLE 11-continued
| Structure | CK2 IC50 (uM) | CK2% inhibition | | |
|---|---|---|---|---|
| | | 5 uM | 2.5 uM | 1.0 uM |
| 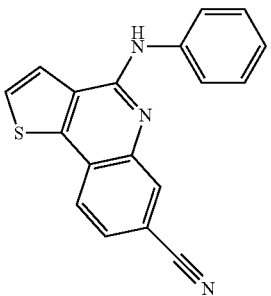 | | 0% | | |
| 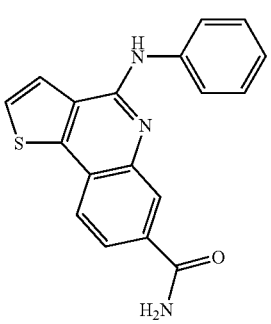 | | 0% | | |
| 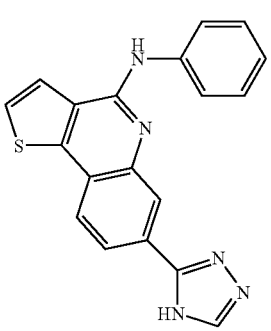 | | 0% | | |
| 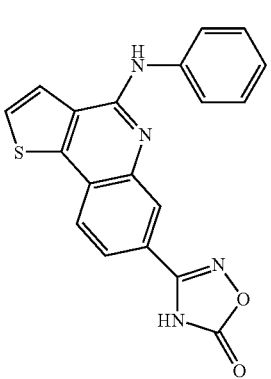 | | 0% | | |

TABLE 11-continued

| Structure | CK2 IC50 (uM) | CK2% inhibition | | |
|---|---|---|---|---|
| | | 5 uM | 2.5 uM | 1.0 uM |
| | | 71% | | |
| | | 84% | | |
| | | 80% | | |
| | | 77% | | |

TABLE 11-continued

| Structure | CK2 IC50 (uM) | CK2% inhibition | | |
|---|---|---|---|---|
| | | 5 uM | 2.5 uM | 1.0 uM |
| | | | | 75% |
| | | | | 61% |
| | | | | 65% |
| | | | | 68% |

TABLE 11-continued

| Structure | CK2 IC50 (uM) | CK2% inhibition 5 uM | 2.5 uM | 1.0 uM |
|---|---|---|---|---|
| (structure) | | | | 77% |
| (structure) | | | | 60% |
| (structure) | | | | |
| (structure) | | | | |

TABLE 11-continued

| Structure | CK2 IC50 (uM) | CK2% inhibition | | |
|---|---|---|---|---|
| | | 5 uM | 2.5 uM | 1.0 uM |

TABLE 11-continued
| | CK2 IC50 | CK2% inhibition | | |
|---|---|---|---|---|
| Structure | (uM) | 5 uM | 2.5 uM | 1.0 uM |
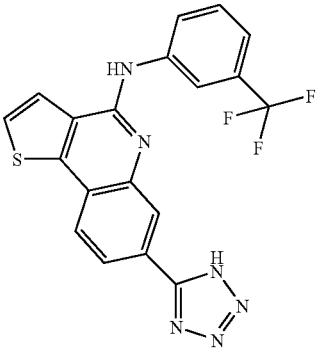
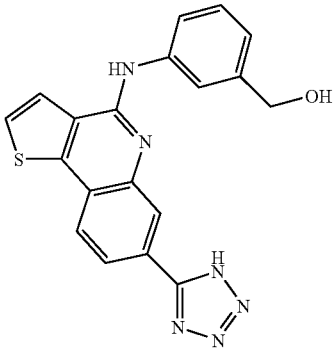
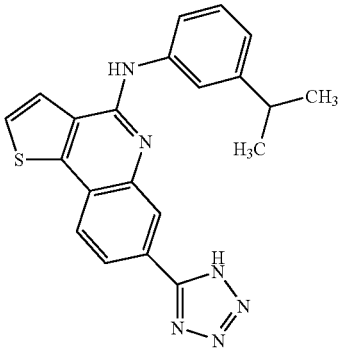
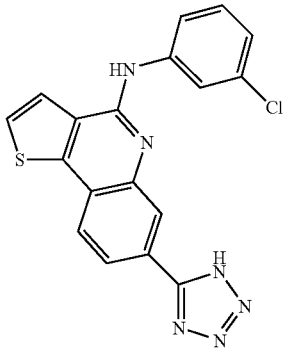

TABLE 11-continued
| Structure | CK2 IC50 (uM) | CK2% inhibition | | |
|---|---|---|---|---|
| | | 5 uM | 2.5 uM | 1.0 uM |
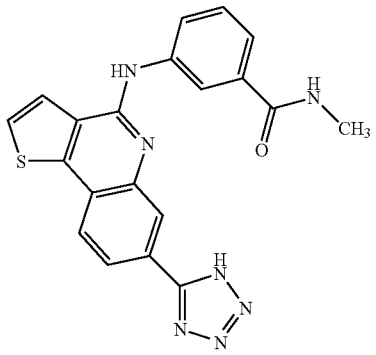
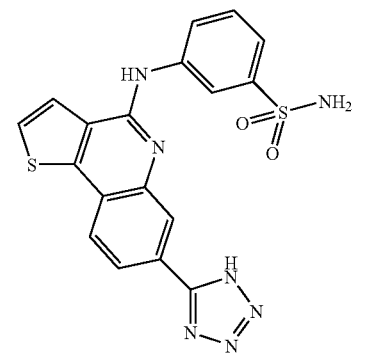
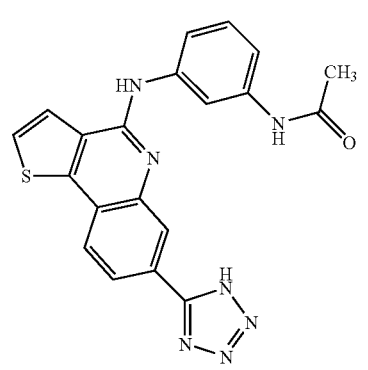
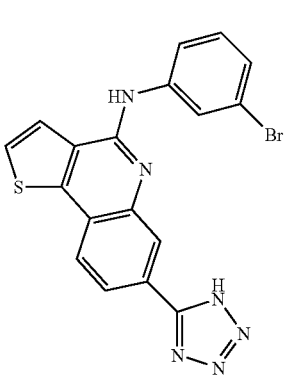

TABLE 11-continued
| Structure | CK2 IC50 (uM) | CK2% inhibition | | |
|---|---|---|---|---|
| | | 5 uM | 2.5 uM | 1.0 uM |
| 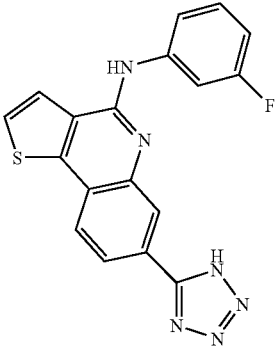 | | | | |
| 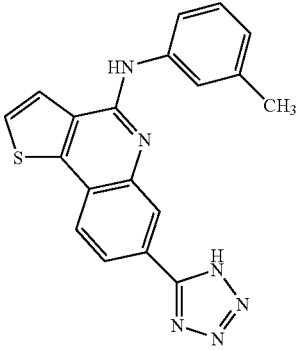 | | | | |
| 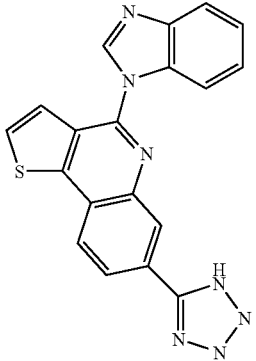 | | | | |
Table 12 shows modulatory effects of compounds on PARP and CK2.
TABLE 12
| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 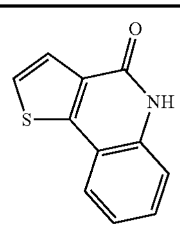 | 0 | — | — | 0 | — |

TABLE 12-continued
| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 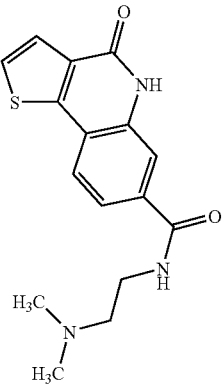 | 85 | — | — | — | — |
| 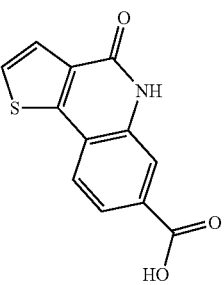 | 90 | 58 | 1 | 77 | 4 |
| 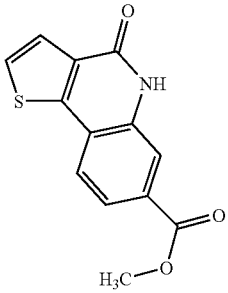 | 84 | 27 | — | 17 | |
| 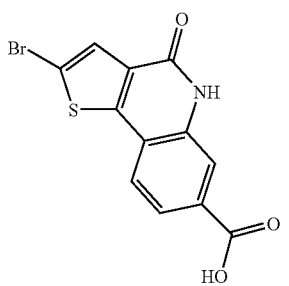 | 84 | 39 | — | 5 | |

TABLE 12-continued
| Structure | PARP % inhib @ 20 uM | PARP % inhib @ 1 uM | PARP IC50 (um) | CK2 % inhib @ 10 uM | CK2 IC50 (uM) |
| --- | --- | --- | --- | --- | --- |
| 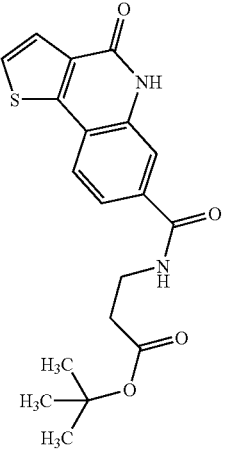 | 82 | 40 | — | 8 | — |
| 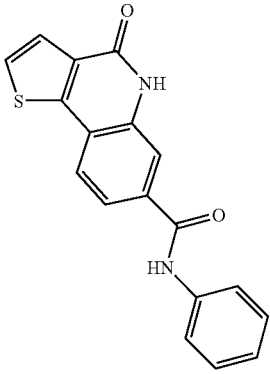 | 22 | 0 | — | 22 | — |
| 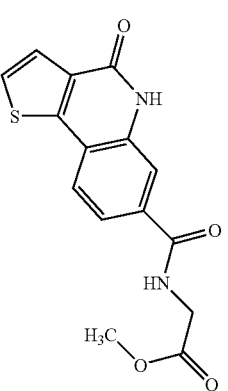 | 93 | 47 | — | 10 | — |

TABLE 12-continued
| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 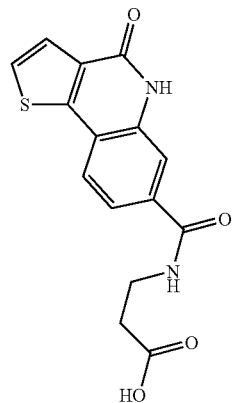 | 95 | 35 | — | 16 | |
| 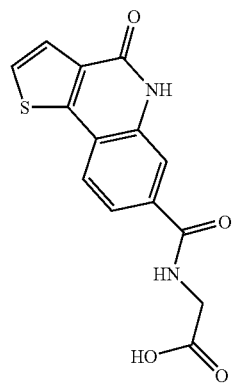 | 97 | 31 | — | 12 | |
| 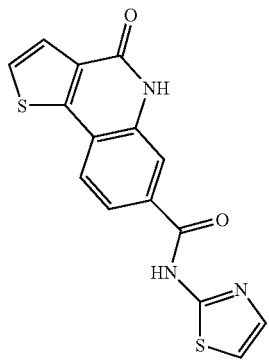 | 52 | 0 | — | 10 | |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 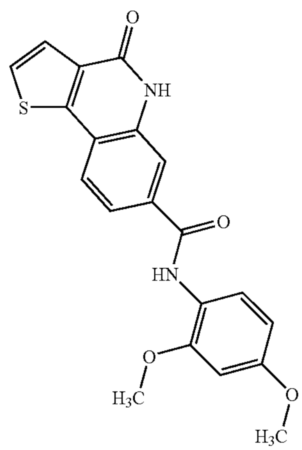 | 32 | 0 | — | | 3 |
| 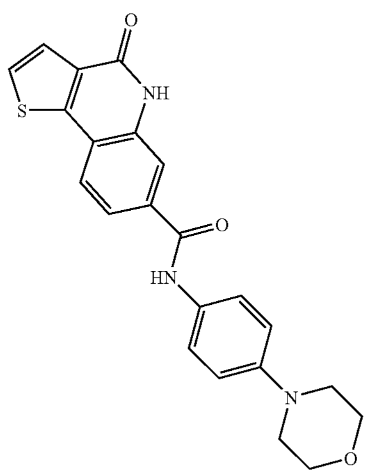 | 37 | 0 | — | | −3 |
| 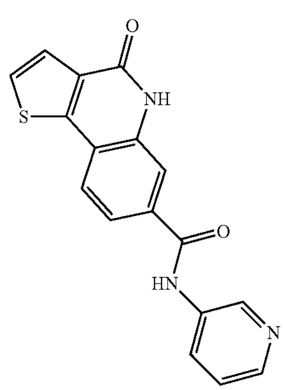 | 62 | 0 | — | | −9 |

TABLE 12-continued
| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 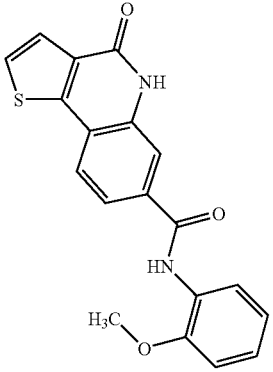 | 24 | 0 | — | −7 | |
| 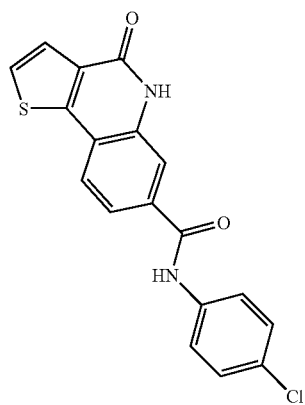 | 55 | 0 | — | −10 | |
| 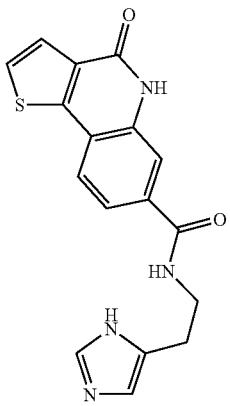 | 97 | 83 | 0.2 | 7 | |

TABLE 12-continued
| Structure | PARP % inhib @ 20 uM | PARP % inhib @ 1 uM | PARP IC50 (um) | CK2 % inhib @ 10 uM | CK2 IC50 (uM) |
| --- | --- | --- | --- | --- | --- |
| 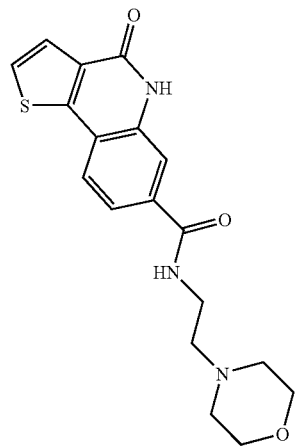 | 96 | 77 | 0.5 | −9 | |
| 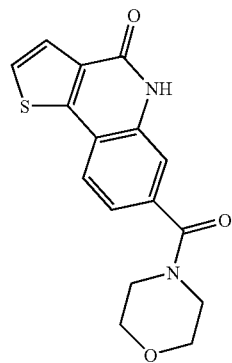 | 95 | 82 | 0.4 | 2 | |
| 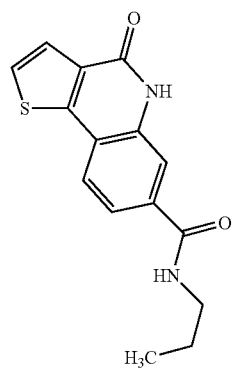 | 88 | 65 | 1 | −34 | |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 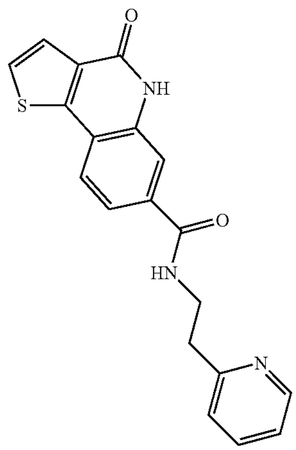 | 83 | 55 | 1 | −24 | |
| 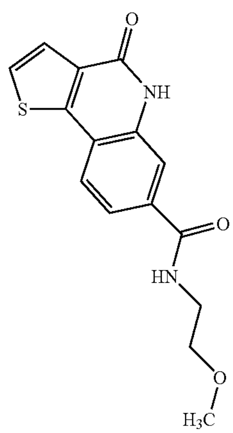 | 93 | 65 | 0.4 | −19 | |
| 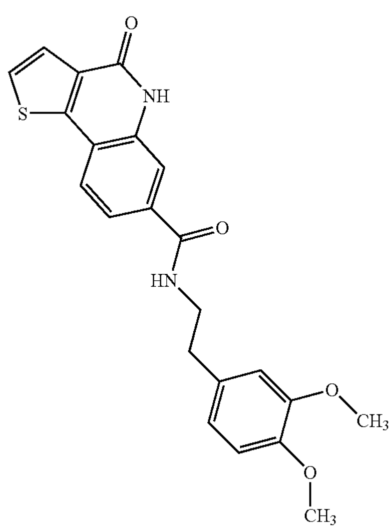 | 67 | 15 | — | −22 | |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| *(structure)* | 97 | 89 | 0.2 | 3 | |
| *(structure)* | 94 | 71 | 0.3 | 7 | — |
| *(structure)* | 90 | 69 | 0.5 | 0 | — |
| *(structure)* | — | 36 | — | 14 | — |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| | — | — | — | −1 | — |
| | — | 24 | — | 5 | — |
| | — | — | — | −16 | — |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| (structure) | — | 72 | 0.3 | −25 | — |
| (structure) | — | 49 | — | 10 | — |
| (structure) | — | — | — | 1 | — |

TABLE 12-continued
| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 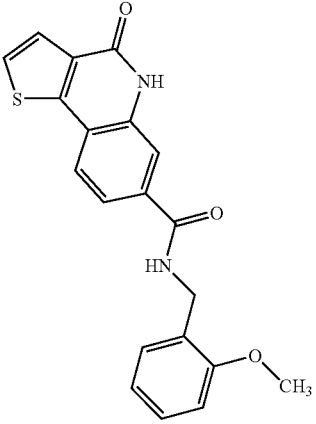 | — | 27 | — | 8 | — |
| 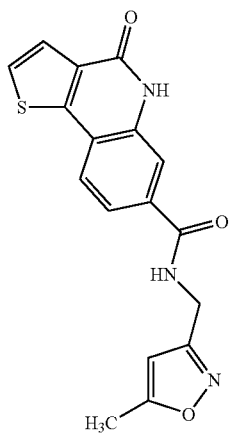 | — | 67 | 0.5 | −13 | — |
| 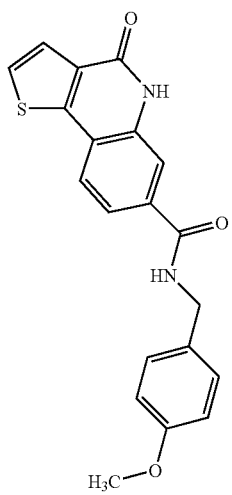 | — | 45 | — | 1 | — |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| | — | 71 | 1 | 3 | — |
| | — | 64 | 0.5 | 1 | — |
| | — | 75 | 1 | −13 | — |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| (structure) | — | 71 | — | −24 | — |
| (structure) | — | 29 | — | −1 | — |
| (structure) | — | 96 | 0.03 | −27 | — |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| (structure: thieno[3,2-c]quinolin-4(5H)-one with 7-carbonyl-(4-aminopiperidine)) | — | 96 | 0.02 | −3 | — |
| (structure: thieno[3,2-c]quinolin-4(5H)-one with 7-carbonyl-NH-(2-carboxyphenyl)) | — | 12 | — | 41 | — |
| (structure: thieno[3,2-c]quinolin-4(5H)-one-7-carboxamide) | — | 79 | 0.06 | −14 | — |
| (structure: 7-(hydroxymethyl)thieno[3,2-c]quinolin-4(5H)-one) | — | 74 | 0.4 | 3 | — |

TABLE 12-continued

| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| *(thieno-quinolinone with N-propyl-OH and COOH)* | — | 21 | — | 48 | 2.8 |
| *(thieno-quinolinone with CN)* | — | 51 | 0.5 | −5 | — |
| *(thieno-quinolinone with tetrazole)* | — | 39 | — | 86 | 0.9 |
| *(thieno-quinolinone with N-CH2CH2-N(CH3)2 and COOH)* | — | 5 | — | 44 | 12.5 |
| *(chloro-thieno-quinoline with methyl ester)* | — | 18 | — | 18 | — |

TABLE 12-continued
| Structure | PARP % inhib @ 20 uM | PARP % inhib @ 1 uM | PARP IC50 (um) | CK2 % inhib @ 10 uM | CK2 IC50 (uM) |
|---|---|---|---|---|---|
| 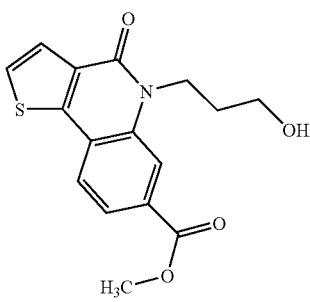 | — | 40 | — | | |
TABLE 13
| Structure | CK2: IC50 (uM) (15 uM ATP) | CK2: IC50 (uM) (20 um ATP) |
|---|---|---|
| 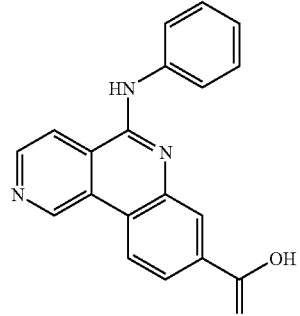 | 0.006 | 0.01 |
| 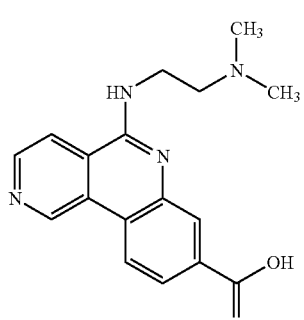 | 0.025 | 0.019 |
| 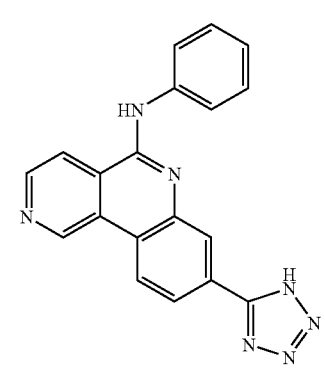 | 0.07 | 0.06 |

TABLE 13-continued

| Structure | CK2: IC50 (uM) (15 uM ATP) | CK2: IC50 (uM) (20 um ATP) |
|---|---|---|
| 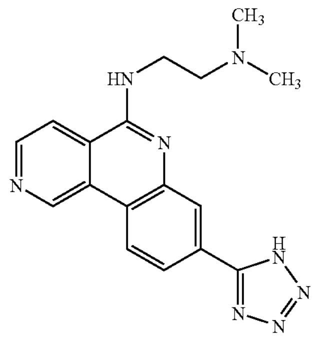 | 0.311 | 0.13 |
| 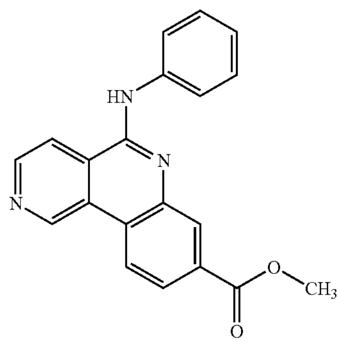 | 0.113 | 0.2 |
| | 0.004 | 0.007 |
| | 0.004 | 0.006 |

TABLE 13-continued
| Structure | CK2: IC50 (uM) (15 uM ATP) | CK2: IC50 (uM) (20 um ATP) |
|---|---|---|
| 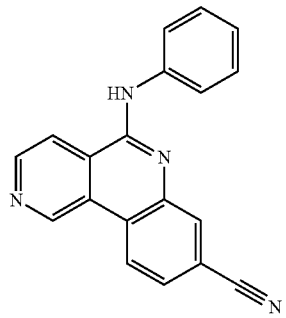 | | |
| 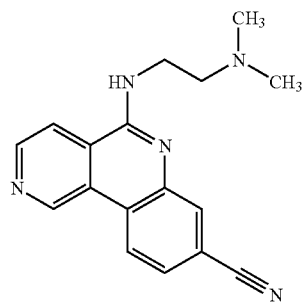 | 1.469 | 1.661 |
| 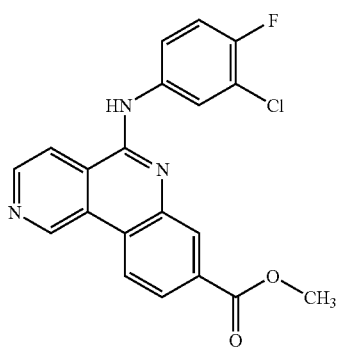 | | |
| 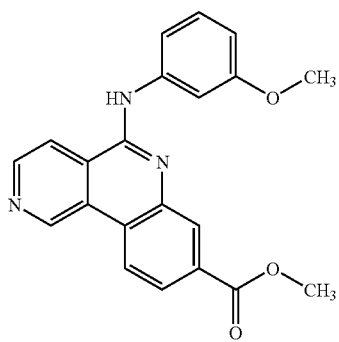 | | |

TABLE 13-continued

| Structure | CK2: IC50 (uM) (15 uM ATP) | CK2: IC50 (uM) (20 um ATP) |
|---|---|---|
| [structure: methyl ester, 4-fluoro-3-chloroanilino pyrimido-quinoline] | | |
| [structure: carboxylic acid, 4-fluoro-3-chloroanilino pyrimido-quinoline] | | 0.01 |
| [structure: phenylamino pyrido-quinoline with 3-methyl-1,2,4-oxadiazole] | | |
| [structure: 3-fluoroanilino pyrido-quinoline carboxylic acid] | | 0.005 |

TABLE 13-continued

| Structure | CK2: IC50 (uM) (15 uM ATP) | CK2: IC50 (uM) (20 um ATP) |
|---|---|---|
| 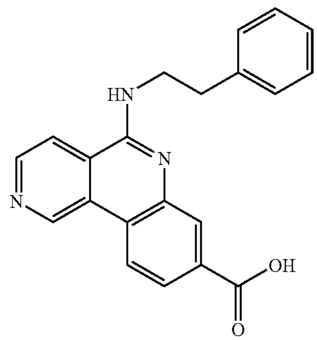 | 0.003 | |
| 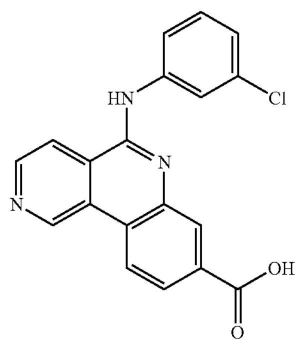 | 0.002 | |
| 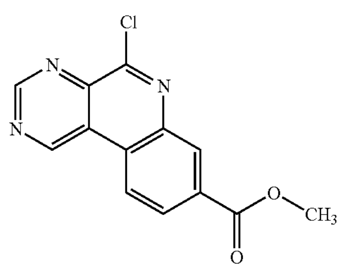 | 0.651 | |
| 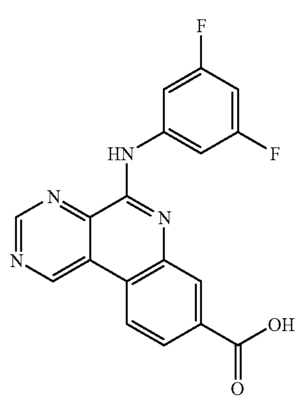 | 0.006 | |

TABLE 13-continued

| Structure | CK2: IC50 (uM) (15 uM ATP) | CK2: IC50 (uM) (20 um ATP) |
|---|---|---|
| 3-fluorophenylamino pyrimido-quinoline carboxylic acid | 0.006 | |
| 3-chlorophenylamino pyrimido-quinoline carboxylic acid | 0.007 | |
| 3-ethynylphenylamino pyrimido-quinoline carboxylic acid | 0.006 | |
| 3-fluorophenylamino pyrido-quinoline tetrazole | 0.047 | |

TABLE 13-continued

| Structure | CK2: IC50 (uM) (15 uM ATP) | CK2: IC50 (uM) (20 um ATP) |
|---|---|---|
| 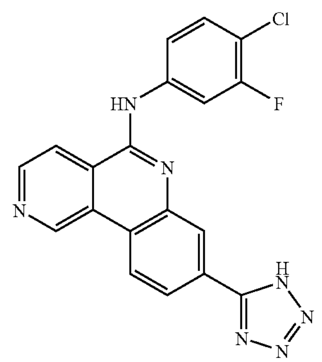 | 0.052 | |
| 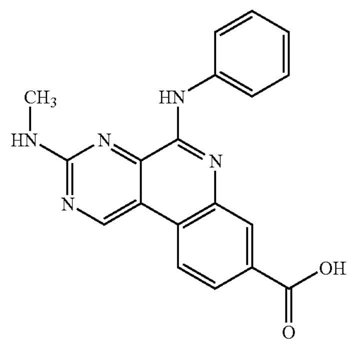 | 0.019 | |
| 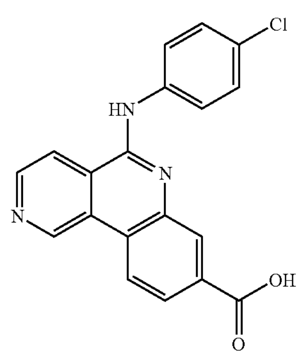 | 0.007 | |
| 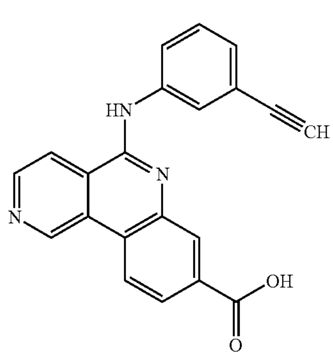 | 0.003 | |

TABLE 13-continued

| Structure | CK2: IC50 (uM) (15 uM ATP) | CK2: IC50 (uM) (20 um ATP) |
|---|---|---|
| 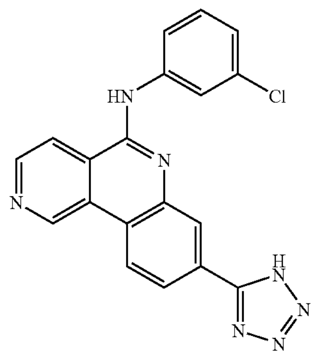 | 0.045 | |
| 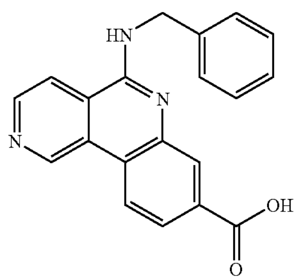 | 0.009 | |
| 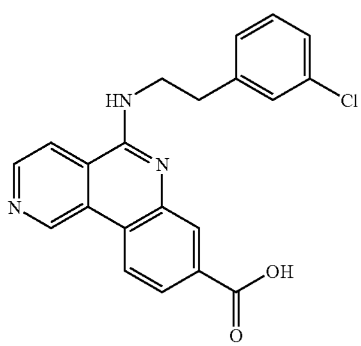 | 0.005 | |
| 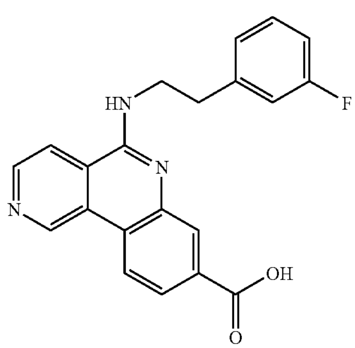 | 0.007 | |

TABLE 13-continued

| Structure | CK2: IC50 (uM) (15 uM ATP) | CK2: IC50 (uM) (20 um ATP) |
|---|---|---|
| 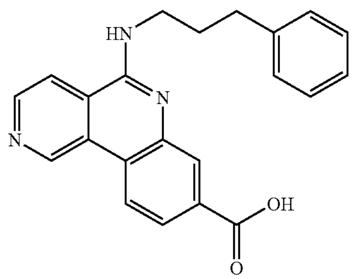 | 0.016 | |
| 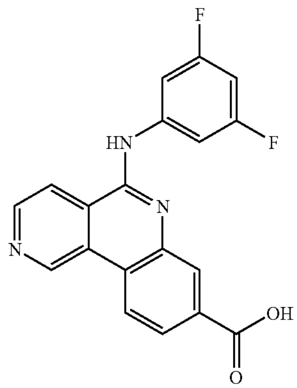 | 0.005 | |
| 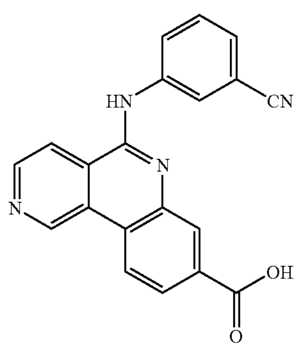 | 0.004 | |
| 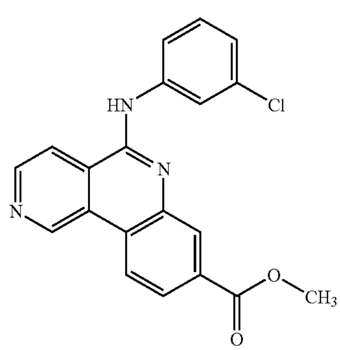 | >0.5 | |

TABLE 13-continued

| Structure | CK2: IC50 (uM) (15 uM ATP) | CK2: IC50 (uM) (20 um ATP) |
|---|---|---|
| | >0.5 | |
| | >0.5 | |
| | >0.5 | |
| 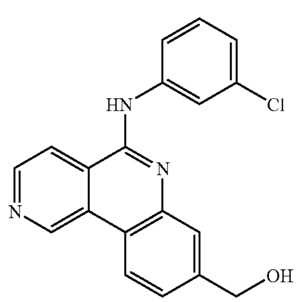 | 0.711 | |

TABLE 13-continued

| Structure | CK2: IC50 (uM) (15 uM ATP) | CK2: IC50 (uM) (20 um ATP) |
|---|---|---|
| 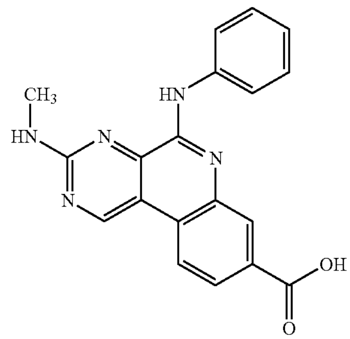 | 0.018 | |
| 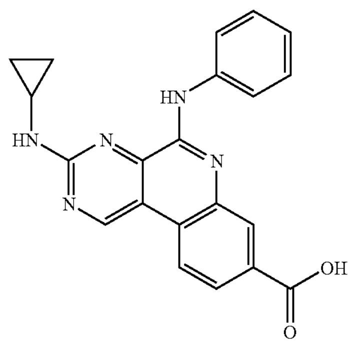 | 0.027 | |
| 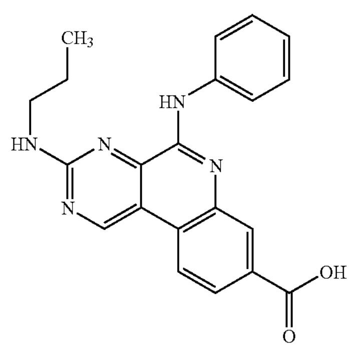 | 0.051 | |
| 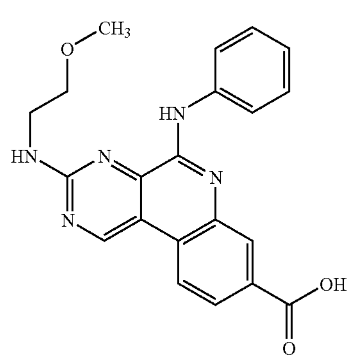 | 0.069 | |

TABLE 13-continued

| Structure | CK2: IC50 (uM) (15 uM ATP) | CK2: IC50 (uM) (20 um ATP) |
|---|---|---|
| *structure* | 0.02 | |
| *structure* | 0.026 | |
| *structure* | 0.056 | |
| *structure* | 0.163 | |

TABLE 13-continued

| Structure | CK2: IC50 (uM) (15 uM ATP) | CK2: IC50 (uM) (20 um ATP) |
|---|---|---|
| | | 0.107 |
| | | 0.089 |
| | | 0.046 |
| | | 0.06 |

TABLE 13-continued
| Structure | CK2: IC50 (uM) (15 uM ATP) | CK2: IC50 (uM) (20 um ATP) |
|---|---|---|
| 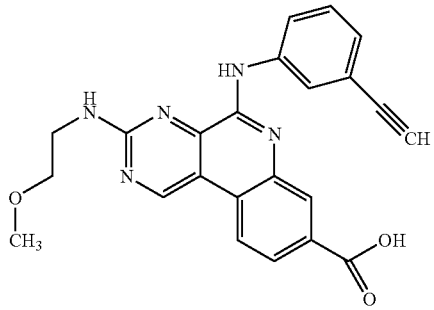 | 0.04 | |
| 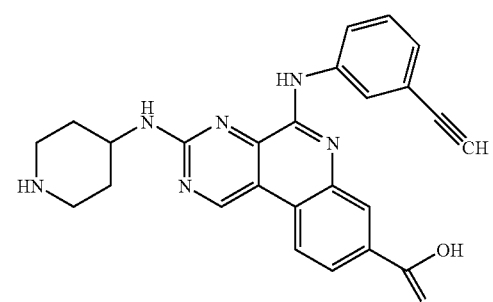 | 0.144 | |
| 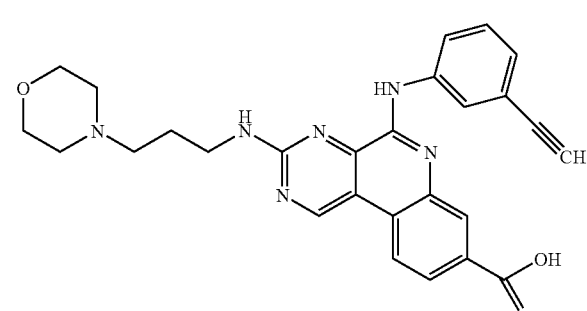 | 0.25 | |
| 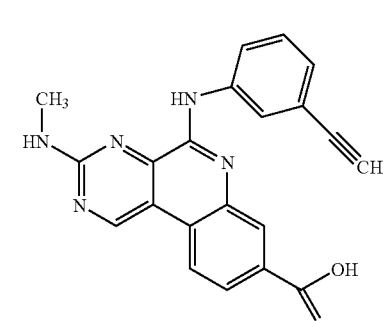 | 0.009 | |

TABLE 13-continued

| Structure | CK2: IC50 (uM) (15 uM ATP) | CK2: IC50 (uM) (20 um ATP) |
|---|---|---|
| 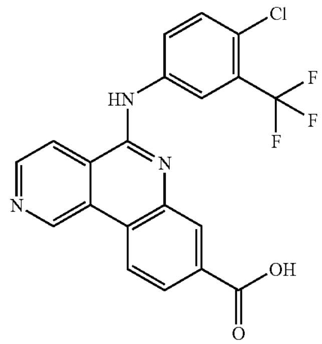 | 0.018 | |
| 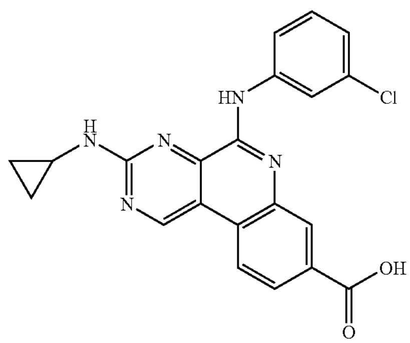 | 0.013 | |
| 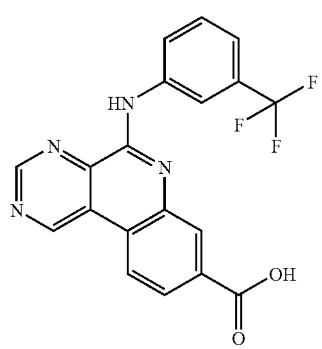 | 0.011 | |
| 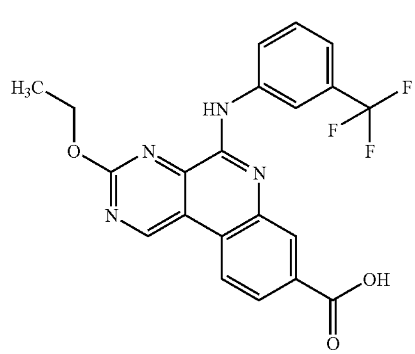 | >0.75 | |

TABLE 13-continued

| Structure | CK2: IC50 (uM) (15 uM ATP) | CK2: IC50 (uM) (20 um ATP) |
|---|---|---|
| | | 0.018 |
| | | >0.75 |
| | | 0.004 |
| | | 0.134 |

TABLE 13-continued

| Structure | CK2: IC50 (uM) (15 uM ATP) | CK2: IC50 (uM) (20 um ATP) |
|---|---|---|
| 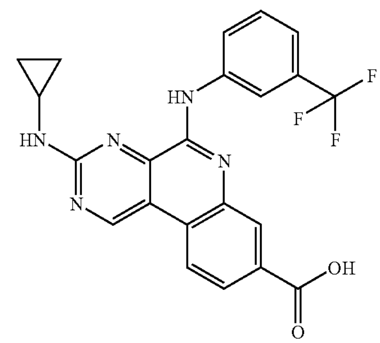 | 0.009 | |
| 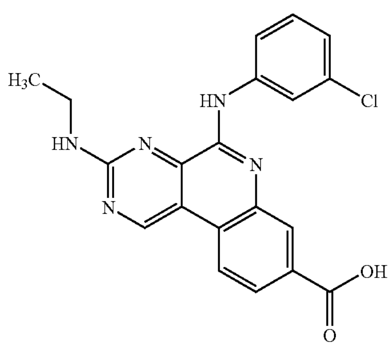 | 0.03 | |
| 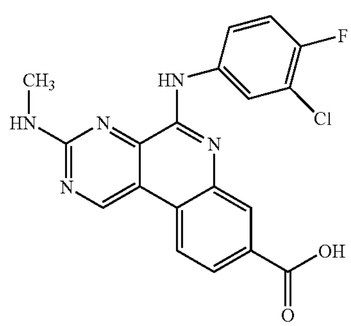 | 0.02 | |
| 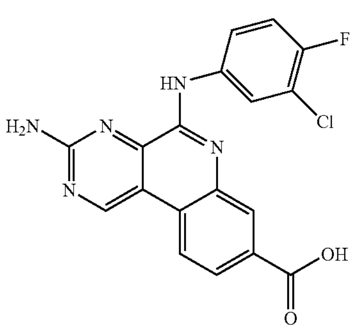 | 0.007 | |

TABLE 13-continued

| Structure | CK2: IC50 (uM) (15 uM ATP) | CK2: IC50 (uM) (20 um ATP) |
|---|---|---|
| 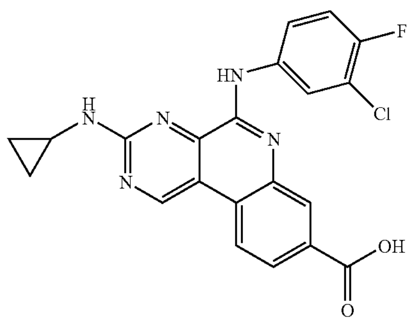 | 0.083 | |
| 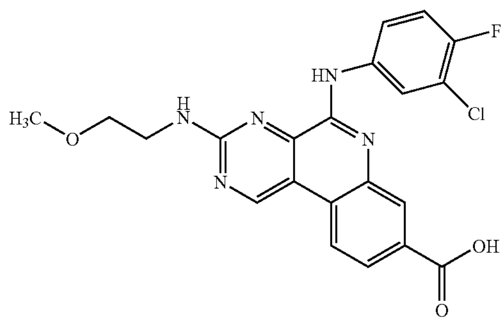 | 0.052 | |
| 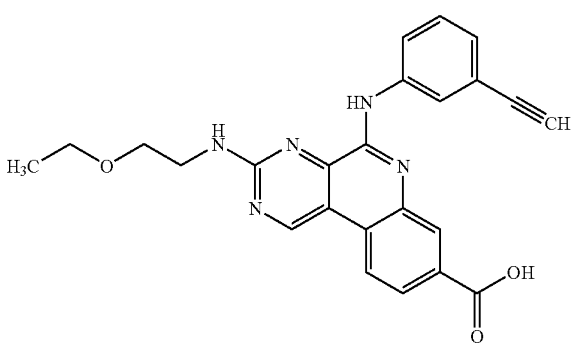 | 0.171 | |
| 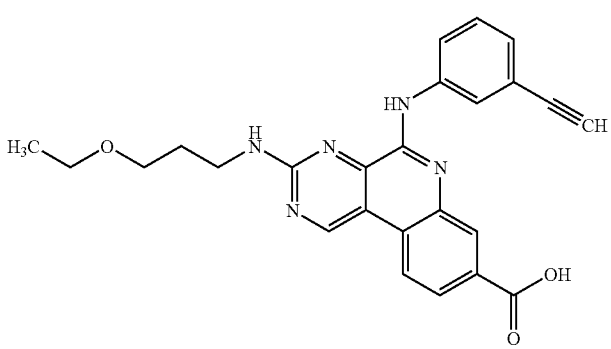 | 0.107 | |

TABLE 13-continued
| Structure | CK2: IC50 (uM) (15 uM ATP) | CK2: IC50 (uM) (20 um ATP) |
|---|---|---|
| 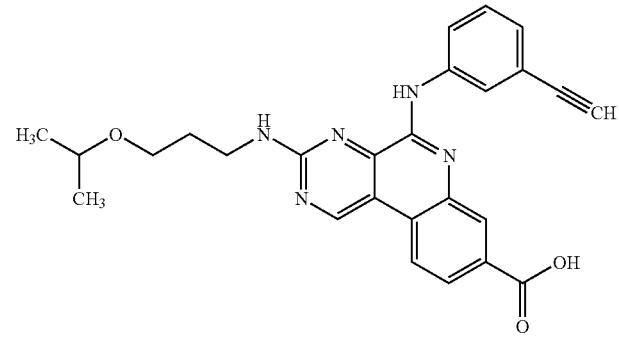 | | 0.349 |
| 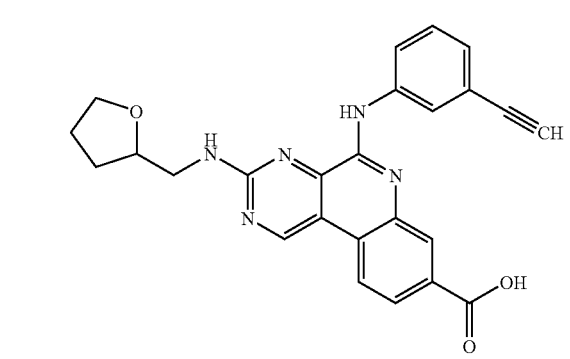 | | 0.114 |
| 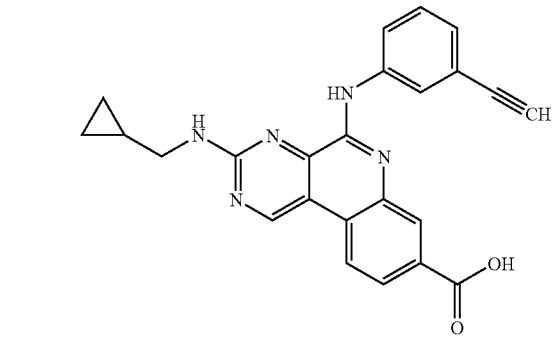 | | 0.05 |
| 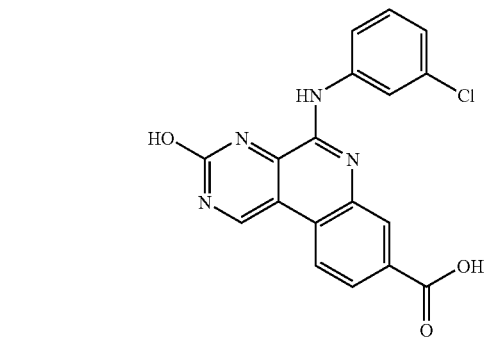 | | 0.214 |

TABLE 13-continued

| Structure | CK2: IC50 (uM) (15 uM ATP) | CK2: IC50 (uM) (20 um ATP) |
|---|---|---|
| 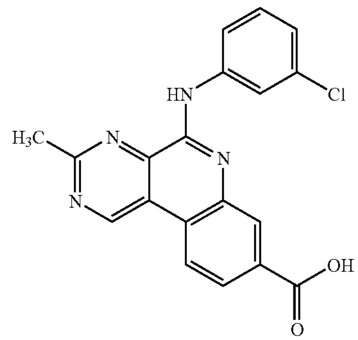 | 0.172 | |
| | >0.75 | |
| | >0.75 | |
| | >0.75 | |

TABLE 13-continued
| Structure | CK2: IC50 (uM) (15 uM ATP) | CK2: IC50 (uM) (20 um ATP) |
|---|---|---|
| 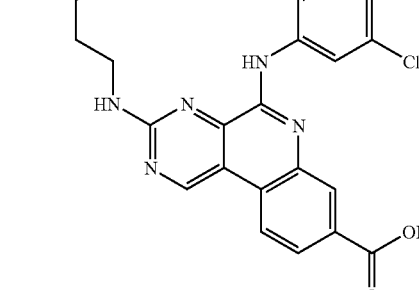 | 0.028 | |
| 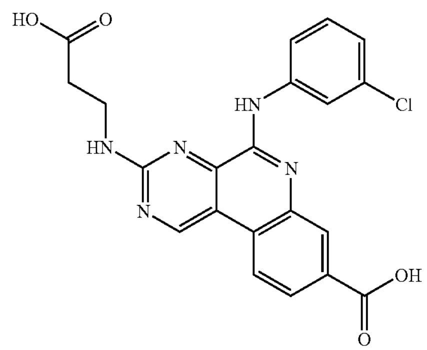 | 0.021 | |
| 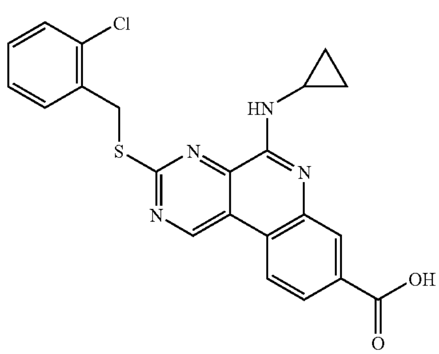 | >0.75 | |
| 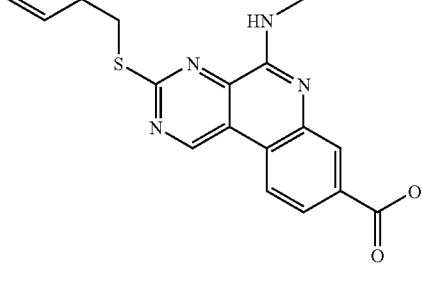 | 0.493 | |

TABLE 13-continued

| Structure | CK2: IC50 (uM) (15 uM ATP) | CK2: IC50 (uM) (20 um ATP) |
| --- | --- | --- |
| 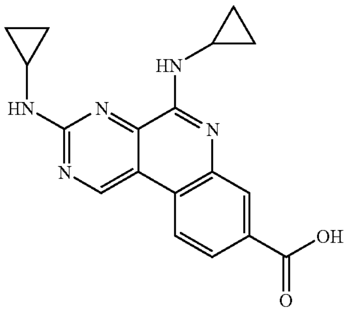 | 0.006 | |
| 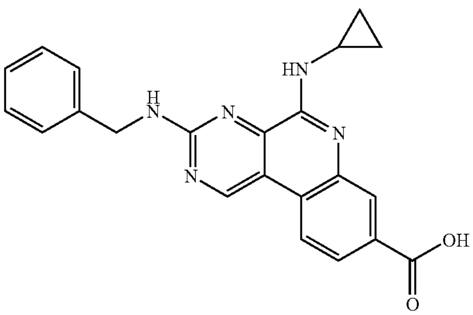 | 0.059 | |
| 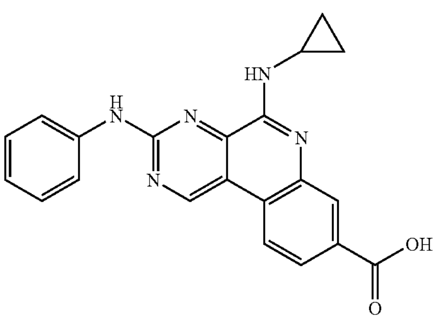 | 0.026 | |
| 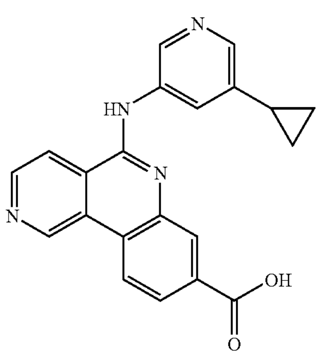 | >0.75 | |

TABLE 13-continued

| Structure | CK2: IC50 (uM) (15 uM ATP) | CK2: IC50 (uM) (20 um ATP) |
|---|---|---|
| 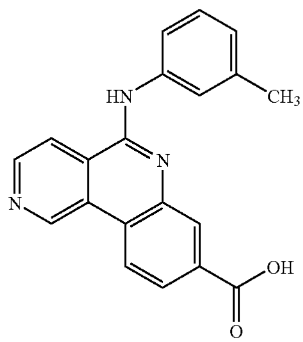 | 0.006 | |
| 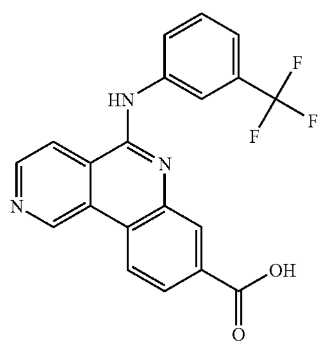 | 0.011 | |
| 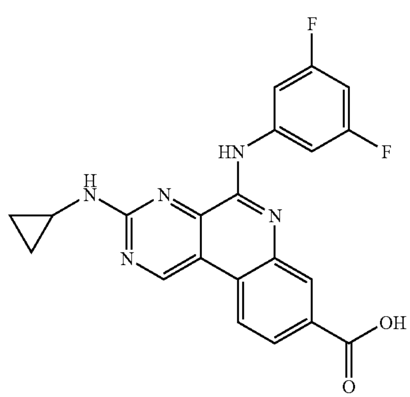 | 0.102 | |
| 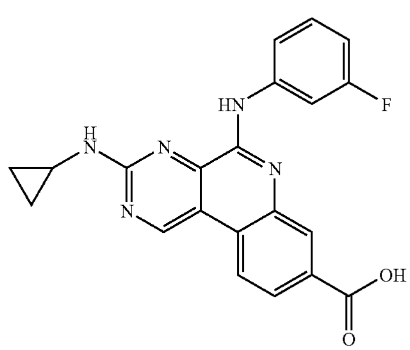 | 0.086 | |

TABLE 13-continued

| Structure | CK2: IC50 (uM) (15 uM ATP) | CK2: IC50 (uM) (20 um ATP) |
|---|---|---|
| | | 0.134 |
| | | 0.018 |
| | | 0.035 |
| | | >0.75 |

TABLE 13-continued
| Structure | CK2: IC50 (uM) (15 uM ATP) | CK2: IC50 (uM) (20 um ATP) |
|---|---|---|
| 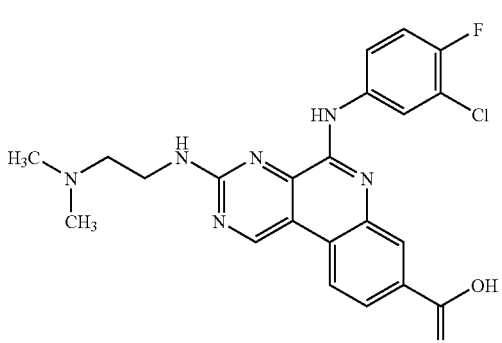 | 0.168 | |
| 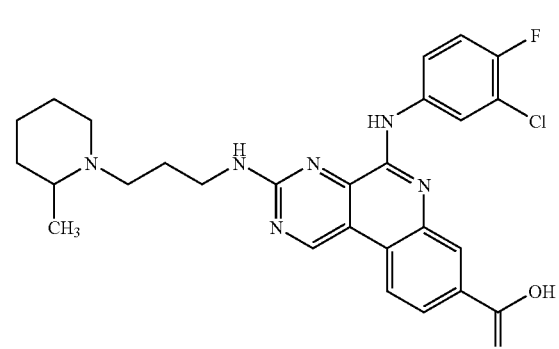 | 0.686 | |
| 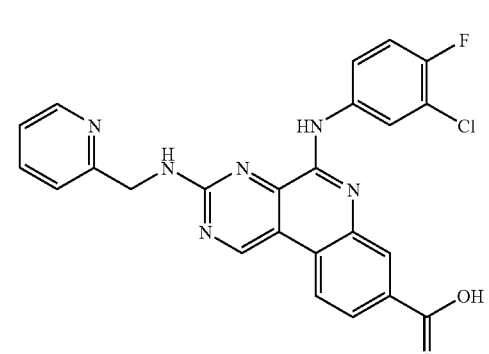 | 0.356 | |
| 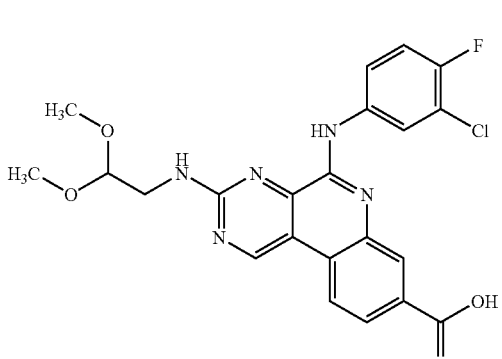 | 0.103 | |

US 7,956,064 B2
TABLE 13-continued
| Structure | CK2: IC50 (uM) (15 uM ATP) | CK2: IC50 (uM) (20 um ATP) |
|---|---|---|
| 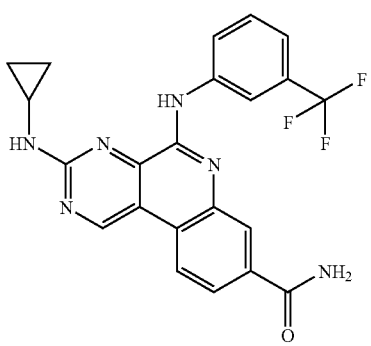 | | >0.75 |
| 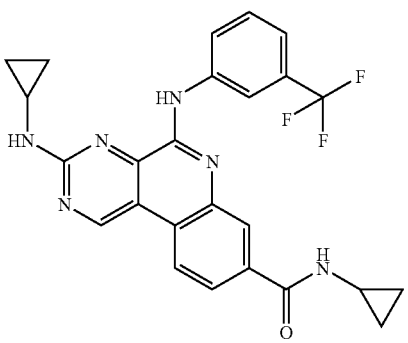 | | >0.75 |
| 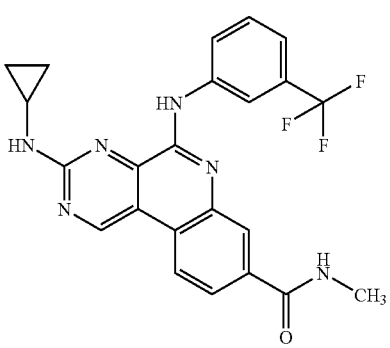 | | >0.75 |
| 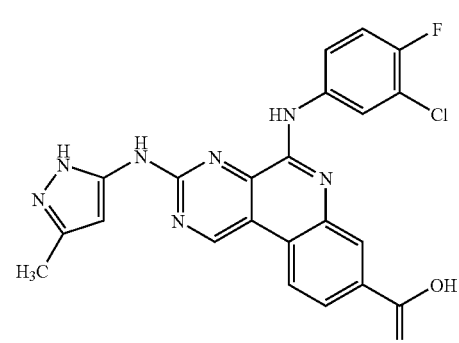 | | 0.513 |

TABLE 13-continued

| Structure | CK2: IC50 (uM) (15 uM ATP) | CK2: IC50 (uM) (20 um ATP) |
|---|---|---|
| 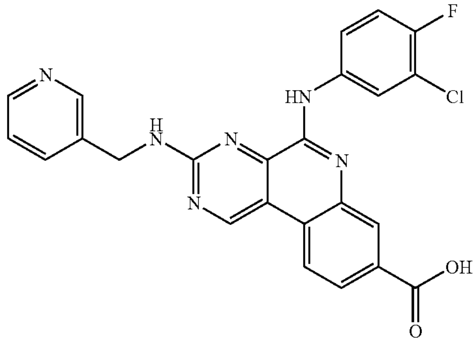 | 0.027 | |
| 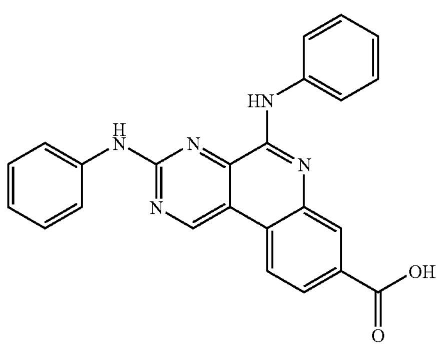 | 0.185 | |
| 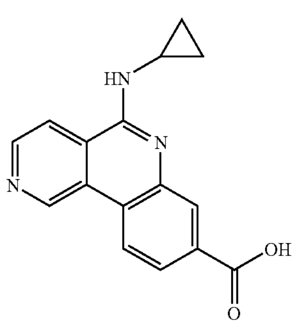 | 0.016 | |
| | | |

TABLE 13-continued

| Structure | CK2: IC50 (uM) (15 uM ATP) | CK2: IC50 (uM) (20 um ATP) |
|---|---|---|
| | >0.75 | |
| | >0.75 | |
| | >0.75 | |
| 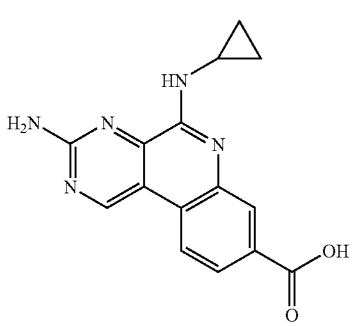 | 0.023 | |

TABLE 13-continued

| Structure | CK2: IC50 (uM) (15 uM ATP) | CK2: IC50 (uM) (20 um ATP) |
|---|---|---|
| | | 0.015 |
| | | 0.014 |
| | | >0.75 |
| | | 0.087 |

TABLE 13-continued

| Structure | CK2: IC50 (uM) (15 uM ATP) | CK2: IC50 (uM) (20 um ATP) |
|---|---|---|
| | | >0.75 |
| | | 0.014 |
| | | 0.093 |
| | | 0.01 |

TABLE 13-continued

| Structure | CK2: IC50 (uM) (15 uM ATP) | CK2: IC50 (uM) (20 um ATP) |
|---|---|---|
| 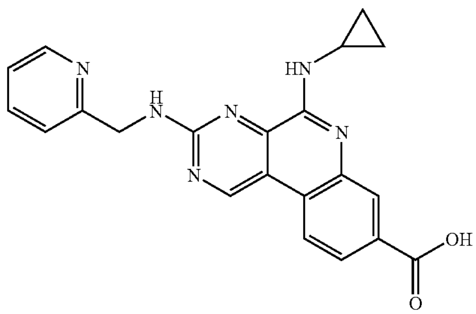 | 0.035 | |
| 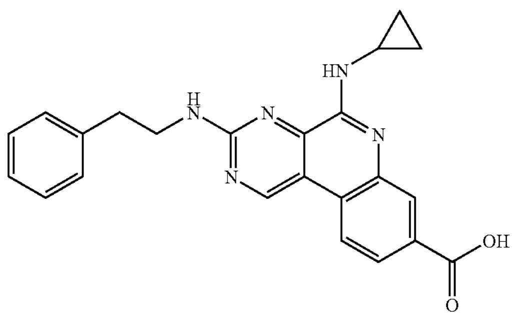 | 0.033 | |
| 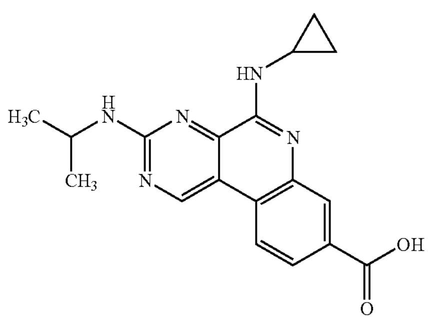 | 0.02 | |
| 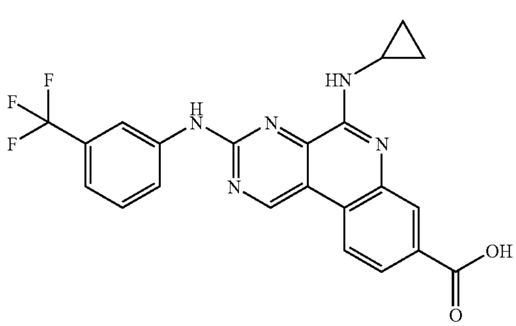 | 0.198 | |

TABLE 13-continued
| Structure | CK2: IC50 (uM) (15 uM ATP) | CK2: IC50 (uM) (20 um ATP) |
|---|---|---|
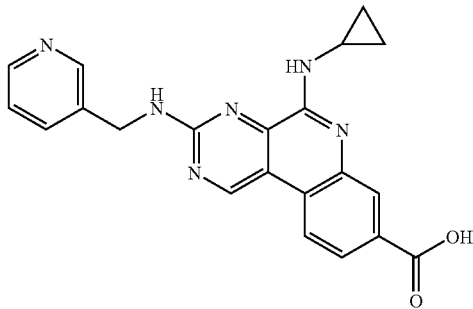
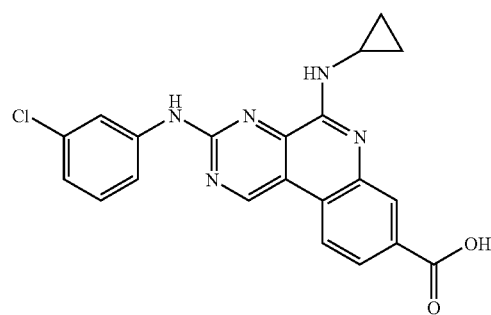
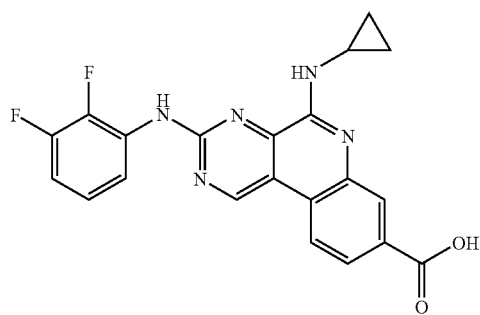
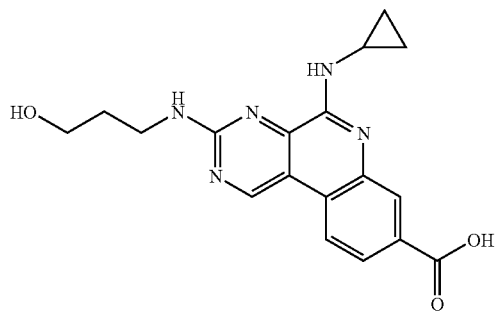

TABLE 13-continued
| Structure | CK2: IC50 (uM) (15 uM ATP) | CK2: IC50 (uM) (20 um ATP) |
|---|---|---|
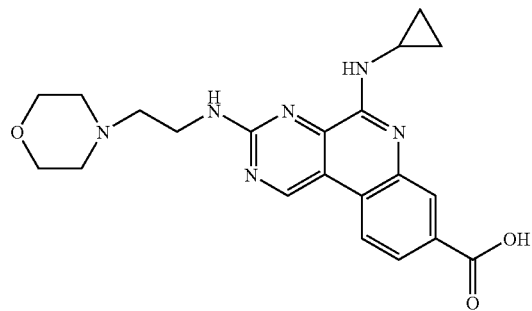
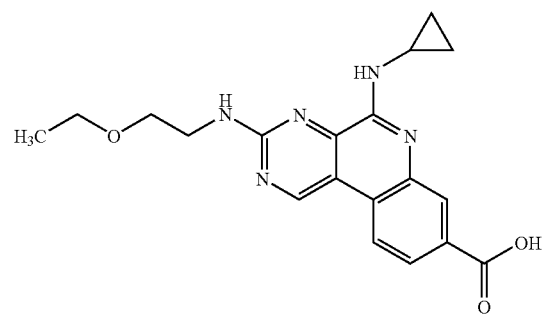
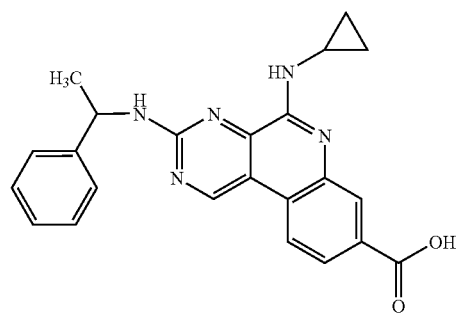
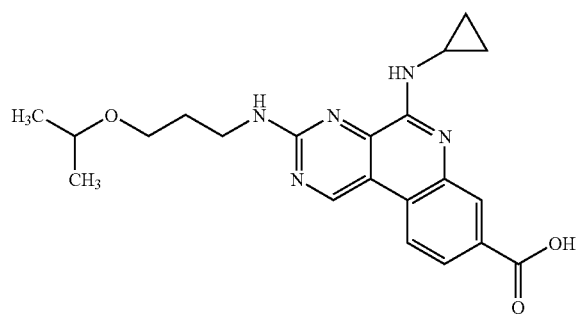

TABLE 13-continued
| Structure | CK2: IC50 (uM) (15 uM ATP) | CK2: IC50 (uM) (20 um ATP) |
|---|---|---|
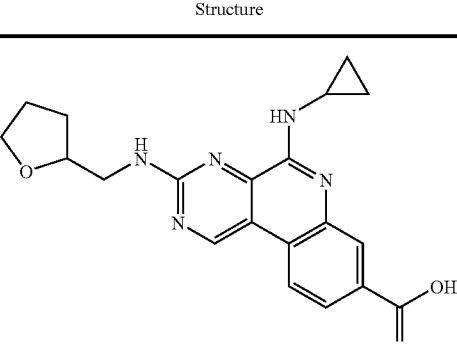
TABLE 14
| Structure | CK2: IC50 (uM) (15 uM ATP) | CK2: IC50(uM) (20 uM ATP) |
|---|---|---|
| 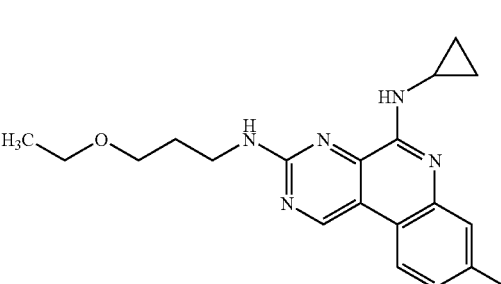 | 0.995 | 1.2 |

TABLE 14-continued
| Structure | CK2: IC50 (uM) (15 uM ATP) | CK2: IC50(uM) (20 uM ATP) |
|---|---|---|
| 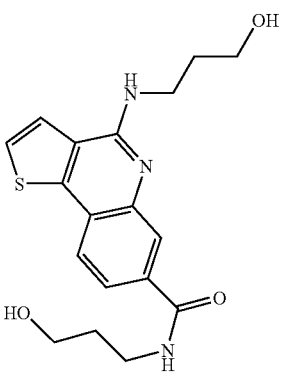 | | |
| 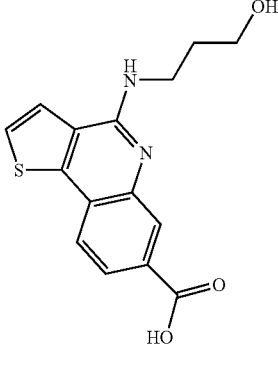 | 0.748 | 0.67 |
| 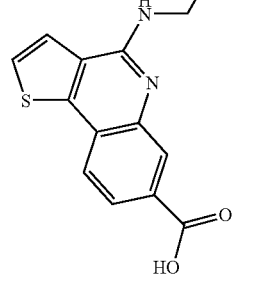 | 1.258 | 1.1 |
| 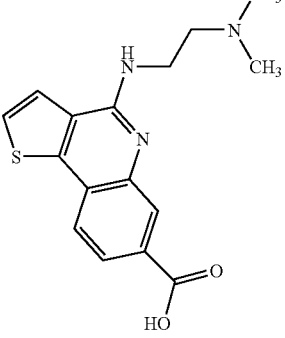 | 0.102 | 0.277 |

TABLE 14-continued

| Structure | CK2: IC50 (uM) (15 uM ATP) | CK2: IC50(uM) (20 uM ATP) |
| --- | --- | --- |
| 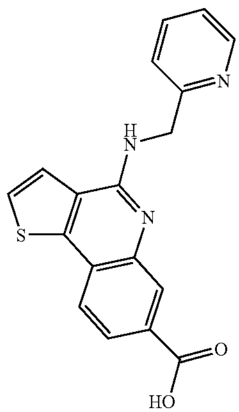 | 0.622 | 0.872 |
| 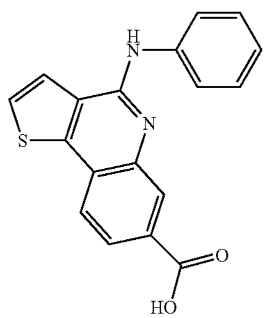 | 0.092 | 0.31 |
| 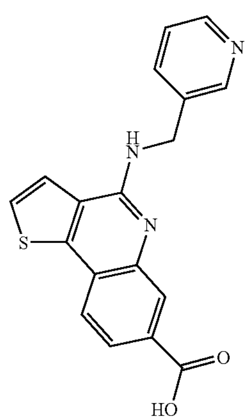 | 0.367 | 0.9 |
| 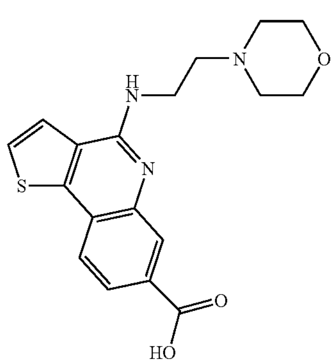 | 0.922 | 1.22 |

TABLE 14-continued
| Structure | CK2: IC50 (uM) (15 uM ATP) | CK2: IC50(uM) (20 uM ATP) |
|---|---|---|
| 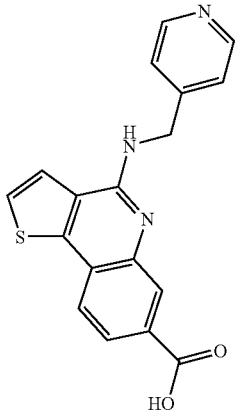 | 0.168 | 0.518 |
| 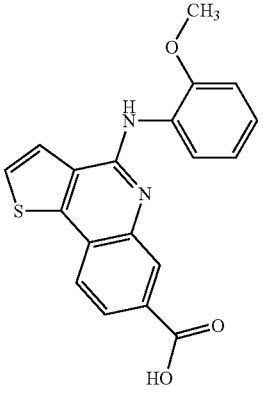 | 0.171 | 0.55 |
| 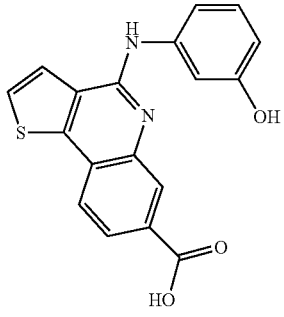 | 0.507 | 0.369 |
| 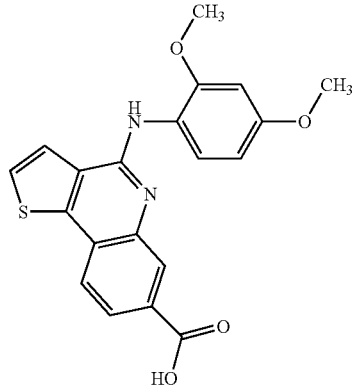 | 0.771 | 2 |

TABLE 14-continued

| Structure | CK2: IC50 (uM) (15 uM ATP) | CK2: IC50(uM) (20 uM ATP) |
|---|---|---|
| 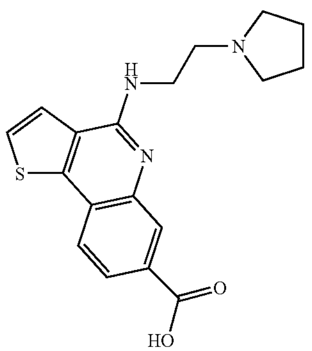 | 0.231 | 0.28 |

TABLE 14-continued

| Structure | CK2: IC50 (uM) (15 uM ATP) | CK2: IC50(uM) (20 uM ATP) |
|---|---|---|
| | | |
| 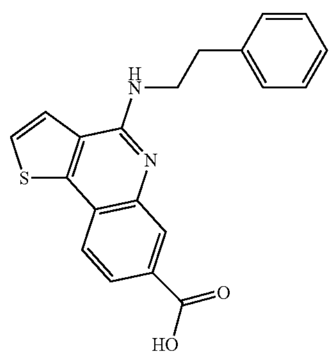 | 0.516 | 1.006 |
| | | |
| | | |

TABLE 14-continued
| Structure | CK2: IC50 (uM) (15 uM ATP) | CK2: IC50(uM) (20 uM ATP) |
|---|---|---|
| 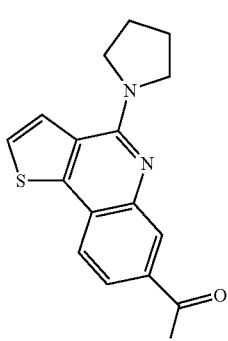 | | |
| 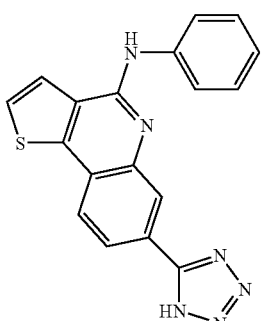 | 0.096 | 0.189 |
| 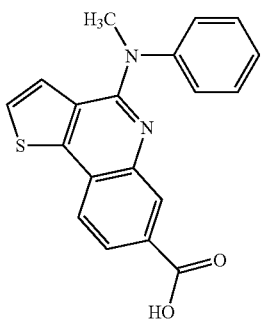 | 1.5 | |
| 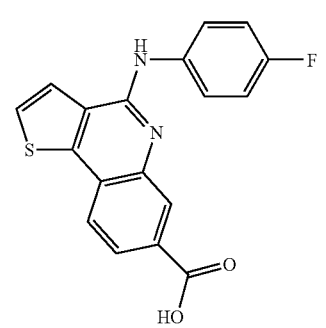 | 0.219 | 0.31 |

TABLE 14-continued
| Structure | CK2: IC50 (uM) (15 uM ATP) | CK2: IC50(uM) (20 uM ATP) |
|---|---|---|
| 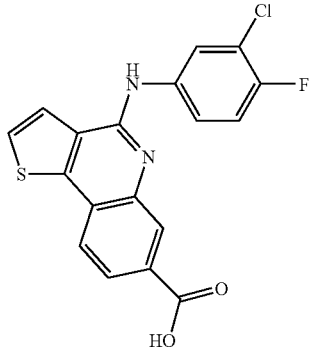 |  | 0.15 |
| 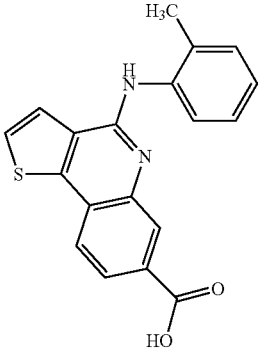 |  | 1.1 |
| 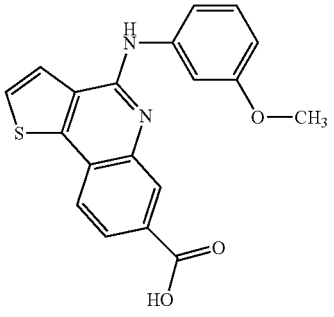 |  | 0.12 |
| 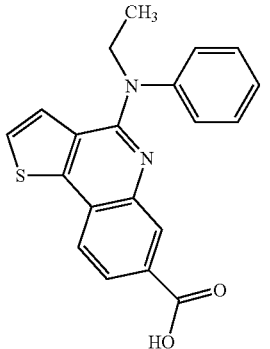 |  |  |

TABLE 14-continued

| Structure | CK2: IC50 (uM) (15 uM ATP) | CK2: IC50(uM) (20 uM ATP) |
| --- | --- | --- |
| (4-chlorophenylamino thieno[3,2-c]quinoline carboxylic acid) |  | 0.21 |
| (2,4-difluorophenylamino thieno[3,2-c]quinoline carboxylic acid) |  | 0.67 |
| (cyclopropylamino thieno[3,2-c]quinoline carboxylic acid) |  | 0.97 |
| (indolinyl thieno[3,2-c]quinoline carboxylic acid) | 0.32 | 0.58 |

TABLE 14-continued
| Structure | CK2: IC50 (uM) (15 uM ATP) | CK2: IC50(uM) (20 uM ATP) |
|---|---|---|
| 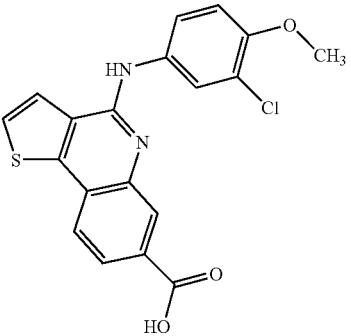 | 0.131 | 0.43 |
| 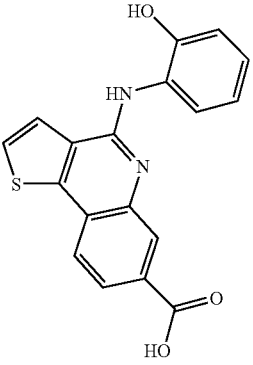 | 0.257 | 0.82 |
| 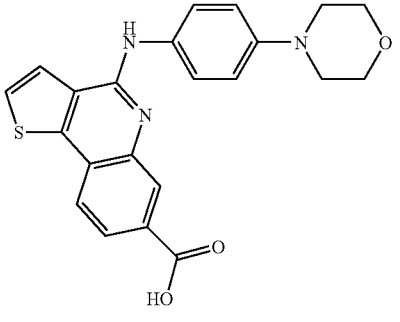 | 0.666 | 1.17 |
| 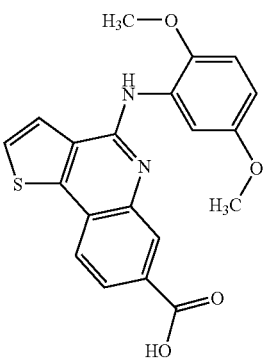 | 0.238 | 0.431 |

TABLE 14-continued
| Structure | CK2: IC50 (uM) (15 uM ATP) | CK2: IC50(uM) (20 uM ATP) |
|---|---|---|
| 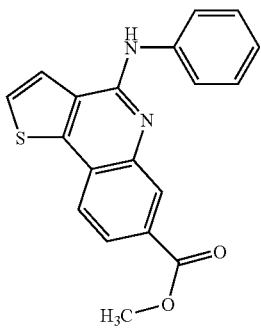 | | |
| 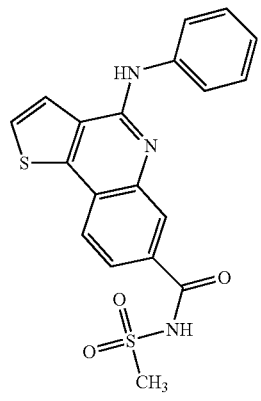 | | |
| 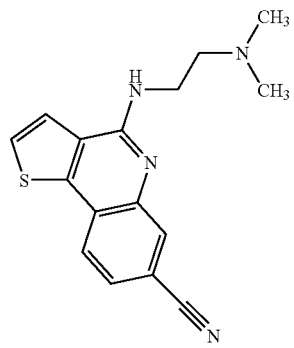 | | |
| 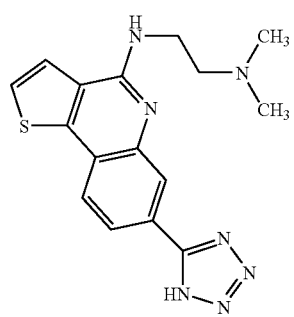 | 0.252 | 0.31 |

TABLE 14-continued

| Structure | CK2: IC50 (uM) (15 uM ATP) | CK2: IC50(uM) (20 uM ATP) |
|---|---|---|
| | | |
| | | |
| | | |
| | | |

TABLE 14-continued
| Structure | CK2: IC50 (uM) (15 uM ATP) | CK2: IC50(uM) (20 uM ATP) |
|---|---|---|
| 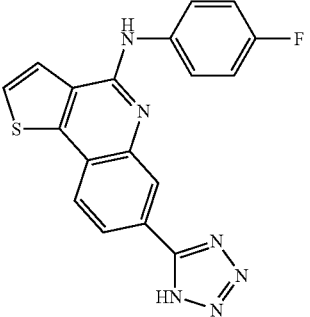 | 0.371 | 0.372 |
| 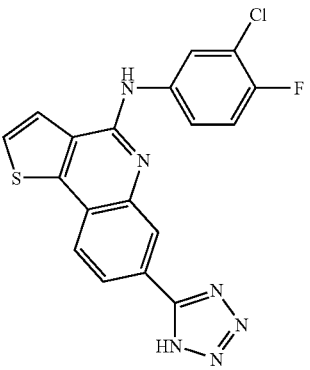 | 0.194 | 0.382 |
| 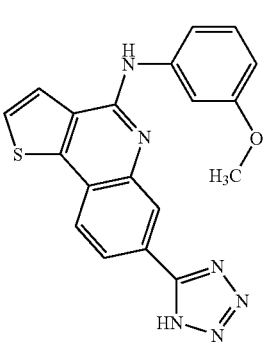 | 0.172 | 0.3 |
| 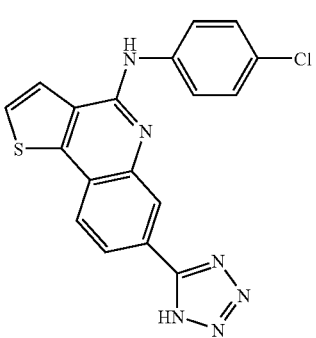 | 0.233 | 0.407 |

TABLE 14-continued
| Structure | CK2: IC50 (uM) (15 uM ATP) | CK2: IC50(uM) (20 uM ATP) |
|---|---|---|
| 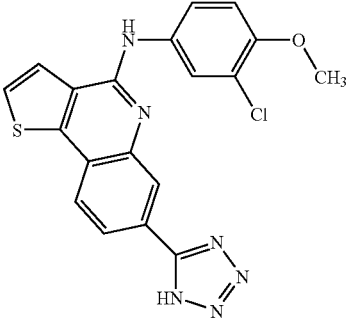 | 0.256 | 0.462 |
| 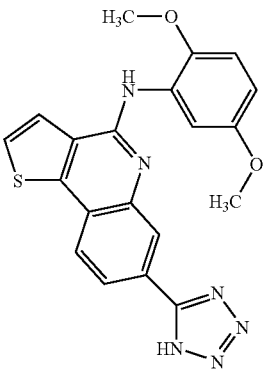 | 0.358 | 10 |
| 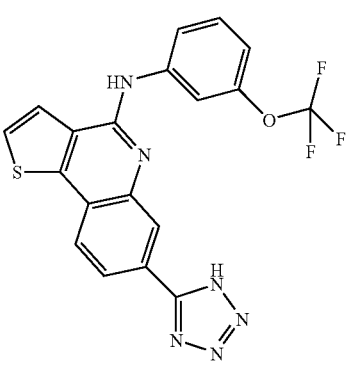 | 0.611 | 0.392 |
| 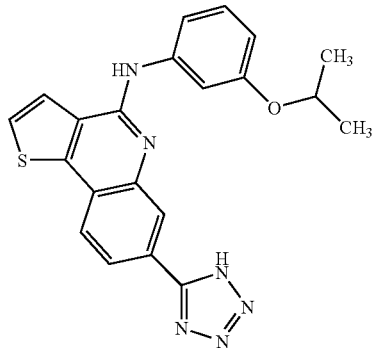 | 0.42 | 0.27 |

TABLE 14-continued

| Structure | CK2: IC50 (uM) (15 uM ATP) | CK2: IC50(uM) (20 uM ATP) |
|---|---|---|
| 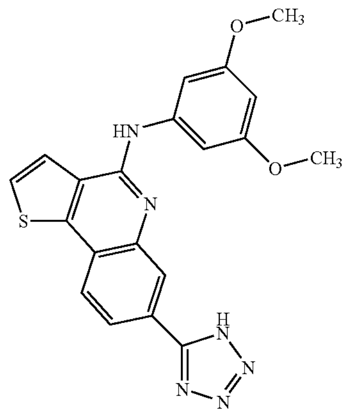 | 0.348 | 0.35 |
| 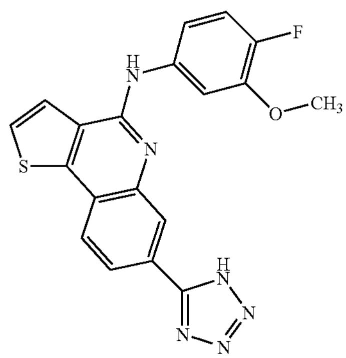 | 0.812 | 0.89 |
| | | |
| | | |

TABLE 14-continued
| Structure | CK2: IC50 (uM) (15 uM ATP) | CK2: IC50(uM) (20 uM ATP) |
|---|---|---|
| 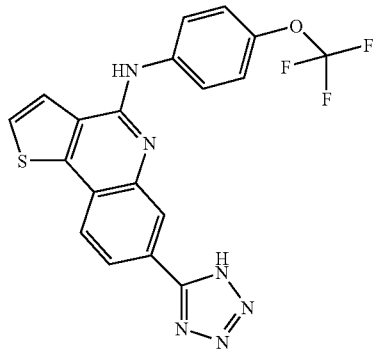 | | |
| 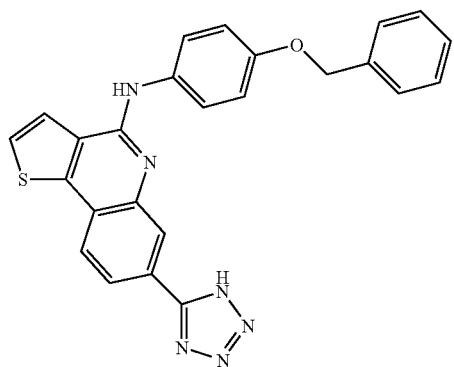 | | |
| 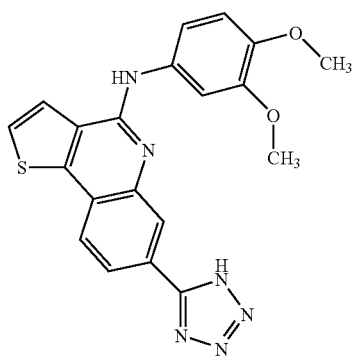 | | |
| 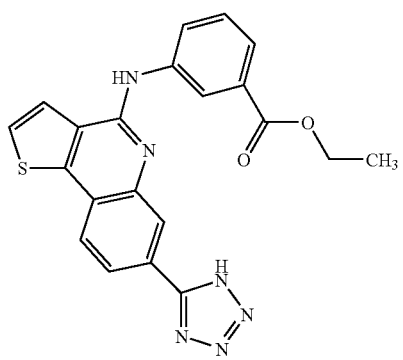 | | |

TABLE 14-continued
| Structure | CK2: IC50 (uM) (15 uM ATP) | CK2: IC50(uM) (20 uM ATP) |
|---|---|---|
| 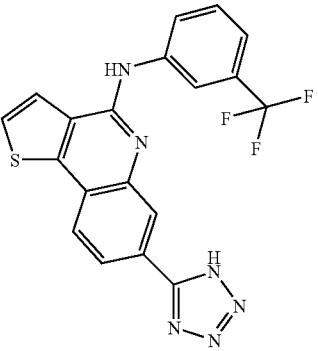 | 0.458 | 0.406 |
| 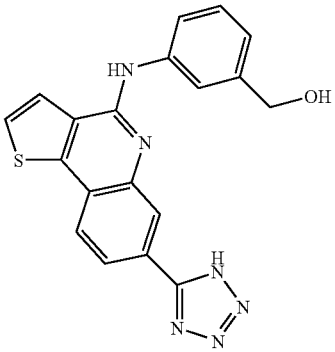 | 0.154 | 0.216 |
| 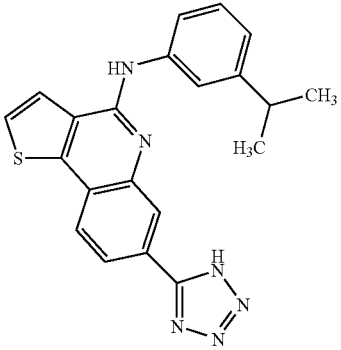 | | |
| 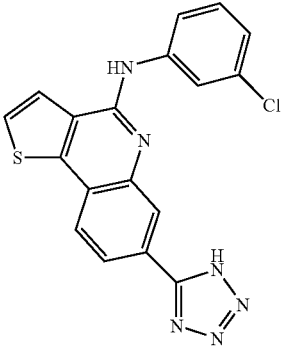 | 0.129 | 0.181 |

TABLE 14-continued
| Structure | CK2: IC50 (uM) (15 uM ATP) | CK2: IC50(uM) (20 uM ATP) |
|---|---|---|
| 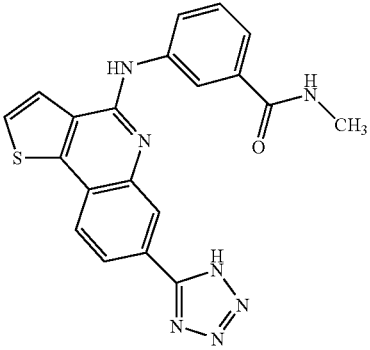 | 0.171 | 0.283 |
| 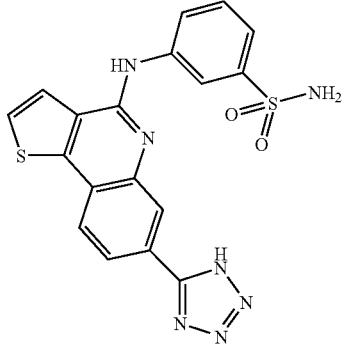 | 0.198 | 0.268 |
| 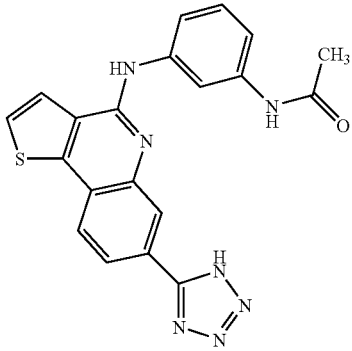 | 0.485 | 0.524 |
| 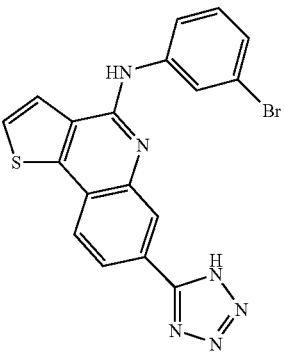 | 0.122 | 0.14 |

TABLE 14-continued

| Structure | CK2: IC50 (uM) (15 uM ATP) | CK2: IC50(uM) (20 uM ATP) |
|---|---|---|
| 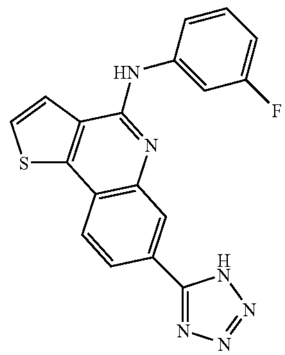 | 0.075 | 0.096 |
| 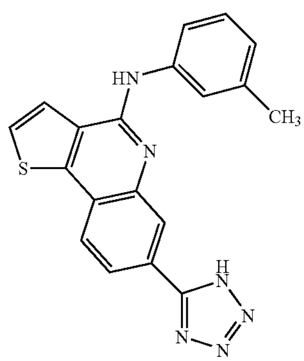 | 0.235 | 0.375 |
| | | |
| 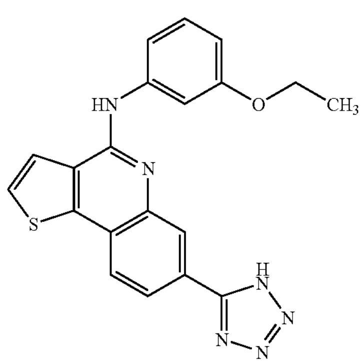 | 0.346 | 0.423 |

TABLE 14-continued
| Structure | CK2: IC50 (uM) (15 uM ATP) | CK2: IC50(uM) (20 uM ATP) |
|---|---|---|
| 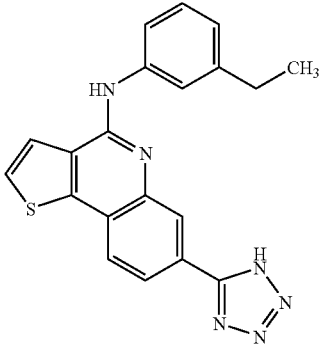 | 0.358 | 0.509 |
| 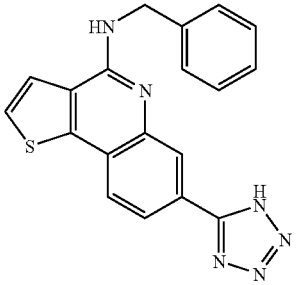 | | |
| 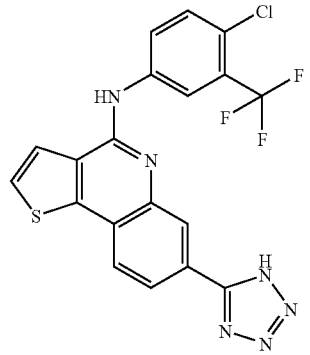 | | |
| 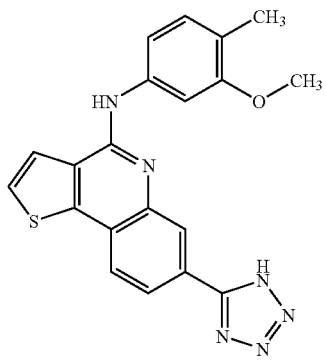 | | |

TABLE 14-continued
| Structure | CK2: IC50 (uM) (15 uM ATP) | CK2: IC50(uM) (20 uM ATP) |
|---|---|---|
| 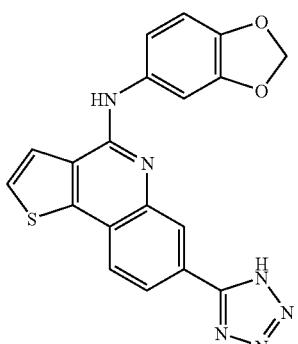 | | |
| 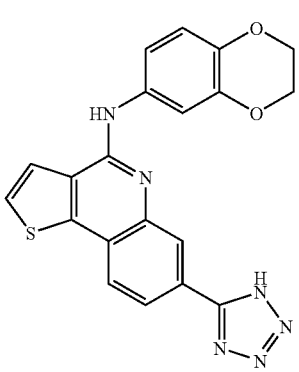 | 0.29 | 0.63 |
| 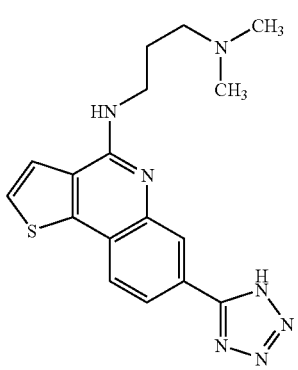 | | |
| 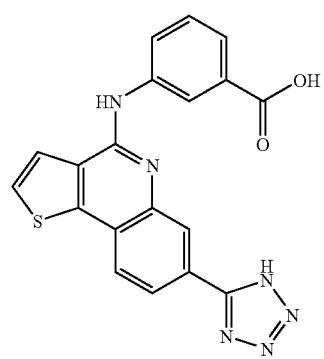 | 0.135 | |

TABLE 14-continued

| Structure | CK2: IC50 (uM) (15 uM ATP) | CK2: IC50(uM) (20 uM ATP) |
|---|---|---|
| *[thieno-quinoline with 3,5-difluoroanilino and carboxylic acid]* | 0.07 | |
| *[thieno-quinoline with 3-fluoroanilino and carboxylic acid]* | 0.068 | |
| *[thieno-quinoline with 3-chloroanilino and carboxylic acid]* | 0.032 | |
| *[thieno-quinoline with 2-fluoro-5-chloroanilino and carboxylic acid]* | 0.07 | |

TABLE 14-continued
| Structure | CK2: IC50 (uM) (15 uM ATP) | CK2: IC50(uM) (20 uM ATP) |
|---|---|---|
| 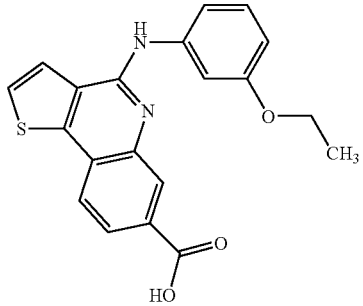 | 0.126 | |
| 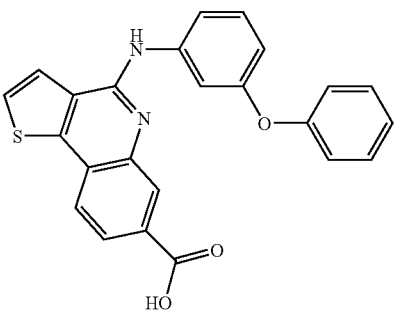 | 0.395 | |
| 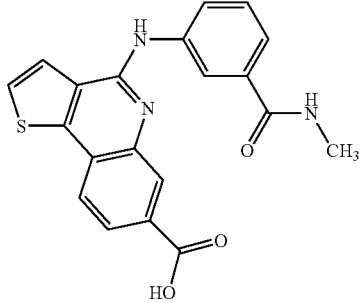 | 0.129 | |
| 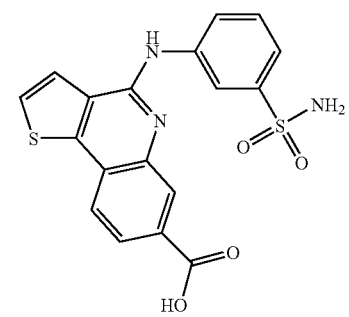 | 0.103 | |
| 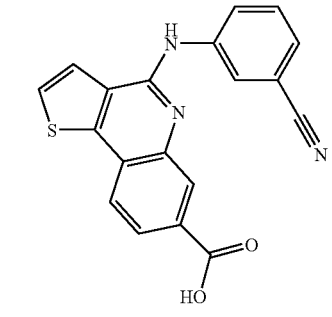 | 0.081 | |

… TABLE 14-continued
| Structure | CK2: IC50 (uM) (15 uM ATP) | CK2: IC50(uM) (20 uM ATP) |
|---|---|---|
| | | 0.028 |
| | | 0.38 |
| | | 0.502 |
| | | 0.549 |
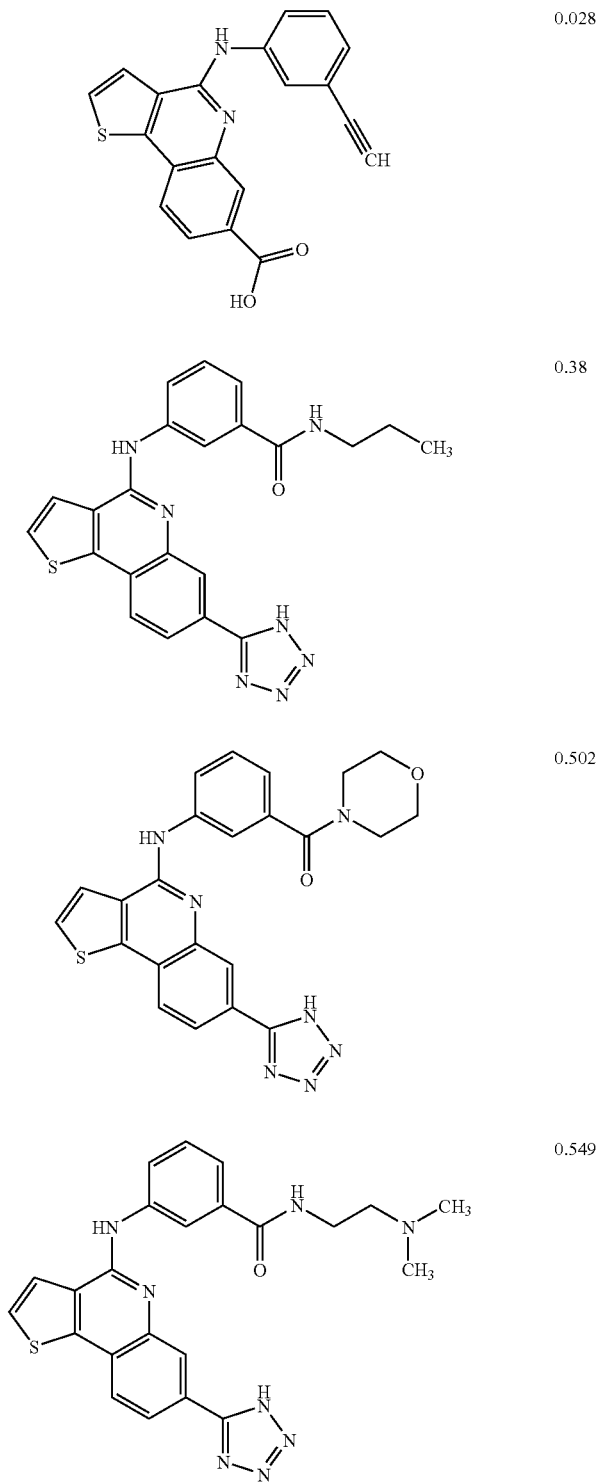

TABLE 14-continued
| Structure | CK2: IC50 (uM) (15 uM ATP) | CK2: IC50(uM) (20 uM ATP) |
|---|---|---|
| 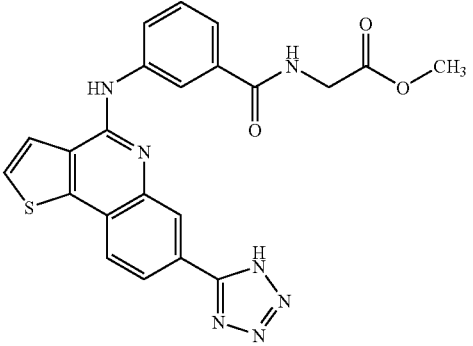 | | 0.24 |
| 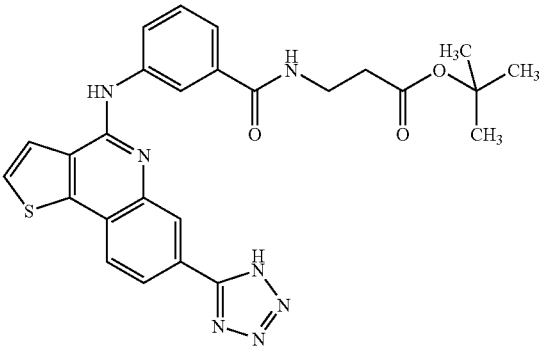 | | |
| 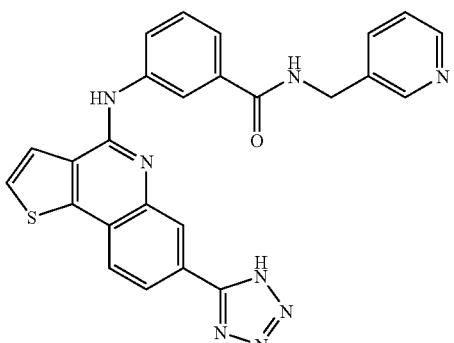 | | 0.363 |
| 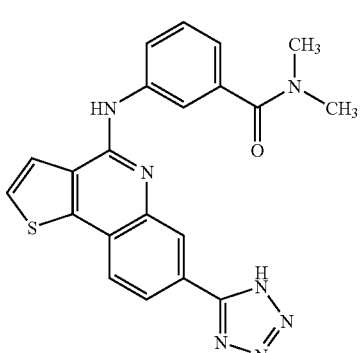 | | 0.318 |

TABLE 14-continued

| Structure | CK2: IC50 (uM) (15 uM ATP) | CK2: IC50(uM) (20 uM ATP) |
|---|---|---|
| 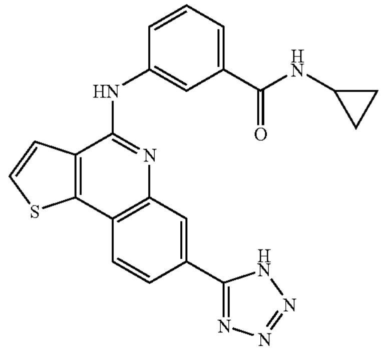 | 0.237 | |
| 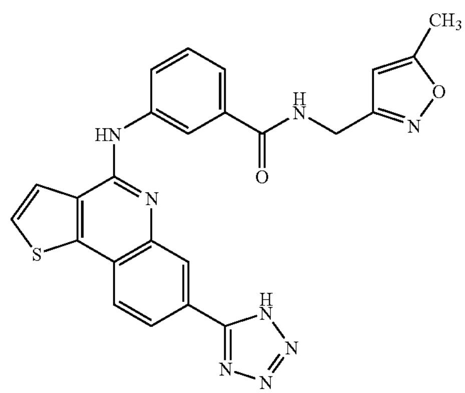 | 0.288 | |
| 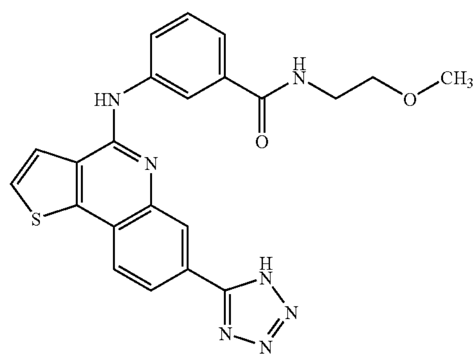 | 0.251 | |
| 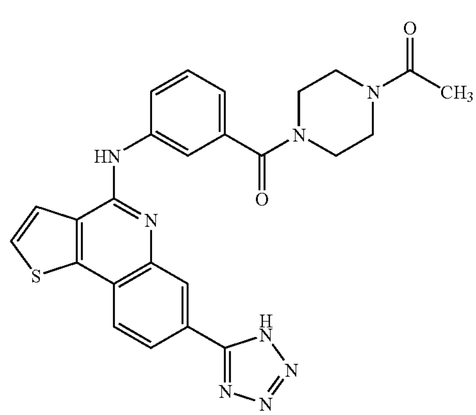 | 0.303 | |

TABLE 14-continued

| Structure | CK2: IC50 (uM) (15 uM ATP) | CK2: IC50(uM) (20 uM ATP) |
|---|---|---|
| 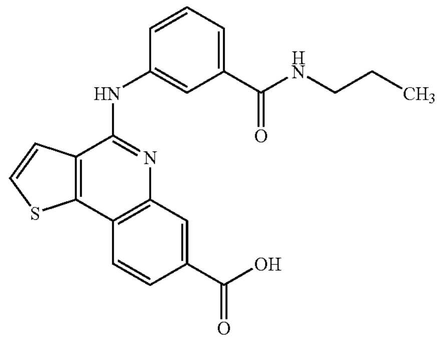 | 0.224 | |
| 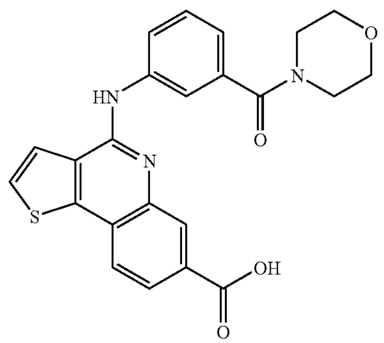 | 0.307 | |
| | | |
| 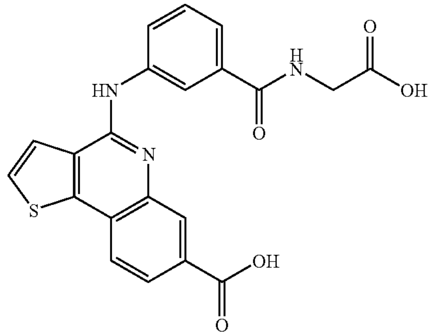 | 0.192 | |

TABLE 14-continued

| Structure | CK2: IC50 (uM) (15 uM ATP) | CK2: IC50(uM) (20 uM ATP) |
| --- | --- | --- |
| 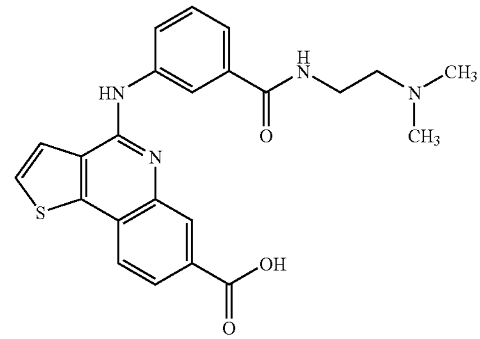 | 0.366 | |
| | | |
| | | |
| | | |

TABLE 14-continued

| Structure | CK2: IC50 (uM) (15 uM ATP) | CK2: IC50(uM) (20 uM ATP) |
|---|---|---|
| | | |
| | | 0.221 |
| | | |
| | | |

TABLE 14-continued
| Structure | CK2: IC50 (uM) (15 uM ATP) | CK2: IC50(uM) (20 uM ATP) |
|---|---|---|
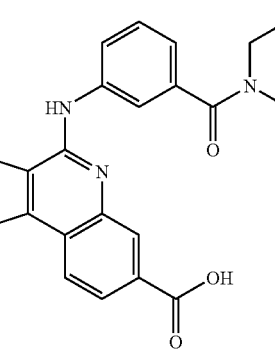
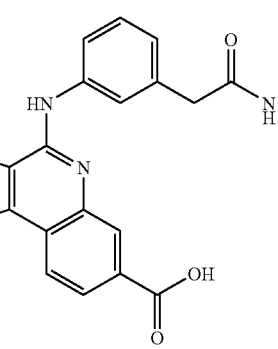
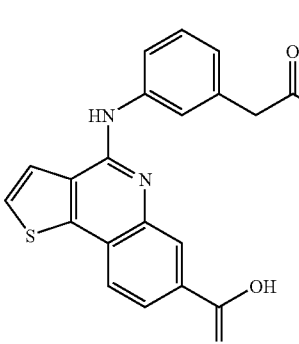
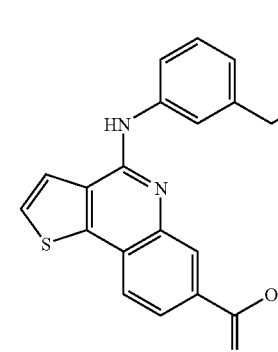

TABLE 14-continued

| Structure | CK2: IC50 (uM) (15 uM ATP) | CK2: IC50(uM) (20 uM ATP) |
|---|---|---|
| | 0.137 | |
| | 0.187 | |
| | 0.335 | |
| | | |

TABLE 14-continued
| Structure | CK2: IC50 (uM) (15 uM ATP) | CK2: IC50(uM) (20 uM ATP) |
|---|---|---|
| 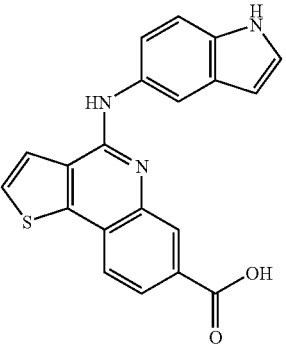 | 0.156 | |
| 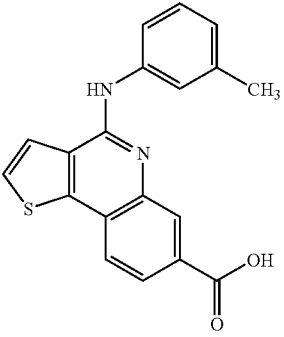 | 0.09 | |
| 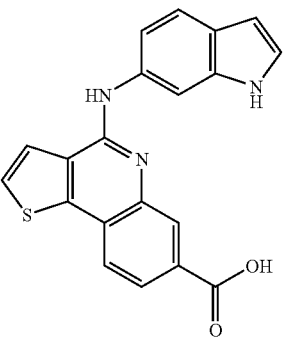 | 0.121 | |
| 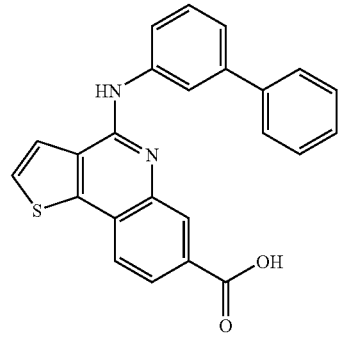 | | |

TABLE 14-continued

| Structure | CK2: IC50 (uM) (15 uM ATP) | CK2: IC50(uM) (20 uM ATP) |
|---|---|---|
| | | 0.281 |
| | | 0.061 |
| | | 0.242 |
| | | 0.091 |

TABLE 14-continued
| Structure | CK2: IC50 (uM) (15 uM ATP) | CK2: IC50(uM) (20 uM ATP) |
|---|---|---|
| 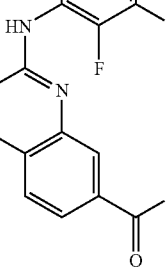 | 0.256 | |
| 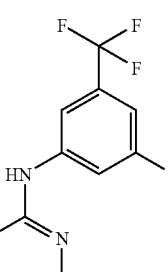 | 0.156 | |
| 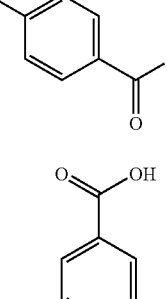 | 0.127 | |
| 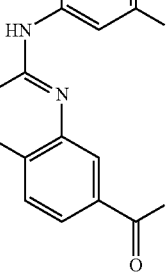 | 0.138 | |

TABLE 14-continued

| Structure | CK2: IC50 (uM) (15 uM ATP) | CK2: IC50(uM) (20 uM ATP) |
|---|---|---|
| 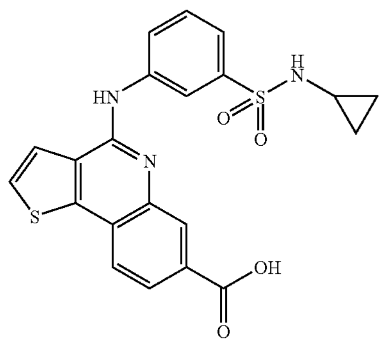 | 0.116 | |
| 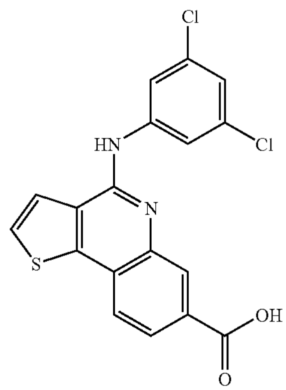 | 0.035 | |
| 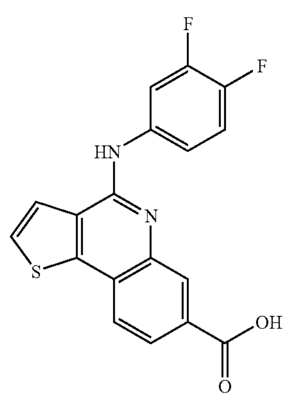 | 0.127 | |
| 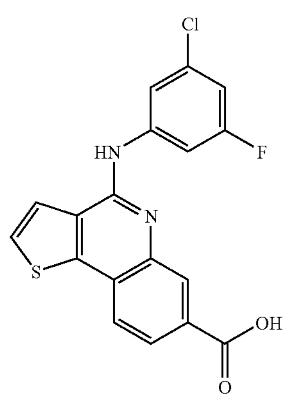 | 0.076 | |

TABLE 14-continued
| Structure | CK2: IC50 (uM) (15 uM ATP) | CK2: IC50(uM) (20 uM ATP) |
|---|---|---|
| 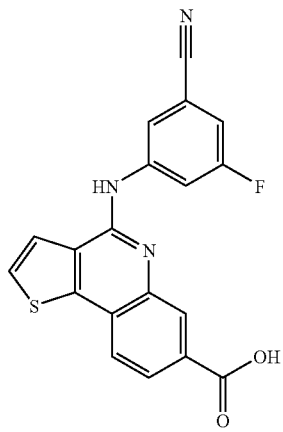 | | 0.131 |
| 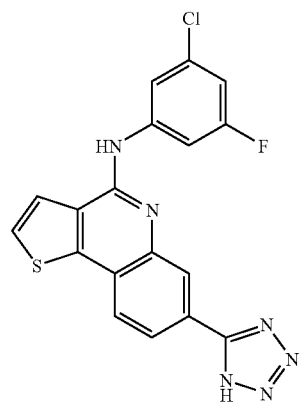 | | 0.289 |
| 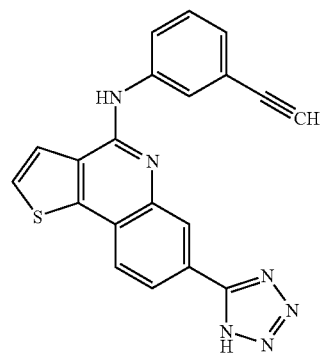 | | 0.141 |

TABLE 14-continued
| Structure | CK2: IC50 (uM) (15 uM ATP) | CK2: IC50(uM) (20 uM ATP) |
|---|---|---|
| 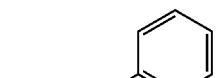 | 0.204 | |
TABLE 15
| Structure | CK2: IC50 (uM) (15 uM ATP) | CK2: IC50 (uM) (20 um ATP) |
|---|---|---|
| 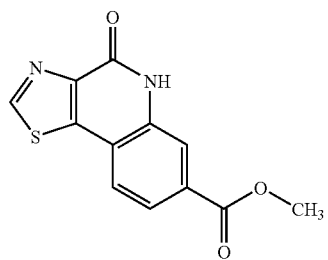 | | |
| 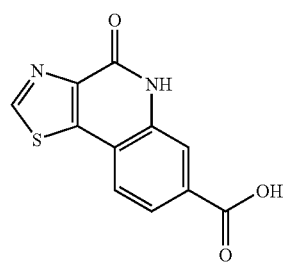 | 4.7 | |
| 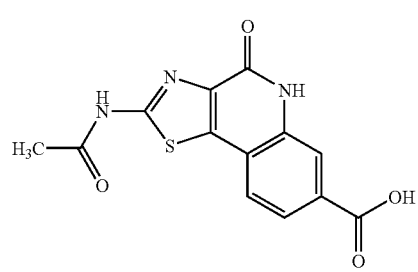 | | |
TABLE 15-continued
| Structure | CK2: IC50 (uM) (15 uM ATP) | CK2: IC50 (uM) (20 um ATP) |
|---|---|---|
| 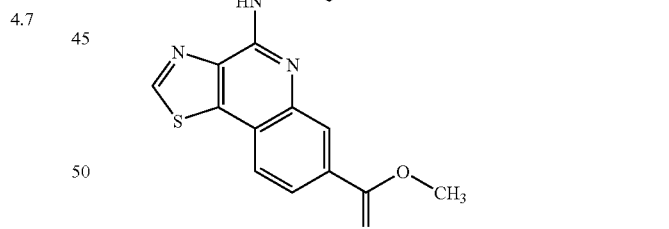 | 3.4 | |
|  | | |
| 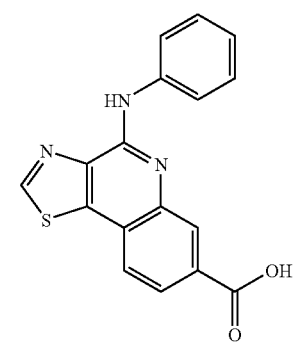 | 0.169 | 0.219 |

TABLE 15-continued

| Structure | CK2: IC50 (uM) (15 uM ATP) | CK2: IC50 (uM) (20 um ATP) |
|---|---|---|
| (3-methoxyphenyl)amino thiazoloquinoline carboxylic acid | 0.037 | |
| (3-chloro-4-fluorophenyl)amino thiazoloquinoline carboxylic acid | 0.12 | |
| (3-fluorophenyl)amino thiazoloquinoline carboxylic acid | 0.146 | |
| (3-ethynylphenyl)amino thiazoloquinoline carboxylic acid | 0.044 | |

Example 5

Cell Proliferation Modulatory Activity

A representative cell-proliferation assay protocol using Alamar Blue dye (stored at 4° C., use 20 ul per well) is described hereafter.

96-Well Plate Setup and Compound Treatment
 a. Split and trypsinize cells.
 b. Count cells using hemocytometer.
 c. Plate 4,000-5,000 cells per well in 100 μl of medium and seed into a 96-well plate according to the following plate layout. Add cell culture medium only to wells B10 to B12. Wells B1 to B9 have cells but no compound added.

|   | 1 2 3 | 4 5 6 | 7 8 9 | 10 11 12 |   |
|---|---|---|---|---|---|
| A | EMPTY | | | | |
| B | NO COMPOUND ADDED | | | Medium Only | |
| C | 10 nM | 100 nM | 1 uM | 10 uM | Control |
| D | 10 nM | 100 nM | 1 uM | 10 uM | Comp1 |
| E | 10 nM | 100 nM | 1 uM | 10 uM | Comp2 |
| F | 10 nM | 100 nM | 1 uM | 10 uM | Comp3 |
| G | 10 nM | 100 nM | 1 uM | 10 uM | Comp4 |
| H | EMPTY | | | | | d. Add 100 μl of 2× drug dilution to each well in a concentration shown in the plate layout above. At the same time, add 100 μl of media into the control wells (wells B10 to B12). Total volume is 200 μl/well.
 e. Incubate four (4) days at 37° C., 5% CO2 in a humidified incubator.
 f. Add 20 μl Alamar Blue reagent to each well.
 g. Incubate for four (4) hours at 37° C., 5% CO2 in a humidified incubator.
 h. Record fluorescence at an excitation wavelength of 544 nm and emission wavelength of 590 nm using a microplate reader.

In the assays, cells are cultured with a test compound for approximately four days, the dye then is added to the cells and fluorescence of non-reduced dye is detected after approximately four hours. Different types of cells can be utilized in the assays (e.g., HCT-116 human colorectal carcinoma cells, PC-3 human prostatic cancer cells and MiaPaca human pancreatic carcinoma cells). Anti-proliferative effects of representative compounds are provided hereafter.

TABLE 16

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | >10 | | | | | | | | | |
| | >10 | | | | | | | | | |
| | >10 | | | | | | | | | |
| | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| [structure] | >10 | | | | | | | | | |
| [structure] | >10 | >50 | 26.02 | 8.90 | >50 | | | | | |
| [structure] | >10 | | | | | | | | | |
| [structure] | >10 | 6.38 | 6.12 | 4.39 | 9.09 | >10 | >10 | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 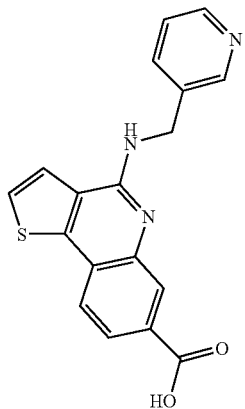 | >10 | | | | | | | | | |
| 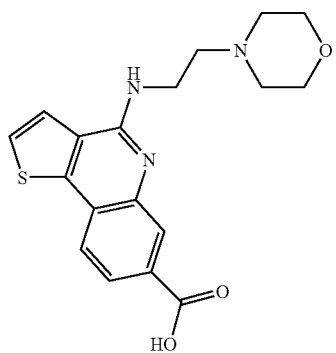 | >10 | | | | | | | | | |
| 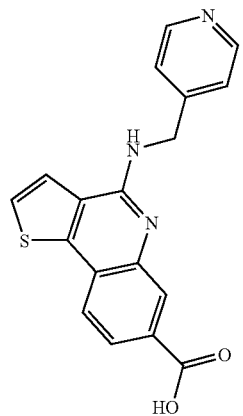 | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| (2-methoxyphenylamino thieno[3,2-c]quinoline carboxylic acid) | >10 | | | | | | | | | |
| (3-hydroxyphenylamino thieno[3,2-c]quinoline carboxylic acid) | >10 | | | | | | | | | |
| (2,4-dimethoxyphenylamino thieno[3,2-c]quinoline carboxylic acid) | >10 | | | | | | | | | |
| (2-pyrrolidin-1-yl-ethylamino thieno[3,2-c]quinoline carboxylic acid) | >10 | | | | | | | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 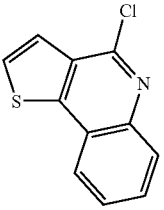 | >10 | | | | | | | | | |
| 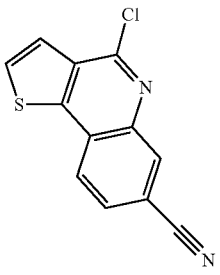 | >10 | | | | | | | | | |
| 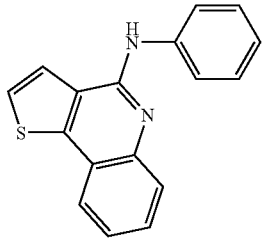 | >10 | | | | | | | | | |
| 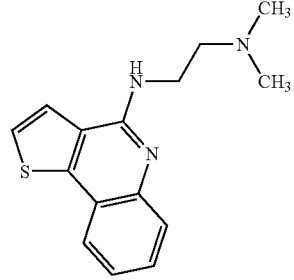 | 2 | | | | | | | | | |
| 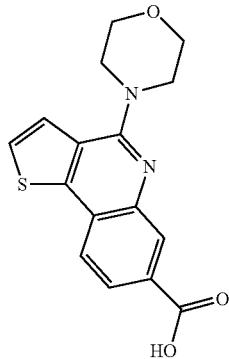 | >10 | | | | | | | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 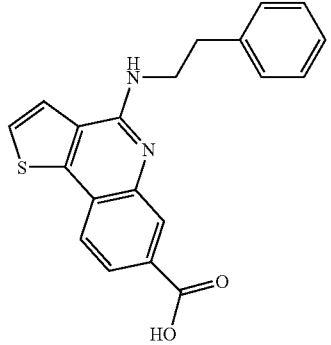 | >10 | | | | | | | | | |
| 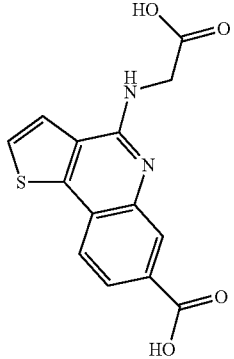 | >10 | | | | | | | | | |
| 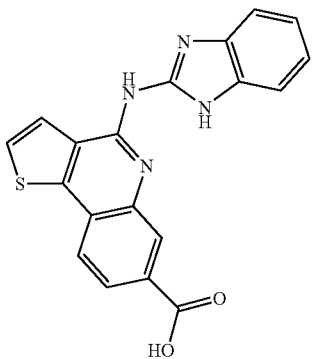 | >10 | | | | | | | | | |
| 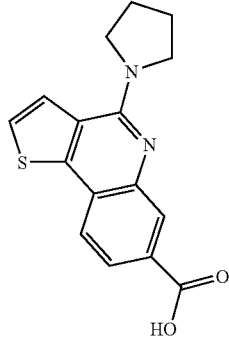 | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | >10 | 21.75 | 16.33 | 11.68 | 19.98 | | | | | |
| | >10 | | | | | | | | | |
| | >10 | | | | | | | | | |
| | >10 | | | | | >10 | | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 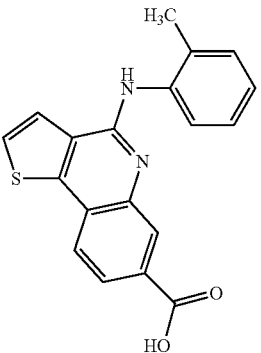 | >10 | | | | | | | | | |
| 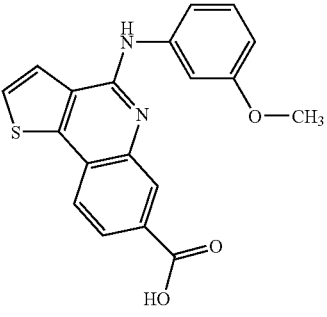 | >10 | | | | | >10 | | | | |
| 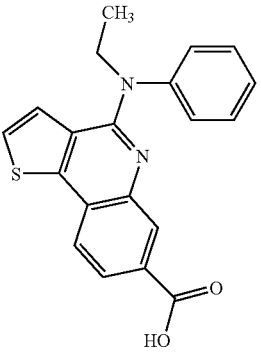 | >10 | | | | | | | | | |
| 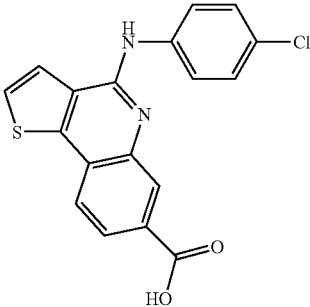 | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | >10 | | | | | | | | | |
| | >10 | | | | | | | | | |
| | >10 | | | | | | | | | |
| | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| (2-hydroxyphenylamino structure) | >10 | | | | | | | | | |
| (4-morpholinophenylamino structure) | >10 | | | | | | | | | |
| (2,5-dimethoxyphenylamino structure) | >10 | | | | | | | | | |
| (phenylamino methyl ester structure) | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| (structure) | >10 | | | | | | | | | |
| (structure) | 0 | | | | | | | | | |
| (structure) | >10 | | | | | | | | | |
| (structure) | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| [structure] | 9 | | | | | | | | | |
| [structure] | 5 | 5.50 | 6.26 | 17.81 | 7.26 | 7.60 | | 14.39 | 1.97 | |
| [structure] | >10 | | | | | | | | | |
| [structure] | >10 | | | | | | | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 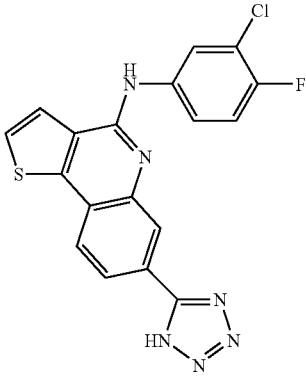 | >10 | | | | | | | | | |
| 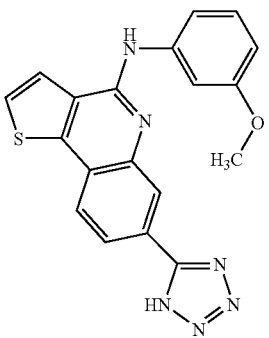 | >10 | | | | | | | | | |
| 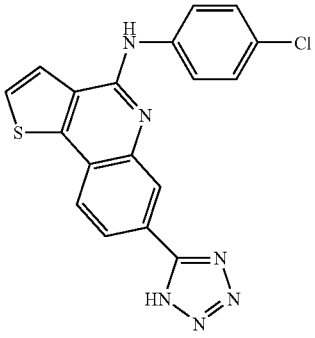 | >10 | | | | | | | | | |
| 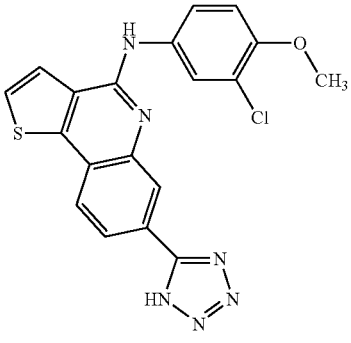 | >10 | | | | | | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| [structure] | >10 | | | | | | | | | |
| [structure] | | | | | | 15.00 | | | | |
| [structure] | | | | | | >10 | | | | |
| [structure] | | | | | | 15.00 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| (structure) | | | | | | >10 | | | | |
| (structure) | | | | | | >10 | | | | |
| (structure) | | | | | | >10 | | | | |
| (structure) | | | | | | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | 15.00 | | | | |
| | | | | | | >10 | | | | |
| | | | | | | >10 | | | | |
| | | | | | | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| (structure with CH2OH) | | | | | | 15.00 | | | | |
| (structure with isopropyl) | | | | | | >10 | | | | |
| (structure with Cl) | 5.23 | 8.89 | 15.19 | 11.95 | 15.00 | >10 | | | | |
| (structure with NHCH3 amide) | 3.01 | 4.22 | 4.01 | 2.79 | >10 | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | >10 | | | |
| | | | | | | 15.00 | | | | |
| | | | | | | >10 | >10 | | | |
| | 3.37 | 5.11 | 3.05 | 2.89 | | 15.00 | 9.55 | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 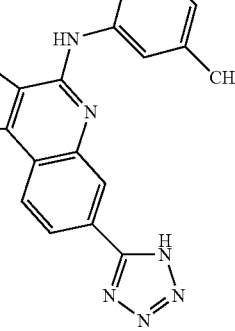 | | | | | | 15.00 | | | | |
| 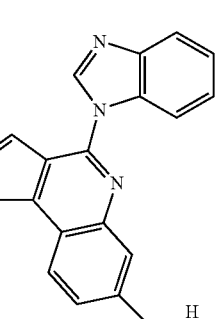 | | | | | | 15.00 | | | | |
| 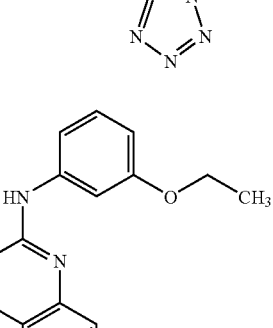 | | | | | | >10 | | | | |
| 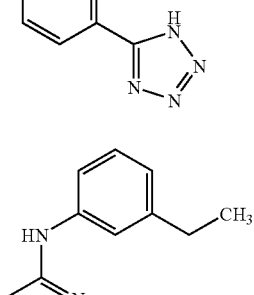 | | | | | | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | | | | |
| | | | | | | >10 | | | | |
| | | | | | | >10 | | | | |
| | | | | | | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| *structure* | | | | | | >10 | | | | |
| *structure* | | | | | | 15.00 | | | | |
| *structure* | | | | | | >10 | | | | |
| *structure* | >50 | 7.43 | 38.80 | >50 | >10 | >10 | >50 | | | >50 |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| [structure] | | >50 | | 18.53 | >50 | >10 | >10 | >50 | | >50 |
| [structure] | | 28.15 | 15.24 | 41.77 | >50 | 15.00 | >10 | >50 | | >50 |
| [structure] | | | | | | 15.00 | >10 | | | |
| [structure] | | >50 | 40.24 | 21.63 | >50 | 15.00 | >10 | >50 | | >50 |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 3,5-difluoroanilino thienoquinoline carboxylic acid | | 7.31 | 5.86 | 8.14 | 6.11 | >10 | 6.36 | 7.45 | | 2.00 |
| 3-fluoroanilino thienoquinoline carboxylic acid | | 8.67 | 5.93 | 8.78 | 2.66 | >10 | 7.28 | 6.23 | | 1.89 |
| 3-chloroanilino thienoquinoline carboxylic acid | | 9.70 | 12.36 | 14.35 | 16.66 | 15.00 | 9.82 | 11.68 | | 5.36 |
| 2-fluoro-5-chloroanilino thienoquinoline carboxylic acid | | 17.59 | 17.64 | 17.51 | >50 | >10 | >10 | 31.06 | | >50 |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| [structure: 4-(3-ethoxyphenylamino)thieno[3,2-c]quinoline-8-carboxylic acid] | | | | | | >10 | >10 | | | |
| [structure: 4-(3-phenoxyphenylamino)thieno[3,2-c]quinoline-8-carboxylic acid] | | | | | | >10 | | | | |
| [structure: 4-(3-(N-methylcarbamoyl)phenylamino)thieno[3,2-c]quinoline-8-carboxylic acid] | 9.07 | 8.69 | 13.85 | 26.72 | >10 | >10 | 6.94 | | 3.56 | |
| [structure: 4-(3-sulfamoylphenylamino)thieno[3,2-c]quinoline-8-carboxylic acid] | 10.96 | 10.16 | 9.90 | 44.93 | >10 | >10 | 7.60 | | 4.60 | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 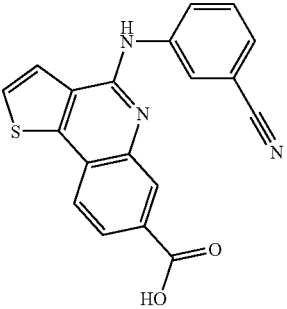 | | 12.31 | 17.61 | 19.07 | >50 | 15.00 | >10 | 16.04 | | 16.64 |
| 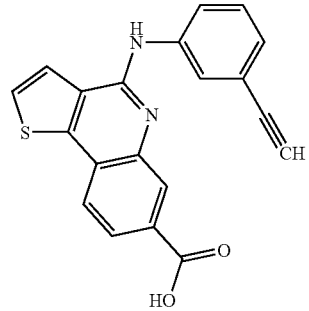 | | 9.96 | 13.57 | 16.90 | 17.78 | 15.00 | >10 | 27.72 | | 23.14 |
| 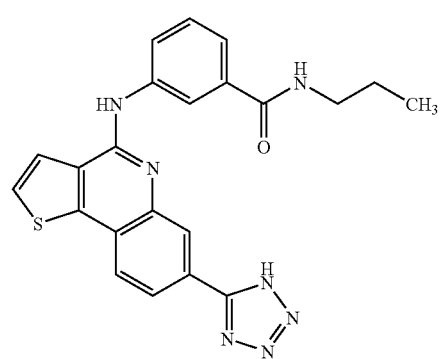 | | | | | | 15.00 | | | | |
| 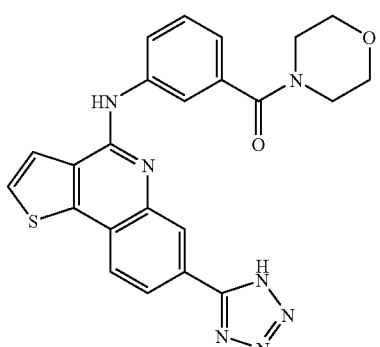 | | | | | | >10 | >10 | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | >10 | | | |
| | | | | | | >10 | >10 | | | |
| | | | | | | >10 | >10 | | | |
| | | | | | | >10 | >10 | | | |
| | | | | | | >10 | >10 | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 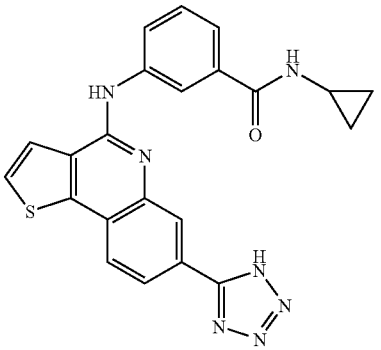 | | 7.79 | 6.97 | 12.66 | 5.31 | >10 | 3.18 | 4.49 | | 3.22 |
| 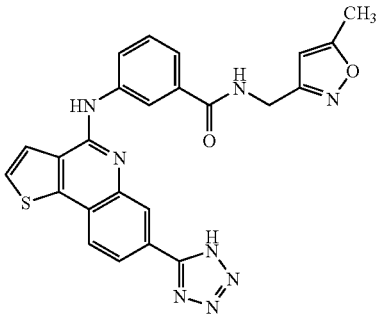 | | | | | | >10 | >10 | | | |
| 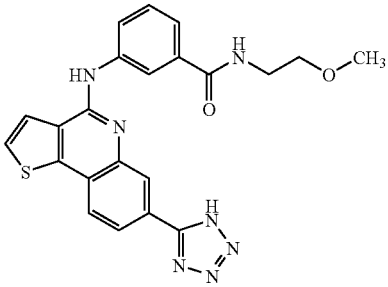 | | | | | | >10 | >10 | | | |
| 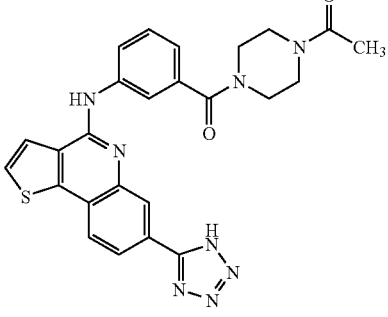 | | | | | | >10 | >10 | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | | | | |
| | | | | | | >10 | | | | |
| | | | | | | >10 | | | | |
| | | | | | | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | | | | |
| | | | | | | >10 | | | | |
| | | | | | | >10 | | | | |
| | | | | | | >10 | | | | |
| | | | | | | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| [structure] | | | | | | >10 | | | | |
| [structure] | | | | | | >10 | | | | |
| [structure] | | | | | | >10 | | | | |
| [structure] | | | | | | >10 | | | | |
| [structure] | | | | | | >10 | | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | | | | |
| | | | | | | >10 | | | | |
| | | | | | | >10 | | | | |
| | | | | | | >10 | >10 | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 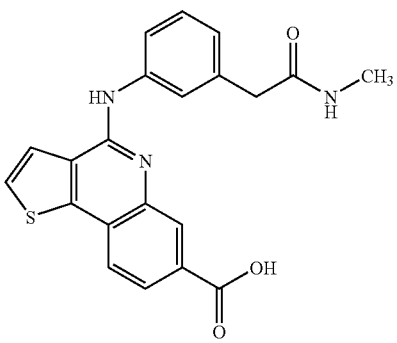 | | | | | | >10 | >10 | | | |
| 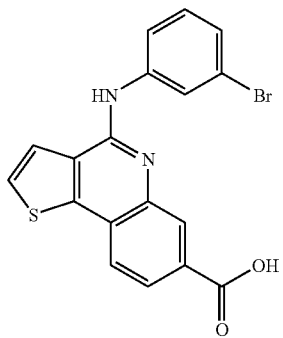 | | | | | | >10 | >10 | | | |
| 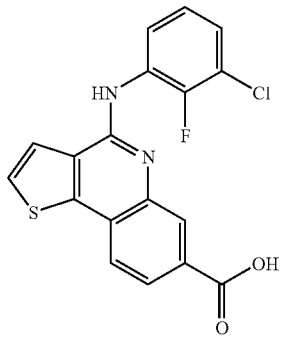 | | | | | | >10 | >10 | | | |
| 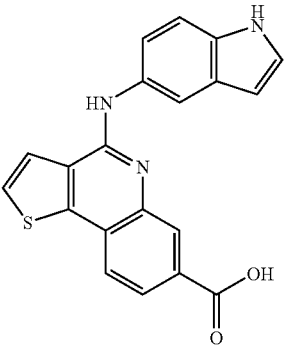 | | | | | | >10 | >10 | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | >10 | | | |
| | | | | | | >10 | >10 | | | |
| | | | | | | >10 | >10 | | | |
| | | | | | | >10 | >10 | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 3-CF3 phenylamino thienoquinoline carboxylic acid | | | | | | >10 | >10 | | | |
| 3-ethyl phenylamino thienoquinoline carboxylic acid | | | | | | >10 | >10 | | | |
| 3-iodo phenylamino thienoquinoline carboxylic acid | | | | | | >10 | 9.44 | | | |
| 2,3-difluoro phenylamino thienoquinoline carboxylic acid | | | | | | >10 | >10 | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| | | | | | | >10 | >10 | | | |
| | | | | | | >10 | >10 | | | |
| | | | | | | >10 | >10 | | | |
| | | | | | | >10 | >10 | | | |

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
|  | | 7.67 | 4.31 | 0.97 | 32.25 | 8.76 | 14.62 | 13.17 | 2.10 | 13.02 |
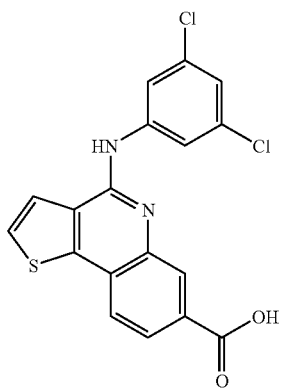
| | | | | | | 0.83 | >10 | | | |
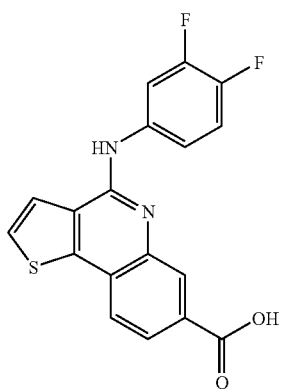
| | | | | | | >10 | >10 | | | |
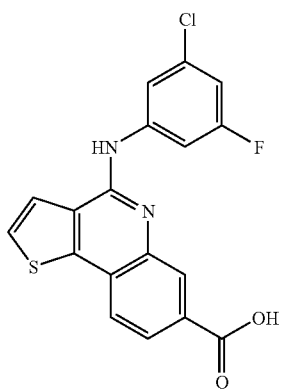

TABLE 16-continued
| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| 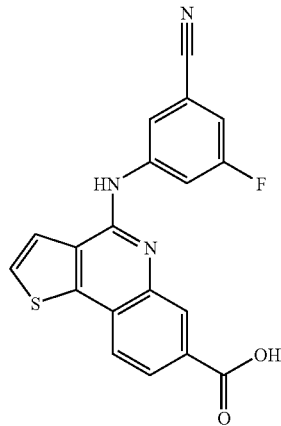 | | | | | | >10 | >10 | | | |
| 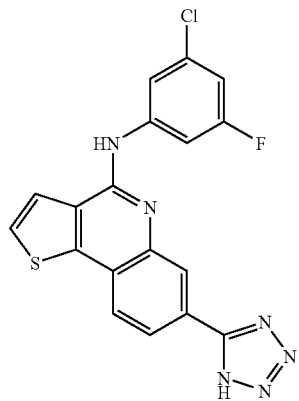 | | | | | | >10 | >10 | | | |
| 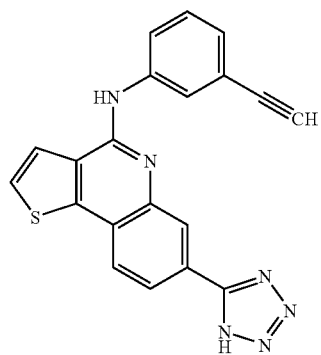 | | | | | | >10 | >10 | | | |

TABLE 16-continued

| Structure | IC50 (uM) HCT-116 | IC50 (uM) Hs578T | IC50 (uM) Jurkat | IC50 (uM) H1299 | IC50 (uM) PC3 | IC50 (uM) HCT-116 | IC50 (uM) MiaPaCa | IC50 (uM) A549 | IC50 (uM) BxPC3 | IC50 (uM) HT29 |
|---|---|---|---|---|---|---|---|---|---|---|
| [structure: 4-(3,5-difluorophenylamino)thieno[3,2-c]quinoline with tetrazole] | | | | | | >10 | >10 | | | |

TABLE 17

| Structure | IC50 (uM) A375 | IC50 (uM) MDAMB231 | IC50 (uM) K-562 | IC50 (uM) Raji | IC50 (uM) PANC1 | IC50 (uM) LNCaP | IC50 (uM) MCF-7 | IC50 (uM) H460 | IC50 (uM) HL-60 | IC50 (uM) COLO 205 | IC50 (uM) SK-OV-3 |
|---|---|---|---|---|---|---|---|---|---|---|---|
| [structure: 4-(3,5-dichlorophenylamino)thieno[3,2-c]quinoline-8-carboxylic acid] | 19.93 | 3.89 | 11.03 | 17.71 | 20.34 | 6.23 | 13.73 | 12.27 | 1.94 | 1.01 | 11.72 |

TABLE 18

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| [structure: phenylamino-substituted diazaphenanthrene carboxylic acid] | 18.36 | 13.29 | 7.51 | 6.84 | 15.43 | 23.67 | 14.86 |

TABLE 18-continued
| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 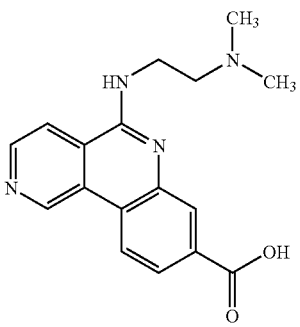 | | >10 | | 3.80 | 17.89 | 23.79 | 12.90 |
| 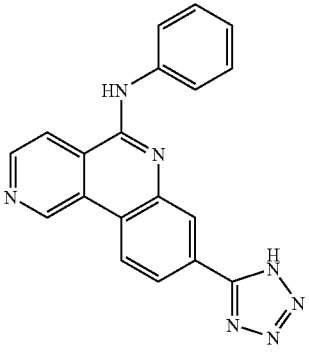 | | >10 | | | | | |
| 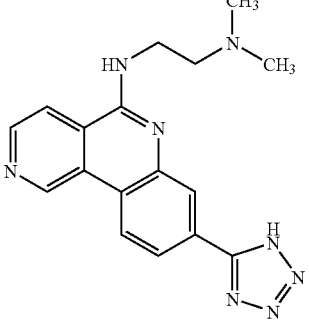 | | >10 | | | | | |
| 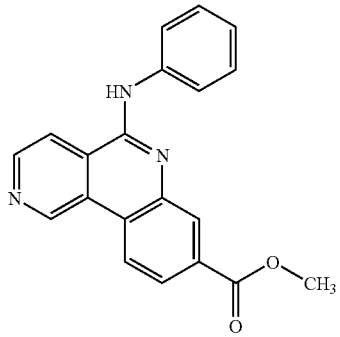 | | 15.00 | | 13.07 | 11.26 | 6.83 | 4.78 |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| *(structure: 3-methoxyphenylamino benzo[c][2,7]naphthyridine carboxylic acid)* | >10 | >10 | 10.73 | 17.39 | 6.52 | 12.90 |  |
| *(structure: 3-chloro-4-fluorophenylamino benzo[c][2,7]naphthyridine carboxylic acid)* | 3.21 | 4.34 | 3.06 | 3.08 | 4.86 | 2.68 | 3.31 |
| *(structure: phenylamino benzo[c][2,7]naphthyridine carbonitrile)* | 6.90 |  |  |  |  |  |  |
| *(structure: (2-(dimethylamino)ethyl)amino benzo[c][2,7]naphthyridine carbonitrile)* | 1.60 |  |  |  |  |  |  |

TABLE 18-continued
| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 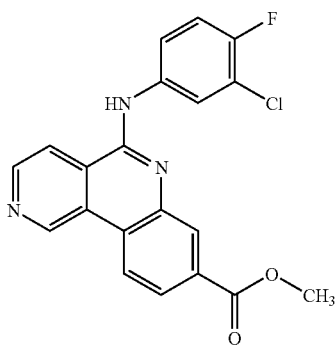 | | 3.94 | | 8.46 | 9.02 | 4.25 | 2.62 |
| 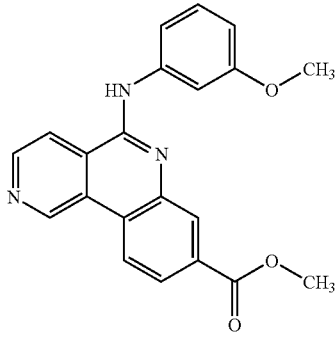 | | 15.00 | | 7.16 | 11.30 | 3.40 | 1.82 |
| 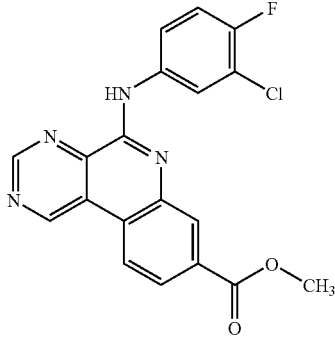 | | >10 | | 15.40 | 15.85 | 20.26 | 3.70 |
| 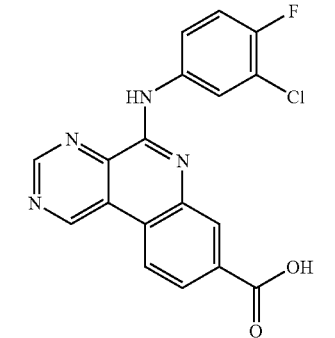 | | >10 | 1.22 | 7.55 | 18.76 | 4.29 | 9.70 |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| (phenylamino structure with oxadiazole-CH3) | >10 | | | | | | |
| (3-fluorophenylamino structure with COOH) | | | 6.86 | 8.32 | 9.23 | 3.19 | 5.89 |
| (phenethylamino structure with COOH) | >10 | 5.08 | 20.96 | 23.58 | 11.11 | 16.53 | |
| (3-chlorophenylamino structure with COOH) | 3.95 | 4.02 | 2.74 | 3.08 | 1.51 | 2.37 | 0.67 |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | 1.71 | 2.92 | | | | |
| 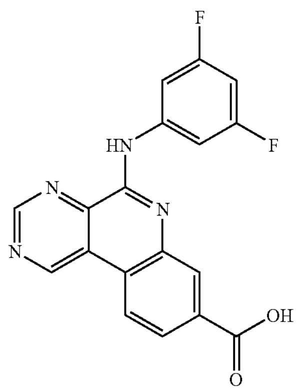 | 2.63 | 4.06 | 0.85 | 6.62 | 7.50 | 2.59 | 5.90 |
| 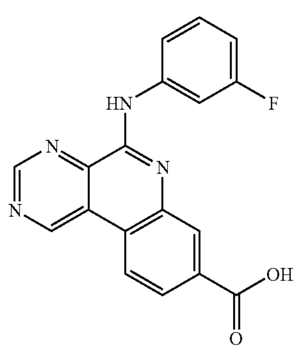 | 5.11 | 7.10 | 3.36 | 7.24 | 4.71 | 1.89 | 3.43 |
| 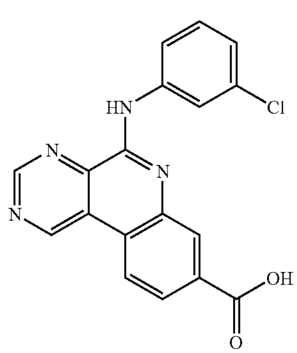 | 5.45 | 7.19 | 2.09 | 3.01 | 9.14 | 0.88 | 11.16 |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 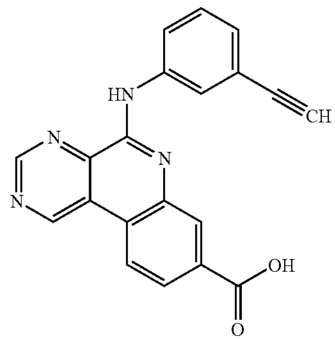 | 4.12 | 5.86 | 0.67 | 1.55 | 3.13 | 1.80 | 2.86 |
| | >10 | >10 | >50 | >50 | | 9.43 | |
| | >10 | >10 | >50 | >50 | | 18.76 | |
| 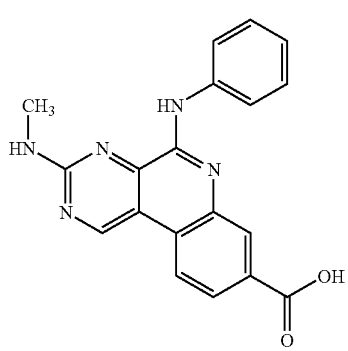 | 1.92 | 2.99 | 1.09 | 2.42 | 3.14 | 0.73 | 1.84 |

TABLE 18-continued
| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 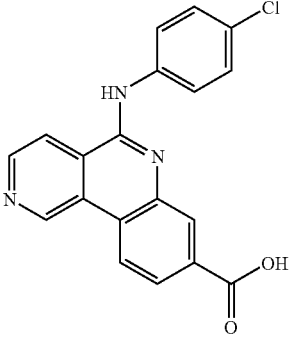 | 4.80 | 6.72 | 2.70 | 1.94 | 8.63 | 2.53 | 6.64 |
| 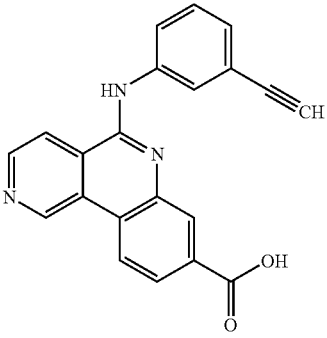 | 7.36 | 10.80 | 3.85 | 3.65 | 16.82 | 2.78 | 4.03 |
| 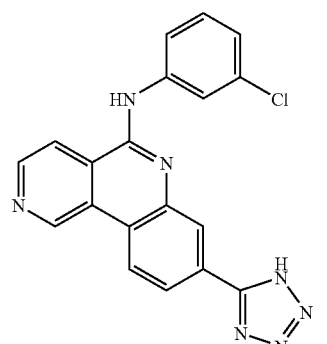 | >10 | >10 | >50 | 46.58 | 14.25 | | |
| 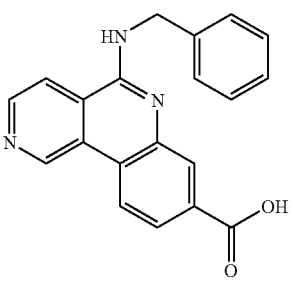 | >10 | 31.22 | | | 17.70 | | |

TABLE 18-continued
| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 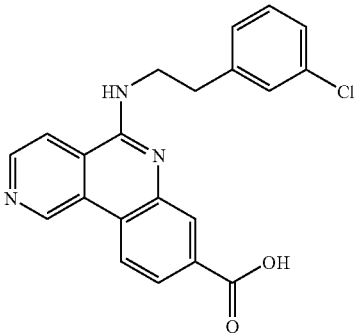 | | >10 | >10 | | 46.55 | 18.88 | 25.01 |
| 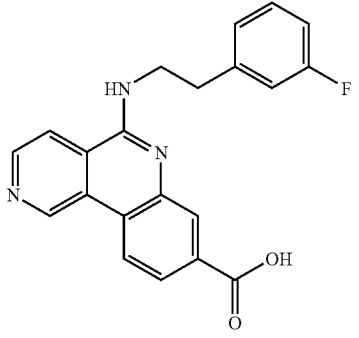 | | >10 | >10 | | 27.00 | 12.22 | 24.57 |
| 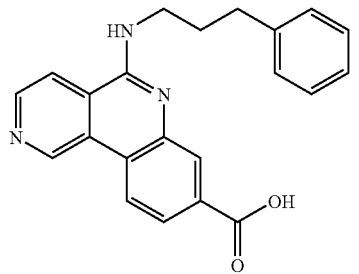 | | >10 | >10 | | 5.25 | 13.23 | 29.95 |
| 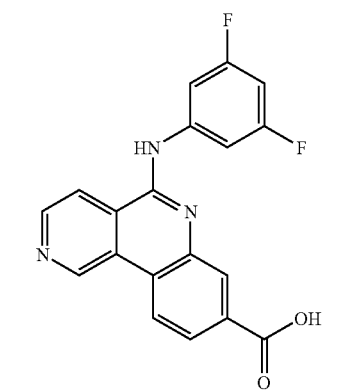 | 5.40 | 4.33 | 1.35 | 8.91 | 10.14 | 2.41 | 9.09 |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | >10 | >10 | | | 26.38 | 22.00 | 35.59 |
| | >10 | >10 | | | | | |
| | 9.56 | >10 | | | | | |
| | 0.97 | 2.82 | | | | | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | | 4.06 | >10 | | | |
| | | | 4.28 | 4.05 | | | |
| | | | 1.94 | 0.68 | | 2.42 | |
| | | | >10 | 2.99 | | 4.53 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | >10 | 3.20 | | | | 5.80 | |
| | >10 | 16.22 | | | | 26.13 | |
| | >10 | 11.88 | | | | 7.90 | |
| | >10 | 14.40 | | | | 18.91 | |

TABLE 18-continued
| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 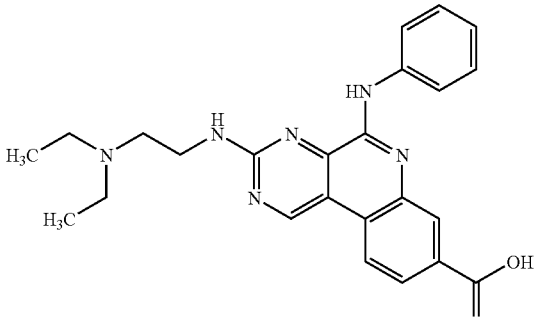 | | >10 | 1.45 | | | 13.07 | |
| 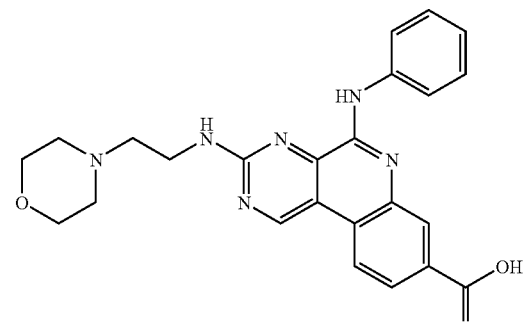 | | >10 | 1.69 | | | 5.70 | |
| 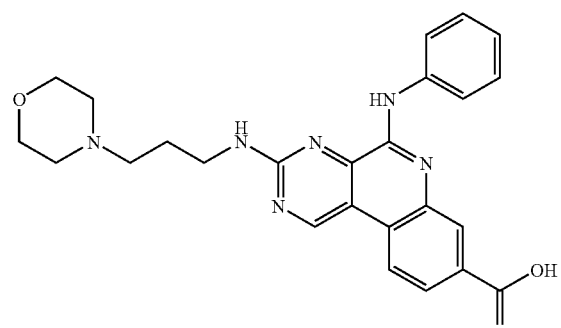 | | >10 | 1.36 | | | 2.18 | |
| 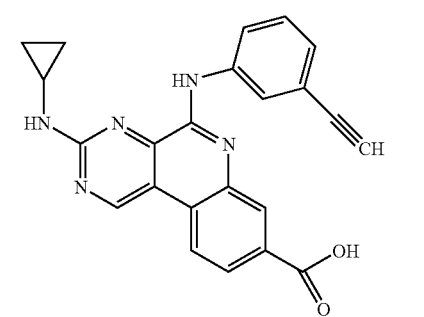 | | 7.30 | 1.20 | | | 1.27 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | >10 | 2.32 | | | 2.67 | |
| | | 8.05 | 1.00 | | | 0.94 | |
| | | >10 | 8.62 | | | 9.55 | |
| | | >10 | 2.26 | | | 3.69 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | 4.69 | 2.34 | | | 1.29 | |
| | | 3.99 | 9.09 | | | 3.05 | |
| | | 7.82 | 0.47 | | | 1.29 | |
| | | >10 | 2.23 | | | 2.53 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | >10 | 18.06 | | | 35.93 | |
| | | >10 | 1.75 | | | 1.09 | |
| | | >10 | >50 | | | 5.83 | |
| | | >10 | 0.88 | | | 1.14 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | >10 | 5.45 | | | | 18.42 | |
| | >10 | 0.65 | | | | 3.13 | |
| | >10 | 0.92 | | | | 3.06 | |
| | >10 | 0.65 | | | | 1.24 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | 11.25 | 0.95 | | | 4.34 | |
| | | >10 | 0.37 | | | 1.54 | |
| | | >10 | 1.08 | | | 0.41 | |
| | | >10 | 0.62 | | | 1.13 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | >10 | 0.87 | | | 0.39 | | |
| | >10 | 2.01 | | | 2.37 | | |
| | >10 | 0.45 | | | 2.04 | | |
| | >10 | 0.48 | | | 0.42 | | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | >10 | >50 | | | >50 | |
| | | >10 | 5.39 | | | 4.95 | |
| | | >10 | >50 | | | 26.98 | |
| | | >10 | 17.06 | | | 4.41 | |

TABLE 18-continued
| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 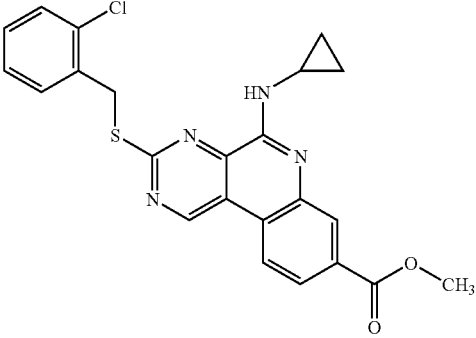 | | >10 | 32.40 | | | 4.67 | |
| 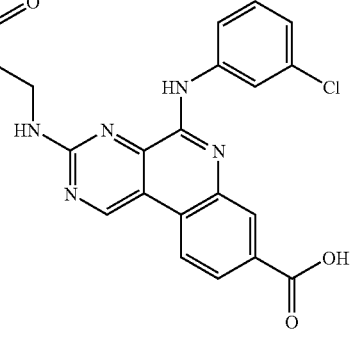 | | >10 | >50 | | | 37.71 | |
| 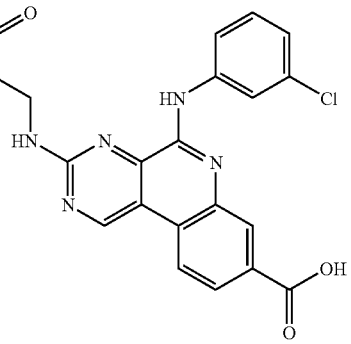 | | >10 | >50 | | | >50 | |
| 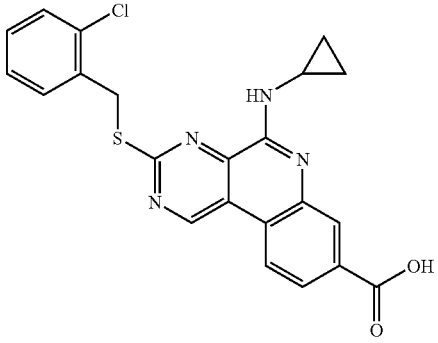 | | >10 | >50 | | | 29.33 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | >10 | >50 | | | 18.50 | |
| | | >10 | 2.83 | | | 3.45 | |
| | | >10 | 14.66 | | | 8.82 | |
| | | >10 | 2.44 | | | 4.60 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | >10 | | | | >50 | |
| | | >10 | 8.33 | | | 3.45 | |
| | | 5.14 | 8.55 | | | 3.15 | |
| | | >10 | 2.32 | | | 6.02 | |

TABLE 18-continued
| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| 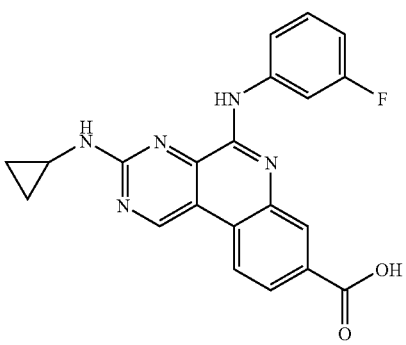 | | >10 | 3.27 | | | | 3.56 |
| 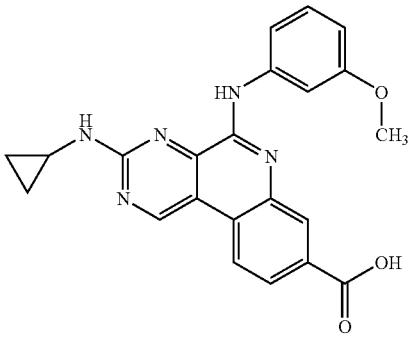 | | >10 | 2.85 | | | | 3.44 |
| 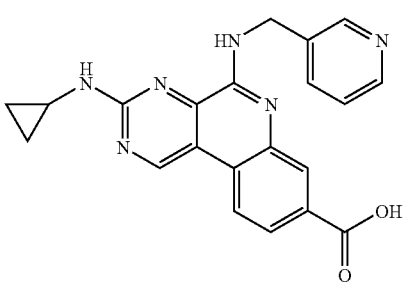 | | >10 | 13.81 | | | | 25.75 |
| 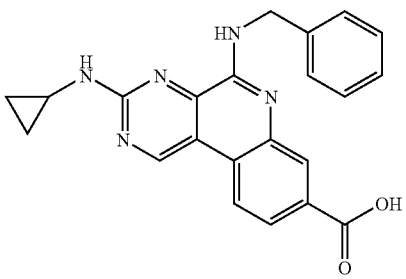 | | >10 | 12.87 | | | | 16.92 |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | >10 | >50 | | | 3.67 | |
| | | >10 | 2.14 | | | 1.25 | |
| | | 9.80 | 3.16 | | | 2.86 | |
| | | >10 | 8.21 | | | 2.59 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | >10 | | 3.41 | | | 1.12 | |
| | >10 | | 3.97 | | | 1.16 | |
| | >10 | | | | | 3.92 | |
| | >10 | | 11.91 | | | 3.65 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | >10 | 18.24 | | | | 1.34 | |
| | >10 | 1.97 | | | | 1.50 | |
| | >10 | 4.50 | | | | 5.11 | |
| | >10 | 5.12 | | | | 8.98 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| | | >10 | 26.48 | | | 37.46 | |
| | | >10 | | | | 1.16 | |
| | | >10 | >50 | | | >50 | |
| | | >10 | >50 | | | 33.95 | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
| --- | --- | --- | --- | --- | --- | --- | --- |
| | | >10 | 0.33 | | | | 3.75 |
| | | >10 | >50 | | | | 26.68 |
| | | >10 | 4.65 | | | | 7.49 |
| | | >10 | | | | | |

TABLE 18-continued

| Structure | IC50 (uM) A375 | IC50 (uM) HCT-116 | IC50 (uM) MiaPaCa | IC50 (uM) H1299 | IC50 (uM) PC3 | IC50 (uM) Jurkat | IC50 (uM) Hs578T |
|---|---|---|---|---|---|---|---|
| [structure: 3-dimethylamino-6-cyclopropylamino pyrimido-quinoline-carboxylic acid] | >10 | | | | | | |

TABLE 19

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| [structure: 6-phenylamino pyrido-quinoline carboxylic acid] | 4.16 | 10.79 | 8.18 | 2.66 | 13.70 | 4.86 | 4.01 |
| [structure: 6-(3-chloro-4-fluorophenylamino) pyrido-quinoline carboxylic acid] | 6.83 | 8.24 | 4.57 | 6.13 | 4.51 | 1.92 | 4.95 |
| [structure: 6-(3-chloro-4-fluorophenylamino) pyrimido-quinoline carboxylic acid] | | | | 1.11 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | 16.65 | | | | | |
| 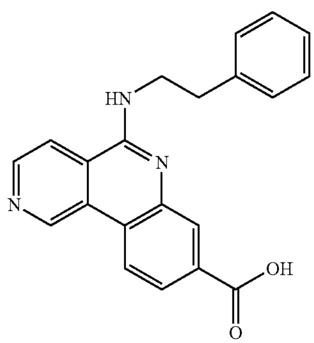 | 47.04 | 14.71 | 8.60 | | | | |
| 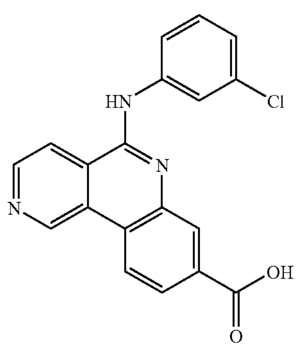 | 6.59 | 17.68 | 4.89 | 6.66 | 3.32 | 2.64 | 2.99 |
| 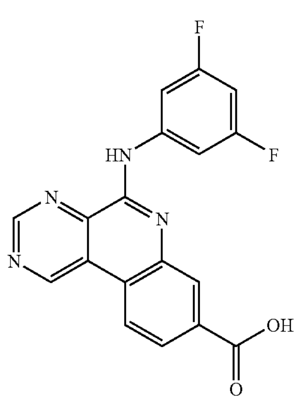 | 24.58 | 2.02 | 1.83 | 3.10 | 8.47 | 1.85 | 2.41 |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| *structure with 3-fluoroanilino and carboxylic acid* | 14.10 | 1.06 | 1.36 | 0.84 | 4.51 | 9.68 | 1.77 |
| *structure with 3-chloroanilino and carboxylic acid* | 28.46 | 1.79 | 1.56 | 1.18 | | 7.35 | 1.13 |
| *structure with 3-ethynylanilino and carboxylic acid* | 21.21 | 1.27 | 1.40 | 4.25 | 3.38 | 4.49 | 1.20 |
| *structure with 3-fluoroanilino and tetrazole* | >50 | >50 | <0.2 | >50 | | | 40.62 |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 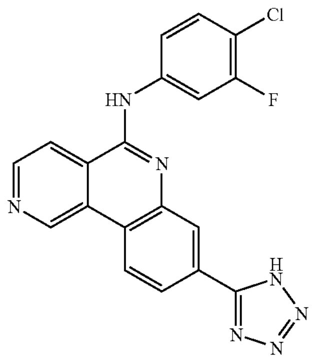 | >50 | 5.94 | 48.24 | >50 | | | >50 |
| 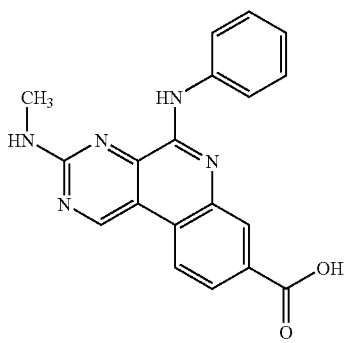 | 13.86 | 3.40 | 1.44 | 2.38 | 4.97 | 0.73 | 1.68 |
| 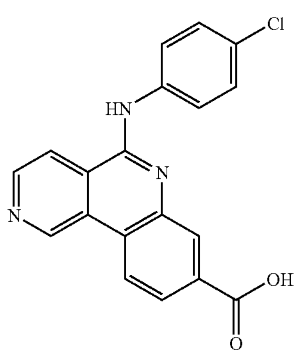 | 9.74 | 0.76 | 7.39 | 3.79 | 5.46 | 3.74 | 8.65 |
| 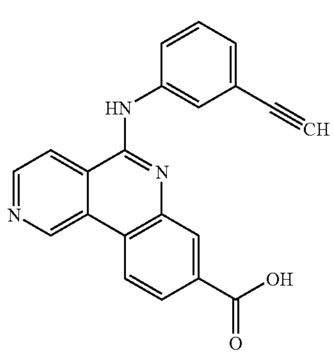 | 30.24 | 1.43 | 17.08 | 11.80 | 4.28 | 5.59 | 3.33 |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 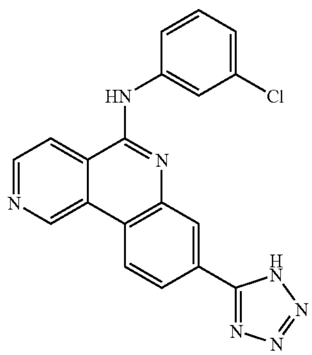 | >50 | >50 | 37.38 | >50 | | | 31.21 |
| | | | | 37.98 | | | |
| 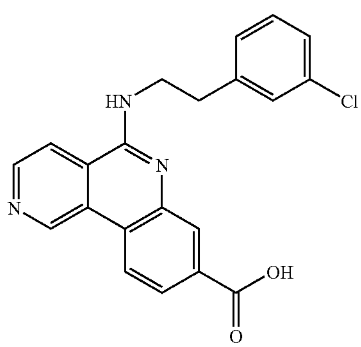 | 32.50 | 47.63 | 13.91 | 14.22 | | | 9.18 |
| 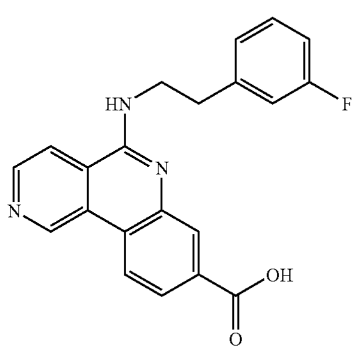 | 47.17 | >50 | 10.30 | 5.83 | | | 8.11 |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
|  | >50 | >50 | 10.43 | 7.66 |  |  | 7.17 |
| 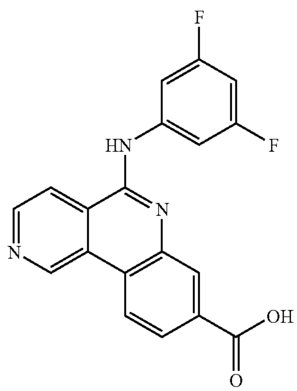 | 27.37 | 1.89 | 10.76 | 11.04 | 6.35 | 4.81 | 3.26 |
|  | >50 | 40.95 | 15.51 | 28.65 |  |  | 9.15 |
|  |  |  |  | 0.73 |  |  |  |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 18.16 | | | |
| | | | | 24.45 | | | |
| | | | | >50 | | | |
| | | | | 48.21 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | >50 | | | |
| | | | | 10.51 | | | |
| | | | | 2.44 | | | |
| | | | | >50 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 4.90 | | | |
| | | | | 10.44 | | | |
| | | | | 4.74 | | | |
| | | | | >50 | | | |
| | | | | 12.45 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 5.21 | | | |
| | | | | 4.43 | | | |
| | | | | 3.93 | | | |
| | | | | 2.93 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 26.52 | | | |
| | | | | 8.28 | | | |
| | | | | 9.82 | | | |
| | | | | 4.12 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 20.77 | | | |
| | | | | 9.19 | | | |
| | | | | 6.87 | | | |
| | | | | 15.77 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 6.53 | | | |
| | | | | 7.12 | | | |
| | | | | 12.63 | | | |
| | | | | 31.58 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 5.22 | | | |
| | | | | 7.05 | | | |
| | | | | 8.38 | | | |
| | | | | 2.63 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | >50 | | | |
| | | | | 5.48 | | | |
| | | | | >50 | | | |
| | | | | 27.18 | | | |

TABLE 19-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 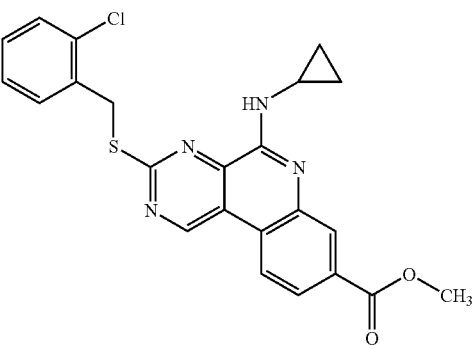 | | | | 7.23 | | | |
| 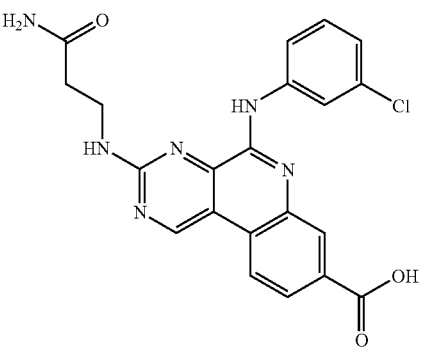 | | | | >50 | | | |
| 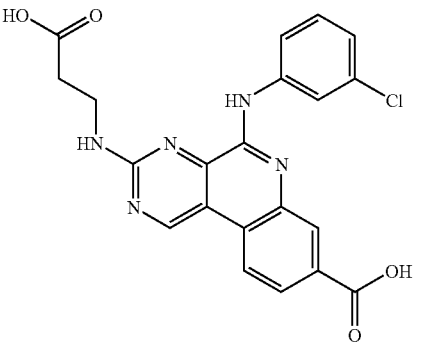 | | | | >50 | | | |
| 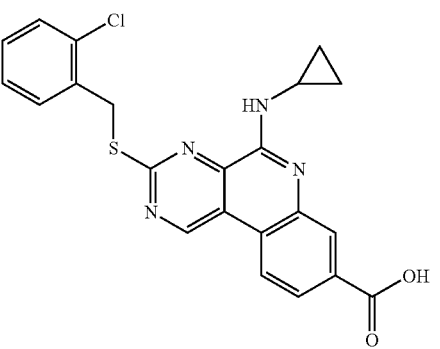 | | | | >50 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | >50 | | | |
| | | | | 7.22 | | | |
| | | | | 23.54 | | | |
| | | | | 6.88 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | >50 | | | |
| | | | | 17.50 | | | |
| | | | | 13.02 | | | |
| | | | | 23.04 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 12.77 | | | |
| | | | | 20.11 | | | |
| | | | | >50 | | | |
| | | | | >50 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | >50 | | | |
| | | | | >50 | | | |
| | | | | 9.66 | | | |
| | | | | 33.72 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | 25.43 | | | |
| | | | | >50 | | | |
| | | | | 39.84 | | | |
| | | | | 10.47 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | >50 | | | |
| | | | | 5.48 | | | |
| | | | | 12.11 | | | |
| | | | | 19.23 | | | |

TABLE 19-continued

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| | | | | >50 | | | |
| | | | | 4.27 | | | |
| | | | | 34.23 | | | |
| | | | | >50 | | | |

TABLE 19-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 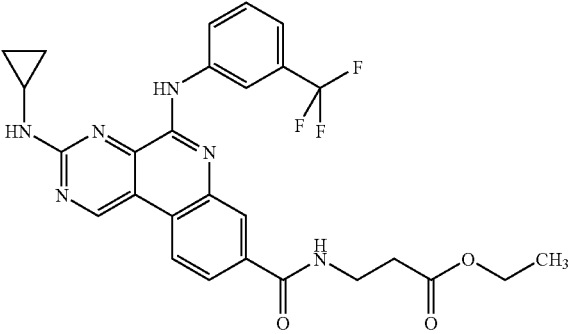 | | | | 2.52 | | | |
| 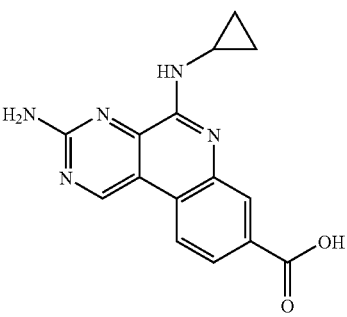 | | | | >50 | | | |
| 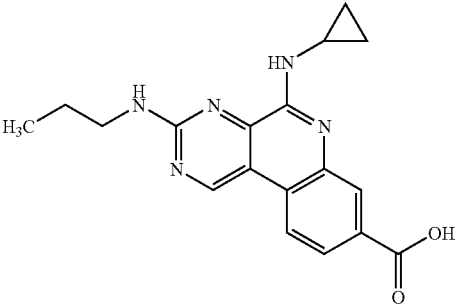 | | | | 4.36 | | | |
TABLE 19b
| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 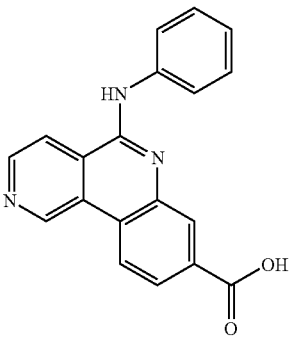 | 10.85 | 8.92 | >50 | 20.65 | 3.84 | 37.52 | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| *[structure: 3-chloro-4-fluoroanilino benzo[c][2,7]naphthyridine carboxylic acid]* | 1.50 | 2.20 | 1.84 | 7.33 | | 8.69 | | |
| *[structure: 3-chloro-4-fluoroanilino pyrimido-quinoline carboxylic acid]* | 3.55 | | 3.37 | | | | | |
| *[structure: phenylamino benzo[c][2,7]naphthyridine with methyl-oxadiazole]* | | | | | | | | |
| *[structure: 3-fluoroanilino benzo[c][2,7]naphthyridine carboxylic acid]* | | | | | | | | 12.78 |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| [structure] | | | | | | | | 46.85 |
| [structure] | 2.75 | 1.96 | 17.81 | 9.03 | 0.53 | 10.26 | 1.56 | 10.46 |
| [structure] | 3.34 | 5.69 | 9.34 | 6.98 | 1.08 | 4.19 | 12.43 | |
| [structure] | 3.48 | 6.16 | 3.79 | 14.37 | | 6.16 | 16.96 | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| (3-chloroanilino pyrimido-quinoline carboxylic acid) | 1.48 | 8.62 | 18.67 | 8.97 | | 4.10 | 12.97 | |
| (3-ethynylanilino pyrimido-quinoline carboxylic acid) | 2.58 | 7.04 | 2.34 | 20.17 | 0.64 | 7.33 | 12.44 | 8.81 |
| (3-fluoroanilino pyrido-quinoline tetrazole) | | | >50 | | | | | |
| (4-chloro-3-fluoroanilino pyrido-quinoline tetrazole) | | | >50 | | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 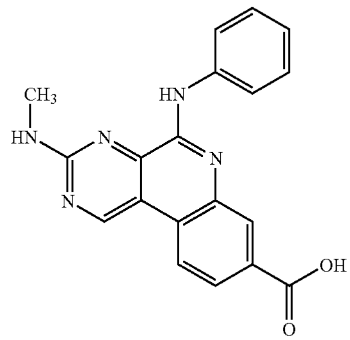 | 1.83 | 9.56 | 15.88 | 1.06 | | 4.06 | 15.34 | 5.68 |
| 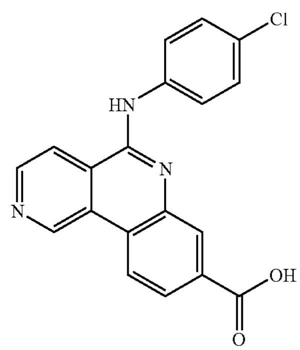 | 6.38 | 1.57 | 25.80 | 15.33 | | 9.10 | 26.85 | |
| 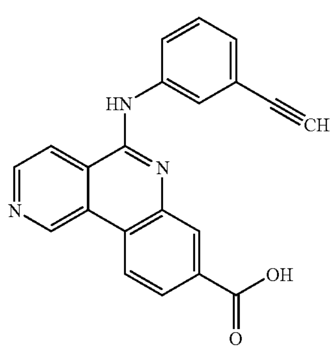 | 3.70 | 4.44 | 4.07 | 23.38 | 0.73 | 13.78 | 45.47 | |
| | | | | >50 | | | | |

TABLE 19b-continued
| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 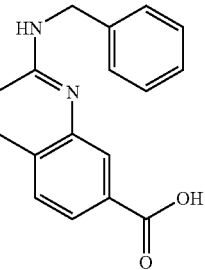 | | | >50 | | >50 | | | |
| 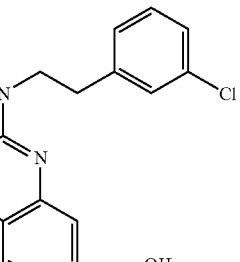 | | | 24.34 | | 28.07 | | | 34.02 |
| 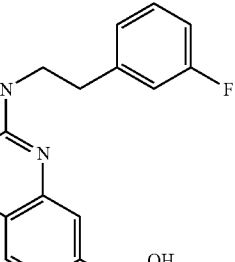 | | | 3.29 | | 28.20 | | | 31.26 |
| 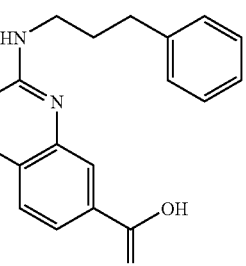 | | | 23.43 | | 34.43 | | | 16.36 |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| (3,5-difluorophenylamino structure) | 1.63 | 3.62 | 24.00 | 10.10 | | 7.53 | 16.64 | |
| (3-cyanophenylamino structure) | 3.62 | | >50 | | | | 41.82 | |
| (cyclopropylamino, phenylamino structure) | 2.16 | | 5.02 | | | | | |
| (propylamino, phenylamino structure) | 5.83 | | 4.28 | | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| (methoxyethylamino phenylamino tricyclic carboxylic acid) | 3.92 | 32.63 | | | | | | |
| (hydroxyethylamino phenylamino tricyclic carboxylic acid) | 23.53 | >50 | | | | | | |
| (hydroxypropylamino phenylamino tricyclic carboxylic acid) | 9.41 | 34.16 | | | | | | |
| (piperidinylamino phenylamino tricyclic carboxylic acid) | 8.36 | >50 | | | | | | |

TABLE 19b-continued
| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 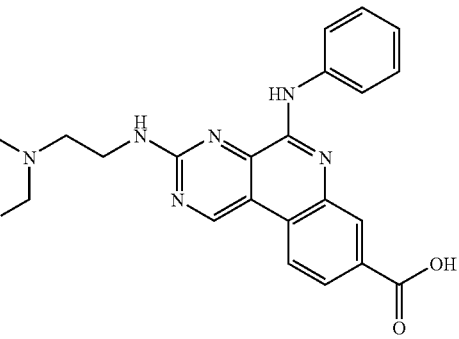 | | | 10.70 | | >50 | | | |
| 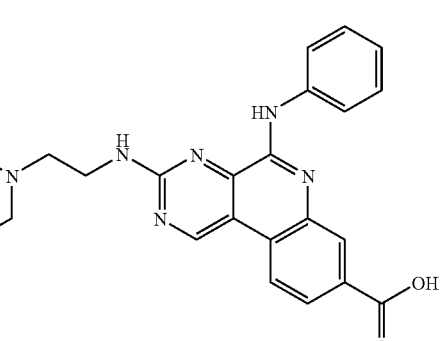 | | | 4.67 | | 27.45 | | | |
| 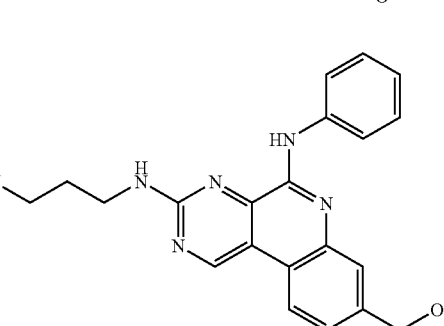 | | | 1.65 | | >50 | | | |
| 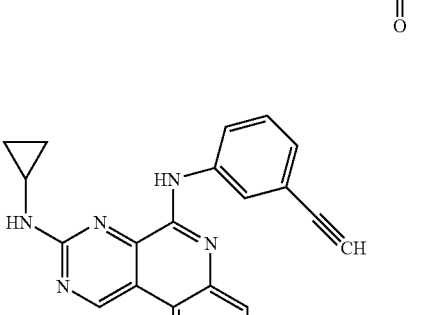 | | | 1.05 | | 5.79 | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | 3.00 | 8.12 | | | | |
| | | | 1.17 | 4.61 | | | | |
| | | | 25.31 | >50 | | | | |
| | | | 3.60 | 11.24 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 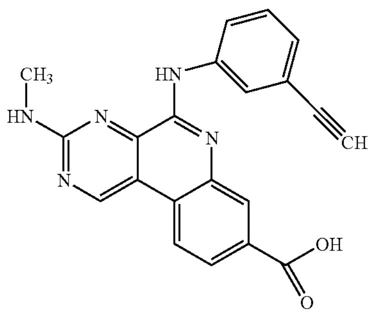 | 1.60 | | | 13.76 | | | | |
| 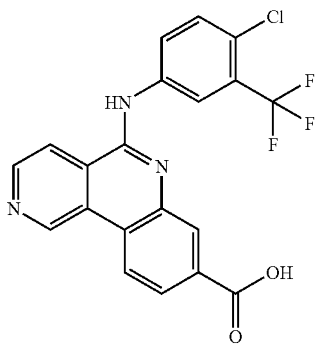 | 2.60 | | | 17.87 | | | | |
| 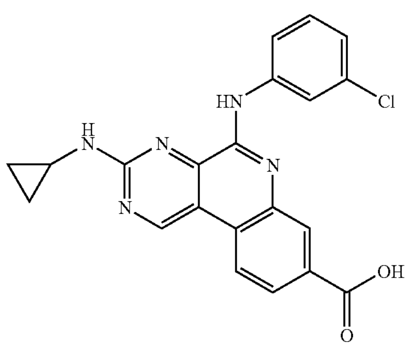 | 1.95 | | | 4.61 | | | | |
| 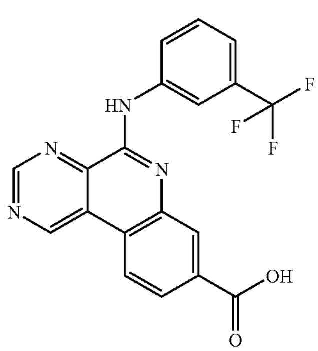 | 4.31 | | | 35.20 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | 49.61 | >50 | | | | |
| | | | 2.56 | 8.30 | | | | |
| | | | 42.69 | >50 | | | | |
| | | | 0.61 | 3.62 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| (structure: 3-isopropylamino, 6-(3-chlorophenylamino) pyrimidoquinoline carboxylic acid) | | | 36.90 | 33.21 | | | | |
| (structure: 3-cyclopropylamino, 6-(3-trifluoromethylphenylamino) pyrimidoquinoline carboxylic acid) | | | 10.01 | 2.03 | | | | |
| (structure: 3-ethylamino, 6-(3-chlorophenylamino) pyrimidoquinoline carboxylic acid) | | | 2.37 | 1.61 | | | | |
| (structure: 3-methylamino, 6-(3-chloro-4-fluorophenylamino) pyrimidoquinoline carboxylic acid) | | | 1.46 | >50 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 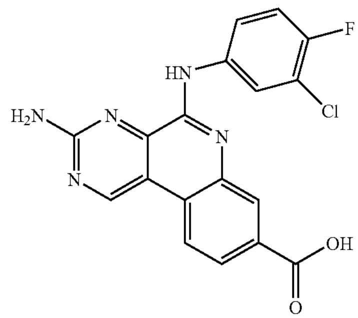 | 0.70 | | | 8.03 | | | | |
| 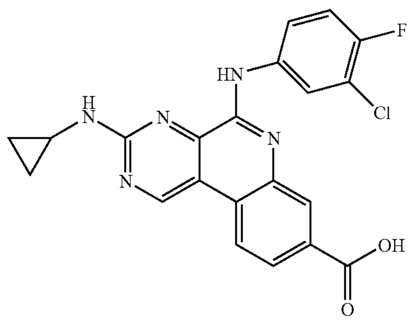 | 9.48 | | | 8.53 | | | | |
| 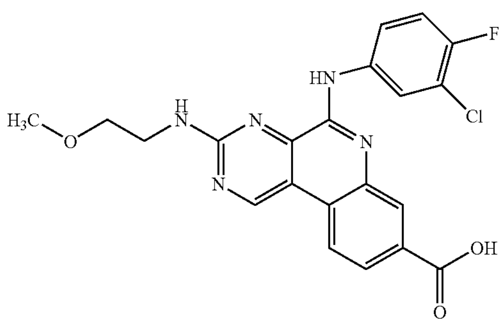 | 1.61 | | | >50 | | | | |
| 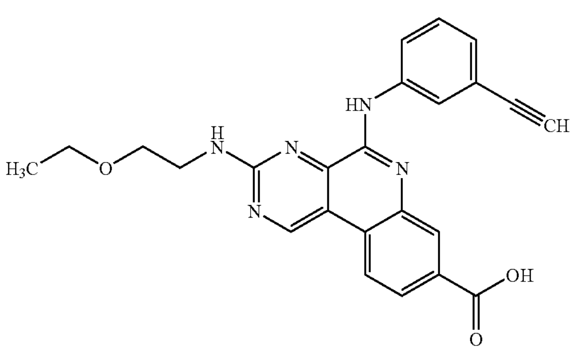 | 0.69 | | | 2.41 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | 0.48 | 1.04 | | | | |
| | | | 0.97 | 3.10 | | | | |
| | | | 1.20 | 6.66 | | | | |
| | | | 0.82 | 1.30 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | 15.85 | | >50 | | | |
| | | | 8.88 | | >50 | | | |
| | | | 40.00 | | >50 | | | |
| | | | 2.62 | | 25.46 | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 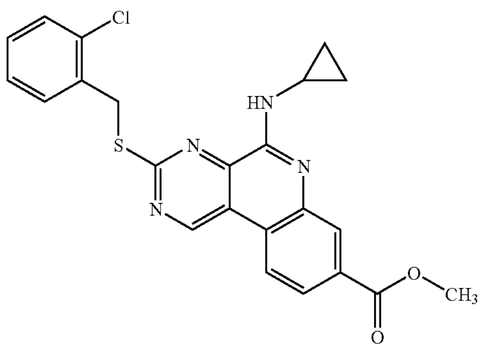 | 2.12 | 3.48 | | | | | | |
| 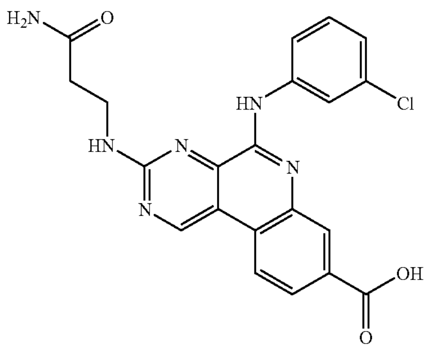 | 20.85 | >50 | | | | | | |
| 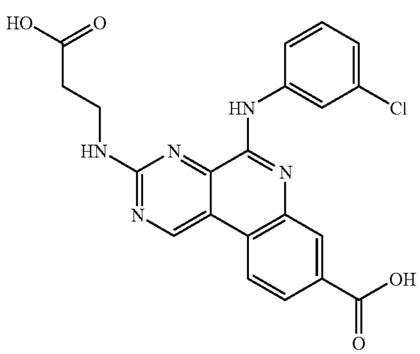 | 43.49 | >50 | | | | | | |
| 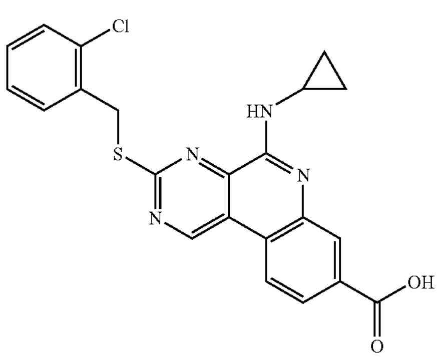 | 45.33 | >50 | | | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | 48.86 | >50 | | | | |
| | | | 2.59 | 2.60 | | | | |
| | | | 10.92 | 25.80 | | | | |
| | | | 3.92 | 4.02 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 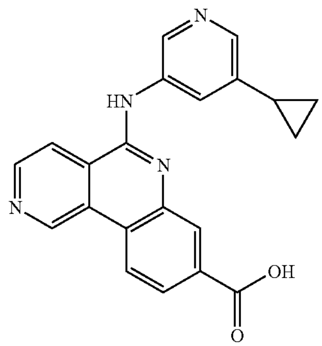 | 38.07 | | | >50 | | | | |
| 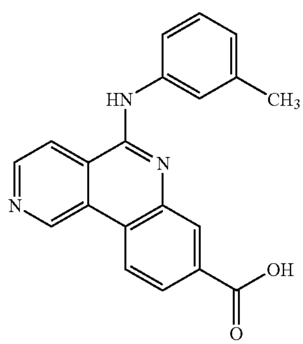 | 2.23 | | | 37.95 | | | | |
| 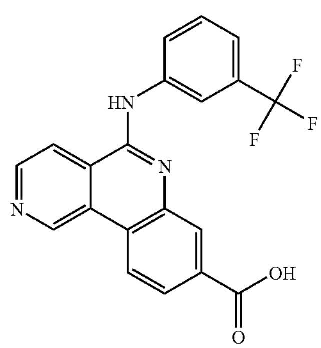 | 2.60 | | | 27.16 | | | | |
| 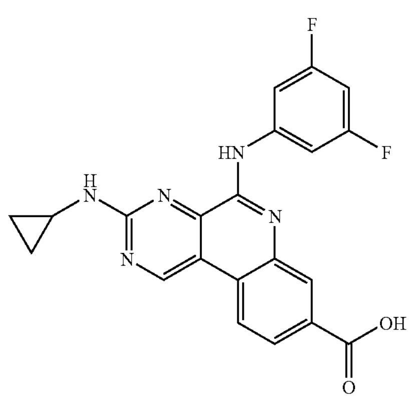 | 14.89 | | | 16.11 | | | | |

TABLE 19b-continued
| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| 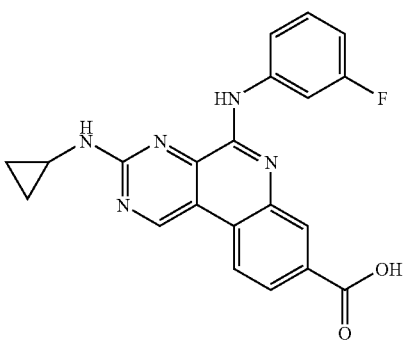 | | | 9.89 | | 2.81 | | | |
| 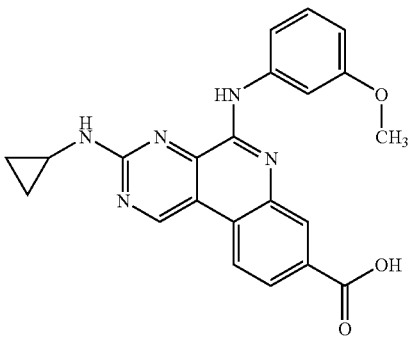 | | | 8.68 | | 3.48 | | | |
| 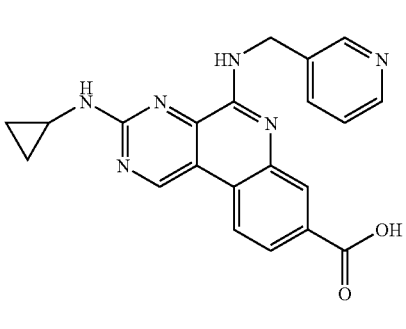 | | | >50 | | >50 | | | |
| 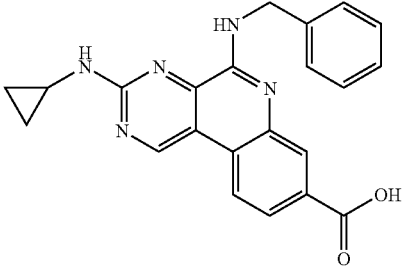 | | | 22.32 | | 19.13 | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| *(morpholine-cyclopropylamino pyrimido-quinoline carboxylic acid)* | | | | >50 | >50 | | | |
| *(dimethylaminoethylamino, 3-chloro-4-fluoroanilino pyrimido-quinoline carboxylic acid)* | | | | 1.52 | 44.94 | | | |
| *(methylpiperidinyl-propylamino, 3-chloro-4-fluoroanilino pyrimido-quinoline carboxylic acid)* | | | | 3.34 | 10.51 | | | |
| *(pyridylmethylamino, 3-chloro-4-fluoroanilino pyrimido-quinoline carboxylic acid)* | | | | 11.12 | >50 | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | 2.86 | | 41.52 | | | |
| | | | 0.33 | | >50 | | | |
| | | | 2.73 | | 16.03 | | | |
| | | | 3.00 | | 18.92 | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | >50 | >50 | | | | |
| | | | 3.16 | 20.88 | | | | |
| | | | 7.33 | | | | | |
| | | | 40.09 | 3.72 | | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| | | | 49.04 | | >50 | | | |
| | | | 0.90 | | 9.88 | | | |
| | | | 7.39 | | >50 | | | |
| | | | 13.03 | | >50 | | | |

TABLE 19b-continued

| Structure | IC50 (uM) BxPC3 | IC50 (uM) COLO205 | IC50 (uM) PanC1 | IC50 (uM) SK-OV-3 | IC50 (uM) MCF-10A | IC50 (uM) H460 | IC50 (uM) HT29 | IC50 (uM) HL-60/MX2 |
|---|---|---|---|---|---|---|---|---|
| *structure: 2-(cyclopropylamino)-5-((3-(trifluoromethyl)phenyl)amino)pyrimido[4,5-c]quinoline-8-carboxamide with ethyl propanoate linker* | 8.76 | | 0.44 | | | | | |
| *structure: 2-amino-5-(cyclopropylamino)pyrimido[4,5-c]quinoline-8-carboxylic acid* | 43.80 | | >50 | | | | | |
| *structure: 5-(cyclopropylamino)-2-(propylamino)pyrimido[4,5-c]quinoline-8-carboxylic acid* | 5.58 | | 1.33 | | | | | |

Example 6

Modulation of Endogenous CK2 Activity

The human leukemia Jurkat T-cell line was maintained in RPMI 1640 (Cambrex) supplemented with 10% fetal calf serum and 50 ng/ml Geutamycin. Before treatment cells were washed, resuspended at a density of about $10^6$ cells/milliliter in medium containing 1% fetal calf serum and incubated in the presence of indicated mounts of drug for two hours. Cells were recovered by centrifugation, lysed using a hypotonic buffer (20 mM Tris/HCl pH 7.4; 2 mM EDTA; 5 mM EGTA; 10 mM mercaptoethanol; 10 mM NaF; 1 uM Okadaic acid; 10% v/v glycerol; 0.05% NP-40; 1% Protease Inhibitor Cocktail) and protein from the cleared lysate was diluted to 1 microgram per microliter in Assay Dilution Buffer (ADB; 20 mM MOPS, pH 7.2, 25 mM β-glycerolphosphate, 5 mM EGTA, 1 mM sodium orthovanadate and 1 mM dithiothreitol). To 20 microliters of diluted protein was added 10 microliters of substrate peptide (RRRDDDSDDD, dissolved in ADB at a concentration of 1 mM) and 10 microliters of PKA Inhibitor cocktail (Upstate). Reactions were initiated by the addition of 10 microliters of ATP Solution (90% 75 mM $MgCl_2$, 100 uM ATP dissolved in ADB; 10% [gamma-$^{33}$P] ATP (stock 1 mCi/100 microliters; 3000 Ci/mmol (Perkin Elmer)) and maintained for 15 min at 32 degrees C. The reactions were quenched with 100 microliters of 0.75% phosphoric acid, then transferred to and filtered through a phosphocellulose filter plate (Millipore). After washing each well 5 times with 0.75% phosphoric acid, the residual radioactivity was measured using a Wallac luminescence counter.

Modulatory activities of two compounds assessed by the assay are shown in FIG. 1. Structures of the compounds are provided below:

Compound 1

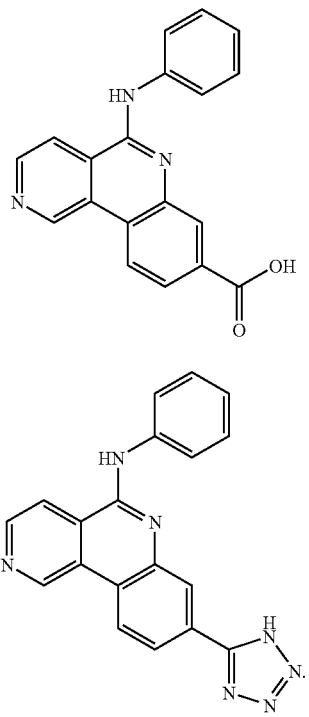

Compound 2

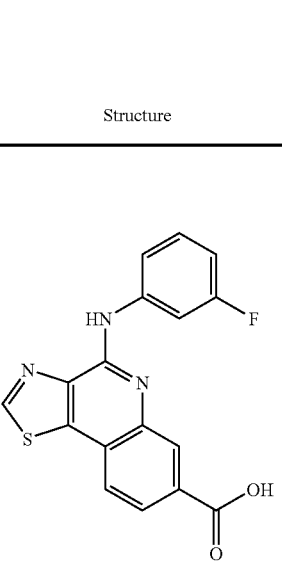

As shown in FIG. 1, each of the two compounds significantly inhibited endogenous CK2 activity as compared to the untreated control. Each of the two compounds also more potently inhibited endogenous CK2 activity as compared to reference compound 4,5,6,7-tetrabromobenzotriazole (TBB), a known CK2 inhibitor (Ruzzene et al., *Biochem J.* 15: 364(Pt 1):41-7 (2002)).

TABLE 20

| Modulation of endogenous CK2 activity | |
|---|---|
| Structure | Modulation of endogenous CK2 activity IC50 (uM) |
| 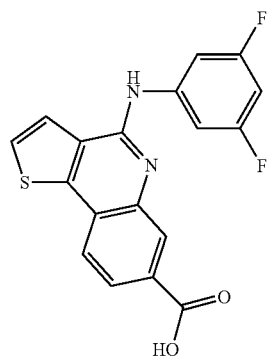 | 25.8 |

TABLE 20-continued

| Modulation of endogenous CK2 activity | |
|---|---|
| Structure | Modulation of endogenous CK2 activity IC50 (uM) |
| 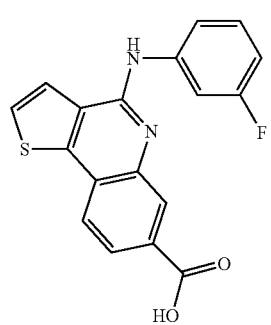 | 4.338 |
| 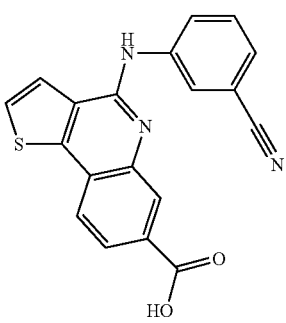 | 3.564 |
| 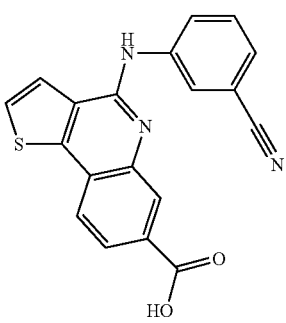 | 10.66 |
| 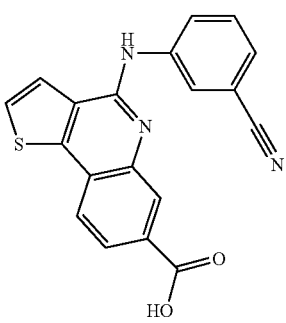 | 8.36 |

TABLE 20-continued

Modulation of endogenous CK2 activity

| Structure | Modulation of endogenous CK2 activity IC50 (uM) |
|---|---|
| (structure) | 50 |
| (structure) | 15.7 |
| (structure) | 50 |
| (structure) | 9.59 |
| (structure) | 37.89 |
| (structure) | 4.426 |
| (structure) | 0.58 |

TABLE 20b

Modulation of endogenous CK2 activity

| Structure | Modulation of endogenous CK2 activity IC50 (uM) |
|---|---|
| (structure: 6-phenylamino pyrido-fused quinoline with carboxylic acid) | 7.4 |
| (structure: 6-(2-(dimethylamino)ethylamino) pyrido-fused quinoline with carboxylic acid) | >50 |
| (structure: 6-phenylamino pyrido-fused quinoline with methyl ester) | 19.87 |
| (structure: 6-(3-methoxyphenylamino) pyrido-fused quinoline with carboxylic acid) | 2.325 |

TABLE 20b-continued

| Modulation of endogenous CK2 activity | |
|---|---|
| Structure | Modulation of endogenous CK2 activity IC50 (uM) |
| *[Structure: benzo[c][2,7]naphthyridine with 3-chloro-4-fluoroanilino and carboxylic acid substituents]* | 0.464 |
| *[Structure: benzo[c][2,7]naphthyridine with 3-chloro-4-fluoroanilino and methyl ester substituents]* | 7.066 |
| *[Structure: benzo[c]naphthyridine with 3-methoxyanilino and methyl ester substituents]* | >50 |
| *[Structure: pyrimido-quinoline with 3-chloro-4-fluoroanilino and methyl ester substituents]* | >50 |

TABLE 20b-continued

| Modulation of endogenous CK2 activity | |
|---|---|
| Structure | Modulation of endogenous CK2 activity IC50 (uM) |
| *[structure: 6-(4-fluoro-3-chlorophenylamino)pyrimido-quinoline carboxylic acid]* | 1.056 |
| *[structure: 6-(3-fluorophenylamino)pyrido-quinoline carboxylic acid]* | 2.933 |
| *[structure: 6-(phenethylamino)pyrido-quinoline carboxylic acid]* | 0.688 |
| *[structure: 6-(3-chlorophenylamino)pyrimido-quinoline carboxylic acid]* | 0.1 |

TABLE 20b-continued

| Modulation of endogenous CK2 activity | |
|---|---|
| Structure | Modulation of endogenous CK2 activity IC50 (uM) |
| [3,5-difluorophenylamino pyrimido-quinoline carboxylic acid] | 0.269 |
| [3-fluorophenylamino pyrimido-quinoline carboxylic acid] | 0.026 |
| [3-ethynylphenylamino pyrimido-quinoline carboxylic acid] | 0.098 |
| [3-fluorophenylamino pyrido-quinoline tetrazole] | 0.63 |

TABLE 20b-continued

| Modulation of endogenous CK2 activity | |
|---|---|
| Structure | Modulation of endogenous CK2 activity IC50 (uM) |
| *(structure: 4-chloro-3-fluoroanilino substituted with tetrazole)* | 0.22 |
| *(structure: 4-chloroanilino with carboxylic acid)* | 0.017 |
| *(structure: 3-ethynylanilino with carboxylic acid)* | 0.07 |
| *(structure: 3-chloroanilino with tetrazole)* | 1.016 |

TABLE 20b-continued

| Structure | Modulation of endogenous CK2 activity IC50 (uM) |
|---|---|
| [structure: 6-[(3-chlorophenethyl)amino]-pyrido-quinoline carboxylic acid] | 0.64 |
| [structure: 6-[(3-fluorophenethyl)amino]-pyrido-quinoline carboxylic acid] | 3.6 |
| [structure: 6-[(3-phenylpropyl)amino]-pyrido-quinoline carboxylic acid] | 2.5 |
| [structure: 6-[(3,5-difluorophenyl)amino]-pyrido-quinoline carboxylic acid] | 1.351 |

TABLE 20b-continued

Modulation of endogenous CK2 activity

| Structure | Modulation of endogenous CK2 activity IC50 (uM) |
|---|---|
| (structure with 2-methoxyethylamino, 3-ethynylphenylamino substituents, and carboxylic acid) | 0.01 |
| (structure with cyclopropylamino, 3-chlorophenylamino substituents, and carboxylic acid) | 0.01 |
| (structure with 3-(trifluoromethyl)phenylamino substituent and carboxylic acid) | 0.098 |
| (structure with amino, 3-chlorophenylamino substituents, and carboxylic acid) | 0.044 |

TABLE 20b-continued

Modulation of endogenous CK2 activity

| Structure | Modulation of endogenous CK2 activity IC50 (uM) |
|---|---|
| (cyclopropyl-HN / HN-3-(trifluoromethyl)phenyl tetracyclic core with COOH) | 0.01 |
| (ethyl-HN / HN-3-chlorophenyl tetracyclic core with COOH) | 0.01 |
| (H2N / HN-3-chloro-4-fluorophenyl tetracyclic core with COOH) | 0.044 |
| (cyclopropyl-HN / HN-3-chloro-4-fluorophenyl tetracyclic core with COOH) | 0.03 |

TABLE 20b-continued

Modulation of endogenous CK2 activity

| Structure | Modulation of endogenous CK2 activity IC50 (uM) |
|---|---|
| 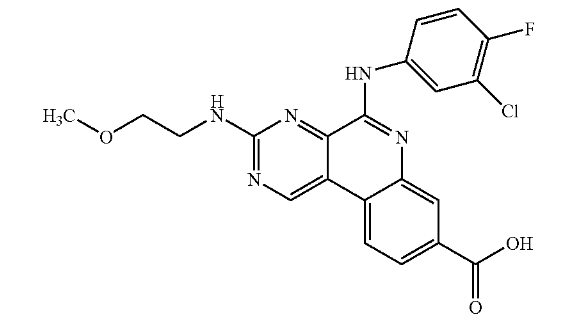 | 0.047 |
| 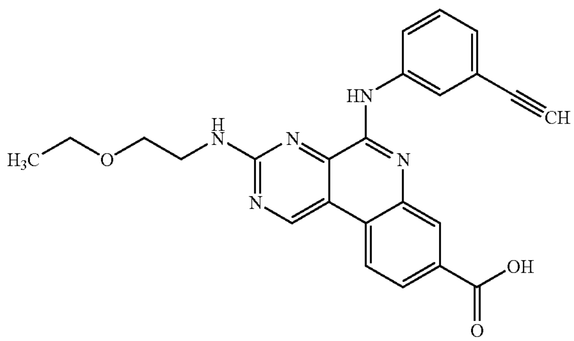 | 0.172 |
| 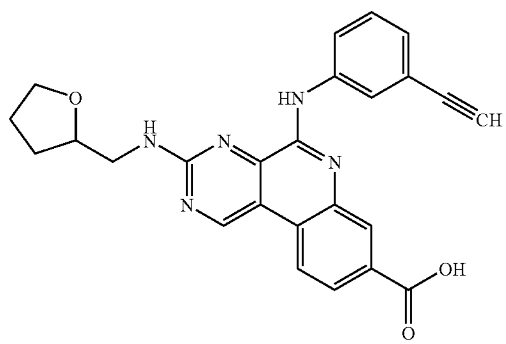 | 0.011 |
| 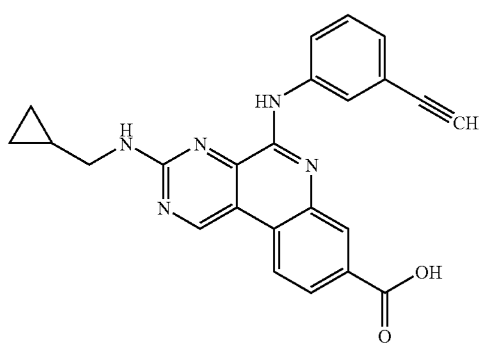 | 0.027 |

Example 7

Evaluation of Pharmacokinetic Properties

The pharmacokinetics properties of drugs were investigated in ICR mice following an intravenous (IV) bolus and oral (PO) doses of drug at 5 mg/kg and 25 mg/kg respectively. Blood samples were collected at predetermined times and the plasma separated. Plasma was separated from the blood samples collected at 5, 15 and 30 minutes and 1, 2, 4, 8 and 24 hours post-dose.

Drug levels were quantified by the LC/MS/MS method described below. Noncompartmental pharmacokinetic analysis was applied for intravenous administration. A linear trapezoidal rule was used to compute AUC(0-24). The terminal $t_{1/2}$ and $C_0$ were calculated using the last three and the first three data points, respectively Bioanalysis was performed using a Quattro Micro LC/MS/MS instrument in the MRM detection mode, with an internal standard (IS). Briefly, 15 □L plasma samples were prepared for analysis using protein precipitation with 120 μL of acetonitrile. The supernatants were transferred into a 96 well plate and subjected to LC-MS/MS analysis using a Phenomenex Polar-RP HPLC column. The mobile phases were 10 mM $NH_4HCO_3$ in water (Solution-A) and 10 mM $NH_4HCO_3$ in methanol (Solution-B). The column was initially equilibrated with 25% Solution-B and followed with 100% Solution B over 5 minutes. The method had a dynamic range from 1 to 10,000 ng/mL. Quantitation of the analytes was performed in the batch mode with two bracketing calibration curves according to the bioanalytical sample list.

Figure 2A:
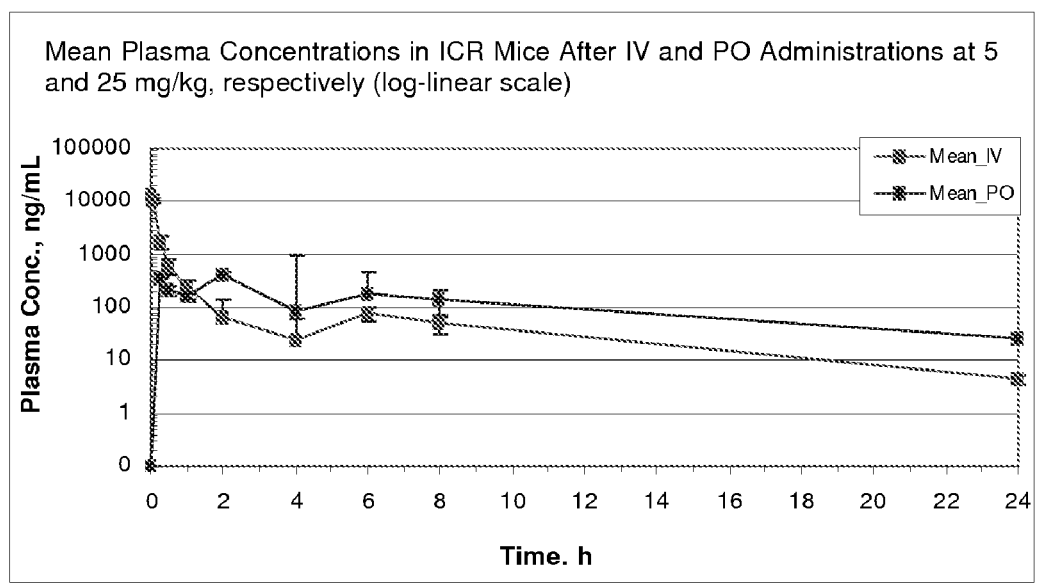
FIGS. 2A and 2B show mean plasma concentrations of compounds described herein over time after intravenous and oral administration to ICR mice.

Pharmacokinetic profiles and estimated pharmacokinetic parameters of compound A1 below are shown in FIG. 2A and in Table 21.

TABLE 21

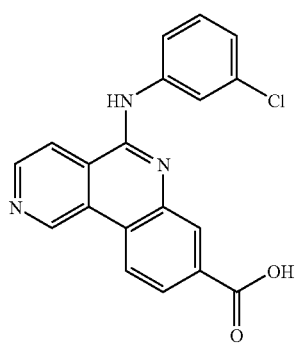

A1

Estimated pharmacokinetic parameters after intravenous and oral dosing at 5 and 25 mg/kg, respectively.

| PK Parameter | IV | PO | Units |
|---|---|---|---|
| Dose | 5 | 25 | mg/kg |
| $AUC_{(0-8\,h)}$ | 2910 | 1580 | |
| $AUC_{(0-24\,h)}$ | 3337 | 2915 | ng·h·mh$^{-1}$ |
| $AUC_{(0-Inf)}$ | 3364 | 3149 | ng·h·ml$^{-1}$ |
| Cmax-obs | N/A | 343 | ng/mL |
| Cp0-exp | 13201 | N/A | ng/mL |
| Tmax | N/A | 0.25 | hr |
| Kel | 0.1586 | 0.1076 | hr$^{-1}$ |
| $t_{1/2}$ | 4.4 | 6.4 | hr |
| Vd | 9.4 | N/A | L/kg |
| $CL_s$ | 1.5 | N/A | L/kg/hr |
| F(0-8 h) | N/A | 10.9 | % |
| F(0-inf h) | N/A | 18.7 | % |

Figure 2B:
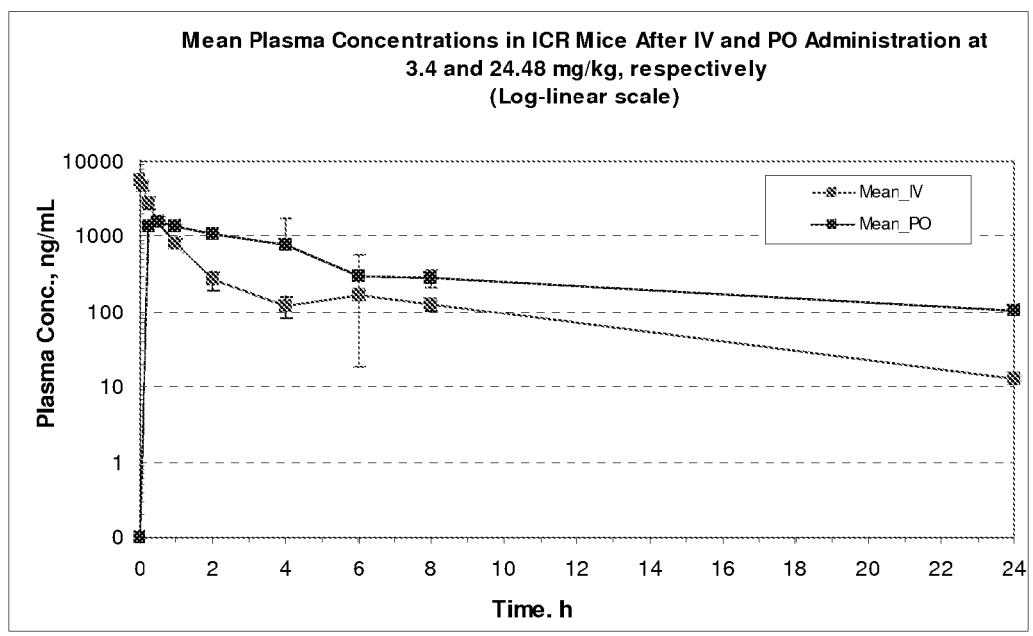

Pharmacokinetic profiles and estimated pharmacokinetic parameters of the test compound below are shown in FIG. 2B and Table 22.

TABLE 22

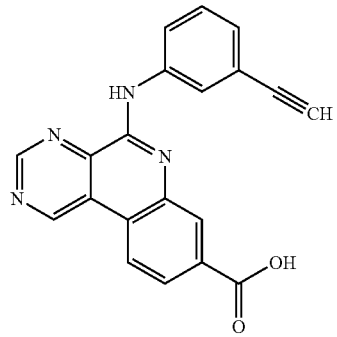

A2

Estimated pharmacokinetic parameters after aIV and PO dose

| PK Parameter | IV | PO | Unit |
|---|---|---|---|
| Dose | 3.4 | 24.5 | mg/kg |
| $AUC_{(0-8\,h)}$ | 3716 | 6005 | |
| $AUC_{(0-24\,h)}$ | 4806 | 9120 | ng·h·ml$^{-1}$ |
| $AUC_{(0-Inf)}$ | 4898 | 10895 | ng·h·ml$^{-1}$ |
| Cmax-obs | 4744 | 1600.5 | ng/mL |
| Cp0-exp | 5631 | N/A | ng/mL |
| Tmax | N/A | 0.5 | hr |
| Kel | 0.1418 | 0.0594 | hr$^{-1}$ |
| $t_{1/2}$ | 4.9 | 11.7 | hr |
| Vd | 4.9 | N/A | L/kg |
| $CL_s$ | 0.7 | N/A | L/kg/hr |
| $F_{(0-24\,h)}$ | N/A | 26.5 | % |
| $F_{(0-Inf)}$ | N/A | 31.1 | % |

Example 8

Evaluation of Compound Efficacy in Tumor Suppression

The in vivo activity of compound A1 and compound A2 (shown previously) was assessed by intravenous and oral administration to tumor-bearing xenograft mice. The in vivo experiments followed protocols approved by the Animal Use and Care Committee. Female NCr nu/nu mice were purchased from Taconic Farms and group housed in a ventilated rack system on a 12/12 light cycle. All housing materials and water were autoclaved prior to use. The mice were fed ad libitum with gamma irradiated laboratory chow and acidified water. Animals were handled under laminar-flow hoods.

Tumor size (mm$^3$) was calculated using the formula (l×w$^2$)/2, where w=width and l=length in mm of the tumor. Tumor weight was estimated with the assumption that 1 mg is equivalent to 1 mm$^3$ of tumor volume.

For intravenous administration of compound A1, animals were inoculated subcutaneously in the right flank with 5×10$^6$ MiaPaca cells. Tumors were monitored twice weekly and then daily as they approached the appropriate size for study. On Day 1 of the study, the animals were randomized into n=5 treatment groups with group mean tumor sizes of 160 mm$^3$.

| Grp 1 | Mean | 160.966 | UTC |
|---|---|---|---|
| Grp 2 | Mean | 161.816 | Gemzar |

-continued

| | | | |
|---|---|---|---|
| Grp 3 | Mean | 161.807 | 30 mg/kg CK2 Compound |
| Grp 4 | Mean | 159.621 | 60 mg/kg CK2 Compound |
| % Dif. | | 1.363 | |
| SD | | 1.034. | |

Figure 3A:
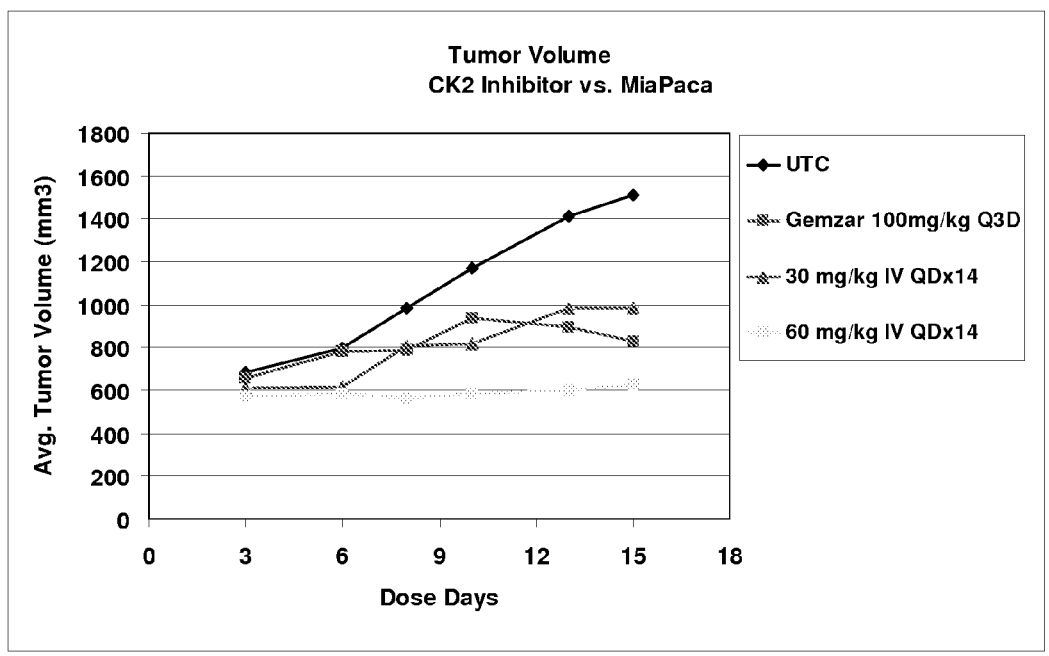
FIGS. 3A and 3B show tumor volume over time and body weight over time, respectively, in tumor-bearing xenograft animals administered a compound described herein.
Figure 3B:
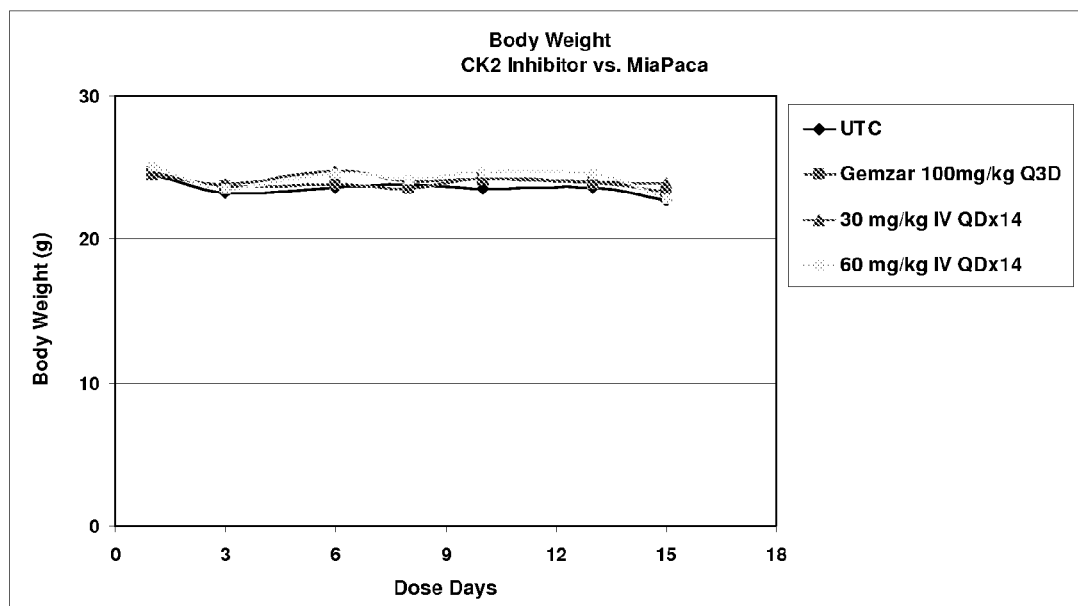
Figure 3C:
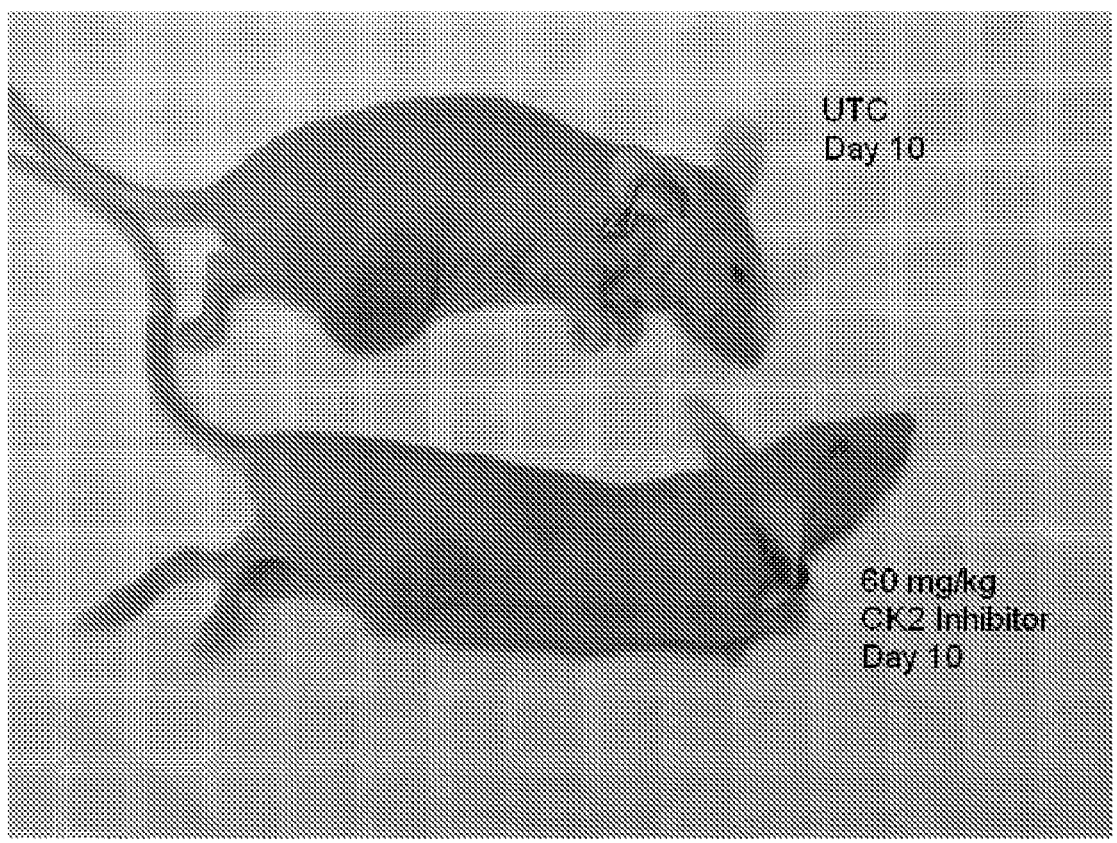
FIGS. 3C and 3D illustrate effects of the compound on tumors in individual animals.
Figure 3D:
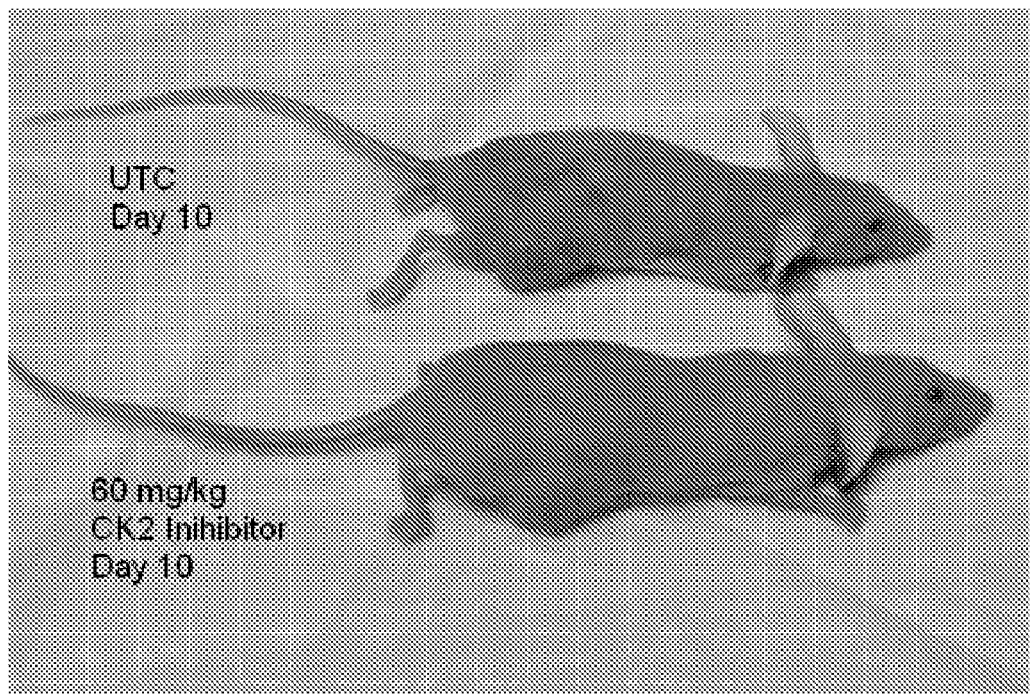

Animals received 14 doses of Vehicle, Gemzar at 100 mg/kg Q3D or compound A1 at either 30 mg/kg or 60 mg/kg by QD intravenous administration. Tumor volume measurements (FIG. 3A) and body weight (FIG. 3B) were recorded on days 3, 6, 8, 10, 13 and 15. Photographs of specific untreated control animals and animals administered 60 mg/kg compound A1 are shown in FIGS. 3C and 3D. Compound A1 is referred to as "CK2 inhibitor" in FIGS. 3A, 3B, 3C and 3D.

Compound A1 also was administered orally to MiaPaca xenograft animals and inhibited tumor growth. Compound A1 was formulated as a sodium salt at 10 mg/mL with 2% PEG 300 and buffered to pH 8.4 using sodium phosphate buffer. Compound A1 when administered orally to the animals at a dose of 100 mg/kg QDx8 and then 200 mg/kg QDx5 significantly inhibited tumor growth relative to an untreated control group. Gemzar™ administered at a dose of 80 mg/kg IP Q3D was used as a positive control. Compound A1 also was delivered by oral administration at 100 mg/kg to animals bearing MCF-7 xenografts and at 150 mg/kg to animals bearing PC-3 xenografts, and in both sets of studies, significantly inhibited tumor growth.

It also was determined that compound A1 reduced CK2 activity in tumors. Assessment of CK2 activity in tumors revealed that tumors from animals treated with compound A1 had about 40% of the CK2 activity of tumors from animals not treated with compound A1 or treated with Gemzar™.

The distribution of compound A1 in the plasma and tumors of animals was assessed. In animals administered 30 mg/kg compound A1 IV, 60 mg/kg compound A1 IV and 200 mg/kg compound A1 orally, about 6.8, 2.2 and 9.5 micromolar compound A1, respectively, was identified in plasma, and about 42.9, 7.0 and 6.4 micromolar compound A1, respectively, was identified in tumors.

Caspase staining also was assessed as a biomarker for compound A1 treatment of tumors. In animals treated with 60 mg/kg of compound A1 by IV administration, caspase-3 cell staining levels were four-fold greater than in untreated control cells. These results suggest caspase-3 staining can be a useful biomarker for monitoring inhibition of cell proliferation and tumor inhibition.

For assessment of compound A2, the compound was delivered by intravenous and intraperitoneal administration to tumor-bearing xenograft mice. Animals were inoculated subcutaneously in the right flank with $5 \times 10^6$ BC-PC3 cells. Tumors were monitored twice weekly and then daily as they approached the appropriate size for study. On Day 1 of the study, the animals were randomized into n=8 treatment groups (n=5 for positive and negative control groups) with group mean tumor sizes of 97 mm$^3$.

| | | | |
|---|---|---|---|
| Grp 1 | Mean | 97.80 | UTC |
| Grp 2 | Mean | 96.95 | Gemzar Q3D |
| Grp 3 | Mean | 96.68 | 50 mg/kg CX-5011 IV BID x10 days |
| Grp 4 | Mean | 98.95 | 60 mg/kg CX-5011 IV QD x17 days |
| Grp 5 | Mean | 96.51 | 100 mg/kg CX-5011 IP BID x17 days |
| % Dif | | 2.50 | |
| SD | | 1.01 | |

Figure 4A:
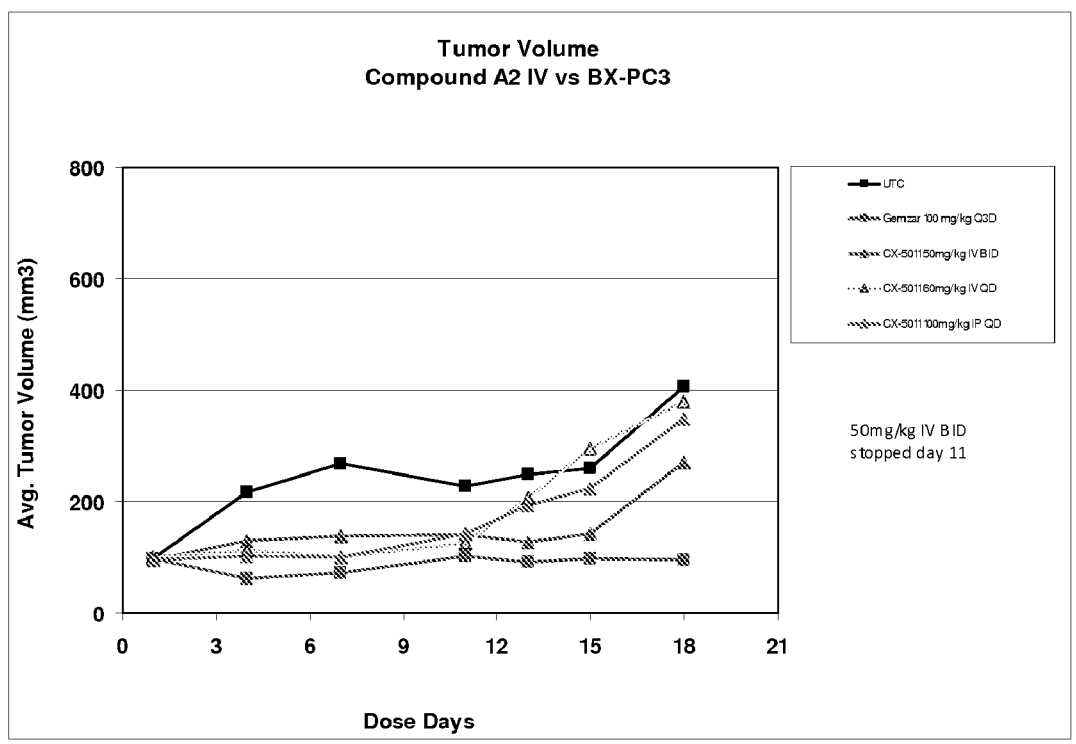
FIGS. 4A and 4B show tumor volume over time and body weight over time, respectively, in tumor-bearing xenograft animals administered a compound described herein.
Figure 4B:
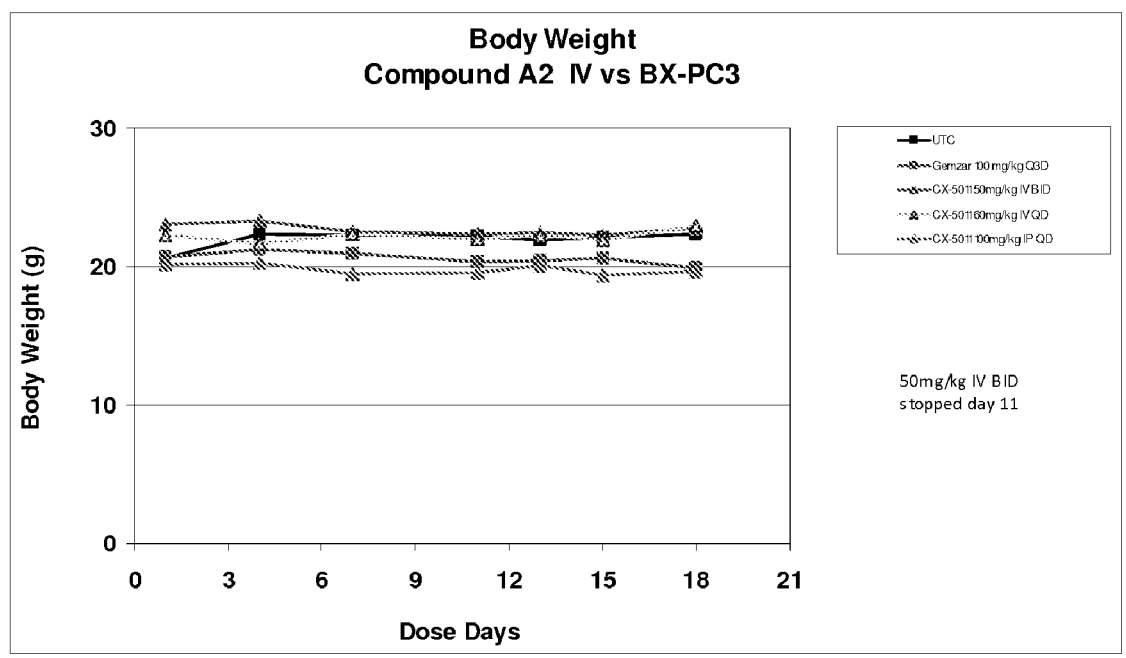

Animals received 17 doses of Vehicle, Gemzar at 100 mg/kg Q3D or compound at either 60 mg/kg QD intravenous administration or 100 mg/kg BID intraperitoneal administration. One group (#3) received 10 doses of compound at 50 mg/kg BID intravenous administration. Tumor volume measurements and body weight were recorded on days 1, 4, 7, 11, 13, 15, and 18, and data showed compound A2 significantly inhibited tumor progression (FIG. 4A) while not significantly altering body weight (FIG. 4B). Delivery of compound A2 to animals bearing MiaPaca xenografts by IV administration at 50 and 60 mg/kg and by IP administration at 100 mg/kg significantly inhibited tumor progression. Also, delivery of compound A2 to animals bearing MDA-MB-231 xenografts by IV administration at 30 and 60 mg/kg and by oral administration at 200 mg/kg significantly inhibited tumor progression. Delivery of compound A2 to animals bearing MiaPaca xenografts by oral administration at 100 mg/kg QDx8 and 200 mg/kg QDx6 significantly inhibited tumor progression. A meglumine salt of compound A2 at pH 10.0 and at 10 mg/mL was utilized as an oral formulation for the studies.

Tumor pharmacokinetic studies of compound A2 were carried out in which 30 mg/kg of the compound was dosed IV QDx6. Plasma, blood and tumor samples were taken on day 1, 4 and 6 and three animals sacrificed for each time point. Steady state was reached after about three days, the terminal slope decreases, the half life about doubles, the minimum concentration was 4-5 times higher after six days and there were no significant differences between day 4 and 6.

Delivery of compound A3 to animals bearing MiaPaca xenografts by IV administration also significantly inhibited tumor progression.

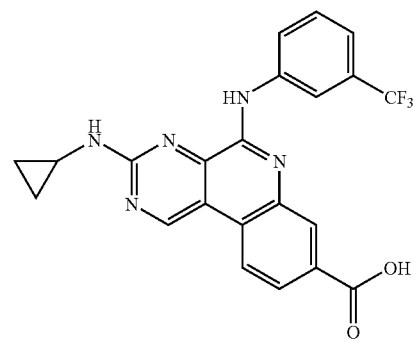

Compound A3

Example 9

Modulation of Non-CK2 Protein Kinase Activity

Compounds described herein are profiled for in vitro modulatory activity against protein kinases other than CK2. The in vitro analysis is conducted using known protocols (e.g., assay protocols described at world-wide web address upstate.com/img/pdf/KP Assay Protocol_Booklet_v3.pdf). Compounds described herein are screened in the assays and prioritized based upon modulatory activity against protein kinases other than CK2 and specificity for CK2 or PARP.

Example 10

Evaluation of Angiogenesis Inhibition by Endothelial Tube Formation Assay

A human endothelial tube formation assay was performed using the 96-well BD BioCoat™ Angiogenesis System from BD Biosciences, using the manufacturer's recommended protocol.

Briefly, HUVEC cells (from ATCC) were suspended in 150 ul of media containing 10% FBS at $4 \times 10^5$ cells/ml in each of the 96-wells of the matrigel coated plate in the presence or absence of various concentrations of compound A2. The plate was incubated for 18 hrs at 37° C. The cells were stained with calcein AM and the results visualized by fluorescent microscopy or by phase contrast. It was observed that compound A2 inhibited tube formation in the assay described above over a concentration range of 1 to 5 μM.

Example 11

Modulation of Protein Kinase Activity in Cell-Free In Vitro Assay

In a PIM-1 assay, test compounds in aqueous solution are added at a volume of 5 ul, to a reaction mixture comprising 5 ul of 5× Reaction buffer (40 mM MOPS, pH 7.0, 1 mM EDTA), 2.5 ul of recombinant human PIM-1 solution (10 ng), 2.5 ul of substrate peptide (KKRNRTLTK) and 10 ul of ATP solution—98% (75 mM MgCl2 37.5 uM ATP) 2% ([γ-33P] ATP: 3000 Ci/mmol—Perkin Elmer). The reactions are incubated for 10 min at 30° C., quenched with 100 ul of 0.75% Phosphoric acid, then transferred to and filtered through a Phosphocellulose filter plate (Millipore). After washing each well 5 times with 0.75% Phosphoric acid, Scintillation fluid (15 ul) is added to each well. The residual radioactivity is measured using a luminescence counter. Compound A2 inhibited PIM-1 with $IC_{50}=189$ nM.

Compound A2 was tested further for its activity against other protein kinases. The following kinase inhibition $IC_{50}$ data were determined using standardized radiometric kinase assays for each individual kinase, which entail filter binding of $^{33}P$ labeled substrate proteins by the kinase of interest. Each $IC_{50}$ value was determined over a range of 10 drug concentrations. Reaction conditions are available from the World Wide Web URL upstate.com/discovery/services/ic50_profiler.q.

| Kinase | IC50 (nM) |
|---|---|
| CDK1/cyclinB(h) | 226 |
| CK2(h) | 2 |
| CK2α2(h) | 1 |
| c-RAF(h) | >1,000 |
| DYRK2(h) | 354 |
| Flt3(h) | 721 |
| Flt4(h) | 815 |
| HIPK3(h) | 56 |
| ZIPK(h) | 34 |

The following kinase inhibition data were determined using standardized radiometric kinase assays for each individual kinase, which entail filter binding of $^{33}P$ labeled substrate proteins by the kinase of interest. Each percentage of activity was determined at 0.5 μM concentration of the drug. Reaction conditions are available at the World Wide Web URL upstate.com/discovery/services/ic50_profiler.q.

| Kinase | % activity at 0.5 μM |
|---|---|
| CK2α2(h) | −7 |
| CK2(h) | −2 |
| Flt4(h) | −1 |
| HIPK3(h) | 10 |
| HIPK2(h) | 11 |
| ZIPK(h) | 12 |
| Flt3(D835Y)(h) | 17 |
| Pim-1(h) | 27 |
| Flt3(h) | 42 |
| Mer(h) | 46 |
| MELK(h) | 49 |
| DYRK2(h) | 50 |
| CDK1/cyclinB(h) | 52 |
| GSK3β(h) | 56 |
| MSK2(h) | 56 |
| DRAK1(h) | 62 |
| CDK2/cyclinA(h) | 63 |
| Lck(h) | 63 |
| Mnk2(h) | 63 |
| SRPK1(h) | 66 |
| KDR(h) | 67 |
| c-RAF(h) | 69 |
| IGF-1R(h) | 73 |
| CDK7/cyclinH/MAT1(h) | 77 |
| NEK2(h) | 77 |
| Rsk1(h) | 78 |
| EGFR(L861Q)(h) | 79 |
| MLK1(h) | 80 |
| p70S6K(h) | 80 |
| LOK(h) | 84 |
| EGFR(L858R)(h) | 89 |
| PKA(h) | 90 |
| TrkA(h) | 90 |
| Abl(h) | 91 |
| EGFR(T790M)(h) | 92 |
| PRAK(h) | 93 |
| Aurora-A(h) | 94 |
| Flt1(h) | 95 |
| MAPK1(h) | 95 |
| MST1(h) | 96 |
| FAK(h) | 97 |
| ROCK-I(h) | 97 |
| CHK1(h) | 99 |
| EphA7(h) | 99 |
| JAK2(h) | 99 |
| PKCα(h) | 99 |
| Tie2(h) | 99 |
| Blk(m) | 100 |
| CDK9/cyclin T1(h) | 100 |
| CK1γ3(h) | 100 |
| cKit(D816H)(h) | 101 |
| IKKα(h) | 101 |
| Src(1-530)(h) | 101 |
| TAK1(h) | 101 |
| Fer(h) | 103 |
| FGFR1(h) | 103 |
| CaMKI(h) | 104 |
| PKBα(h) | 104 |
| CK1γ1(h) | 105 |
| IR(h) | 105 |
| PKG1α(h) | 105 |
| eEF-2K(h) | 106 |
| Plk3(h) | 106 |
| Ron(h) | 106 |
| CK1γ2(h) | 107 |
| FGFR2(h) | 107 |
| MAPKAP-K2(h) | 107 |
| PKD2(h) | 107 |
| ARK5(h) | 108 |
| CDK6/cyclinD3(h) | 108 |
| DDR2(h) | 109 |
| Lyn(h) | 109 |
| PDGFRα(h) | 109 |
| PDGFRα(D842V)(h) | 109 |
| Rse(h) | 109 |
| Yes(h) | 109 |
| BRK(h) | 110 |
| PDGFRβ(h) | 110 |

-continued

| Kinase | % activity at 0.5 μM |
|---|---|
| PDK1(h) | 110 |
| Ros(h) | 110 |
| cKit(V560G)(h) | 111 |
| Hck(h) | 111 |
| PKCθ(h) | 111 |
| ALK(h) | 112 |
| PAK2(h) | 112 |
| cKit(h) | 114 |
| Fyn(h) | 114 |
| ASK1(h) | 116 |
| Snk(h) | 117 |
| Bmx(h) | 118 |
| ZAP-70(h) | 118 |
| IRAK4(h) | 119 |
| EGFR(T790M, L858R)(h) | 121 |
| Met(h) | 122 |
| EGFR(h) | 123 |
| EphA5(h) | 125 |
| ErbB4(h) | 126 |
| MKK7β(h) | 133 |
| MEK1(h) | 136 |
| Fes(h) | 139 |
| EphB4(h) | 144 |
| CSK(h) | 146 |
| Fms(h) | 174 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following aspects.

A1. A compound having a structure of Formula I, II, III or IV:

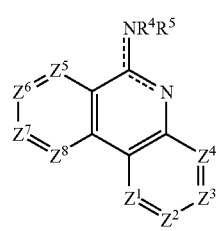

Formula I

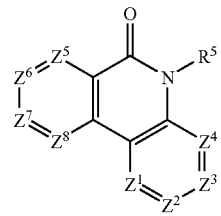

Formula II

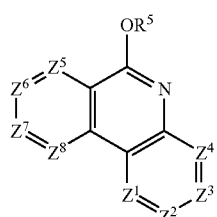

Formula III

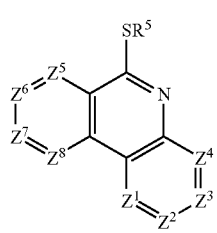

Formula IV and pharmaceutically acceptable salts, esters and tautomers thereof; wherein:
  each $Z^1$, $Z^2$, $Z^3$, and $Z^4$ is N or $CR^3$;
  each of $Z^5$, $Z^6$, $Z^7$ and $Z^8$ is N or $CR^6$;
  none, one or two of $Z^1$-$Z^4$ are N and none, one or two of $Z^5$-$Z^8$ are N;
    each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group,
    or each $R^3$ and each $R^6$ is independently halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, polar substituent, carboxy bioisostere, COOH or $NO_2$,
      wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
      and wherein two R on the same atom or on adjacent atoms can be linked to form a 3-8 membered ring, optionally containing one or more N, O or S;
      and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$,
        wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or an optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member;

provided that when —$NR^4R^5$ in Formula (I) is —NHΦ, where Φ is optionally substituted phenyl:

if all of $Z^5$-$Z^8$ are CH or one of $Z^5$-$Z^8$ is N, at least one of $Z^1$-$Z^4$ is $CR^3$ and at least one $R^3$ must be a non-hydrogen substituent; or if each $R^3$ is H, then Φ must be substituted; or if all of $Z^5$-$Z^8$ are CH or one of $Z^5$-$Z^8$ is N, then $Z^2$ is not C—OR', and $Z^3$ is not $NH_2$, $NO_2$, NHC(=O)R' or NHC(=O)—OR', where R" is C1-C4 alkyl.

A2. The compound of embodiment A1, wherein the polar substituent is a substituent having an electric dipole, and optionally a dipole moment.

A3. The compound of embodiment A1 or A2, wherein the polar substituent accepts or donates a hydrogen bond.

A4. The compound of any one of embodiments A1-A3, wherein the polar substituent is selected from a carboxy, a carboxy bioisostere or other acid-derived moiety that exists predominately as an anion at a pH of about 7 to 8.

A5. The compound of any one of embodiments A1-A3, wherein the polar substituent contains an OH or NH, an ether oxygen, an amine nitrogen, an oxidized sulfur or nitrogen, a carbonyl, a nitrile, and a nitrogen-containing or oxygen-containing heterocyclic ring whether aromatic or non-aromatic.

A6. The compound of any one of embodiments A1-A5, wherein the polar substituent is a carboxylate.

A7. The compound of any one of embodiments A1-A5, wherein the polar substituent is a carboxylate or carboxylic acid.

A8. The compound of any one of embodiments A1-A3, wherein the polar substituent is a carboxy bioisostere selected from the group consisting of:

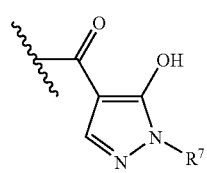
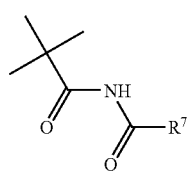

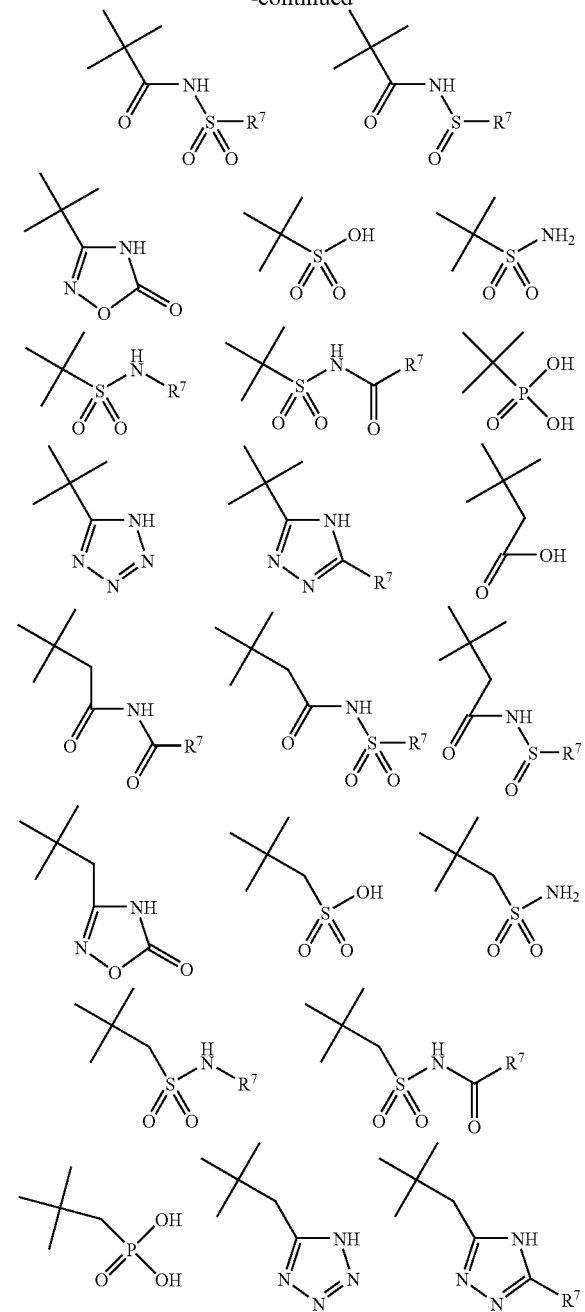

and salts of the foregoing, wherein each $R^7$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring; or $R^7$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring.

A9. The compound of any one of embodiments A1-A3, wherein the polar substituent is selected from the group consisting of carboxylic acid, carboxylic ester, carboxamide, tetrazole, triazole, carboxymethanesulfonamide, oxadiazole, oxothiadiazole, thiazole, aminothiazole and hydroxythiazole.

A10. The compound of any one of embodiments A1-A9, wherein the polar substituent is at a position on the ring containing $Z^1$-$Z^4$.

A11. The compound of embodiment any one of embodiments A1-A10, wherein the ring containing $Z^1$-$Z^4$ includes one, two, three or four polar substituents.

A12. The compound of any one of embodiments A1-A10, wherein each of $Z^1$-$Z^4$ is $CR^3$ and one of the $R^3$ substituents is a polar substituent A13. The compound of any one of embodiments A1-A10, wherein the ring containing $Z^1$-$Z^4$ is selected from one of the following structures

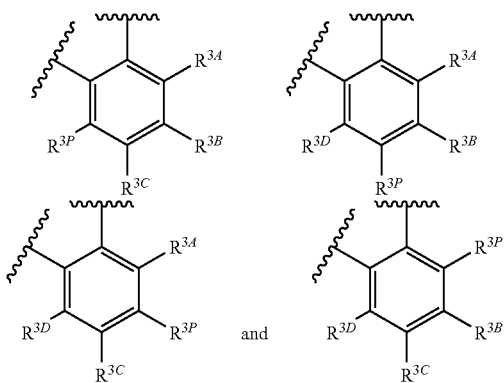

wherein $R^{3P}$ is a polar substituent and each $R^{3A}$, $R^{3B}$, $R^{3C}$ and $R^{3D}$ independently is selected from $R^3$ substituents.

A14. The compound of any one of embodiments A1-A10, wherein at least one of $Z^1$-$Z^4$ and $Z^5$-$Z^8$ is a nitrogen atom.

A15. The compound of embodiment A14, the ring containing $Z^1$-$Z^4$ or the ring containing $Z^5$-$Z^8$ is independently an optionally substituted pyridine, pyrimidine or pyridazine ring.

A16. The compound of embodiment A14, wherein the ring containing $Z^5$-$Z^8$ is selected from the group consisting of

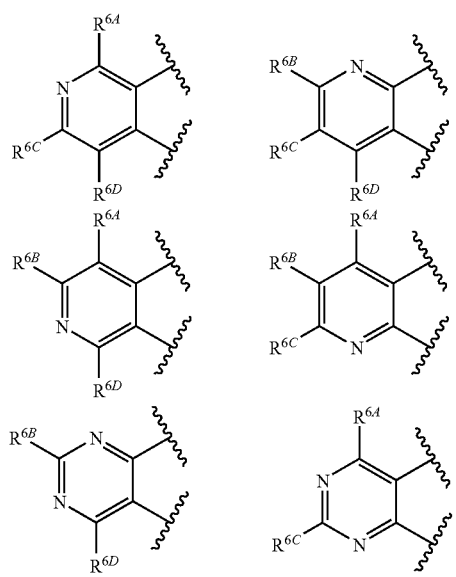

-continued

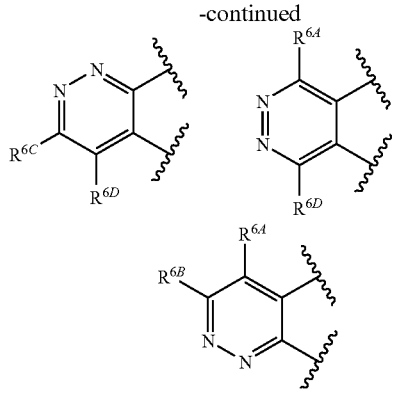

wherein each $R^{6A}$, $R^{6B}$, $R^{6C}$ and $R^{6D}$ independently is selected from $R^6$ substituents defined in embodiment A1.

A17. The compound of any one of embodiments A1-A17, wherein $R^4$ is H.

A18. The compound of any one of embodiments A1-A17, wherein $R^5$ is an optionally substituted 3-8 membered ring.

A19. The compound of any one of embodiments A1-A17, wherein $R^5$ is a $C_{1-10}$ alkyl group substituted with an optionally substituted 3-8 membered ring.

A20. The compound of embodiment A18, wherein $R^5$ is an optionally substituted six-membered carbocyclic or heterocyclic ring.

A21. The compound of embodiment A20, wherein $R^5$ is an optionally substituted phenyl ring.

A22. The compound of embodiment A21, wherein the compound has a structure of Formula I, $R^4$ is H or $CH_3$ and $R^5$ is a phenyl substituted with one or more halogen or acetylene substituents.

A23. The compound of embodiment A22, wherein the one or more halogen or acetylene substituents are on the phenyl ring at the 3-position, 4-position or 5-position, or combinations thereof.

A24. The compound of any one of embodiments A1-A17, wherein $R^5$ is a $C_{1-3}$ alkyl substituted with an optionally substituted phenyl, pyridyl or morpholino ring substituent, or substituted with —$NR^4R^5$ (e.g., —$N(CH_3)_2$).

A25. The compound of embodiment A1, wherein the polar substituent is a carboxy, carboxyalkyl (e.g., carboxymethyl), tetrazole or amide (e.g., —$CONH_2$) substituent.

A26. The compound of embodiment A1, wherein the $R^6$ substituent is a —$NR^4R^5$ substituent.

A27. The compound of embodiment A26, wherein the $R^6$ substituent is a —NH—(C1-C6 alkyl) moiety.

A28. The compound of embodiment A1, wherein each of $Z^1$, $Z^2$, $Z^3$, and $Z^4$ is $CR^3$.

A29. The compound of embodiment A1, wherein at least one $R^3$ is H.

A30. The compound of embodiment A1, wherein at least two $R^3$ are H.

A31. The compound of embodiment A1, wherein at least one $R^6$ is H.

A32. The compound of embodiment A1, wherein at least two $R^6$ are H.

A33. The compound of embodiment A13, wherein each $R^{3A}$, $R^{3C}$ and $R^{3D}$ is H and $R^{3B}$ is a polar substituent.

A34. A composition that comprises a compound of embodiment A1 and a pharmaceutically acceptable carrier.

B1. A compound having a structure of Formula V, VI, VII or VIII:

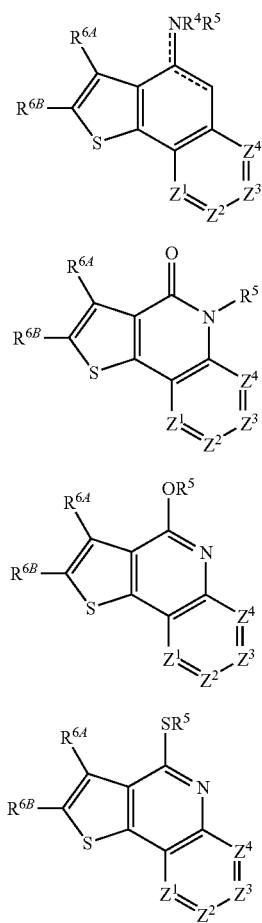

Formula V

Formula VI

Formula VII

Formula VIII and pharmaceutically acceptable salts, esters and tautomers thereof; wherein:

each $Z^1$, $Z^2$, $Z^3$, and $Z^4$ independently is N or $CR^3$ and none, one or two of $Z^1$, $Z^2$, $Z^3$, and $Z^4$ is N;

each $R^3$, $R^{6A}$ and $R^{6B}$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$, $R^{6A}$ and $R^{6B}$ independently is halo, OR, NR$_2$, NROR, NRNR$_2$, SR, SOR, SO$_2$R, SO$_2$NR$_2$, NRSO$_2$R, NRCONR$_2$, NRCOOR, NRCOR, CN, COOR, polar substituent, carboxy bioisostere, CONR$_2$, OOCR, COR, or NO$_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, $R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —NR$^4$R$^5$, $R^4$ and $R^5$ together with N may form an optionally substituted 3-8 membered ring, which may optionally contain an additional heteroatom selected from N, O and S as a ring member;

provided that if $R^5$ in Formula IV is phenyl, substituted phenyl, —CH(CH$_3$)—(CH$_2$)$_3$—NEt$_2$, —(CH$_2$)$_3$-piperazine-(CH$_2$)$_3$—NH$_2$, cyclohexane or butyl, then one or more of $R^3$ present is a non-hydrogen moiety.

B2. The compound of embodiment B1, provided that at least one $R^3$ present is a polar substituent.

B3. The compound of embodiment B1, wherein the polar substituent accepts or donates a hydrogen bond.

B4. The compound of embodiment B1, wherein the polar substituent is selected from a carboxy, a carboxy bioisostere or other acid-derived moiety that exists predominately as an anion at a pH of about 7 to 8.

B5. The compound of embodiment B1, wherein the polar substituent contains an OH or NH, an ether oxygen, an amine nitrogen, an oxidized sulfur or nitrogen, a carbonyl, a nitrile, and a nitrogen-containing or oxygen-containing heterocyclic ring whether aromatic or non-aromatic.

B6. The compound of embodiment B1, wherein the polar substituent is a carboxylic acid, or a salt, an ester or a bioisostere thereof.

B7. The compound of embodiment B6, wherein the polar substituent is a carboxylic acid or a salt thereof.

B8. The compound of embodiment B1, wherein the polar substituent is a bioisostere selected from the group consisting of:

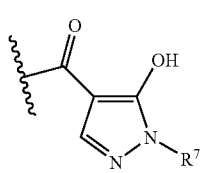 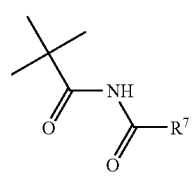

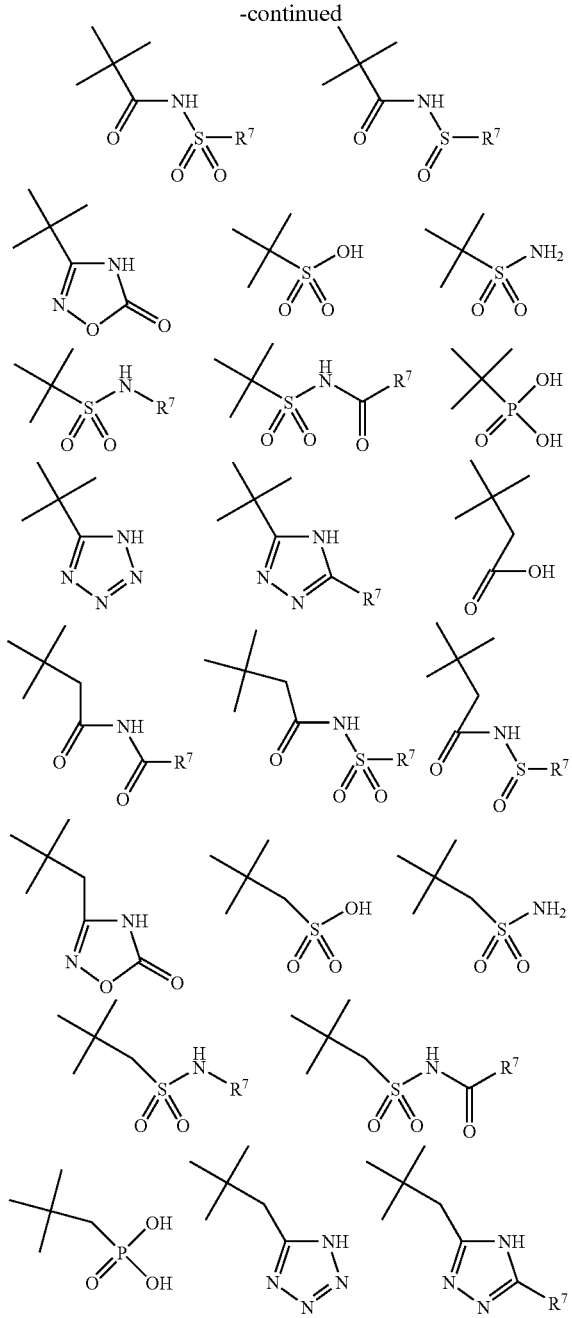

and salts of the foregoing, wherein each $R^7$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring; or $R^7$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring.

B9. The compound of embodiment B1, wherein the polar substituent is selected from the group consisting of carboxylic acid, carboxylic ester, carboxamide, tetrazole, triazole, carboxymethanesulfonamide, oxadiazole, oxothiadiazole, thiazole, aminothiazole and hydroxythiazole.

B10. The compound of any one of embodiments B1-B9, wherein the polar substituent is at a position on the ring containing $Z^1$-$Z^4$.

B11. The compound of any one of embodiments B1-B10, wherein the ring containing $Z^1$-$Z^4$ includes one, two, three or four polar substituents.

B12. The compound of any one of embodiments B1-B9, wherein each of $Z^1$-$Z^4$ is $CR^3$ and one of the $R^3$ substituents is a polar substituent B13. The compound of any one of embodiments B1-B9, wherein the ring containing $Z^1$-$Z^4$ is selected from one of the following structures

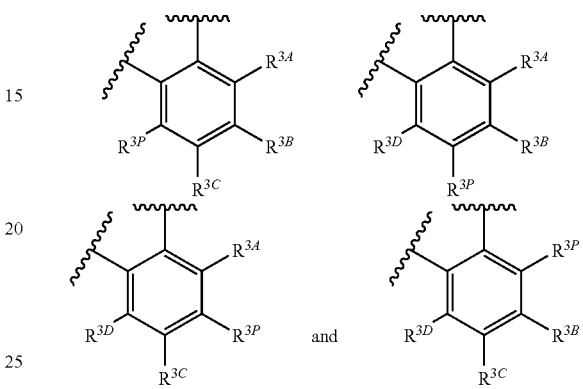

wherein $R^{3P}$ is a polar substituent and each $R^{3A}$, $R^{3B}$, $R^{3C}$ and $R^{3D}$ independently is selected from $R^3$ substituents.

B14. The compound of any one of embodiments B1-B13, wherein at least one of $Z^1$-$Z^4$ is a nitrogen atom.

B15. The compound of embodiment B14, the ring containing $Z^1$-$Z^4$ is independently an optionally substituted pyridine, pyrimidine or pyridazine ring.

B16. The compound of any one of embodiments B1-B15, wherein $R^4$ is H.

B17. The compound of any one of embodiments B1-B16, wherein $R^5$ is an optionally substituted 3-8 membered ring.

B18. The compound of any one of embodiments B1-B16, wherein $R^5$ is a $C_{1-10}$ alkyl group substituted with an optionally substituted 3-8 membered ring.

B19. The compound of embodiment B18, wherein $R^5$ is an optionally substituted six-membered carbocyclic or heterocyclic ring.

B20. The compound of embodiment B19, wherein $R^5$ is an optionally substituted phenyl ring.

B21. The compound of embodiment B20, wherein the compound has a structure of Formula V, $R^4$ is H or $CH_3$ and $R^5$ is a phenyl substituted with one or more halogen or acetylene substituents.

B22. The compound of embodiment B21, wherein the one or more halogen or acetylene substituents are on the phenyl ring at the 3-position, 4-position or 5-position, or combinations thereof.

B23. The compound of any one of embodiments B1-B16, wherein $R^5$ is a $C_{1-3}$ alkyl substituted with an optionally substituted phenyl, pyridyl or morpholino ring substituent, or substituted with —$NR^4R^5$ (e.g., —$N(CH_3)_2$).

B24. The compound of embodiment B1, wherein the polar substituent is a carboxy, carboxyalkyl (e.g., carboxymethyl), tetrazole or amide (e.g., —$CONH_2$) substituent.

B25. The compound of embodiment B1, wherein the $R^6$ substituent is a —$NR^4R^5$ substituent.

B26. The compound of embodiment B25, wherein the $R^6$ substituent is a —NH—(C1-C6 alkyl) moiety.

B27. The compound of embodiment B1, wherein each of $Z^1$, $Z^2$, $Z^3$, and $Z^4$ is $CR^3$.

B28. The compound of embodiment B1, wherein at least one $R^3$ is H.

B29. The compound of embodiment B1, wherein at least two $R^3$ are H.

B30. The compound of embodiment B1, wherein at least one of $R^{6A}$ and $R^{6B}$ is H.

B31. The compound of embodiment B1, wherein each of $R^{6A}$ and $R^{6B}$ is H.

B32. The compound of embodiment B13, wherein each $R^{3A}, R^{3C}, R^{3D}, R^{6A}$ and $R^{6B}$ is H and $R^{3B}$ is a polar substituent.

C1. A compound having a structure of Formula IX, X, XI or XII:

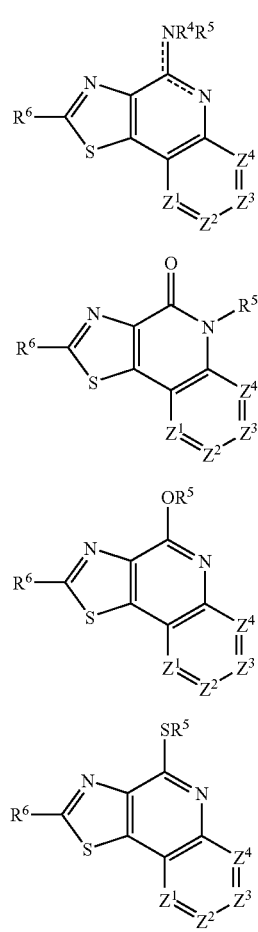

and pharmaceutically acceptable salts, esters and tautomers thereof; wherein:

each $Z^1, Z^2, Z^3$, and $Z^4$ is N or $CR^3$ and none, one or two of $Z^1, Z^2, Z^3$, and $Z^4$ is N;

each $R^3$ and $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ and $R^6$ can be halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, polar substituent, carboxy bioisostere, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member.

C2. The compound of embodiment C1, provided that at least one $R^3$ present is a polar substituent.

C3. The compound of embodiment C1, wherein the polar substituent accepts or donates a hydrogen bond.

C4. The compound of embodiment C1, wherein the polar substituent is selected from a carboxy, a carboxy bioisostere or other acid-derived moiety that exists predominately as an anion at a pH of about 7 to 8.

C5. The compound of embodiment C1, wherein the polar substituent contains an OH or NH, an ether oxygen, an amine nitrogen, an oxidized sulfur or nitrogen, a carbonyl, a nitrile, and a nitrogen-containing or oxygen-containing heterocyclic ring whether aromatic or non-aromatic.

C6. The compound of embodiment C1, wherein the polar substituent is a carboxylate.

C7. The compound of embodiment C1, wherein the polar substituent is a carboxylic acid.

C8. The compound of embodiment C1, wherein the polar substituent is a bioisostere selected from the group consisting of:

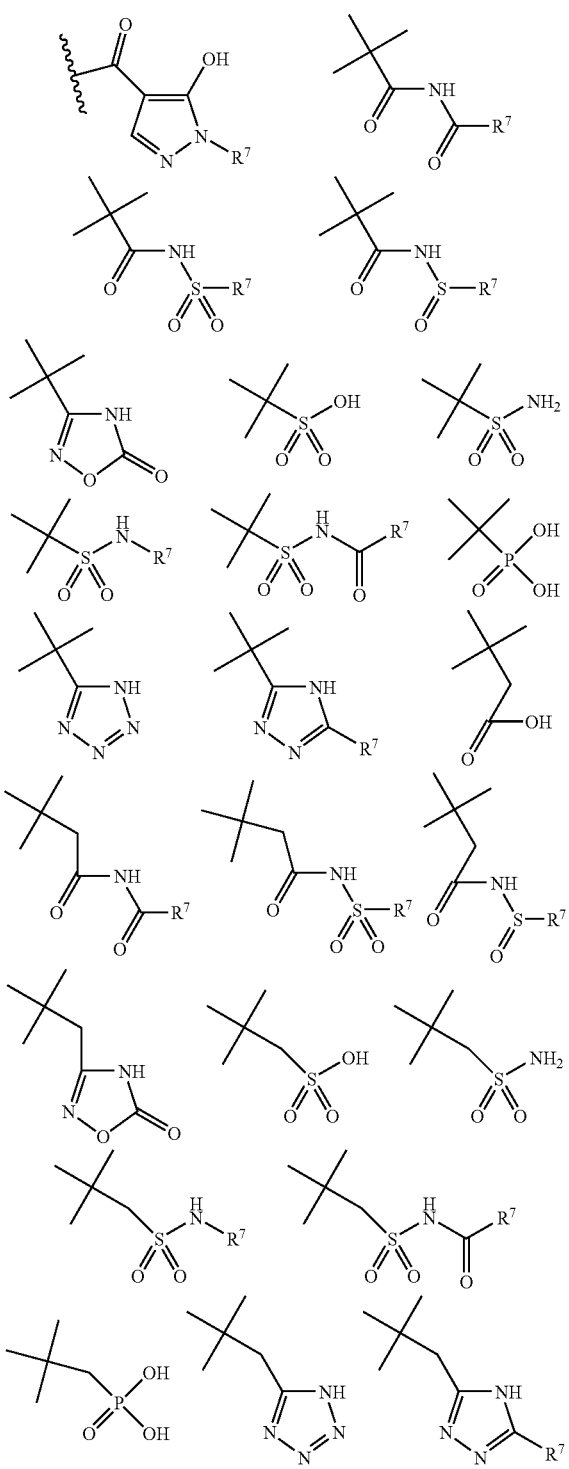

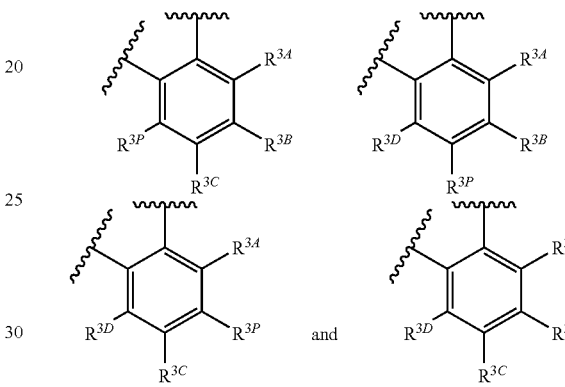

and salts of the foregoing, wherein each $R^7$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring; or $R^7$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring.

C9. The compound of embodiment C1, wherein the polar substituent is selected from the group consisting of carboxylic acid, carboxylic ester, carboxamide, tetrazole, triazole, carboxymethanesulfonamide, oxadiazole, oxothiadiazole, thiazole, aminothiazole and hydroxythiazole.

C10. The compound of any one of embodiments C1-C9, wherein the polar substituent is at a position on the ring containing $Z^1$-$Z^4$.

C11. The compound of embodiment C10, wherein the ring containing $Z^1$-$Z^4$ includes two, three or four polar substituents.

C12. The compound of any one of embodiments C1-C9, wherein each of $Z^1$-$Z^4$ is $CR^3$ and one of the $R^3$ substituents is a polar substituent C13. The compound of embodiment C1, wherein the ring containing $Z^1$-$Z^4$ is selected from one of the following structures wherein $R^{3P}$ is a polar substituent and each $R^{3A}$, $R^{3B}$, $R^{3C}$ and $R^{3D}$ independently is selected from $R^3$ substituents.

C14. The compound of any one of embodiments C1-C13, wherein at least one of $Z^1$-$Z^4$ is a nitrogen atom.

C15. The compound of embodiment C14, the ring containing $Z^1$-$Z^4$ is independently an optionally substituted pyridine, pyrimidine or pyridazine ring.

C16. The compound of any one of embodiments C1-C15, wherein $R^4$ is H.

C17. The compound of any one of embodiments C1-C16, wherein $R^5$ is an optionally substituted 3-8 membered ring.

C18. The compound of any one of embodiments C1-C16, wherein $R^5$ is a $C_{1-10}$ alkyl group substituted with an optionally substituted 3-8 membered ring.

C19. The compound of embodiment C18, wherein $R^5$ is an optionally substituted six-membered carbocyclic or heterocyclic ring.

C20. The compound of embodiment C19, wherein $R^5$ is an optionally substituted phenyl ring.

C21. The compound of embodiment C20, wherein the compound has a structure of Formula IX, $R^4$ is H or $CH_3$ and $R^5$ is a phenyl substituted with one or more halogen or acetylene substituents.

C22. The compound of embodiment C21, wherein the one or more halogen or acetylene substituents are on the phenyl ring at the 3-position, 4-position or 5-position, or combinations thereof.

C23. The compound of any one of embodiments C1-C16, wherein $R^5$ is a $C_{1-3}$ alkyl substituted with an optionally substituted phenyl, pyridyl or morpholino ring substituent, or substituted with —$NR^4R^5$ (e.g., —$N(CH_3)_2$).

C24. The compound of embodiment C1, wherein the polar substituent is a carboxy, carboxyalkyl (e.g., carboxymethyl), tetrazole or amide (e.g., —$CONH_2$) substituent.

C25. The compound of embodiment C1, wherein the $R^6$ substituent is a $-NR^4R^5$ substituent.

C26. The compound of embodiment C25, wherein the $R^6$ substituent is a $-NH-(C1-C6\ alkyl)$ moiety.

C27. The compound of embodiment C1, wherein each of $Z^1$, $Z^2$, $Z^3$, and $Z^4$ is $CR^3$.

C28. The compound of embodiment C1, wherein at least one $R^3$ is H.

C29. The compound of embodiment C1, wherein at least two $R^3$ are H.

C30. The compound of embodiment C1, wherein $R^6$ is H.

C31. The compound of embodiment C13, wherein each $R^{3A}$, $R^{3C}$, $R^{3D}$ and $R^6$ is H and $R^{3B}$ is a polar substituent.

C32. The compound of embodiment C1, wherein the compound has a structure of Formula IX, $R^4$ and $R^5$ are not both hydrogen, and $R^4$ and $R^5$ independently are H, $-Y^0$ or $-LY^1$, wherein $Y^0$ is an optionally substituted 5-membered ring or optionally substituted 6-membered ring, $Y^1$ is an optionally substituted 5-membered aryl ring or optionally substituted 6-membered aryl ring, and L is a C1-C20 alkyl linker or C1-C20 alkylene linker.

C33. The compound of embodiment C1, provided that if $R^5$ in Formula IX is phenyl, substituted phenyl, $-CH(CH_3)-(CH_2)_3-NEt_2$, $-(CH_2)_3$-piperazine-$(CH_2)_3-NH_2$, cyclohexane or butyl, then one or more of $R^3$ present is a non-hydrogen moiety.

C34. A pharmaceutical composition comprising a compound of embodiment C1 and a pharmaceutically acceptable carrier.

E1. A method for identifying a candidate molecule that interacts with a PARP protein, which comprises contacting a composition containing a PARP protein and a compound having a structure of Formula I, II, III, IV, V, VI, VII, VIII, IX, X, XI, XII, XIII, XIV, XV or XVI with a candidate molecule under conditions in which the compound and the protein interact, and determining whether the amount of the compound that interacts with the protein is modulated relative to a control interaction between the compound and the protein without the candidate molecule, whereby a candidate molecule that modulates the amount of the compound interacting with the protein relative to the control interaction is identified as a candidate molecule that interacts with the protein.

E2. The method of embodiment E1, wherein the PARP protein comprises the amino acid sequence of SEQ ID NO: 1 or a substantially identical variant thereof.

E3. The method of embodiment E1 or E2, wherein the protein is in a cell.

E4. The method of any one of embodiments E1-E3, wherein the protein is in a cell-free system.

E5. The method of any one of embodiments E1-E4, wherein the protein, the compound or the molecule is in association with a solid phase.

E6. The method of any one of embodiments E1-E5, wherein the interaction between the compound and the protein is detected via a detectable label.

E7. The method of embodiment E6, wherein the protein comprises a detectable label.

E8. The method of embodiment E6, wherein the compound comprises a detectable label.

E9. The method of any one of embodiments E1-E5, wherein the interaction between the compound and the protein is detected without a detectable label.

F1. A method for modulating the activity of a PARP protein, which comprises contacting a system comprising the protein with a compound having a structure of Formula I, II, III, IV, V, VI, VII, VIII, IX, X, XI, XII, XIII, XIV, XV or XVI in an amount effective for modulating the activity of the protein.

F2. The method of embodiment F1, wherein the activity of the protein is inhibited.

F3. The method of F1 or F2, wherein the system is a cell.

F4. The method of any one of embodiments F1-F3, wherein the system is a cell-free system.

F5. The method of any one of embodiments F1-F4, wherein the protein or the compound is in association with a solid phase.

G1. A method for inhibiting cell proliferation, which comprises contacting cells with a compound having a structure of Formula I, II, III, IV, V, VI, VII, VIII, IX, X, XI, XII, XIII, XIV, XV or XVI in an amount effective to inhibit proliferation of the cells.

G2. The method of embodiment G1, wherein the cells are in a cell line.

G3. The method of embodiment G2, wherein the cells are in a cancer cell line.

G4. The method of embodiment G3, wherein the cancer cell line is a breast cancer, prostate cancer, pancreatic cancer, lung cancer, hemopoietic cancer, colorectal cancer, skin cancer, ovary cancer cell line.

G5. The method of embodiment G4, wherein the cancer cell line is a breast cancer, prostate cancer or pancreatic cancer cell line.

G6. The method of embodiment G1, wherein the cells are in a tissue.

G7. The method of embodiment G1, wherein the cells are in a subject.

G8. The method of embodiment G1, wherein the cells are in a tumor.

G9. The method of embodiment G1, wherein the cells are in a tumor in a subject.

G10. The method of any one of embodiments G1-G9, which further comprises inducing cell apoptosis.

G11. The method of embodiment G1, wherein the cells are from an eye of a subject having macular degeneration.

G12. The method of embodiment G1, wherein the cells are in a subject having macular degeneration.

H1. A method for treating a condition related to aberrant cell proliferation, which comprises administering a compound having a structure of Formula I, II, III, IV, V, VI, VII, VIII, IX, X, XI, XII, XIII, XIV, XV or XVI to a subject in need thereof in an amount effective to treat the cell proliferative condition.

H2. The method of embodiment H1, wherein the cell proliferative condition is a tumor-associated cancer.

H3. The method of embodiment H1 or H2, wherein the cancer is of the breast, prostate, pancreas, lung, colorectum, skin, or ovary H4. The method of embodiment H1, wherein the cell proliferative condition is a non-tumor cancer.

H5. The method of embodiment H4, wherein the non-tumor cancer is a hemopoietic cancer.

H6. The method of embodiment H1, wherein the cell proliferative condition is macular degeneration.

I1. A method to treat cancer or an inflammatory disorder in a subject in need of such treatment, comprising:

administering to the subject a therapeutically effective amount of a therapeutic agent having a structure of Formula I, II, III, IV, V, VI, VII, VIII, IX, X, XI, XII, XIII, XIV, XV or XVI or a pharmaceutically acceptable salt thereof; and administering to the subject a molecule that inhibits PARP or CK2 in an amount that is effective to enhance a desired effect of the therapeutic agent.

I2. The method of embodiment I1, wherein the molecule that inhibits PARP or CK2 is a compound having a structure of Formula I, II, III, IV, V, VI, VII, VIII, IX, X, XI, XII, XIII, XIV, XV or XVI, or a pharmaceutically acceptable salt thereof.

I3. The method of embodiment I1, wherein the therapeutic agent is:

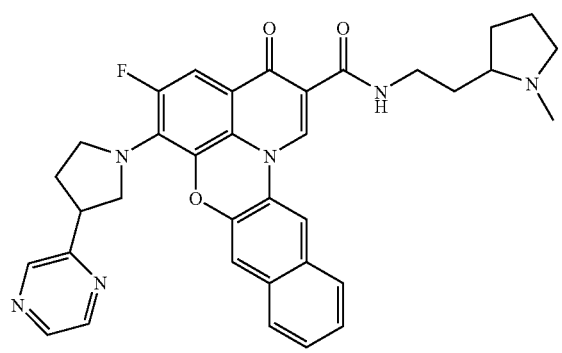

or a specific isomer or mixture of isomers thereof, or a pharmaceutically acceptable salt thereof.

I4. The method of any of embodiments I1-I3, wherein the therapeutic agent and the molecule that inhibits PARP or CK2 are administered at substantially the same time.

I5. The method of any of embodiments I1-I3, wherein the therapeutic agent and molecule that inhibits PARP or CK2 are used concurrently by the subject.

I6. The method of any of embodiments I1-I3, wherein the therapeutic agent and the molecule that inhibits PARP or CK2 are combined into one pharmaceutical composition.

I7. A pharmaceutical composition comprising a therapeutic agent of any of formulas TA1-1, TA2, TA3-1, TA4-1, TA5-1 or TA6 admixed with a molecule that inhibits PARP or CK2, or a pharmaceutically acceptable salt thereof.

I8. The pharmaceutical composition of embodiment I7, wherein the molecule that inhibits PARP or CK2 is a PARP inhibitor and is a known compound shown above, or is GPI 15427, GPI 16539.

I9. The pharmaceutical composition of embodiment I7, wherein the molecule that inhibits PARP or CK2 is a compound of Formula I, II, III, IV, V, VI, VII, VIII, IX, X, XI, XII, XIII, XIV, XV or XVI as described herein, or a pharmaceutically acceptable salt thereof.

I10. The pharmaceutical composition of embodiment I9, wherein the therapeutic agent is a compound of formula TA2 or a pharmaceutically acceptable salt thereof.

I11. A therapeutic composition comprising:
a therapeutically effective amount of a therapeutic agent of the formula TA2:

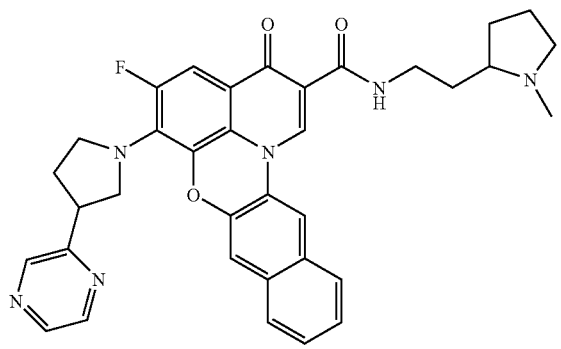

or a specific isomer or mixture of isomers thereof, or a pharmaceutically acceptable salt thereof,
admixed with an amount of a PARP inhibitor or a pharmaceutically acceptable salt of a PARP inhibitor, wherein the PARP inhibitor is selected from the group consisting of GPI 15427, GPI 16539, and the known compounds shown above; and
wherein the amount of the PARP inhibitor or the pharmaceutically acceptable salt of a PARP inhibitor is an amount that is effective to enhance a desired effect of the therapeutic agent.

M1. A compound having a structure of Formulae XIII, XIV, XV and XVI:

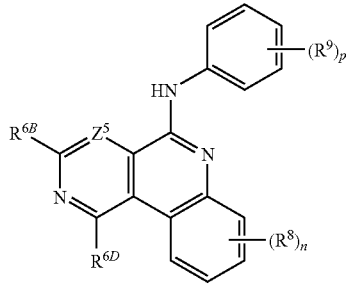

Formula XIII

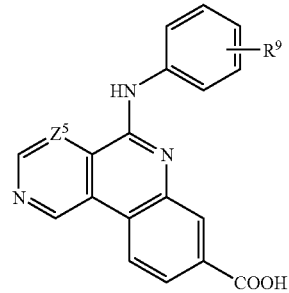

Formula XIV

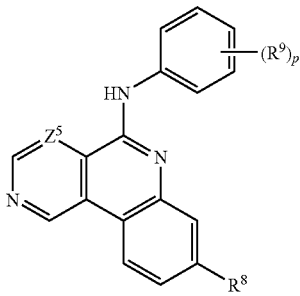

Formula XV

Formula XVI

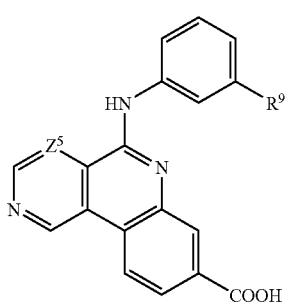

and pharmaceutically acceptable salts, esters, prodrugs and tautomers thereof; wherein:

$Z^5$ is N or $CR^{6A}$;

each $R^{6A}$, $R^{6B}$, $R^{6C}$ and $R^8$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^{6A}$, $R^{6B}$, $R^{6C}$ and $R^8$ independently is halo, $CF_3$, CFN, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, carboxy bioisostere, $CONR_2$, OOCR, COR, or $NO_2$, $R^9$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or $R^9$ is independently halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

n is 0 to 4; and p is 0 to 4.

M2. The compound of embodiment M1, wherein $Z^5$ is N.

M3. The compound of embodiment M1, wherein $R^8$ is a caboxy moiety or carboxy bioisostere.

M4. The compound of embodiment M3, wherein the carboxy moiety is a carboxylate or carboxylic acid.

M5. The compound of embodiment M1, wherein $R^9$ is selected from —C≡CR, —C≡CH, —$CH_3$, —$CH_2CH_3$, —$CF_3$, —CFN, —C≡N, —OR and halogen.

M6. The compound of embodiment M5, wherein $R^9$ is selected from halogen, —C≡CR or —C≡CH.

M7. The compound of embodiment M6, wherein $R^9$ is halogen.

M8. The compound of embodiment M7, wherein $R^9$ is chloro.

M9. The compound of embodiment M7, wherein $R^9$ is bromo.

M10. The compound of embodiment M6, wherein $R^9$ is —C≡CH.

M11. The compound of embodiment M8, which has the following structure

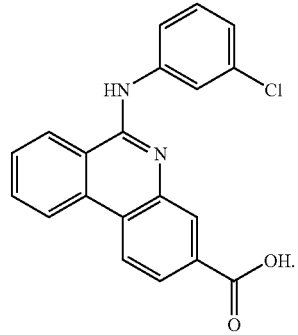

M12. The compound of embodiment M10, which has the following structure

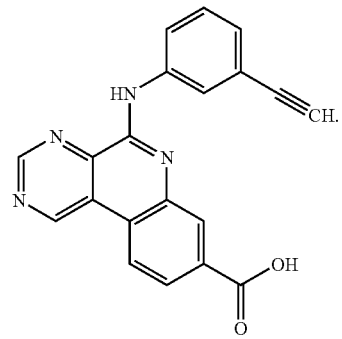

M13. The compound of embodiment M1, wherein p is one or two.

M14. The compound of embodiment M1, wherein p is one.

M15. The compound of embodiment M1, wherein n is one or two.

M16. The compound of embodiment M1, wherein n is one.

N1. A method for identifying a candidate molecule that interacts with a serine-threonine protein kinase, which comprises:

contacting a composition containing a serine-threonine protein kinase and a compound having a structure of Formula I, II, III, IV, V, VI, VII, VIII, IX, X, XI, XII, XIII, XIV, XV or XVI under conditions in which the compound and the protein interact with a candidate molecule, and determining whether the amount of the compound that interacts with the protein is modulated relative to a control interaction between the compound and the protein without the candidate molecule, whereby a candidate molecule that modulates the amount of the compound interacting with the protein relative to the control interaction is identified as a candidate molecule that interacts with the protein.

N2. The method of embodiment N1, wherein the serine-threonine protein kinase is a human serine-threonine protein kinase.

N3. The method of embodiment N1, wherein the serine-threonine protein kinase is selected from the group consisting of CK2, CK2α2, Pim-1, CDK1/cyclinB, c-RAF, Mer, MELK, DYRK2, Flt3, Flt3 (D835Y), Flt4, HIPK3, HIPK2, ZIPK and ZIPK.

N4. The method of embodiment N1, wherein the serine-threonine protein kinase contains one or more of the following amino acids at positions corresponding to those listed in human CK2: leucine at position 45, methionine at position 163 and isoleucine at position 174.

N5. The method of embodiment N4, wherein the serine threonine protein kinase is selected from the group consisting of CK2, STK10, HIPK2, HIPK3, DAPK3, DYK2 and PIM-1.

N6. The method of embodiment N1, wherein the protein, the compound or the molecule is in association with a solid phase.

N7. The method of embodiment N1, wherein the interaction between the compound and the protein is detected via a detectable label.

O1. A method for modulating a serine-threonine protein kinase activity, which comprises contacting a system comprising a serine-threonine protein kinase protein with a compound of Formula I, II, III, IV, V, VI, VII, VIII, IX, X, XI, XII, XIII, XIV, XV or XVI in an amount effective for modulating the activity of the protein.

O2. The method of embodiment O1, wherein the protein kinase activity is the transfer of a gamma phosphate from adenosine triphosphate to a peptide or protein substrate.

P1. A method for treating pain or inflammation in a subject, which comprises administering a compound of Formula I, II, III, IV, V, VI, VII, VIII, IX, X, XI, XII, XIII, XIV, XV or XVI to a subject in need thereof in an amount effective to treat the pain or the inflammation.

P2. A method for identifying a compound that reduces inflammation or pain, which comprises:

contacting a system with a compound of Formula I, II, III, IV, V, VI, VII, VIII, IX, X, XI, XII, XIII, XIV, XV or XVI; and detecting a pain signal or inflammation signal in the system, whereby a compound that modulates the pain signal or inflammation signal relative to a control molecule is identified as a compound that reduces inflammation of pain.

P3. A method for inhibiting angiogenesis in a subject, which comprises administering a compound of Formula I, II, III, IV, V, VI, VII, VIII, IX, X, XI, XII, XIII, XIV, XV or XVI to a subject in need thereof in an amount effective to inhibit the angiogenesis.

P4. A method for identifying a compound that modulates angiogenesis, which comprises contacting a system with a compound of Formula I, II, III, IV, V, VI, VII, VIII, IX, X, XI, XII, XIII, XIV, XV or XVI; and detecting angiogenesis or an angiogenesis signal in the system, whereby a compound that modulates the angiogenesis or angiogenesis signal relative to a control molecule is identified as a compound that modulates angiogenesis.

Q1. A compound of formula (A):

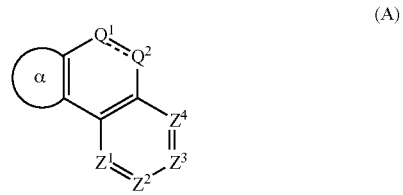

(A)

wherein the group labeled α represents a 5-6 membered aromatic or heteroaromatic ring fused onto the ring containing $Q^1$, wherein α is a 6-membered aryl ring optionally containing one or more nitrogen atoms as ring members, or a five membered aryl ring selected from thiophene and thiazole;

$Q^1$ is C=X, $Q^2$ is $NR^5$, and the bond between $Q^1$ and $Q^2$ is a single bond; or $Q^1$ is C—X—$R^5$, $Q^2$ is N, and the bond between $Q^1$ and $Q^2$ is a double bond; and wherein X represents O, S or $NR^4$;

each $Z^1$, $Z^2$, $Z^3$, and $Z^4$ is N or $CR^3$ and one or more of $Z^1$, $Z^2$, $Z^3$, and $Z^4$ is $CR^3$;

each of $Z^5$, $Z^6$, $Z^7$ and $Z^8$ is $CR^6$ or N;

each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ and each $R^6$ can be halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, $R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member;

or a pharmaceutically acceptable salt, ester or prodrug thereof;

provided that when $Q^1$ in Formula (A) is C—NHΦ, where Φ is optionally substituted phenyl:

if the ring labeled α is a six-membered ring containing at least one N as a ring member, at least one $R^3$ present must be a polar substituent, or if each $R^3$ is H, then Φ must be substituted; and if the ring labeled α is phenyl, and three of $Z^1$-$Z^4$ represent CH, then $Z^2$ cannot be C—OR", and $Z^3$ cannot be $NH_2$, $NO_2$, NHC(=O)R" or NHC(=O)—OR", where R" is C1-C4 alkyl.

---

What is claimed is:

1. A compound having a structure of Formulae XIII, XIV, XV or XVI:

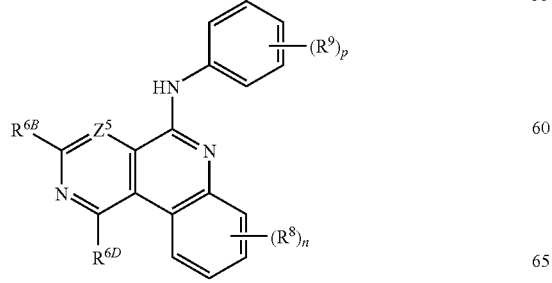

Formula XIII

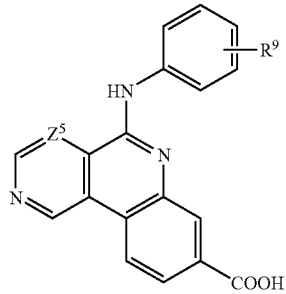

Formula XIV

-continued

Formula XV

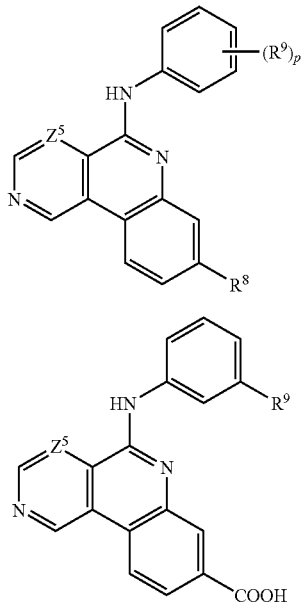

Formula XVI

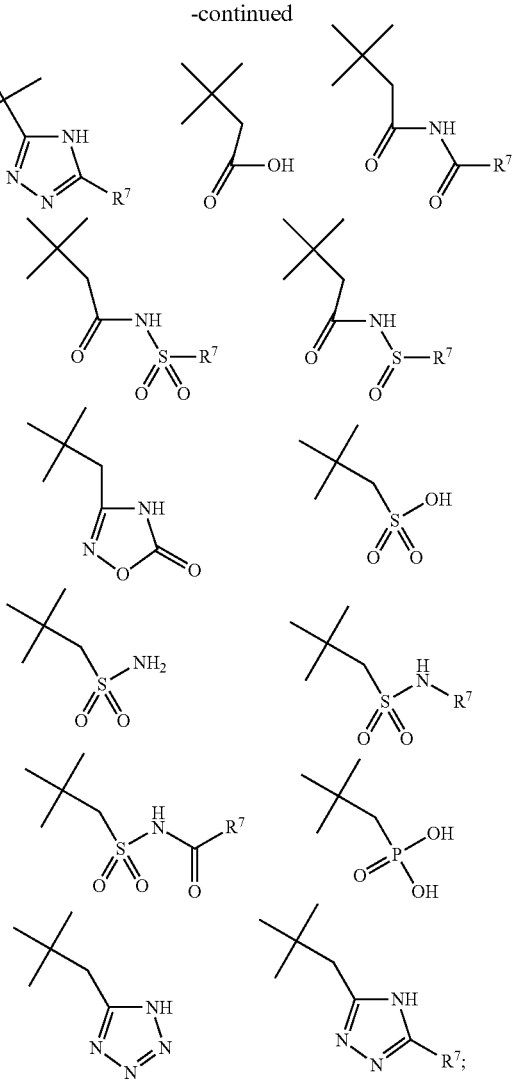

or a pharmaceutically acceptable salt thereof; wherein:
$Z^5$ is $CR^{6A}$;
each $R^{6A}$, $R^{6B}$, $R^{6D}$ and $R^8$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group,
or each $R^{6A}$, $R^{6B}$, $R^{6D}$ and $R^8$ independently is halo, $CF_3$, CFN, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, carboxy bioisostere, carboxylate, carboxylic acid, $CONR_2$, OOCR, COR, or $NO_2$, wherein carboxy bioisostere is selected from the group consisting of

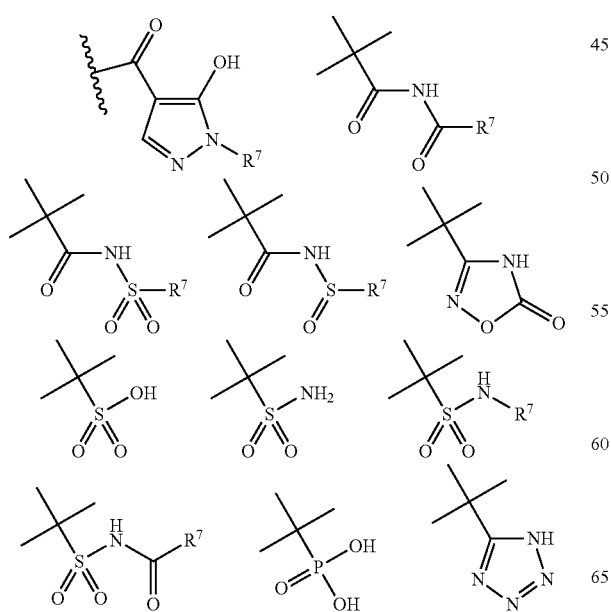

$R^9$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or $R^9$ is independently halo, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', SO₂R', SO₂NR'₂, NR'SO₂R', NR'CONR'₂, NR'COOR', NR'COR', CN, COOR', CONR'₂, OOCR', COR', and NO₂, wherein each R' is independently H, C1-C6 alkyl, C2-C6 heteroalkyl, C1-C6 acyl, C2-C6 heteroacyl, C6-C10 aryl, C5-C10 heteroaryl, $C_{7-12}$ arylalkyl, or $C_{6-12}$ heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

n is 0 to 4; and p is 0 to 4.

2. The compound of claim 1, wherein $R^8$ is a carboxylate or carboxylic acid.

3. The compound of claim 1, wherein $R^9$ is selected from —C≡CR, —C≡CH, —CH₃, —CH₂CH₃, —CF₃, —C≡N, —OR and halogen.

4. The compound of claim 3, wherein $R^9$ is selected from halogen, —C≡CR or —C≡CH.

5. The compound of claim 4, wherein $R^9$ is halogen.

6. The compound of claim 5, wherein $R^9$ is chloro.

7. The compound of claim 5, wherein $R^9$ is bromo.

8. The compound of claim 4, wherein $R^9$ is —C≡CH.

9. A compound of the formula:

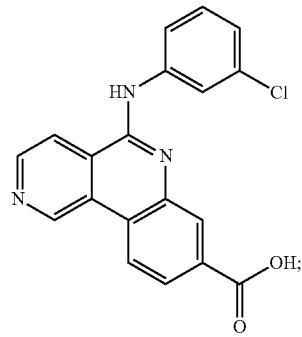

or a pharmaceutically acceptable salt thereof.

10. The compound of claim 4, wherein p is one or two.

11. The compound of claim 4, wherein p is one.

12. The compound of claim 4, wherein n is one or two.

13. The compound of claim 4, wherein n is one.

14. A method for treating pain in a subject, which comprises administering a compound of Formula XIII, XIV, XV, or XVI, or a pharmaceutically acceptable salt thereof, to a subject in need thereof in an amount effective to treat the pain.

* * * * *